(12) United States Patent
Nishio et al.

(10) Patent No.: US 9,045,789 B2
(45) Date of Patent: Jun. 2, 2015

(54) METHOD FOR PRODUCING A TARGET SUBSTANCE BY FERMENTATION

(71) Applicant: AJINOMOTO CO., INC., Tokyo (JP)

(72) Inventors: Yousuke Nishio, Kanagawa (JP); Youko Yamamoto, Kanagawa (JP); Kazuteru Yamada, Kanagawa (JP); Kosuke Yokota, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 13/914,872

(22) Filed: Jun. 11, 2013

(65) Prior Publication Data

US 2013/0295621 A1 Nov. 7, 2013

Related U.S. Application Data

(63) Continuation of application No. PCT/JP2012/078725, filed on Nov. 6, 2012.

(60) Provisional application No. 61/558,685, filed on Nov. 11, 2011.

(30) Foreign Application Priority Data

Nov. 11, 2011 (JP) ................................. 2011-247031

(51) Int. Cl.
*C12P 13/14* (2006.01)
*C12P 7/50* (2006.01)
(Continued)

(52) U.S. Cl.
CPC . *C12P 13/14* (2013.01); *C12P 7/50* (2013.01); *C12N 15/52* (2013.01); *C12N 9/0006* (2013.01); *C12N 9/0008* (2013.01); *C12N 9/16* (2013.01); *C12Y 103/05001* (2013.01); *C12N 9/88* (2013.01); *C12Y 101/01113* (2013.01); *C12Y 102/01026* (2013.01); *C12Y 301/01068* (2013.01); *C12Y 402/01082* (2013.01); *C12P 7/58* (2013.01); *C12P 13/001* (2013.01);
(Continued)

(58) Field of Classification Search
None
See application file for complete search history.

(56) References Cited

U.S. PATENT DOCUMENTS 5,977,331 A 11/1999 Asakura et al.
6,197,559 B1 3/2001 Moriya et al.
(Continued)

FOREIGN PATENT DOCUMENTS

EP 1577396 9/2005
JP 2005-261433 9/2005

OTHER PUBLICATIONS

Weimberg, "Pentose oxidation by Pseudomonas fragi", Journal of Biological Chemistry, vol. 236, No. 3, pp. 629-635, 1961.*
(Continued)

*Primary Examiner* — Rebecca Prouty
*Assistant Examiner* — Richard Ekstrom
(74) *Attorney, Agent, or Firm* — Shelly Guest Cermak; Cermak Nakajima & McGowan LLP

(57) ABSTRACT

A target substance can be produced by culturing a bacterium having an ability to produce 2-ketoglutaric acid or a derivative thereof, and an ability to produce xylonic acid from xylose, which is imparted with xylonate dehydratase activity, 2-keto-3-deoxyxylonate dehydratase activity and 2-ketoglutaric semialdehyde dehydrogenase activity, or in which these activities are enhanced, in a medium containing xylose as a carbon source to produce and accumulate the target substance in the medium, and collecting the target substance from the medium.

6 Claims, 4 Drawing Sheets

(a)

(b)

(51) Int. Cl.

| | |
|---|---|
| C12N 15/52 | (2006.01) |
| C12N 9/04 | (2006.01) |
| C12N 9/02 | (2006.01) |
| C12N 9/16 | (2006.01) |
| C12N 9/88 | (2006.01) |
| C12P 7/58 | (2006.01) |
| C12P 13/00 | (2006.01) |
| C12P 13/04 | (2006.01) |
| C12P 13/10 | (2006.01) |
| C12P 13/24 | (2006.01) |

(52) U.S. Cl.
CPC ............... *C12P13/04* (2013.01); *C12P 13/10* (2013.01); *C12P 13/24* (2013.01)

(56) References Cited

U.S. PATENT DOCUMENTS

| | | | |
|---|---|---|---|
| 6,267,309 | B1 | 7/2001 | Chieffalo et al. |
| 6,331,419 | B1 | 12/2001 | Moriya et al. |
| 6,682,912 | B2 | 1/2004 | Moriya et al. |
| 6,962,805 | B2 | 11/2005 | Asakura et al. |
| 7,037,690 | B2 | 5/2006 | Hara et al. |
| 7,090,998 | B2 | 8/2006 | Ishikawa et al. |
| 7,205,132 | B2 | 4/2007 | Hirano et al. |
| 7,244,581 | B2 * | 7/2007 | Sode .............................. 435/14 |
| 7,344,874 | B2 | 3/2008 | Hara et al. |
| 7,695,946 | B2 | 4/2010 | Usuda et al. |
| 7,696,315 | B2 | 4/2010 | Usuda et al. |
| 7,785,845 | B2 * | 8/2010 | Hara et al. .................... 435/110 |
| 7,785,858 | B2 | 8/2010 | Kozlov et al. |
| 7,794,989 | B2 | 9/2010 | Nakamura et al. |
| 7,915,018 | B2 | 3/2011 | Rybak et al. |
| 7,923,226 | B2 * | 4/2011 | Frost .............................. 435/158 |
| 7,927,844 | B2 | 4/2011 | Nakamura et al. |
| RE42,350 | E | 5/2011 | Izui et al. |
| 8,003,367 | B2 | 8/2011 | Marchenko et al. |
| 8,012,722 | B2 | 9/2011 | Chinen et al. |
| 8,058,035 | B2 | 11/2011 | Hara et al. |
| 8,129,151 | B2 | 3/2012 | Moriya et al. |
| 8,192,963 | B2 | 6/2012 | Nishio et al. |
| 8,206,954 | B2 | 6/2012 | Takikawa et al. |
| 8,222,007 | B2 | 7/2012 | Hara et al. |
| 8,278,074 | B2 | 10/2012 | Nakamura et al. |
| 2005/0214913 | A1 | 9/2005 | Marchenko et al. |
| 2005/0233308 | A1 | 10/2005 | Nishio et al. |
| 2007/0004014 | A1 | 1/2007 | Tsuji et al. |
| 2009/0286290 | A1* | 11/2009 | Hara et al. .................... 435/107 |
| 2010/0190217 | A1 | 7/2010 | Doi et al. |
| 2011/0076730 | A1* | 3/2011 | Frost et al. .................... 435/106 |
| 2012/0129233 | A1 | 5/2012 | Tajima et al. |
| 2013/0217078 | A1* | 8/2013 | Tang et al. ........................ 435/99 |
| 2013/0260423 | A1* | 10/2013 | Knudsen et al. ................ 435/99 |

OTHER PUBLICATIONS

Berghäll, S., et al., "Identification in the mould Hypocrea jecorina of a gene encoding an NADP+:D-xylose dehydrogenase," FEMS Microbiol. Lett., 2007;277:249-253.

Brouns, S. J. J.., et al., "Identification of the Missing Links in Prokaryotic Pentose Oxidation Pathways: Evidence for Enzyme Recruitment," J. Bio. Chem. 2006;281:27378-27388.

Dahms, A. S., et al., "D-xylose Dehydrogenase," Methods in Enzymology 1982;89:226-228.

Ely, B., "Genetics of *Caulobacter crescentus*," Methods in Enzymology 1991;204:372-384.

Fernandes, S., et al., "Xylose reductase from the thermophilic fungus Talaromyces emersonii: cloning and heterologous expression of the native gene (Texr) and a double mutant (Texr[K271R+N273D]) with altered coenzyme specificity," J. Biosci. 2009;34(6):881-890.

Gonzalez, R., et al., "Global Gene Expression Differences Associated with Changes in Glycolytic Flux and Growth Rate in *Escherichia coli* during the Fermentation of Glucose and Xylose," Biotechnol. Prog. 2002;18:6-20.

Hartman, A. L., et al., "The Complete Genome Sequence of Haloferax volcanii DS2, a Model Archaeon," PLoS ONE 2010;5(3),e9605:1-20.

Hosoya, S., et al., "Identification and characterization of the Bacillus subtilis D-glucarate/galactarate utilization operon ycbCDEFGHJ," FEMS Microbiol. Lett. 2002;210:193-199.

Johnsen, U., et al., "Novel Xylose Dehydrogenase in the Halophilic Archaeon Haloarcula marismortui," J. Bacteriol. 2004;186(18):6198-6207.

Johnsen, U., et al., "D-Xylose Degradation Pathway in the Halophilic Archaeon Haloferax volcanii," J. Biol. Chem. 2009;284(40):27290-27303.

Kawaguchi, H., et al., "Engineering of a Xylose Metabolic Pathway in *Corynebacterium glutamicum*," Appl. Environmen. Microbiol. 2006;72(5):3418-3428.

Meijnen, J.-P., et al., "Establishment of Oxidative D-Xylose Metabolism in Pseudomonas putida S12," Appl. Environmen. Microbiol. 2009;75(9):2784-2791.

Meisenzahl, A. C., et al., "Isolation and Characterization of a Xylose-Dependent Promoter from *Caulobacter crescentus*," J. Bacteriol. 1997;179(3):592-600.

Nichols, N. N., et al., "Use of catabolite repression mutants for fermentation of sugar mixtures to ethanol," Appl. Microbiol. Biotechnol. 2001;56:120-125.

Nierman, W. C., et al., "Complete genome sequence of *Caulobacter crescentus*," PNAS 2001;98(7):4136-4141.

Nygård, Y., et al., "Bioconversion of D-xylose to D-xylonate with Kluyveromyces lactis," Metabolic Engineering 2011;13:383-391.

Sasaki, M., et al., "Engineering of pentose transport in *Corynebacterium glutamicum* to improve simultaneous utilization of mixed sugars," Appl. Microbiol. Biotechnol. 2009;85:105-115.

Song, S., et al., "Organization and Regulation of the D-Xylose Operons in *Escherichia coli* K-12: XylR Acts as a Transcriptional Activator," J. Bacteriol. 1997;179(22):7025-7032.

Stephens, C., et al., "Regulation of D-Xylose Metabolism in *Caulobacter crescentus* by a LacI-Type Repressor," J. Bacteriol. 2007;189(24):8828-8834.

Tao, H., et al., "Engineering a Homo-Ethanol Pathway in *Escherichia coli*: Increased Glycolytic Flux and Levels of Expression of Glycolytic Genes during Xylose Fermentation," J. Bacteriol. 2001;183(10):2979-2988.

Toivari, M. H., et al., "Microbial D-xylonate production," Appl. Microbiol. Biotechnol. 2012;96:1-8.

Toivari, M. H., et al., "Saccharomyces cerevisiae engineered to produce D-xylonate," Appl. Microbiol. Biotechnol. 2010;88:751-760.

Watanabe, S., et al., "Enzyme Catalysis and Regulation: α-Ketoglutaric Semialdehyde Dehydrogenase Isozymes Involved in Metabolic Pathways of D-Glucarate, D-Galactarate, and Hydroxy-L-proline: Molecular and Metabolic Convergent Evolution," J. Biol. Chem. 2007;282:6685-6695.

Thanbichler, M., et al., "A comprehensive set of plasmids for vanillate- and xylose-inducible gene expression in *Caulobacter crescentus*," Nucl. Acids Res. 2007;35(20),e137:1-16.

Aghaie, A., et al., "Metabolism and Bioenergetics: New Insights into the Alternative d-Glucarate Degradation Pathway," J. Biol. Chem. 2008;283(23):15638-15646.

Watanabe, S., et al., "Enzyme Catalysis and Regulation: Identification and Characterization of l-Arabonate Dehydratase, l-2-Keto-3-deoxyarabonate Dehydratase, and l-Arabinolactonase Involved in an Alternative Pathway of l-Arabinose Metabolism: Novel Evolutionary Insight Into Sugar Metabolism," J. Biol. Chem. 2006;281(44):33521-33536.

Gopinath, V., et al., "Amino acid production from rice straw and wheat bran hydrolysates by recombinant pentose-utilizing *Corynebacterium glutamicum*," Appl. Microbiol. Biotechnol. 2011;92:985-996.

Liu, H., et al., "High yield production of D-xylonic acid from D-xylose using engineered *Escherichia coli*," Bioresource Technol. 2012;115:244-248.

Stephens, C., et al., "Genetic Analysis of a Novel Pathway for D-Xylose Metabolism in *Caulobacter crescentus*," J. Bacteriol. 2007;189(5):2181-2185.

International Search Report for PCT Patent App. No. PCT/JP2012/078725 (Jan. 22, 2013).

International Preliminary Report on Patentability for PCT Patent App. No. PCT/JP2012/078725 (May 22, 2014).

* cited by examiner

METHOD FOR PRODUCING A TARGET SUBSTANCE BY FERMENTATION

This application is a Continuation of, and claims priority under 35 U.S.C. §120 to, International Application No. PCT/JP2012/078725, filed Nov. 6, 2012, and claims priority therethrough under 35 U.S.C. §119 to Japanese Patent Application No. 2011-247031, filed Nov. 11, 2011, and U.S. Provisional Patent Application No. 61/558,685, filed Nov. 11, 2011, the entireties of which are incorporated by reference herein. Also, the Sequence Listing filed electronically herewith is hereby incorporated by reference (File name: 2013-06-11T_US-471_Seq_List; File size: 263 KB; Date recorded: Jun. 11, 2013).

BACKGROUND OF THE INVENTION

1. Field of the Invention

The present invention relates to a method for producing a target substance such as L-amino acids by fermentation using a microorganism. More precisely, the method for producing a target substance by fermentation uses xylose as a raw material.

2. Brief Description of the Related Art

Methods for producing target substances such as L-amino acids by fermentation using a bacterium include methods of using a wild-type bacterium (wild-type strain), methods of using an auxotrophic strain derived from a wild-type strain, methods of using a metabolic regulation mutant strain derived from a wild-type strain which is resistant to various drugs, methods of using a strain having properties of both auxotrophic strain and metabolic regulation mutant, and so forth.

For example, L-glutamic acid is mainly produced by fermentation using an L-glutamic acid-producing bacterium of the so-called coryneform bacteria belonging to the genus *Brevibacterium, Corynebacterium* or *Microbacterium* or a mutant strain thereof (refer to, for example, Akashi K. et al., Amino Acid Fermentation, Japan Scientific Societies Press, pp. 195-215, 1986). As methods for producing L-glutamic acid by using other strains, methods utilizing a microorganism belonging to the genus *Bacillus, Streptomyces, Penicillium*, or the like (refer to, for example, U.S. Pat. No. 3,220,929), methods utilizing a microorganism belonging to the genus *Pseudomonas, Arthrobacter, Serratia, Candida*, or the like (refer to, for example, U.S. Pat. No. 3,563,857), methods utilizing a microorganism belonging to the genus *Bacillus*, or *Aerobacter aerogenes* (currently *Enterobacter aerogenes*), or the like (refer to, for example, Japanese Patent Publication (Kokoku) No. 32-9393), methods utilizing a mutant strain of *Escherichia coli* (refer to, for example, Japanese Patent Laid-open (Kokai) No. 5-244970), and so forth are known. Furthermore, methods of producing L-glutamic acid using a microorganism belonging to the genus *Klebsiella, Erwinia, Pantoea*, or *Enterobacter* (refer to, e.g., Japanese Patent Laid-open No. 2000-106869, Japanese Patent Laid-open No. 2000-189169 and Japanese Patent Laid-open No. 2000-189175) have also been disclosed.

In recent years, recombinant DNA techniques have been used in the production of target substances by fermentation. For example, L-amino acid productivity of a bacterium is improved by enhancing expression of a gene encoding an L-amino acid biosynthetic enzyme (U.S. Pat. No. 5,168,056 and U.S. Pat. No. 5,776,736), or by enhancing uptake of a carbon source into the L-amino acid biosynthesis system (U.S. Pat. No. 5,906,925).

Conventional industrial production of substances by fermentation typically employ saccharides, i.e., glucose, fructose, sucrose, blackstrap molasses, starch hydrolysate, and so forth as a carbon source, but they are relatively expensive, and use of biomass raw materials derived from plants and the like has also advanced in recent years.

Although raw materials including edible portions such as starch and fats and oils are mainly used as such biomass raw materials at present, it is necessary to shift such biomass raw materials to those which include non-edible portions, specifically, cellulose, hemicellulose, lignin, and so forth in the future. Non-edible biomass such as cellulose and hemicellulose are converted into pentoses or hexoses via a pretreatment using heat or acid, and a saccharification treatment using a cellulase enzyme, and then they can be used as raw materials in fermentation (Japanese Patent Laid-open based on PCT application (Kohyo) No. 9-507386 and Japanese Patent Laid-open based on PCT application No. 11-506934). If mixed saccharides of pentoses or hexoses are used as the raw materials for amino acid fermentation etc., *Escherichia coli* preferentially assimilates glucose, and as a result, the phenomena of two-step proliferation (diauxy), delayed growth etc. have been observed (Nichols N. N. et al., Appl. Microbiol. Biotechnol., 2001 July, 56(1-2):120-125 and Gonzalez, R., Biotechnol. Prog., 2002 January-February, 18(1):6-20)

In *Escherichia coli*, a xylose assimilation pathway utilizing xylose isomerase encoded by the xylA gene and xylulokinase encoded by the xylB gene is known, and it is also known that L-amino acids can be produced from xylose by introducing that pathway into *Escherichia coli* or *Corynebacterium glutamicum* (Tao H. et al., J. Bacteriol., 2001 May, 183 (10): 2979-2988, European Patent No. 1577396, Gopinath, V. et al., Appl. Microbiol. Biotechnol., 2011 Jul., 28).

It has also been reported that *Caulobacter crescentus* and *Haloferax volcanii* utilize a pathway of converting xylose into 2-ketoglutaric acid via xylonic acid in five steps, not using the conventionally known pathway as described above (Stephens, C. et al., J. Bacteriol., 2007 March, 189 (5):2181-2185). Moreover, examples of expression of that pathway in *Escherichia coli* are also known (Huaiwei, L et al., Bioresour Technol., 2011 Aug., 22, U.S. Pat. No. 7,923,226).

SUMMARY OF THE INVENTION

Aspects of the Invention

An aspect of the present invention is to provide a microorganism that can efficiently produce a target substance such as L-glutamic acid in a medium containing xylose, and a method for producing a target substance using such a microorganism.

Means for Achieving the Aspects

The development of a microorganism by utilizing the pathway of converting xylose into 2-ketoglutaric acid via xylonic acid for the purpose of developing an amino acid-producing bacterium having a pentose- or hexose-assimilating ability by breeding is described. As a result, a microorganism expressing such a pathway as described above can efficiently assimilate xylose.

It is an aspect of the present invention to provide a method for producing a target substance comprising culturing a bacterium having an ability to produce the target substance in a medium containing xylose so that the target substance accumulates in the medium, and collecting the target substance from the medium, wherein:

the target substance is 2-ketoglutaric acid or a derivative thereof, the bacterium has an ability to produce xylonic acid from xylose, and activities of the enzymes xylonate dehydratase, 2-keto-3-deoxyxylonate dehydratase and 2-ketoglutaric semialdehyde dehydrogenase have been imparted to or enhanced in the bacterium.

It is a further aspect of the present invention to provide the method as described above, wherein said activities are imparted to or enhanced in the bacterium by introducing expressible forms of genes coding for the enzymes into the bacterium.

It is a further aspect of the present invention to provide the method as described above,
wherein the genes are derived from, or native to, a microorganism belonging to a genus selected from the group consisting of *Caulobacter, Escherichia, Agrobacterium, Herbaspirillum, Actinoplanes, Cupriavidus, Pseudomonas, Zobellia, Thermobacillus, Arthrobacter, Azospirillum, Halomonas, Bacillus*, and *Aspergillus*.

It is a further aspect of the present invention to provide the method as described above, wherein the bacterium can produce xylonic acid from xylose because of any one of the following characteristics:

(A) xylose dehydrogenase activity, or xylose dehydrogenase activity and xylonolactonase activity have been imparted to or enhanced in the bacterium, or (B) the bacterium has glucose dehydrogenase activity that can catalyze a reaction producing xylonic acid from xylose.

It is a further aspect of the present invention to provide the method as described above, wherein the glucose dehydrogenase uses pyrroloquinoline quinone as a coenzyme, and the bacterium has glucose dehydrogenase activity because it has pyrroloquinoline quinone-producing ability, or it is cultured in a medium containing pyrroloquinoline quinone.

It is a further aspect of the present invention to provide the method as described above, wherein the bacterium can produce xylonic acid from xylose because a gene coding for xylose dehydrogenase, or expressible forms of genes coding for xylose dehydrogenase and xylonolactonase have been introduced in to said bacterium.

It is a further aspect of the present invention to provide the method as described above, wherein the bacterium has been modified so that activity of 2-ketoglutarate dehydrogenase is reduced.

It is a further aspect of the present invention to provide the method as described above, wherein the bacterium has been further modified so that activity of succinate dehydrogenase is reduced.

It is a further aspect of the present invention to provide the method as described above, wherein the bacterium is an enterobacterium or a coryneform bacterium.

It is a further aspect of the present invention to provide the method as described above, wherein the bacterium is a bacterium belonging to the genus *Pantoea*.

It is a further aspect of the present invention to provide the method as described above, wherein the bacterium is *Pantoea ananatis*.

It is a further aspect of the present invention to provide the method as described above, wherein the bacterium is a bacterium belonging to the genus *Escherichia*.

It is a further aspect of the present invention to provide the method as described above, wherein the bacterium is *Escherichia coli*.

It is a further aspect of the present invention to provide the method as described above, wherein the bacterium is a bacterium belonging to the genus *Corynebacterium*.

It is a further aspect of the present invention to provide the method as described above, wherein the bacterium is *Corynebacterium glutamicum*.

It is a further aspect of the present invention to provide the method as described above, wherein the 2-ketoglutaric acid derivative is a substance selected from the group consisting of L-glutamic acid, L-glutamine, L-arginine, L-citrulline, L-ornithine, L-proline, putrescine, and γ-aminobutyric acid.

DESCRIPTION OF THE PREFERRED EMBODIMENTS

Figure 1:
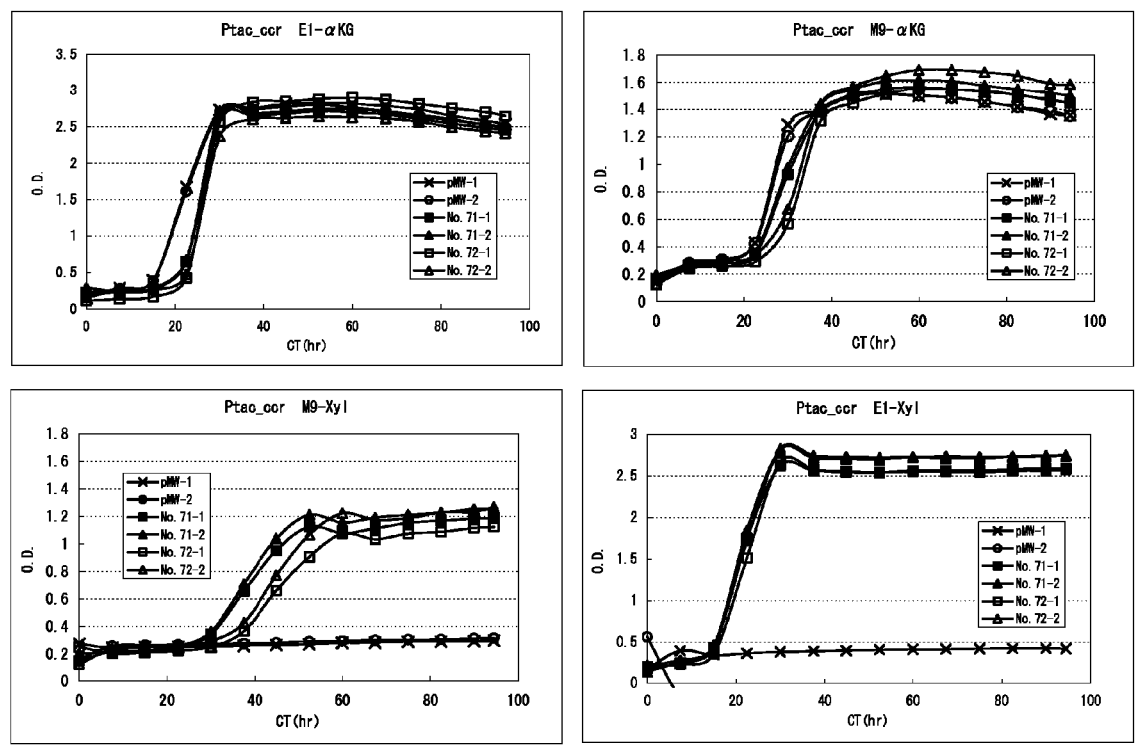
FIG. 1 depicts graphs showing results of a growth complementation test for *C. crescentus*-derived NXA operon-expressing strain using an icd gene-deficient strain. E1-αKG, M9-αKG, M9-Xyl, and E1-Xyl represent M9 minimal medium or E1 synthetic medium containing 2-ketoglutaric acid or xylose as the sole carbon source, respectively.

The method in accordance with the presently described subject matter can be a method for producing a target substance by culturing a bacterium having an ability to produce the target substance in a medium containing xylose as a carbon source to produce and accumulate the target substance in the medium, and collecting the target substance from the medium, wherein:

the target substance is 2-ketoglutaric acid or a derivative thereof, and the bacterium has an ability to produce xylonic acid from xylose, and activities of the enzymes xylonate dehydratase, 2-keto-3-deoxyxylonate dehydratase and 2-ketoglutaric semialdehyde dehydrogenase have been imparted to or enhanced in the bacterium.

The target substance can be 2-ketoglutaric acid (α-ketoglutaric acid, αKG) or a derivative thereof. Examples of the derivative of 2-ketoglutaric acid can include L-glutamic acid, L-glutamine, L-arginine, L-citrulline, L-ornithine, L-proline, putrescine, and γ-aminobutyric acid.

The "ability to produce a target substance" can mean an ability of the bacterium to produce a target substance to such an extent that the target substance can be collected from cells or medium, when it is cultured in the medium, and/or an ability to produce the target substance in a larger amount as compared to that obtainable with a wild-type strain or a non-modified strain cultured under the same conditions. The bacterium may have an ability to produce two or more kinds of target substances.

The target substance can include a compound in a free form and/or a salt thereof, for example, sulfate, hydrochloride, carbonate, ammonium salt, sodium salt, potassium salt, and so forth.

<1> Bacterium

The bacterium in accordance with the presently described subject matter can be a bacterium having an ability to produce xylonic acid from xylose, and in which the activities of xylonate dehydratase, 2-keto-3-deoxyxylonate dehydratase, and 2-ketoglutaric semialdehyde dehydrogenase have been imparted, or in which these activities have been enhanced.

The bacterium can be a bacterium that does not inherently have the activities of xylonate dehydratase, 2-keto-3-deoxyxylonate dehydratase, and 2-ketoglutaric semialdehyde dehydrogenase, but in which these enzymatic activities can be imparted, or it can be a bacterium which inherently has these enzymatic activities and in which these enzymatic activities can be enhanced.

The ability to produce xylonic acid from xylose can be attained by, for example, one or both of:
1) impartation or enhancement of xylose dehydrogenase activity, and
2) possession of glucose dehydrogenase activity that can catalyze the reaction producing xylonic acid from xylose.

Examples of a microorganism to which xylose dehydrogenase activity can be imparted or enhanced can include *Escherichia* bacteria and coryneform bacteria, and examples of a microorganism that has glucose dehydrogenase include *Pantoea* bacteria, and so forth.

In addition to xylose dehydrogenase activity, xylonolactonase activity may also be enhanced.

The bacteria belonging to these genera will be explained later.

Xylonic acid produced from xylose is converted into 2-ketoglutaric acid by xylonate dehydratase, 2-keto-3-deoxyxylonate dehydratase, and 2-ketoglutaric semialdehyde dehydrogenase. The pathway in which xylose is converted into 2-ketoglutaric acid by xylonate dehydratase, 2-keto-3-deoxyxylonate dehydratase, and 2-ketoglutaric semialdehyde dehydrogenase is also called the Weimberg pathway (J. Biol. Chem., 236:629-636). The Weimberg pathway and the pathway in which xylose is converted into xylonic acid by xylose dehydrogenase and/or xylonolactonase may be collectively referred to as the NXA (Novel Xylose Assimilation) pathway.

Whether a bacterium has the Weimberg pathway, or this pathway has been introduced into a bacterium can be determined by measuring enzymatic activities of xylonate dehydratase, 2-keto-3-deoxyxylonate dehydratase, and 2-ketoglutaric semialdehyde dehydrogenase in an extract of the bacterium, or confirming assimilation of xylonic acid, which accumulates in a strain not having the Weimberg pathway. Furthermore, whether a bacterium has the NXA pathway or this pathway has been introduced into a bacterium can be determined by measuring enzymatic activities of xylose dehydrogenase and/or xylonolactonase in addition to the aforementioned enzymes. Furthermore, these enzymatic activities can also be determined by measuring xylonic acid produced from xylose.

Xylonate dehydratase is an enzyme that reversibly catalyzes the following reaction (EC4.2.1.82), and can also be called D-xylo-aldonate dehydratase, D-xylonate dehydratase, or D-xylonate hydro-lyase.

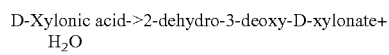
D-Xylonic acid->2-dehydro-3-deoxy-D-xylonate+ H$_2$O

The xylonate dehydratase activity can be measured by, for example, mixing a D-xylonic acid solution and a test sample to allow the reaction, then terminating the reaction with addition of a stop solution which includes 1% aqueous solution of semicarbazide hydrochloride and a 1.5% aqueous solution of sodium acetate, and measuring the absorbance of the diluted reaction solution at 250 nm (Dahms, A. S., et al., Methods Enzymol., 1982, 90 Pt E:302-5).

2-keto-3-deoxyxylonate dehydratase (2-keto-3-deoxy-xylonate dehydratase) is an enzyme that can reversibly catalyze the following reaction (EC4.2.1-).

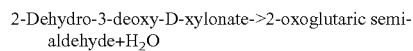
2-Dehydro-3-deoxy-D-xylonate->2-oxoglutaric semi-aldehyde+H$_2$O

The 2-keto-3-deoxyxylonate dehydratase activity can be measured by, for example, mixing a solution of 2-keto-3-deoxyxylonic acid as the substrate and a test sample to allow the reaction, and then measuring the decrease of 2-keto-3-deoxyxylonic acid.

2-ketoglutaric semialdehyde dehydrogenase is an oxidoreductase that can reversibly catalyze the following reaction (EC1.2.1.26).

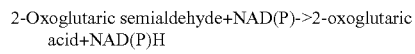
2-Oxoglutaric semialdehyde+NAD(P)->2-oxoglutaric acid+NAD(P)H

The 2-ketoglutaric semialdehyde dehydrogenase activity can be measured by, for example, measuring reduction of NAD(P). For example, the activity of this enzyme can be measured by adding 2-ketoglutaric semialdehyde to a mixture of pyrophosphoric acid (pH 8.5), NAD(P), and a test sample, and measuring the absorbance of the reaction mixture at 340 nm (Adams, E., et al., J. Biol. Chem., 1967, 242, 1802-1814).

Xylose dehydrogenase (D-xylose-1-dehydrogenase) is a dismutase for a pentose and glucuronic acid, and is an oxidoreductase that can reversibly catalyze the following reaction (EC1.1.1.175).

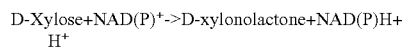
D-Xylose+NAD(P)$^+$->D-xylonolactone+NAD(P)H+ H$^+$

The D-xylose-1-dehydrogenase activity can be measured by, for example, mixing xylose, a test sample, and NAD(P) to allow the reaction, and measuring absorbance of the reaction mixture at 340 nm (Stephens, C. et al., J. Bacteriol., 2007, 189(5):181-2185).

The xylose dehydrogenase of *Caulobacter crescentus* can catalyze the reaction which converts D-xylose into xylonic acid.

Xylonolactonase is an enzyme that reversibly catalyzes the following reaction (EC3.1.1.68).

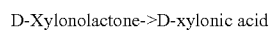
D-Xylonolactone->D-xylonic acid

The xylonolactonase activity can be measured by, for example, mixing xylonolactone and a test sample to allow the reaction, and quantifying the remaining xylonolactone according to the hydroxamate method (Appl. Microbiol. Biotechnol., 29:375-379, 1988; Appl. Microbiol., Biotechnol., 27:333-336, 1988).

The genes coding for the enzymes xylonate dehydratase, 2-keto-3-deoxyxylonate dehydratase, and 2-ketoglutaric semialdehyde dehydrogenase can be derived from, or native to, any microorganism having the Weimberg pathway, and examples include, for example, genes derived from, or native to, a microorganim such as a bacterium belonging to the genus *Caulobacter, Escherichia, Agrobacterium, Herbaspirillum, Actinoplanes, Cupriavidus, Pseudomonas, Zobellia, Thermobacillus, Arthrobacter, Azospirillum, Halomonas, Bacillus*, or a filamentous fungus belonging to the genus *Aspergillus*.

An example of the *Caulobacter* bacteria can include *Caulobacter crescentus*.

As *Caulobacter crescentus*, the CB-15 strain and the CB-13 strain are known, and are stored at the American Type Culture Collection (Address: P.O. Box 1549, Manassas, Va. 20108, United States of America) as ATCC 19089 and ATCC 33532, respectively. Furthermore, the NA-1000 strain (J. Bacteriol., 192:3678-88, 2010) and the K31 strain can also be used.

The genome sequences of the *Caulobacter crescentus* CB15, NA1000, and K31 strains are registered as GenBank Accession Nos. AE005673, CP001340, and CP000927, respectively.

The genes of the enzymes of the *Caulobacter crescentus* CB15, NA1000, and K31 strains are registered at GenBank with the following gene symbols.

Furthermore, as for 2-keto-deoxyxylonate dehydratase, xylX gene homologues of bacteria belonging to the genus *Agrobacterium, Pseudomonas, Zobellia, Thermobacillus*, or *Arthrobacter*, such as *Agrobacterium tumefaciens, Cupriavidus necator, Pseudomonas elodea, Zobellia galactanivorans, Thermobacillus composti*, and *Arthrobacter globiformis*, may also be used.

Furthermore, as for 2-ketoglutaric semialdehyde dehydrogenase, genes of bacteria belonging to the genus *Azospirillum, Halomonas*, or *Bacillus*, such as xylA gene homologues of *Azospirillum brasilense* and *Halomonas boliviensis*, and ycbD of *Bacillus subtilis*, may also be used.

The nucleotide sequences of the aforementioned genes and amino acid sequences encoded by them are shown in Table 11.

In *Caulobacter crescentus*, the genes of the five enzymes of the NXA pathway constitute an operon structure as described later. The nucleotide sequence of this operon is registered at GenBank as Accession No. AAK22808_*Caulobacter_crescentus*. The nucleotide sequence of this operon is shown in SEQ ID NO: 23. The amino acid sequences of 2-keto-3-deoxyxylonate dehydratase, 2-ketoglutaric semialdehyde dehydrogenase, xylose dehydrogenase, and xylonolactonase encoded by this operon are shown in SEQ ID NOS: 24 to 27, respectively. Furthermore, the nucleotide sequence of the xylD gene in this operon, and the amino acid sequences of xylonate dehydratase encoded by it are shown in SEQ ID

TABLE 1

| Gene | Enzyme | EC number | Gene symbol (GenBank) | | |
|---|---|---|---|---|---|
| | | | CB15 | NA1000 | K31 |
| xylD | Xylonate dehydratase | EC4.2.1.82 | CC_0823 | CCNA_00866 | Caul_4000 |
| xylX | 2-keto-3-deoxyxylonate dehydratase | EC: 4.2.1 | CC_0822 | CCNA_00865 | |
| xylA | 2-Ketoglutaric semialdehyde dehydrogenase | EC: 1.2.1.26 | CC_0821 | CCNA_00864 | Caul_4001 |
| xylB | Xylose dehydrogenase | EC: 1.1.1.175 | CC_0820 | CCNA_00863 | Caul_4002 |
| xylC | Xylonolactonase | EC: 3.1.1.68 | CC_0819 | CCNA_00862 | Caul_4003 |

In addition, the xylose dehydrogenase gene and the 2-ketoglutaric semialdehyde dehydrogenase gene of *Caulobacter crescentus* can be referred to as ccrxylB and ccrxylA, respectively.

Furthermore, examples of the enzymes of the NXA (Novel Xylose Assimilation) pathway can include, besides those of *Caulobacter* bacteria, for example, xylose dehydrogenase of *Hypocrea jecorina* (*Trichoderma ressei*) (FEMS Microbiol. Lett., 277, 249-254, 2007); ycbD of *Bacillus subtilis* (2-ketoglutaric semialdehyde dehydrogenase, typeIII); 2-ketoglutaric semialdehyde dehydrogenase (typeII) of *Pseudomonas putida*; 2-ketoglutaric semialdehyde dehydrogenase, typeI, typeII, typeIII of *Azospirillum brasilense* (J. Bac. Chem., 282, 6685-6695, 2007 for these), and their homologues.

In particular, as the xylonate dehydratase gene, the yjhG gene and yagF gene of a bacterium belonging to the genus *Escherichia* such as *Escherichia coli* can be used. The yjhG gene of *Escherichia coli* is shown in SEQ ID NO: 34, and the yagF gene of *Escherichia coli* is shown in SEQ ID NO: 36. Furthermore, as for xylonate dehydratase, xylD gene homologues of microorganisms belonging to the genus *Agrobacterium, Herbaspirillum, Actinoplanes*, or *Aspergillus*, such as *Agrobacterium tumefaciens, Herbaspirillum seropedicae, Actinoplanes missouriensis*, and *Aspergillus oryzae*, may also be used.

NOS: 28 and 29, respectively. The nucleotide sequence of SEQ ID NO: 28 corresponds to the positions 5509 to 7296 of the sequence of SEQ ID NO: 23.

Although two sites are suggested as the start codon of xylX, the positions 1175 to 1177 are described as the start codon in SEQ ID NO: 23. Two start codons are suggested also for xylD, and the positions 1 to 3 or the positions 13 to 15 of SEQ ID NO: 28 may be used as the start codon. When the positions 13 to 15 are considered as the start codon, the amino acid sequence of xylonate dehydratase of SEQ ID NO: 29 begins from the Leu at the position 5.

Although glucose dehydrogenase can reversibly catalyze the following reaction (EC1.1.1.119), the phrase "glucose dehydrogenase that can catalyze the reaction which produces xylonic acid from xylose" can mean an enzyme that can convert D-xylose into D-xylonolactone by using pyrroloquinoline quinone as a coenzyme.

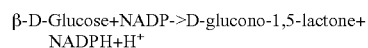
β-D-Glucose+NADP->D-glucono-1,5-lactone+ NADPH+H$^+$

Pyrroloquinoline quinone can be produced by a native ability possessed by the microorganism, or can be added to the medium (Appl. Environ. Microbiol., 2009 May, 75(9) 2784-2791).

In the bacterium that produces 2-ketoglutaric acid or a derivative thereof, the decomposition pathway of 2-ketoglutaric acid can be attenuated or deleted. To attenuate or delete the decomposition pathway of 2-ketoglutaric acid, the activities or activity of α-ketoglutarate dehydrogenase and/or succinate dehydrogenase are(is) attenuated or deleted. The α-ketoglutarate dehydrogenase, which can henceforth also be referred to as "α-KGDH", activity can mean an activity of catalyzing the reaction in which α-ketoglutaric acid (2-oxoglutaric acid) is oxidatively decarboxylated to generate succinyl-CoA. The aforementioned reaction is catalyzed by three kinds of enzyme subunits, α-KGDH (E1o, α-ketoglutarate dehydrogenase, EC:1.2.4.2), dihydrolipoamide S-succinyltransferase (E2o, EC: 2.3.1.61), and dihydrolipoamide dehydrogenase (E3, EC:1.8.1.4). That is, these three subunits catalyze the following reactions, respectively, and the collective activity of catalyzing a reaction by a combination of these three reactions can be called the α-KGDH activity. The α-KGDH activity can be confirmed by measurement according to the method of Shiio et al. (Isamu Shiio and Kyoko Ujigawa-Takeda, Agric. Biol. Chem., 44 (8), 1897-1904, 1980).

E1o: 2-oxoglutarate+[dihydrolipoyllysine-residue succinyltransferase]lipoyllysine=[dihydrolipoyllysine-residue succinyltransferase]S-succinyldihydrolipoyllysine+$CO_2$ E2o: CoA+enzyme N6-(S-succinyldihydrolipoyl)lysine=succinyl-CoA+enzyme N6-(dihydrolipoyl)lysine E3: protein N6-(dihydrolipoyl)lysine+NAD=protein N6-(lipoyl)lysine+NADH+$H^+$ α-KGDH can also be called oxoglutarate dehydrogenase or 2-oxoglutarate dehydrogenase.

In Enterobacteriaceae bacteria such as *Pantoea ananatis*, the protein subunits having these three enzymatic activities, respectively, form a complex. The subunits are encoded by sucA, sucB and lpd, respectively, and the sucA and sucB genes are present downstream from the succinate dehydrogenase iron-sulfur protein gene (sdhB) (U.S. Pat. No. 6,331,419). Although these genes are described as genes of *Enterobacter agglomerans* AJ13355 in the aforementioned patent, this strain was later reclassified into *Pantoea ananatis*.

As genes coding for α-KGDH of enterobacteria, the nucleotide sequences of the sucA gene, the sucB gene and the sucC and the amino acid sequences of the subunits of *Pantoea ananatis* are disclosed in European Patent Application Laid-open No. 2100957 A1. Furthermore, the sucA, sucB and sucC genes coding for α-KGDH of *Escherichia coli* have been opened to public as Genbank NP_415254 and NP_415255, respectively.

In coryneform bacteria, the E1o subunit is encoded by the odhA gene (registered as NCgl1084 of GenBank Accession No. NC_003450, which is also called the sucA gene), and the E3 subunit is encoded by the lpd gene (GenBank Accession No. Y16642). On the other hand, it is estimated that the E2o subunit is encoded by the odhA gene together with the E1o subunit as a bifunctional protein (Usuda et al., Microbiology, 142, 3347-3354, 1996), or encoded by the gene registered as NCgl2126 of GenBank Accession No. NC_003450, which is different from the odhA gene. Therefore, although the odhA gene can code for the E1o subunit, it can also code for E2o.

The nucleotide sequence of the odhA gene of *Brevibacterium lactofermentum* and the amino acid sequence of the E1o subunit encoded thereby (WO2006/028298), the nucleotide sequence of the aforementioned NCgl2126 of GenBank Accession No. NC_003450 and the amino acid sequence of the E2o subunit encoded thereby, as well as the nucleotide sequence of the aforementioned NCgl1084 of GenBank Accession No. NC_003450 and the amino acid sequence of the E1o subunit encoded thereby are disclosed in European Patent Application Laid-open No. 2100957 A1.

Genes coding for each of the α-KGDH subunits, and the gene cluster containing them may be generically called the "genes coding for α-KGDH".

The succinate dehydrogenase, which can also be referred to as "SDH", is the enzyme EC:1.3.99.1, which can reversibly catalyze the following reaction. SDH activity can mean the activity for catalyzing this reaction:

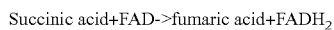

Succinic acid+FAD->fumaric acid+$FADH_2$

SDH is made up of three or four subunit structures, depending on type of microorganism, and the activity thereof can be decreased or deleted by modifying at least one of these proteins so that it does not normally function. Specifically, SDH is made up of the following subunits (names of genes coding for the subunits are described in parentheses), and the membrane anchor protein is encoded solely by sdhC or by sdhC and sdhD depending on species.

SDHA: flavoprotein subunit (sdhA)
SDHB: Fe—S protein subunit (sdhB)
SDHC: membrane anchor protein (sdhC)
SDHD: membrane anchor protein (sdhD)

Furthermore, the SDH subunit complex may have the activities of both SDH and fumarate reductase. For example, the SDH subunit complex of coryneform bacteria has the activities of both SDH and fumarate reductase (WO2005/021770).

The SDH activity can be confirmed by measuring reduction of 2,6-dichloroindophenol (DCIP) as an indicative index. A specific method is described in Tatsuki Kurokawa and Junshi Sakamoto, Arch. Microbiol., (2005) 183:317-324.

The genes coding for the SDH subunits, and the operon containing them may be generically called the "genes coding for SDH."

As genes coding for SDH of enterobacteria, the nucleotide sequences of such genes of *Pantoea ananatis* and the amino acid sequences of the subunits are disclosed in WO2008/075483.

As the genes coding for SDH of coryneform bacteria, for example, there are disclosed the sequences of the sdh operon of *Corynebacterium glutamicum* (GenBank accession No. NCgl0359 (sdhC) NCgl0360 (sdhA) NCgl0361 (sdhB)), and the sdh operon of *Brevibacterium flavum* (Japanese Patent Laid-open No. 2005-095169, European Patent Application Laid-open No. 1672077 A1, WO2008/075483).

For reducing or deleting the activities of α-KGDH and SDH, the methods described later for reduction of activity of an enzyme that catalyzes a reaction branching from the biosynthesis pathway of L-glutamic acid, and produces other compounds, can be used.

Furthermore, an activity of an enzyme that incorporates xylose into cells may further be enhanced in the microorganism.

An example of an enzyme that can catalyze incorporation of xylose into cells can include D-xylose permease, and an example of a gene which encodes for D-xylose permease can include the xylE gene. The nucleotide sequence of the xylE gene of *Escherichia coli* coding for D-xylose permease, and the amino acid sequence encoded by this gene are shown in SEQ ID NOS: 30 and 31, respectively.

Furthermore, xylose isomerase (xylA) and xylulose kinase (xylB) can be attenuated in the microorganism. The xylose isomerase (xylA) gene and xylulose kinase (xylB) gene of *Escherichia coli* are disclosed as NC000913.1 gi:16131436 and 16131435, respectively.

Xylonic acid may accumulate in the medium, and especially in *Escherichia coli*, the activity of xylonate dehydratase can be further enhanced. For example, the activity can be 10 μmol/min/mg protein or higher, 15 μmol/min/mg protein or higher, or 17 μmol/min/mg protein or higher.

Methods for imparting activity of a target enzyme to a microorganism or for increasing activity of a target enzyme of a microorganism will be explained below.

When the activity of a target enzyme is not native to the chosen microorganism, the activity of the target enzyme can be imparted to the microorganism by introducing the gene encoding the target enzyme into the microorganism. Furthermore, when the microorganism has the activity of the target enzyme, the activity can be increased by introducing a non-native target enzyme gene, increasing the copy number of the endogenous target enzyme gene, or modifying an expression control sequence such as a promoter of the target enzyme gene to increase expression of the gene. The expression "introduce a target enzyme gene" can mean not only to introduce a target enzyme gene into a microorganism in which activity of the target enzyme is not native, but also to introduce a foreign target enzyme gene into a microorganism having activity of the target enzyme, and also to introduce an endogenous target enzyme gene into a microorganism having activity of the target enzyme to increase expression of the endogenous target enzyme gene.

In order to introduce a target enzyme gene, for example, the target enzyme gene is cloned into an appropriate vector, and a host microorganism is transformed with the obtained vector.

Examples of the vector which can be used for transformation can include a plasmid which can autonomously replicate in the chosen microorganism. Examples of a plasmid autonomously replicable in a microorganism belonging to the family Enterobacteriaceae include pUC19, pUC18, pBR322, RSF1010, pHSG299, pHSG298, pHSG399, pHSG398, pSTV28, pSTV29, pTWV228, pTWV229 (pHSG, pSTV and pTWV series vectors are available from Takara Bio), pMW119, pMW118, pMW219, pMW218 (pMW series vectors are available from Nippon Gene), and so forth. Furthermore, plasmids for coryneform bacteria include pAM330 (Japanese Patent Laid-open No. 58-67699), pHM1519 (Japanese Patent Laid-open No. 58-77895), pSFK6 (Japanese Patent Laid-open No. 2000-262288), pVK7 (U.S. Patent Published Application No. 2003/0175912), pAJ655, pAJ611, pAJ1844 (Japanese Patent Laid-open No. 58-192900), pCG1 (Japanese Patent Laid-open No. 57-134500), pCG2 (Japanese Patent Laid-open No. 58-35197), pCG4, pCG11 (Japanese Patent Laid-open No. 57-183799), pHK4 (Japanese Patent Laid-open No. 5-7491), and so forth.

Examples of transformation methods include treating recipient cells with calcium chloride to increase permeability for DNA, which has been reported for *Escherichia coli* K-12 (Mandel, M. and Higa, A., J. Mol. Biol., 1970, 53:159-162), preparing competent cells from cells which are at the growth phase, followed by transformation with DNA, which has been reported for *Bacillus subtilis* (Duncan, C. H., Wilson, G. A. and Young, F. E., 1977, Gene, 1:153-167), and so forth. Alternatively, a method of making DNA-recipient cells into protoplasts or spheroplasts, which can easily take up recombinant DNA, followed by introducing recombinant DNA into the DNA-recipient cells, which is known to be applicable to *Bacillus subtilis*, actinomycetes, and yeast (Chang, S, and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Sci., USA, 75:1929-1933) can also be employed. In addition, transformation of microorganisms can also be performed by the electric pulse method (Japanese Patent Laid-open No. 2-207791).

The target enzyme gene can also be introduced into the chromosome of the host microorganism. The target enzyme gene can be introduced into a chromosome of a microorganism randomly using a transposon or Mini-Mu (Japanese Patent Laid-open No. 2-109985, U.S. Pat. No. 5,882,888, European Patent Publication No. 805867 B1), or by homologous recombination using a sequence present on the chromosomal DNA in multiple copies as a target, such as repetitive DNA, and an inverted repeat located at the end of a transposable element. Alternatively, a target gene can be introduced into a chromosome by using the Red driven integration method (WO2005/010175). Moreover, a target gene can also be introduced into a chromosome by transduction using a phage such as P1 phage, or by using a conjugative transfer vector. Furthermore, it is also possible to introduce a target enzyme gene using a gene unnecessary for production of target substance as a target, as described in WO03/040373. One or plural copies of the target enzyme gene can be introduced into a target sequence by such methods as described above.

Transfer of a target gene on a chromosome can be confirmed by Southern hybridization using a probe having a sequence complementary to the target gene or a part thereof.

Although it is sufficient that a copy number of the introduced target gene is not less than 1, the copy number can be 2 or more, 3 or more, or 5 or more. As for the xylonate dehydratase gene as the target gene, in particular, 2 or more copies of the gene can be introduced.

Furthermore, the activity of a target enzyme gene can be optimized by substituting or mutating an expression control sequence such as a promoter of the target enzyme gene in combination as described later. In particular, the xylonate dehydratase gene can be overexpressed by substituting or mutating an expression control sequence instead of or together with the aforementioned increase of the copy number.

Examples of the method for increasing expression of a target enzyme gene include replacing an expression control sequence such as a promoter of the target enzyme gene with one having an appropriate strength on a chromosomal DNA or a plasmid to enhance expression of the gene. For example, the thr promoter, lac promoter, trp promoter, trc promoter, pL promoter, tac promoter, and so forth are known as frequently used promoters. Furthermore, variants of the tac promoter used in the examples described below (PtacA promoter, PtacB promoter) can also be used. Methods for evaluating the strength of promoters and strong promoters are described in the paper of Goldstein and Doi (Goldstein, M. A. and Doi R. H., 1995, Prokaryotic promoters in biotechnology, Biotechnol. Annu. Rev., 1, 105-128), and so forth.

Furthermore, it is also possible to substitute several nucleotides into the promoter region of a gene to strengthen it, as disclosed in International Publication WO00/18935. Substitution of an expression control sequence can be performed in the same manner as, for example, that of the gene substitution using a temperature-sensitive plasmid. Examples of vectors having a temperature-sensitive replication origin and effective in *Escherichia coli* and *Pantoea ananatis* include, for example, the temperature-sensitive plasmid pMAN997 described in International Publication WO99/03988, derivatives thereof, and so forth. Furthermore, substitution of an expression control sequence can also be performed by a method utilizing a linear DNA such as the method called "Red-driven integration" using Red recombinase of λ phage (Datsenko, K. A. and Wanner, B. L., 2000, Proc. Natl. Acad. Sci. USA. 97:6640-6645), and the method using a combination of the Red-driven integration method and the λ phage excision system (Cho, E. H., Gumport, R. I., Gardner, J. F., J. Bacteriol. 184: 5200-5203 (2002)) (refer to WO2005/010175). Modification of an expression control sequence can be combined with increasing the copy number of a gene.

Furthermore, it is known that substitution of several nucleotides in a spacer between the ribosome-binding site (RBS) and translation initiation codon, especially a sequence immediately upstream from the initiation codon, greatly affects the mRNA translation efficiency, and therefore this sequence can be modified to improve the translation amount.

When a target gene is introduced into the aforementioned amplification plasmid or chromosome, any promoter can be used to express the gene so long as the chosen promoter functions in the chosen microorganism. The promoter can be the native promoter for the chosen gene, or a modified promoter. Expression of a gene can also be controlled by suitably choosing a promoter that strongly functions in the chosen microorganism, or by making the −35 and −10 regions of the promoter closer to the consensus sequence.

Whether a target enzyme activity is enhanced or not can be confirmed by comparing the target enzyme activities of a modified strain to a parent or non-modified strain. If the target enzyme activity of the modified strain is increased as compared to the parent or non-modified strain, the target enzyme activity is enhanced. Furthermore, when the parent strain does not have the target enzyme activity, if the target enzyme activity can be detected in the modified strain, the target enzyme activity is enhanced.

The target enzyme gene can be obtained by PCR using oligonucleotides prepared on the basis of the aforementioned sequence information or sequence information of gene or protein known for the microorganism as primers, or hybridization using an oligonucleotide prepared on the basis of the aforementioned sequence information as a probe from a chromosomal DNA or chromosomal DNA library of a microorganism having the target enzyme.

Moreover, the target enzyme and the gene coding for it may be a homologue or artificial modification thereof, or a protein having a conservative mutation, or a gene coding for it, so long as the enzymatic activity is maintained.

Such a homologue, artificial modification thereof, or a protein having a conservative mutation or genes coding for these can be referred to as a conservative variant.

The conservative variant of a target enzyme may be, for example, a protein having the aforementioned amino acid sequence of the enzyme, but can include substitution, deletion, insertion, addition or the like of one or several amino acid residues at one or several positions.

Although the number of the "one or several" amino acid residues may differ depending on the position in the three-dimensional structure or the types of amino acid residues of the protein, specifically, it can be 1 to 20, 1 to 10, or 1 to 5. The conservative mutation is typically a conservative substitution. The conservative substitution is a mutation wherein substitution takes place mutually among Phe, Trp, and Tyr, if the substitution site is an aromatic amino acid; among Leu, Ile and Val, if the substitution site is a hydrophobic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having a hydroxyl group. Substitutions considered conservative substitutions can include, specifically, substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Gly, Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Be, Leu, Val or Phe for Met, substitution of Trp, Tyr, Met, Be or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. The aforementioned amino acid substitutions, deletions, insertions, additions, inversions or the like may be a result of a naturally-occurring mutation or a variation due to an individual difference or a difference of species of a microorganism from which the genes are derived (mutant or variant). Such proteins can be obtained by, for example, modifying a nucleotide sequence of a wild-type target enzyme gene by site-specific mutagenesis so that the amino acid residues at the specific sites of the encoded protein include substitutions, deletions, insertions, or additions of amino acid residues.

Furthermore, such a protein having a conservative mutation as described above may have a homology of, for example, 80% or more, 90% or more, 95% or more, 97% or more, 98% or more, or 99% or more, to the entire amino acid sequence, and having a function equivalent to that of the wild-type protein. In this specification, "homology" can mean "identity".

So long as the wild-type target enzyme gene codes for such an amino acid sequence as described above, it is not limited to genes of *Caulobacter crescentus, Haloferax volcanii*, and the like, but it may be any that have an equivalent codon for an arbitrary codon.

The wild-type gene can also be a DNA that is able to hybridize with a nucleotide sequence complementary to the nucleotide sequence of each enzyme gene, or a probe that can be prepared from the complementary sequence, under stringent conditions, and codes for a protein having functions equivalent to those of the wild-type target enzyme. The "stringent conditions" can refer to conditions under which a so-called specific hybrid is formed, and a non-specific hybrid is not formed. Examples of the stringent conditions include those under which highly homologous DNAs hybridize to each other, for example, DNAs not less than 80% homologous, not less than 90% homologous, not less than 95% homologous, not less than 97% homologous, not less than 98% homologous, or not less than 99% homologous, hybridize to each other, and DNAs less homologous than the above do not hybridize to each other, or conditions corresponding to washing of typical Southern hybridization, i.e., conditions of washing once, or 2 or 3 times, at a salt concentration and temperature of 1×SSC, 0.1% SDS at 60° C., 0.1×SSC, 0.1% SDS at 60° C., or 0.1×SSC, 0.1% SDS at 68° C.

As the probe, a part of a sequence that is complementary to the target enzyme gene may also be used. Such a probe can be prepared by PCR using oligonucleotides prepared on the basis of a known gene sequence as primers and a DNA fragment containing the nucleotide sequence as a template. For example, when a DNA fragment having a length of about 300 bp is used as the probe, the washing conditions of the hybridization may be, for example, 50° C., 2×SSC and 0.1% SDS.

The aforementioned descriptions concerning conservative variants of the above-mentioned proteins and genes coding for them can be similarly applied to the other genes described below for the bacteria that produce target substances.

The microorganism can inherently have an ability to produce a target substance, or the ability may be imparted by breeding using a mutation method, a recombinant DNA technique, or the like.

Microorganisms can include, but are not limited to, bacteria belonging to the family Enterobacteriaceae such as those of genera *Escherichia, Pantoea*, and *Enterobacter*, coryneform bacteria such as *Corynebacterium glutamicum* and *Brevibacterium lactofermentum*, and *Bacillus* bacteria such as *Bacillus subtillis*.

Coryneform bacteria include those bacteria having been originally classified into the genus *Brevibacterium*, but are now classified into the genus *Corynebacterium* (Int. J. Syst. Bacteriol., 41, 255 (1981)), and include bacteria belonging to the genus *Brevibacterium*, which is closely related to the genus *Corynebacterium*. Examples of such coryneform bacteria are listed below.

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum*
*Brevibacterium flavum*
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Corynebacterium ammoniagenes*
*Brevibacterium album*
*Brevibacterium cerinum*
*Microbacterium ammoniaphilum*

Specific examples of these bacteria include the following:
*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium glutamicum* ATCC 13020, ATCC 13032, ATCC 13060
*Corynebacterium lilium* ATCC 15990
*Corynebacterium melassecola* ATCC 17965
*Corynebacterium thermoaminogenes* AJ12340 (FERM BP-1539)
*Corynebacterium herculis* ATCC 13868
*Brevibacterium divaricatum* ATCC 14020
*Brevibacterium flavum* ATCC 13826, ATCC 14067
*Brevibacterium immariophilum* ATCC 14068
*Brevibacterium lactofermentum* ATCC 13869 (*Corynebacterium glutamicum* ATCC 13869)
*Brevibacterium roseum* ATCC 13825
*Brevibacterium saccharolyticum* ATCC 14066
*Brevibacterium thiogenitalis* ATCC 19240
*Brevibacterium ammoniagenes* ATCC 6871, ATCC 6872
*Brevibacterium album* ATCC 15111
*Brevibacterium cerinum* ATCC 15112
*Microbacterium ammoniaphilum* ATCC 15354

These strains are available from the American Type Culture Collection (ATCC) (Address: P.O. Box 1549, Manassas, Va. 20108, United States of America). That is, a registration number is assigned to each of the strains. Strains can be ordered using the assigned registration numbers listed in the catalogue of the ATCC (www.atcc.org/). The AJ12340 strain was deposited on Oct. 27, 1987 at National Institute of Bioscience and Human Technology of Agency of Industrial Science and Technology (currently independent administrative agency, National Institute of Technology and Evaluation, International Patent Organism Depositary, Tsukuba Central 6, 1-1, Higashi 1-Chome, Tsukuba-shi, Ibaraki-ken, 305-8566, Japan), as the accession number of FERM BP-1539 based on Budapest Treaty.

Microorganisms belonging to the family Enterobacteriaceae can include, but are not limited to, bacteria belonging to the genera *Escherichia, Enterobacter, Pantoea, Klebsiella, Serratia, Erwinia, Salmonella, Morganella* or the like and which are able to produce a target substance. Specifically, bacteria belonging to the family Enterobacteriaceae according to the classification shown in NCBI (National Center for Biotechnology Information) database (www.ncbi.nlm.nih.gov/htbin-post/Taxonomy/wgetorg?mode=Tree&id=1236&lvl=3&keep=1&srchmode=1&unlock) can be used. Among the bacteria of the family Enterobacteriaceae, bacteria belonging to the genus *Escherichia, Enterobacter*, or *Pantoea* can be used as a parent strain.

*Escherichia* bacteria which can be used as the parent strain include, but are not limited to, *Escherichia* bacteria reported by Neidhardt et al. (Neidhardt, F. C. et al., *Escherichia coli* and *Salmonella Typhimurium*, American Society for Microbiology, Washington D.C., 1029 table 1), such as *Escherichia coli*. Specific examples of *Escherichia coli* include *Escherichia coli* W3110 (ATCC 27325), and MG1655 (ATCC 47076) strains, which are derived from the wild-type (prototype) *Escherichia coli* K12 strain, and so forth.

In particular, *Pantoea* bacteria, *Erwinia* bacteria, and *Enterobacter* bacteria are classified as γ-proteobacteria, and are taxonomically very close to one another (J. Gen. Appl. Microbiol., December 1997, 43(6), 355-361; International Journal of Systematic Bacteriology, October 1997, pp. 1061-1067). In recent years, some bacteria belonging to the genus *Enterobacter* were reclassified as *Pantoea agglomerans, Pantoea dispersa*, or the like, on the basis of DNA-DNA hybridization experiments etc. (International Journal of Systematic Bacteriology, July 1989, 39(3). p. 337-345). Furthermore, some bacteria belonging to the genus *Erwinia* were re-classified as *Pantoea ananas* or *Pantoea stewartii* (refer to International Journal of Systematic Bacteriology, January 1993, 43(1), pp. 162-173). In addition, *Pantoea ananas* was then further re-classified as *Pantoea ananatis*.

Examples of the *Enterobacter* bacteria include *Enterobacter agglomerans* (currently re-classified as *Pantoea ananatis* etc.), *Enterobacter aerogenes*, and so forth. Specifically, the strains exemplified in European Patent Application Laid-open No. 952221 can be used. A typical strain of the genus *Enterobacter* is *Enterobacter agglomeranses* ATCC 12287 (currently re-classified as *Pantoea ananatis*).

Typical strains of the *Pantoea* bacteria include *Pantoea ananatis, Pantoea stewartii, Pantoea agglomerans*, and *Pantoea citrea*. Specific examples include the following strains:
*Pantoea ananatis* AJ13355 (FERM BP-6614, European Patent Application Laid-open No. 0952221)
*Pantoea ananatis* AJ13356 (FERM BP-6615, European Patent Application Laid-open No. 0952221)

Although these strains are described as *Enterobacter agglomerans* in European Patent Application Laid-open No. 0952221, they have been reclassified as *Pantoea ananatis* on the basis of nucleotide sequence analysis of 16S rRNA etc., as described above.

The *Pantoea ananatis* AJ13355 strain was isolated from soil in Iwata-shi, Shizuoka, Japan as a strain that can proliferate in a medium containing L-glutamic acid and a carbon source at low pH. The SC17 strain was selected as a low viscous substance-producing mutant strain from the AJ13355 strain (U.S. Pat. No. 6,596,517). The *Pantoea ananatis* AJ13355 strain was deposited at the National Institute of Bioscience and Human-Technology, Agency of Industrial Science and Technology, Ministry of International Trade and Industry (currently, National Institute of Technology and Evaluation, International Patent Organism Depositary, Address: Tsukuba Central 6, 1-1, Higashi 1-Chome, Tsukuba-shi, Ibaraki-ken, 305-8566, Japan) on Feb. 19, 1998 and assigned an accession number of FERM P-16644. The deposit was then converted to an international deposit under the provisions of Budapest Treaty on Jan. 11, 1999 and assigned an accession number of FERM BP-6614. The *Pantoea ananatis* SC17 strain was given the private number AJ416, and deposited on Feb. 4, 2009 at National Institute of Technology and Evaluation, International Patent Organism Depository (Address: Tsukuba Central 6, 1-1, Higashi 1-Chome, Tsukuba-shi, Ibaraki-ken, 305-8566, Japan), and assigned an accession number of FERM BP-11091.

Examples of L-glutamic acid-producing *Pantoea ananatis* bacteria further include SC17 sucA/RSFCPG+pSTVCB, AJ13601, NP106, and NA1 strains. The SC17sucA/RSFCPG+pSTVCB strain was obtained by introducing the plasmid RSFCPG containing the citrate synthase gene (gltA), phosphoenolpyruvate carboxylase gene (prpC), and glutamate dehydrogenase gene (gdhA) derived from *Escherichia coli*, and the plasmid pSTVCB containing the citrate synthase gene (gltA) derived from *Brevibacterium lactofermentum*, into the SC17sucA strain, which is a sucA gene-deficient strain derived form the SC17 strain (U.S. Pat. No. 6,596,517). The AJ13601 strain was selected from the SC17sucA/RSFCPG+pSTVCB strain for its resistance to L-glutamic acid of high concentration at a low pH. Furthermore, the NP106 strain was derived from the AJ13601 strain by eliminating the RSFCPG+pSTVCB plasmid (WO2010/027045). The AJ13601 strain was deposited at National Institute of Technology and Evaluation, International Patent Organism Depositary (Tsukuba Central 6, 1-1, Higashi 1-Chome, Tsukuba-shi, Ibaraki-ken, Japan, postal code: 305-8566) on Aug. 18, 1999, and assigned an accession number FERM P-17516. Then, the deposit was converted into an international deposit under the provisions of the Budapest Treaty on Jul. 6, 2000, and assigned an accession number FERM BP-7207. This strain was originally identified as *Enterobacter agglomerans* when it was isolated, and deposited as *Enterobacter agglomerans*. However, it was recently re-classified as *Pantoea ananatis* on the basis of nucleotide sequencing of 16S rRNA and so forth.

The NA1 strain is a strain corresponding to the NP106 strain having RSFPPG (WO2008/020654) in which the gltA gene of RSFCPG described above is replaced with the methyl citrate synthase gene (prpC) (WO2010/027045).

Examples of the *Erwinia* bacteria include *Erwinia amylovora* and *Erwinia carotovora*, and examples of the *Klebsiella* bacteria include *Klebsiella planticola*. Specific examples include the following strains:

*Erwinia amylovora* ATCC 15580
*Erwinia carotovora* ATCC 15713
*Klebsiella planticola* AJ13399 (FERM BP-6600, European Patent Laid-open No. 955368)
*Klebsiella planticola* AJ13410 (FERM BP-6617, European Patent Laid-open No. 955368).

Hereinafter, methods for imparting an ability to produce a target substance to such microorganisms as described above, or methods for enhancing an ability to produce a target substance of such microorganisms are described.

To impart an ability to produce a target substance, methods conventionally employed in the breeding of coryneform bacteria or bacteria of the genus *Escherichia* (see "Amino Acid Fermentation", Gakkai Shuppan Center (Ltd.), 1st Edition, published May 30, 1986, pp. 77-100) can be used. Such methods include acquisition of an auxotrophic mutant, a target substance analogue-resistant strain, or a metabolic regulation mutant, construction of a recombinant strain in which expression of a target substance biosynthesis enzyme is enhanced, and so forth. In the breeding of target substance-producing bacteria, imparted properties such as an auxotrophic mutation, analogue resistance, or metabolic regulation mutation may be one or more. The expression of target substance biosynthesis enzyme(s) can be enhanced alone or in combinations of two or more. Furthermore, imparting properties such as an auxotrophic mutation, analogue resistance, or metabolic regulation mutation may be combined with enhancing the biosynthesis enzymes.

An auxotrophic mutant strain, analogue-resistant strain, or metabolic regulation mutant strain with an ability to produce a target substance can be obtained by subjecting a parent strain or wild-type strain to conventional mutatagenesis, such as exposure to X-rays or UV irradiation, or treatment with a mutagen such as N-methyl-N'-nitro-N-nitrosoguanidine, etc., and then selecting those which exhibit autotrophy, analogue resistance, or a metabolic regulation mutation and which also have an ability to produce a target substance. Moreover, a target substance-producing bacterium can also be obtained by enhancing activity of a biosynthesis enzyme of the target substance by gene recombination.

Hereinafter, examples of a method for imparting an ability to produce a target substance and microorganisms to which an ability to produce a target substance is imparted will be explained.

Examples of a method for imparting or enhancing an ability to produce a target substance by breeding can include, for example, a method of modifying a microorganism so that expression of a gene coding for an enzyme involved in biosynthesis of a target substance is enhanced. For example, examples of enzymes involved in L-glutamic acid biosynthesis include glutamate dehydrogenase (gdhA), glutamine synthetase (glnA), glutamate synthetase (gltBD), aconitate hydratase (acnA, acnB), citrate synthase (gltA), phosphoenolpyruvate carboxylase (ppc), pyruvate carboxylase, pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), glucose phosphate isomerase (pgi), methyl citrate synthase (prpC), and so forth. The gene names are in the parentheses following the enzyme names (the same shall apply to the following descriptions).

Expression of the aforementioned genes can be enhanced by the method described for the enhancement of the activities of the enzymes of the aforementioned NXA pathway.

Examples of microorganisms which can be modified so that expression of the citrate synthase gene, pyruvate dehydrogenase gene, and/or glutamate dehydrogenase gene is/are enhanced can include the microorganisms described in WO00/18935, European Patent Application Laid-open No. 1010755, and so forth.

Moreover, a modification for imparting the L-glutamic acid-producing ability may also be performed by reducing or deleting activity of an enzyme that catalyzes a reaction which branches off from the L-glutamic acid biosynthetic pathway and produces a compound other than L-glutamic acid. Examples of such enzymes can include 2-oxoketoglutarate dehydrogenase, succinate dehydrogenase, isocitrate lyase, acetohydroxy acid synthase, acetolactate synthase, formate acetyltransferase, lactate dehydrogenase, glutamate decarboxylase, 1-pyrroline dehydrogenase, acetyl-CoA hydrase (International Patent Publication WO2006/057450), and so forth.

In order to reduce or eliminate the activity of a target enzyme, a mutation may be introduced into the gene of the enzyme on a genome by a usual mutagenesis method or gene recombination technique so that intracellular activity of the enzyme is reduced or eliminated. Such a mutation can be introduced by, for example, using genetic recombination to eliminate the gene coding for the enzyme on the genome or to modify an expression control sequence such as a promoter or the Shine-Dalgarno (SD) sequence. It can also be achieved by introducing an amino acid substitution (missense mutation), a stop codon (nonsense mutation), or a frame shift mutation for adding or deleting one or two nucleotides into the regions coding for the enzyme on the genome, or partially or totally deleting the gene (J. Biol. Chem., 272:8611-8617, 1997). The enzymatic activity can also be decreased or eliminated by constructing a gene coding for a mutant enzyme, in which the coding region is totally or partially deleted, and substituting it for a normal gene on a genome by homologous recombination or the like, or by introducing a transposon or IS factor into the gene.

For example, in order to introduce a mutation that decreases or eliminates the activities of the above-mentioned enzymes by genetic recombination, the following methods can be used. A mutant gene can be prepared by modifying a partial sequence of a target gene so that it does not encode an enzyme that can function normally, and then a bacterium belonging to the family Enterobacteriaceae can be transformed with a DNA containing the mutant gene to cause recombination of a corresponding gene on the genome with the mutant gene to substitute the mutant gene for the target gene on the genome. Examples of such gene substitution using homologous recombination include methods of using a linear DNA such as the method called Red-driven integration (Datsenko, K. A, and Wanner, B. L., 2000, Proc. Natl. Acad. Sci. USA, 97:6640-6645), and the method utilizing the Red driven integration in combination with an excisive system derived from λ phage (Cho, E. H., Gumport, R. I., Gardner, J. F., 2002, J. Bacteriol., 184:5200-5203, refer to WO2005/010175, Russian Patent Application No. 2006134574), a method of using a plasmid containing a temperature sensitive replication origin (U.S. Pat. No. 6,303,383, Japanese Patent Laid-open No. 05-007491), and so forth. Furthermore, such site-specific mutagenesis based on gene substitution using homologous recombination can also be performed by using a plasmid which is not able to replicate in a host.

Furthermore, the ability to produce L-glutamic acid in coryneform bacteria can also be achieved by a method of amplifying the yggB gene (NCgl 1221; NP_600492. Reports small-conductance. [gi:19552490], WO2006/070944), and a method of introducing a mutant yggB gene in which a mutation is introduced into the coding region.

Examples of methods to enhance L-glutamic acid-producing ability include introducing genes encoding D-xylulose-5-phosphate phosphoketolase and/or fructose-6-phosphate phosphoketolase (these are collectively called phosphoketolase). Examples of microorganisms which have enhanced activity of phosphoketolase include the following microorganisms (WO2006/016705):

*Brevibacterium lactofermentum* ATCC 13869ΔsucA (pVK9-xfp)

*Brevibacterium lactofermentum* ATCC 13869ΔsucA (pVK9-PS2_xpkA)

L-Glutamic acid-producing ability can also be imparted by enhancing the 6-phosphogluconate dehydratase activity, the 2-keto-3-deoxy-6-phosphogluconate aldolase activity, or both. An example of a microorganism in which 6-phosphogluconate dehydratase activity and the 2-keto-3-deoxy-6-phosphogluconate aldolase activity are increased include the microorganism disclosed in Japanese Patent Laid-open No. 2003-274988. Furthermore, L-glutamic acid-producing ability can also be imparted by amplifying the yhfK and ybjL genes, which are L-glutamic acid secretion genes (WO2005/085419, WO2008/133161).

As an L-glutamic acid-producing microorganism, a microorganism having an ability to produce L-glutamic acid in a liquid medium in an amount exceeding the saturation concentration of L-glutamic acid when it is cultured under acidic conditions (henceforth also referred to as an L-glutamic acid accumulation ability under acidic condition) can be used. For example, by obtaining a strain in which resistance to L-glutamic acid in a low pH environment is improved according to the method described in European Patent Application Laid-open No. 1078989, the ability to produce L-glutamic acid in an amount exceeding the saturation concentration can be imparted.

Other methods for imparting or enhancing L-glutamic acid-producing ability can include methods of imparting resistance to an organic acid analogue, respiratory inhibitor, or the like, and methods of imparting sensitivity to a cell wall synthesis inhibitor. Examples include a method of imparting monofluoroacetic acid resistance (Japanese Patent Laid-open No. 50-113209), a method of imparting adenine resistance or thymine resistance (Japanese Patent Laid-open No. 57-065198), a method of attenuating urease (Japanese Patent Laid-open No. 52-038088), a method of imparting malonic acid resistance (Japanese Patent Laid-open No. 52-038088), a method of imparting resistance to benzopyrons or naphthoquinones (Japanese Patent Laid-open No. 56-1889), a method of imparting HOQNO resistance (Japanese Patent Laid-open No. 56-140895), a method of imparting α-ketomalonic acid resistance (Japanese Patent Laid-open No. 57-2689), a method of imparting guanidine resistance (Japanese Patent Laid-open No. 56-35981), a method of imparting sensitivity to penicillin (Japanese Patent Laid-open No. 4-88994), and so forth.

Specific examples of such resistant bacteria include the following strains.

*Brevibacterium flavum* AJ3949 (FERM BP-2632, refer to Japanese Patent Laid-open No. 50-113209)

*Corynebacterium glutamicum* AJ11628 (FERM P-5736, refer to Japanese Patent Laid-open No. 57-065198)

*Brevibacterium flavum* AJ11355 (FERM P-5007, refer to Japanese Patent Laid-open No. 56-1889)

*Corynebacterium glutamicum* AJ11368 (FERM P-5020, refer to Japanese Patent Laid-open No. 56-1889)

*Brevibacterium flavum* AJ11217 (FERM P-4318, refer to Japanese Patent Laid-open No. 57-2869)

*Corynebacterium glutamicum* AJ11218 (FERM P-4319, refer to Japanese Patent Laid-open No. 57-2869)

*Brevibacterium flavum* AJ11564 (FERM BP-5472, refer to Japanese Patent Laid-open No. 56-140895)

*Brevibacterium flavum* AJ11439 (FERM BP-5136, refer to Japanese Patent Laid-open No. 56-35981)

*Corynebacterium glutamicum* H7684 (FERM BP-3004, refer to Japanese Patent Laid-open No. 04-88994)

*Brevibacterium lactofermentum* AJ11426 (FERM P-5123, refer to Japanese Patent Laid-open No. 56-048890)

*Corynebacterium glutamicum* AJ11440 (FERM P-5137, refer to Japanese Patent Laid-open No. 56-048890)

*Brevibacterium lactofermentum* AJ11796 (FERM P-6402, refer to Japanese Patent Laid-open No. 58-158192)

Examples of microorganisms having L-glutamine-producing ability can include bacteria in which glutamate dehydrogenase activity is enhanced, bacteria in which glutamine synthetase (glnA) activity is enhanced, and bacteria in which glutaminase gene is disrupted (European Patent Application Laid-open Nos. 1229121 and 1424398). Enhancement of the glutamine synthetase activity can also be attained by disruption of the glutamine adenylyltransferase (glnE) or disruption of the PII control protein (glnB). Furthermore, a strain belonging to the genus *Escherichia* and having a mutant glutamine synthetase in which the tyrosine residue in the 397 position is replaced with another amino acid residue is an example of a L-glutamine-producing bacterium (U.S. Patent Published Application No. 2003/0148474).

Other methods for imparting or enhancing the L-glutamic acid-producing ability can include a method of imparting 6-diazo-5-oxo-norleucine resistance (Japanese Patent Laid-open No. 3-232497), a method of imparting purine analogue resistance and methionine sulfoxide resistance (Japanese Patent Laid-open No. 61-202694), a method of imparting α-ketomalonic acid resistance (Japanese Patent Laid-open No. 56-151495), and so forth. Specific examples of coryneform bacteria having L-glutamic acid-producing ability include the following strains.

*Brevibacterium flavum* AJ11573 (FERM P-5492, Japanese Patent Laid-open No. 56-161495)

*Brevibacterium flavum* AJ11576 (FERM BP-10381, Japanese Patent Laid-open No. 56-151495)

*Brevibacterium flavum* AJ12212 (FERM P-8123, Japanese Patent Laid-open No. 61-202694)

Examples of microorganisms having L-proline-producing ability can include, for example, bacteria having γ-glutamyl kinase which is desensitized to feedback inhibition by L-proline, and bacteria in which L-proline decomposition system is attenuated. The method of modifying bacteria by using a DNA coding for γ-glutamyl kinase desensitized to feedback inhibition by L-proline is disclosed in Dandekar, A. M., Uratsu S. L., J. Bacteriol., 170, 12:5943-5 (1988). Furthermore, examples of the method for obtaining a bacterium in which the L-proline decomposition system is attenuated can include, for example, a method of introducing a mutation into a proline dehydrogenase gene for reducing the enzymatic activity. Examples of bacteria having L-proline-producing ability include the *Escherichia coli* NRRL B-12403 strain and NRRL B-12404 strain (British Patent No. 2075056), *Escherichia coli* VKPM B-8012 strain (U.S. Patent Published Application No. 2002/0058315), and strains having the mutant plasmid disclosed in German Patent No. 3127361 or the mutant plasmid disclosed in the reference of Bloom F. R. et al. (The 15th Miami Winter Symposium, 1983, p. 34).

Furthermore, microorganisms having L-proline-producing ability can also include the *Escherichia coli* 702 strain (VKPMB-8011), which is a 3,4-dehydroxyproline and azetidine-2-carboxylate resistant strain, 702ilvA strain (VKPMB-8012 strain), which is an ilvA-deficient strain of the 702 strain, *E. coli* strains of which activity of protein encoded by the b2682, b2683, b1242 or b3434 gene is enhanced (Japanese Patent Laid-open No. 2002-300874), and so forth.

Examples of L-proline-producing strains of coryneform bacteria can include the DL-3,4-dehydroproline resistant strain (FERM BP-1219, U.S. Pat. No. 4,224,409), the strains in which citrate synthetase activity increases 1.4 times or more as compared to the parent strains thereof (FERM P-5332, FERM P-5333, FERM P-5342, FERMP-5343, Japanese Patent No. 1426823), and the strain to which acetic acid auxotrophy is imparted (FERM P-5931).

Examples of microorganisms having an L-arginine-producing ability include *Escherichia coli* mutants strains having resistance to α-methylmethionine, p-fluorophenylalanine, D-arginine, arginine hydroxamate, AEC (S-(2-aminoethyl)-cysteine), α-methylserine, β-2-thienylalanine, or sulfaguanidine (refer to Japanese Patent Laid-open No. 56-106598). The *Escherichia coli* strain 237, which contains highly active N-acetylglutamate synthase having a mutation for resistance to feedback inhibition by L-arginine (Russian Patent Application No. 2000117677), is also an L-arginine-producing bacterium. The strain 237 was deposited at the Russian National Collection of Industrial Microorganisms (VKPM) (GNII Genetika) on Apr. 10, 2000 under an accession number of VKPM B-7925, and the original deposit was converted to an international deposit based on Budapest Treaty on May 18, 2001. The *Escherichia coli* 382 strain, which is a derivative of the 237 strain and is an L-arginine-producing strain having improved ability to assimilate acetic acid (Japanese Patent Laid-open No. 2002-017342), may also be used. The *Escherichia coli* 382 strain was deposited at the Russian National Collection of Industrial Microorganisms (VKPM) on Apr. 10, 2000 under accession number of VKPM B-7926.

As a microorganism having an L-arginine-producing ability, microorganisms in which the expression amount of one or more genes coding for an L-arginine biosynthetic enzyme is increased can also be used. Examples of the L-arginine biosynthetic enzyme can include one or more enzymes selected from N-acetylglutaminate synthetase (argA), N-acetylglutamyl phosphate reductase (argC), ornithine acetyl transferase (argJ), N-acetylglutamate kinase (argB), acetylornithine transaminase (argD), acetylornithine deacetylase (argE), ornithine carbamoyl transferase (argF), argininosuccinic acid synthetase (argG), argininosuccinic acid lyase (argH), and carbamoyl phosphate synthase (carAB). A mutant N-acetylglutamate synthase gene (argA) coding for the enzyme in which the amino acid sequence corresponding to the 15 to 19 positions of the wild-type enzyme is replaced and the feedback inhibition by L-arginine is thereby canceled can be used (European Patent Application Laid-open No. 1170361).

Although the L-arginine-producing coryneform bacteria are not particularly limited so long as a coryneform bacterium having an L-arginine-producing ability is chosen, examples can include wild-type strains of coryneform bacteria; coryneform bacteria resistant to certain agents including sulfa drugs, 2-thiazolealanine, -amino-hydroxyvaleric acid, and so forth; coryneform bacteria exhibiting auxotrophy for L-histidine, L-proline, L-threonine, L-isoleucine, L-methionine or L-tryptophan in addition to the resistance to 2-thiazolealanine (Japanese Patent Laid-open No. 54-44096); coryneform bacteria resistant to ketomalonic acid, fluoromalonic acid or monofluoroacetic acid (Japanese Patent Laid-open No. 57-18989); coryneform bacteria resistant to argininol (Japanese Patent Laid-open No. 62-24075); coryneform bacteria resistant to X-guanidine (X represents a derivative of aliphatic acid or aliphatic chain, Japanese Patent Laid-open No. 2-186995), and so forth.

A coryneform bacterium having L-arginine-producing ability can be bred to be resistant to 5-azauracil, 6-azauracil, 2-thiouracil, 5-fluorouracil, 5-bromouracil, 5-azacytosine, 6-azacytosine and so forth; resistant to arginine hydroxamate and 2-thiouracil; resistant to arginine hydroxamate and 6-azauracil (Japanese Patent Laid-open No. 49-126819); resistant to a histidine analogue or tryptophan analogue (Japanese Patent Laid-open No. 52-114092); auxotrophic for at least one of methionine, histidine, threonine, proline, isoleucine, lysine, adenine, guanine and uracil (or uracil precursor) (Japanese Patent Laid-open No. 52-99289); resistant to arginine hydroxamate (Japanese Patent Publication No. 51-6754); auxotrophic for succinic acid or resistant to a nucleic acid base analogue (Japanese Patent Laid-open No. 58-9692); deficient in arginine decomposition ability, resistant to an arginine antagonist and canavanine and auxotrophic for lysine (Japanese Patent Laid-open No. 52-8729); resistant to arginine, arginine hydroxamate, homoarginine, D-arginine and canavanine, or resistant to arginine hydroxamate and 6-azauracil (Japanese Patent Laid-open No. 53-143288); resistant to canavanine (Japanese Patent Laid-open No. 53-3586), or the like.

Specific examples of coryneform bacteria having L-arginine-producing ability include the following strains.

*Brevibacterium flavum* AJ11169 (FERM P-4161)
*Brevibacterium lactofermentum* AJ12092 (FERM P-7273)
*Brevibacterium flavum* AJ11336 (FERM P-4939)
*Brevibacterium flavum* AJ11345 (FERM P-4948)
*Brevibacterium lactofermentum* AJ12430 (FERM BP-2228)

Furthermore, a strain deficient in ArgR, which is an arginine repressor (U.S. Published Patent Application No. 2002/0045223), and a strain in which glutamine synthetase activity is increased (U.S. Published Patent Application No. 2005/0014236) can also be used.

L-Citrulline and L-ornithine share common biosynthetic pathways with L-arginine, and the ability to produce L-citrulline and L-ornithine can be imparted by increasing the enzymatic activities of N-acetylglutamate syntase (argA), N-acetylglutamylphosphate reductase (argC), ornithine acetyltransferase (argJ), N-acetylglutamate kinase (argB), acetylornithine transaminase (argD), and acetylornithine deacetylase (argE) (WO2006/35831).

As an γ-aminobutyric acid (GABA)-producing bacterium, a strain in which activity of glutamate decarboxylase is enhanced (Microb. Cell Fact., 2010, Nov. 12; 9:85; Amino Acids, 2010 November, 39(5):1107-16; U.S. Patent Published Application No. 2010/0324258) can be used.

As a putrescine-producing bacterium, a strain in which 4-hydroxybutyrate reductase, succinyl-CoA reductase (aldehyde forming), and 4-hydroxybutyrate dehydrogenase are enhanced (WO2011/047101), and a strain of which γ-aminobutyraldehyde dehydrogenase is enhanced (FEBS Lett., 2005 Aug. 1, 579 (19):4107-12), can be used.

<2> Method for Producing Target Substance

By culturing such a bacterium as described above in a medium containing xylose as a carbon source to produce and accumulate a target substance in the medium, and collecting the target substance from the medium, the target substance can be produced.

As the medium used for the culture, a typical media containing a carbon source, nitrogen source and mineral salts as well as organic trace nutrients such as amino acids and vitamins as required can be used. Either a synthetic medium or a natural medium may be used.

As the carbon source, so long as xylose is present, other carbon sources, for example, sugars such as glucose, glycerol, fructose, sucrose, maltose, mannose, galactose, arabinose, starch hydrolysates and molasses can be used. In addition, organic acids such as acetic acid and citric acid, and alcohols such as ethanol can also be used each alone or in combination with other carbon sources.

Although the ratio of xylose to other carbon sources is not particularly limited, the ratio of xylose:other carbon source (weight ratio) can be 1:0.1 to 100, 1:0.1 to 10, 1:0.1 to 5, 1:1 to 5, or 1:1 to 3.

The concentration of the carbon source in the medium is not particularly limited so long as the concentration is suitable for producing the chosen target substance. However, the concentration of the carbon source in the medium can be about 0.1 to 50 w/v %, about 0.5 to 40 w/v %, or about 1 to 30%.

Xylose, or a mixture of xylose and a hexose such as glucose, can be obtained from a supply source of biomass that is not fully used. Such pentoses and hexoses can be released from biomass by hydrolysis with steam and/or a acid, hydrolysis with diluted acid, hydrolysis with an enzyme such as cellulase, or an alkaline treatment. When the substrate is a cellulose-type material, cellulose is hydrolyzed into saccharides simultaneously or successively, and the saccharides can be used for the production of the target substance. Since hemicellulose is generally more easily hydrolyzed into saccharides as compared to cellulose, a cellulose-type material can be hydrolyzed beforehand, the pentoses separated, and then the cellulose hydrolyzed by a treatment with steam, acid, alkali, cellulase, or a combination of these, to produce hexoses.

Xylose in the medium may also be supplied by converting each of the hexoses to xylose (D-xylose) using a microorganism mutated to have a pathway for converting glucose, galactose or arabinose into xylose.

As the nitrogen source, ammonia, urea, ammonium salts such as ammonium sulfate, ammonium carbonate, ammonium chloride, ammonium phosphate and ammonium acetate, nitric acid salts and so forth can be used. As the organic trace nutrients, amino acids, vitamins, fatty acids, nucleic acids, nutrients containing the foregoing substances such as peptone, casamino acid, yeast extract, soybean protein decomposition product and so forth can be used. When an auxotrophic mutant strain that requires an amino acid or the like for its growth is used, the required nutrient can be supplemented. As the mineral salts, phosphoric acid salts, magnesium salts, calcium salts, iron salts, manganese salts and so forth can be used.

The culture can be performed under aerobic conditions, while the fermentation temperature can be controlled to be 20 to 45° C., and pH to be 3 to 9. To adjust the pH, an inorganic or organic acidic or alkaline substance, ammonia gas, and so forth can be used. A substantial amount of the target substance can be accumulated in the culture medium or cells after 10 to 120 hours of culture under such conditions as described above.

Moreover, when the target substance is L-glutamic acid, the culture can be performed to produce and accumulate L-glutamic acid by precipitating L-glutamic acid in a liquid medium adjusted to satisfy a condition under which L-glutamic acid is precipitated. Examples of the condition under which L-glutamic acid is precipitated include, for example, pH of 5.0 to 4.0, 4.5 to 4.0, more 4.3 to 4.0, or 4.0. In order to simultaneously obtain both improvement of growth under acidic conditions and efficient precipitation of L-glutamic acid, the pH can be 5.0 to 4.0, 4.5 to 4.0, or 4.3 to 4.0. The culture may be performed at the aforementioned pH for the whole culture period or for only a portion of it.

The target substance collected may contain microbial cells, medium components, moisture, and by-product metabolites of the microorganism in addition to the target substance. Purity of the collected target substance is 50% or higher, 85% or higher, or 95% or higher (Japanese Patent No. 1214636, U.S. Pat. Nos. 5,431,933, 4,956,471, 4,777,051, 4,946,654, 5,840,358, 6,238,714, U.S. Patent Published Application No. 2005/0025878).

The target substance can be collected from the culture medium after completion of the culture by a combination of conventionally known methods such as ion-exchange resin method (Nagai, H. et al., Separation Science and Technology, 39(16), 3691-3710), membrane separation (Japanese Patent Laid-open Nos. 9-164323 and 9-173792), crystallization (WO2008/078448, WO2008/078646), and other methods.

Furthermore, when the target substance deposits in the medium, it can be collected by centrifugation, filtration or the like. A target substance deposited in the medium and a target substance dissolved in the medium may be isolated together after the target substance dissolved in the medium is crystallized.

EXAMPLES

Hereafter, the present invention will be still more specifically explained with reference to the following non-limiting examples.

The medium compositions used in the following examples are shown below.

LB Medium:

| | |
|---|---|
| Bacto tryptone | 10 g/L |
| Yeast extract | 5 g/L |
| NaCl | 5 g/L |
| pH 7.0 | |

LBGM9:

The same components as those of the LB medium, plus minimal medium components (5 g/L of glucose, 2 mM of magnesium sulfate, 3 g/L of monopotassium phosphate, 0.5 g/L of sodium chloride, 1 g/L of ammonium chloride, 6 g/L of disodium phosphate)

MSII-Glucose Medium:

| | |
|---|---|
| Group A | |
| Glucose | 40 g/L |
| $MgSO_4 \cdot 7H_2O$ | 0.5 g/L |
| Group B | |
| $(NH_4)_2SO_4$ | 20 g/L |
| $KH_2PO_4$ | 2 g/L |
| NaCl | 0.5 g/L |
| Yeast extract | 2 g/L |
| $CaCl_2 \cdot 7H_2O$ | 0.25 g/L |
| $FeSO_4 \cdot 7H_2O$ | 20 mg/L |
| $MnSO_4 \cdot nH_2O$ | 20 mg/L |
| Trace elements* | 4 ml/l |
| L-Lys | 200 mg/L |
| DL-Met | 200 mg/L |
| DAP | 200 mg/L | a. The components of Groups A and B were separately autoclaved at 120° C. for 20 minutes, and then mixed.

| *Trace elements | |
|---|---|
| $CaCl_2 \cdot 2H_2O$ | 0.66 g/L |
| $ZnSO_4 \cdot 7H_2O$ | 0.18 g/L |
| $CuSO_4 \cdot 5H_2O$ | 0.16 g/L |
| $MnSO_4 \cdot 4H_2O$ | 0.15 g/L |
| $CoCl_2 \cdot 6H_2O$ | 0.18 g/L |
| $H_3BO_3$ | 0.10 g/L |
| $Na_2MoO_4$ | 0.30 g/L |

MSII-Xylose Medium:

The same components as those of the MSII-Glucose medium except that glucose (40 g/L) is replaced with xylose (40 g/L).

MSII-GX Medium:

The same components as those of the MSII-Glucose medium except that glucose (40 g/L) is replaced with a mixture of glucose (20 g/L) and xylose (20 g/L)

MSII-SX Medium:

The same components as those of the MSII-Glucose medium except that glucose (40 g/L) is replaced with a mixture of sucrose (20 g/L) and xylose (20 g/L).

E1 Synthetic Medium:

| | |
|---|---|
| Group A | |
| $NH_4Cl$ | 20 mM |
| $MgSO_4 \cdot 7H_2O$ | 2 mM |
| $Na_2HPO_4$ | 40 mM |
| $KH_2PO_4$ | 30 mM |
| $CaCl_2$ | 0.01 mM |
| $FeSO_4 \cdot 7H_2O$ | 0.01 mM |
| $MnSO_4 \cdot 4$ to $5H_2O$ | 0.01 mM |
| Citrate | 5 mM |
| pH Free | |
| Filter-sterilized | |
| Group B-1 | |
| Carbon source | 50 (or 100) mM |
| Filter-sterilized | |
| Group B-2 | |
| Thiamine HCl | 1 mM | b. This component was added to the component of the group B-1 after filter sterilization (0.22 μm).

| Group C | |
|---|---|
| MES-NaOH (pH 6.8) | 50 mM |
| Filter sterilized (0.22 μm) | | c. Solutions containing the components of the groups A to C at 5-fold higher concentrations were prepared as stock solutions.

CM-Dex Medium:

| | |
|---|---|
| Polypeptone | 10 g/L |
| Yeast extract | 10 g/L |
| Glucose | 5 g/L |
| $KH_2PO_4$ | 1 g/L |
| Urea | 3 g/L |
| $MgSO_4 \cdot 7H_2O$ | 0.4 g/L |
| $FeSO_4 \cdot 7H_2O$ | 0.01 g/L |
| $MnSO_4 \cdot 5H_2O$ | 0.01 g/L |
| Bean filtrate | 1.2 g/L (T-N) |
| Soybean hydrolysate | |
| pH 7.5 adjusted with KOH | |

Glc Medium:

| Glucose | 80 g/L |
| --- | --- |
| (NH4)$_2$SO$_4$ | 30 g/L |
| KH$_2$PO$_4$ | 1 g/L |
| MgSO$_4$•7H$_2$O | 0.4 g/L |
| FeSO$_4$•7H$_2$O | 0.01 g/L |
| MnSO$_4$•5H$_2$O | 0.01 g/L |
| Vitamin B1 | 200 µg/L |
| Biotin | 60 µg/L |
| Bean filtrate | 0.48 g/L (T-N) |
| Soybean hydrolysate | |
| pH 8.0 adjusted with KOH | |

Xyl Medium (Biotin Restricted)

The same components as those of the Glc medium except that glucose (80 g/L) is replaced with xylose (80 g/L), and minus biotin.

MS Medium:

| Group A | |
| --- | --- |
| Glucose or xylose | 40 g/L |
| Glucose and xylose (1:1) | 40 g/L |
| MgSO$_4$•7H$_2$O | 1 g/L |
| Group B | |
| (NH4)$_2$SO$_4$ | 20 g/L |
| KH$_2$PO$_4$ | 1 g/L |
| Yeast Extract | 2 g/L |
| FeSO$_4$•7H$_2$O | 10 mg/L |
| MnSO$_4$•nH$_2$O | 10 mg/L |

The components of Groups A and B were separately autoclaved at 120° C. for 20 minutes, and then mixed, and 50 g/L of calcium carbonate according to the Japan Pharmacopoeia was added.

Example 1

Introduction of NXA Pathway into *Pantoea ananatis*

Construction of plasmid pTWV228Ptac_ccrNXA for introduction of NXA Pathway

The NXA pathway has been reported in *C. crescentus* (Stephens, C. et al., J. Bacteriol., 189(5):181-2185, 2007). To obtain the genes coding for the enzymes of the NXA pathway of *C. crescentu*, the following methods were employed.

The genome of *C. crescentus* has a length of about 4 Mb, in which five genes form an operon structure (Journal of Bacteriology, 189:2181-2185, 2007). The genome was extracted from the published strain of *C. crescentus* (CB-15 (ATCC 19089, available from ATCC), and the genes were cloned and an expression vector for the genes constructed.

The expression vectors were constructed by using Clontech In-Fusion Cloning Kit.

The following four kinds of DNA fragments were amplified by PCR using chromosomal DNA of *C. crescentus* CB-15 (ATCC 19089) for the following i), ii) and iii), and pMW119 for the following iv) as the templates. The primers used for PCR are indicated in the parentheses.

i) tac promoter sequence (henceforth referred to as "Ptac", PtwvPtacf: SEQ ID NO: 1, 0823Ptacr: SEQ ID NO: 2)
ii) Fragment containing xylX, ccrxylA, ccrxylB and xylC (Ptac0823f: SEQ ID NO: 3, 0819r: SEQ ID NO: 4)
iii) xylD and downstream region thereof of about 120 bp (0819f: SEQ ID NO: 5, 219 cc0819r: SEQ ID NO: 6)
iv) pMW119/SmaI (219f: SEQ ID NO: 7, 219r: SEQ ID NO: 8)

Then, by PCR using the purified PCR products of i) and ii) as the template, as well as PtwvPtacf and 0819r as the primers, a fragment Ptac_xylXccrAccrBC consisting of the foregoing PCR products ligated together was amplified. The in-fusion reaction was performed with these three of the obtained Ptac_xylXccrAccrBC and the PCR products of iii) and iv) using Clontech In-Fusion Cloning Kit, *E. coli* JM109 strain was transformed with the reaction product, and the target plasmid pMW119 Ptac_ccrNXA was obtained from a transformant.

Then, by using pMW119 Ptac_ccrNXA as the template, as well as PtwvPtacf and 219CC0819r as the primers, ccrNXA operon containing Ptac was amplified. The in-fusion reaction was performed with the obtained amplified product and pTWV228 which had been digested with SmaI; the *E. coli* JM109 strain was transformed with the reaction product, and the target plasmid pTWV228Ptac_ccrNXA was obtained from a transformant.

(2) Construction of Plasmid pUT-MuKm Containing pUT399 Carrying Kanamycin Resistant Mini-Mu pUT399 is a plasmid having the replication origin of R6K and the mob region required for conjugative transfer, and is not replicable in a strain which lacks the pir gene (available from Biomedal, refer to R. Simon., et al., BIO/TECHNOLOGY NOVEMBER 1983, 784-791; U.S. Pat. No. 7,090,998).

pCE1134 (Japanese Patent Laid-open No. 2-109985) is a plasmid containing MudII1734, and carries a Km resistance gene and the lacXYZ gene in the Mini-Mu unit. By the method described below, a DNA fragment not having the lacXYZ region was prepared from the Mini-Mu unit of pCE1134, and cloned into pUT399.

By PCR using pCE1134 as the template, as well as primers attL-F (SEQ ID NO: 9) and nptII-R (SEQ ID NO: 10), a fragment containing the repressor MuCts of the MuAB gene coding for the left end and transposase, and the Km resistance gene, was obtained. Furthermore, by using pCE1134 as the template, as well as primers attR-F (SEQ ID NO: 11) and attR-R (SEQ ID NO: 12), a fragment containing the right end was similarly obtained. Crossover PCR was performed by using these 2 fragments as the template, as well as the primers attL-F and attR-R, and the obtained fragment of about 2.3 kb was introduced into pUT399 at the SmaI site. In this way, the plasmid pUT-MuKm was obtained.

Since the Mini-Mu unit constructed as described above has the Km resistance gene and the 8-base recognizing NotI site as a cloning site in the transposition unit, various genes can be cloned into it.

(3) Substitution of Drug Resistance Gene of pTWV228Ptac_ccrNXA

The ampicillin resistance gene of pTWV228Ptac_ccrNXA was replaced with the kanamycin resistance gene by the λRed method.

By using pUT_MuKm as the template, as well as primers Ap-Km-fw (SEQ ID NO: 13) and Ap-Km-ry (SEQ ID NO: 14), a sequence containing the kanamycin resistance gene (ntpII fragment) was amplified.

The PCR was performed by using PrimeSTAR HS Polymerase (Takara Bio) according the protocol attached to this enzyme.

A helper plasmid RSF_Red_TER (U.S. Patent Published Application No. 2009/0286290A1, WO2008/075483) was introduced into *E. coli* JM109 having pTWV228Ptac_ccrNXA, and the cells were cultured in 50 ml of the LB medium (containing 1 mM IPTG, 100 mg/L of ampicillin, and 25 mg/L of chloramphenicol) at 37° C. until OD660 value became 0.4.

The aforementioned RSF_Red_TER is a helper plasmid for inducing λ-dependent integration (Red-driven integration, λRed method), and it can induce expression of gam, bet and exo genes of λ with the lad gene. This plasmid also contains the levansucrase gene (sacB), and can eliminate a plasmid from a cell with this gene in a medium containing sucrose. Furthermore, this plasmid also contains the chloramphenicol resistance gene.

The cells cultured as described above were collected, washed twice with a 10% glycerol solution by centrifugation, and suspended 1 mL of a 10% glycerol solution. Then, the cells were transformed with the ntpII fragment obtained above by electroporation, and the transformants were subjected to selection on the LB agar medium containing 40 mg/L of kanamycin. The obtained transformants were inoculated on the LB agar medium (containing 1 mM IPTG, 10% sucrose, and 40 mg/L of kanamycin), and cultured overnight at 37° C. to obtain a single clone. It was confirmed that the obtained transformant could not grow on the LB agar medium containing 100 mg/L of ampicillin, and thereby it was confirmed that the ampicillin resistance gene of pTWV228Ptac_ccrNXA was replaced with the kanamycin resistance gene. The obtained plasmid was designated pTWVPtac_ccrNXA_Km.

(4) Construction of Plasmid Containing xylD

The construction was performed by using Clontech In-Fusion Cloning Kit.

First, by PCR using a plasmid containing pUC18 in which each gene was cloned as the template, as well as xylD_IFS_5742-10-5 (SEQ ID NO: 15) and xylD_IFS_5742-10-6 (SEQ ID NO: 16) as the primers, a DNA fragment containing xylD was amplified. Specifically, it was cloned into a pUC18 plasmid in which the SfiI site had been removed by the method described below.

By PCR using the genomic DNA of the C. crescentus CB-15 strain as the template, CC0819-01F_4691-88-7 (SEQ ID NO: 17) and CC0819-01R_5659-9-1 (SEQ ID NO: 18), as well as CC0819-02F_5659-9-2 (SEQ ID NO: 19) and CC0819-02R_4691-88-10 (SEQ ID NO: 20) as the primers, fragments of 1130 bp and 653 bp were amplified, respectively. Then, pUC18 which had been digested with SmaI, and the two amplified fragments described above, were assembled by the in vitro assembly method (Nature Methods, 6(5), 343-345, 2009) to obtain pUC18-xylD in which the SfiI site was removed, and the xylD gene was inserted.

Separately, pSTV28-Ptac-Ttrp was digested with SmaI in a conventional manner. The in-fusion reaction was performed with the DNA fragment of the xylD gene and the vector DNA fragment, the E. coli JM109 strain was transformed with the reaction product, and the target plasmid pSTVPtac_xylD_Ttrp was obtained from a transformant.

pSTV28-Ptac-Ttrp was constructed as follows.

A DNA fragment (PtacTtrp) having the tac promoter (having the sequence of SEQ ID NO: 32) and the sequence of the trp terminator was synthesized, and ligated between the KpnI-BamHI sites of the pMW219 vector to obtain pMW219-Ptac-Ttrp. The same amounts of pSTV28 and pMW219-Ptac-Ttrp both digested with KpnI and BamHI were mixed, and ligated, JM109 was transformed with the ligation product, and a plasmid was extracted from a colony that showed Cm resistance. It was confirmed that the obtained plasmid showed bands of about 400 bp and 3 kbp (correctly 389 bp and 2994 bp), which were expected as a result of the double digestion with KpnI and BamHI, and thus pSTV28-Ptac-Ttrp was obtained.

(4) L-Glutamic Acid Production with *Pantoea ananatis* Having the NXA Pathway

The *P. ananatis* NA1 strain was transformed with pTWVPtac_ccrNXA_Km by electroporation (refer to U.S. Pat. No. 6,682,912). For the strain containing pTWVPtac_ccrNXA_Km, a plate medium with LBGM9 supplemented with kanamycin at a final concentration of 40 mg/L was used.

Cells of the *P. ananatis* NA1 strain and the transformant strain cultured overnight at 34° C. on the LBGM9 plate were each scraped off in an amount corresponding to ⅙ of the plate, inoculated into 5 ml of the MSII-Xylose or MSII-GX medium contained in a large test tube, and cultured at 34° C. and 120 rpm for 48 hours, and residual saccharide, amounts of accumulated L-glutamic acid (Glu), and xylonic acid were measured. The results are shown in Tables 2 and 3.

TABLE 2

| | Glu production in MSII-GX medium | | | | | |
|---|---|---|---|---|---|---|
| Strain | OD660 (x51) | Consumed Glc (g/L) | Consumed Xyl (g/L) | Glu (g/L) | Yield (%) | Xylonic acid (g/L) |
| NA1 | 0.129 ± 0.001 | 21.8 | 22.9 | 11.5 ± 0.1 | 25.7 ± 0.3 | 18.4 ± 0.2 |
| NA1/pTWV228Ptac_ccrNXA_Km | 0.134 ± 0.006 | 21.8 | 22.9 | 31.3 ± 0.1 | 69.8 ± 0.1 | 0.0 |

TABLE 3

| | Glu production in MSII-Xylose medium | | | | |
|---|---|---|---|---|---|
| Strain | OD660 (x51) | Consumed Xyl (g/L) | Glu (g/L) | Yield (%) | Xylonic acid (g/L) |
| NA1 | 0.019 ± 0.006 | 0.0 | 0.0 | 0.0 | 0.0 |
| NA1/pTWV228Ptac_ccrNXA_Km | 0.069 ± 0.008 | 41.0 | 32.7 ± 0.9 | 80.5 ± 2.2 | 10.1 ± 1.9 |

When the *P. ananatis* NA1 strain was cultured with the mixed carbon source of glucose and xylose (MSII-GX medium), the glutamic acid yield was 25.7% (Table 2). In this case, accumulation of xylonic acid was observed, and thus it was suggested that most of xylose was converted into xylonic acid. It is estimated that the accumulation of xylonic acid with the *P. ananatis* NA1 strain was provided by the activity of glucose dehydrogenase of *P. ananatis*.

On the other hand, when the *P. ananatis* NA1 strain containing pTWVPtac_ccrNXA_Km was cultured with the mixed carbon source of glucose and xylose (MSII-GX medium), the glutamic acid yield was significantly higher as compared to the parent strain (yield: 69.9%). If it is taken into consideration that the parent strain hardly produces glutamic acid from xylose, and it is assumed that the glutamic acid yield from glucose of the strain containing pTWVPtac_ccrNXA_Km is equivalent to that of the parent strain, the yield of glutamic acid produced from xylose via the NXA pathway is about 86%. In fact, when the culture was performed with xylose as the sole carbon source (MSII-Xylose), the strain containing pTWVPtac_ccrNXA_Km produced Glu at a yield of 80% (Table 3).

Example 2

Introduction of NXA Pathway into *Escherichia coli*

Expression of NXA Pathway in *E. Coli*
By using a strain deficient in isocitrate dehydrogenase (Δicd), which is an enzyme of the TCA cycle and produces αKG from isocitric acid, expression of the NXA pathway was attempted by growth complementation in a minimal medium containing xylose as the sole carbon source. Since the icd gene-deficient strain cannot produce αKG, it cannot grow in a minimal medium containing xylose as the sole carbon source. However, if the ability to produce αKG from xylose can be imparted by introducing the NXA pathway, then this strain acquires the ability to grow in such a medium.

Specifically, the JW1122 strain, which is an icd gene-deficient strain of Keio Collection (cgsc.biology.yale.edu/Person.php?ID99553, available from *E. coli* Genetic Resource Center at Yale CGSC, The Coli Genetic Stock Center), was used as a host bacterial strain, and by introducing and expressing the NXA pathway in that strain using a plasmid, it was examined whether the NXA pathway could function also in *E. coli*.

In Table 4, the constructed plasmids and the results of growth complementation in the icd gene-deficient strain are shown. It was confirmed that the strain introduced with a plasmid pMW119 Ptac_ccrNXA (prepared in Example 1) containing the NXA pathway operon (xylX, ccrxylA, ccrxylB, xylC, xylD) and the tac promoter in combination could grow on the M9 minimal medium (plate) (Sambrook, J. et al., Molecular Cloning, Cold Spring Harbor Laboratory Press (1989)) containing xylose as the sole carbon source.

A similar study was also performed using liquid culture. Growth (O.D.) in the M9 minimal medium and the E1 synthetic medium containing xylose or αKG as the sole carbon source was measured over time by using a culture apparatus for 36 samples. The results are shown in FIG. 1. Like the plate culture, the NXA pathway-introduced strain favorably grew on the M9 or E1 medium containing xylose as the sole carbon source, whereas the vector control strain did not grow in such a medium. It was considered that these results were obtained because the strain grew by assimilating xylose via the NXA pathway, i.e., the NXA pathway derived from *C. crescentus* functioned also in *E. coli*.

TABLE 4

| Vector | Promoter | Gene | Growth in the M9-xylose medium |
|---|---|---|---|
| pTWV229 | Native | xylX ccrxylA | X |

TABLE 4-continued

| Vector | Promoter | Gene | Growth in the M9-xylose medium |
|---|---|---|---|
| pMW119 | Ptac | ccrxylB xylC xylD xylX ccrxylA ccrxylB xylC xylD | ○ |
| pTWV228 | Ptac | xylX ccrxylA ccrxylB xylC xylD | ○ |

Figure 2:
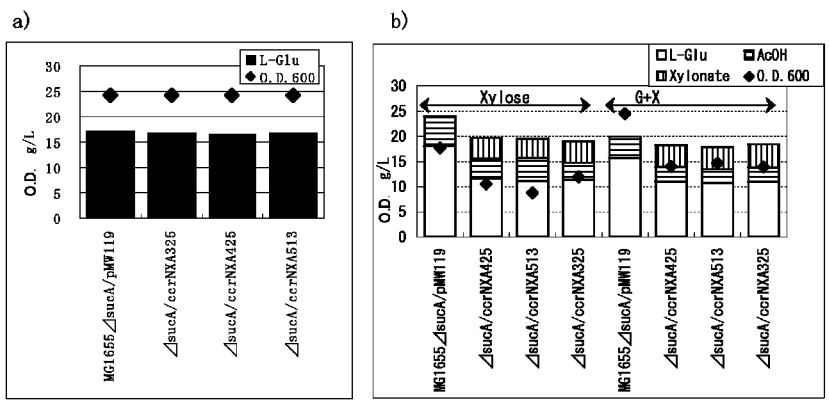
FIG. 2 depicts graphs showing results of L-glutamic acid production culture of *E. coli* L-glutamic acid-producing strain expressing the *E. coli* ccrNXA operon.

(2) Expression of NXA Pathway in *E. Coli* L-Glutamic Acid-Producing Strain
As *E. coli* L-glutamic acid-producing strain, MG1655ΔsucA (U.S. Patent Published Application No. 2005/0106688), which is an αKGDH-deficient strain, was used. pMW119 Ptac_ccrNXA or pMW119 as a control was introduced into the above strain to obtain MG1655ΔsucA/pMW119Ptac_ccrNXA and MG1655ΔsucA/pMW119. These strains were each cultured as a flask culture in the MS culture medium containing glucose (40 g/L), xylose (40 g/L), or glucose and xylose (20 g/L each) as the carbon source. The culture was performed for 24 hours in the medium containing only glucose as the carbon source, and for 48 hours in the other media. The results are shown in FIG. 2. The numerals 325, 425 and 513 attached to the strain names shown in the figure are clone numbers.

When a mixture of glucose and xylose was used as the carbon source, while the control strain (MG1655ΔsucA/pMW119) accumulated 15 to 16 g/L of L-glutamic acid, the ccrNXA operon-expressing strain (MG1655ΔsucA/pMW119Ptac_ccrNXA) produced about 12 g/L L-glutamic acid of, and thus tended to show reduced accumulation and yield of L-glutamic acid. Also when xylose was used as the sole carbon source, the same result was obtained. As for by-products, the resulting culture was analyzed for organic acids and xylonic acid. As a result, it was found that acetic acid and xylonic acid were mainly produced.

(3) Analysis of Rate-Limiting Point of NXA Pathway in *E. Coli*
Since xylonic acid, which is an intermediate of the NXA pathway, was detected in the culture supernatant of the ccrNXA operon-expressing *E. coli* L-glutamic acid-producing bacterium as described above, it was considered that it was highly possible that a part of incorporated xylose was assimilated via the NXA pathway. Furthermore, the following problems were estimated.

i) While xylose incorporated into the cells may be assimilated by both the xylose-assimilating system characteristic to *E. coli* and the NXA pathway, a certain amount of xylose may be utilized by the *E. coli* system due to the difference in activity or substrate specificity of the first enzyme of the *E. coli* system, xylose isomerase (XylA), and the first enzyme of the NXA pathway, xylose dehydrogenase (XDH), and thus the flow rate of metabolic flux using the NXA pathway may become smaller.

ii) There may be a rate-limiting point in the NXA pathway, or an unknown bypass pathway, and therefore αKG may not be produced.

It was considered that the problem of i) might be ameliorated by increasing the amounts of the enzymes of the NXA pathway by replacing the low-copy NXA operon expression vector (pMW119) to a medium copy number type vector (pTWV228), and thereby increasing the uptake amount of the substrate into the ccrNXA pathway.

It was also considered that the problem of ii) might be overcome by improving the strain by breeding based on analysis of rate-limiting point and results thereof.

On the basis of the above considerations, the following was performed:

a) construction of a strain from a strain deficient in the E. coli-specific xylose-assimilating pathway (ΔsucAΔxylA) as a host, in which the ccrNXA operon is expressed and thus carbon flux is forced through the NXA pathway, and evaluation thereof by culture, b) construction of a ccrNXA operon expression vector using a medium copy number vector, construction of a strain using such a expression vector, and evaluation thereof by culture, and c) analysis of rate-limiting point.

By deleting the E. coli-specific xylose-assimilating gene xylA from MG1655ΔsucA according to the λ-Red method using primers xylA-H1P1-5742-5-1 (SEQ ID NO: 21) and xylA-H2P2-5742-5-2 (SEQ ID NO: 22), MG1655ΔsucAΔxylA strain was obtained. pMW119Ptac_ccrNXA was introduced into this strain to obtain a ccrNXA operon-expressing strain deficient in xylA.

Figure 3:
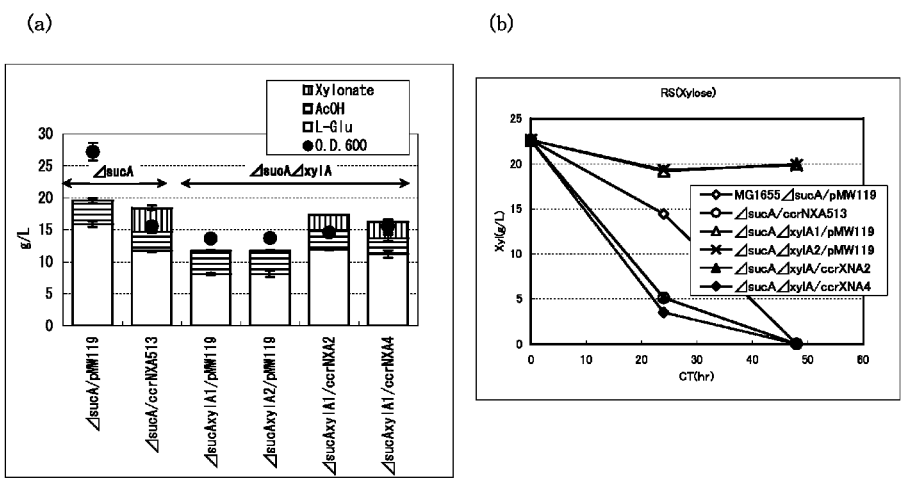
FIG. 3 depicts graphs showing results of L-glutamic acid production culture of a ccrNXA operon-expressing strain using a strain deficient in the xylose assimilation pathway characteristic to *E. coli* as a host.

The results of the L-glutamic acid production culture performed by culturing the ccrNXA operon-expressing strain deficient in xylA in the same manner as that described in the above section (3) are shown in FIG. 3. In FIG. 3, "ccrNXA" represents pMW119Ptac_ccrNXA, and the following numerals represent the clone numbers.

Whereas the vector control strain of the ΔsucAΔxylA strain could not assimilate xylose, and could form cells and produce L-glutamic acid from only glucose, the ccrNXA operon-expressing strain showed consumption of xylose and production of L-glutamic acid, which was considered to be derived form xylose. However, it was found that the L-glutamic acid accumulation amount thereof was smaller than that obtained with the model strain (ΔsucA strain), and it accumulated xylonic acid, which is a metabolic intermediate of the ccrNXA pathway. From these results, it was suggested that the metabolic flux of the whole ccrNXA pathway might be insufficient. Furthermore, since by-production of αKG was not observed, it was considered that supply of NADPH required for expression of the activity of GDH did not pose any problem at this stage.

Figure 4:
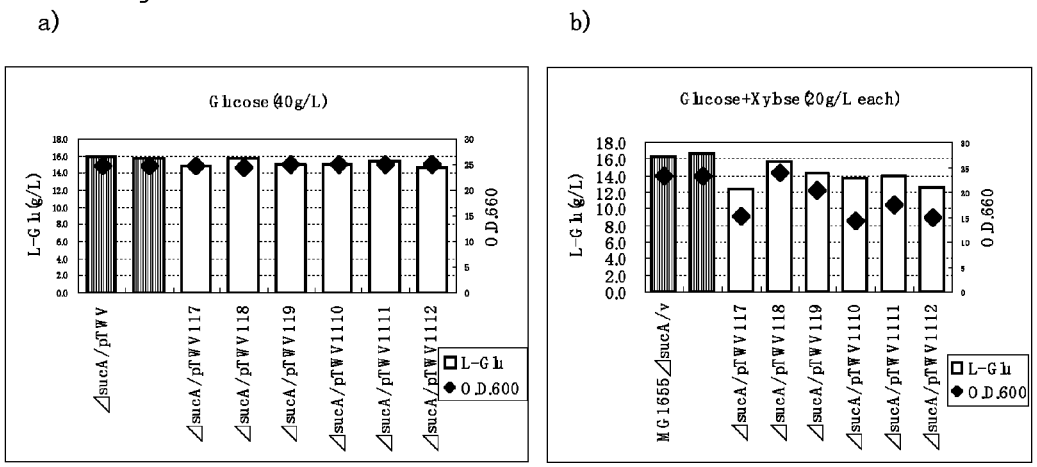
FIG. 4 depicts graphs showing results of L-glutamic acid production culture of a ccrNXA operon-expressing strain utilizing a medium copy number type plasmid.

Then, a ccrNXA operon expression vector was constructed using a medium copy number vector. The ccrNXA operon containing the tac promoter region was amplified by using pMW119 Ptac_ccrNXA as the template, as well as PtwvPtacf (SEQ ID NO: 1) and 0819r (SEQ ID NO: 4) as the primers. pTWV228 was digested with SmaI, and used together with the PCR fragment of the ccrNXA operon containing the tac promoter region to perform the in-fusion reaction, the E. coli JM109 strain was transformed with the reaction product, and the target plasmid pTWVPtac_ccrNXA was obtained from a transformant. This plasmid was introduced into the MG1655ΔsucA strain, and the obtained strain was cultured in the same manner as that described in the above section (3). The results are shown in FIG. 4. In the figure, "ΔsucA" represents the MG1655ΔsucA strain, and "/pTWV" and "/v" mean that the strain harbored pTWV228. Furthermore, pTWV110 to pTWV119 indicate clone numbers of pTWV228Ptac_ccrNXA.

When only glucose was used as the carbon source, the medium copy number ccrNXA operon-expressing strain produced L-glutamic acid in an amount substantially equivalent to that observed with the control strain. However, when the mixed culture system of glucose and xylose was used, the accumulation of L-glutamic acid tended to decrease. Furthermore, results of sibling strains also fluctuated. One of the conceivable reasons is the elimination of the medium copy number expression vector. Furthermore, like the strains described above, accumulation of xylonic acid was observed.

In order to confirm whether the activities of the enzymes of the ccrNXA pathway were increased by the increase in copy number of the NXA operon, the activity of XDH, which is the first enzyme of the NXA pathway, was measured. The results are shown in Table 5. "7513" and "1110" in the strain names mentioned in Table 5 are clone numbers.

TABLE 5

Results of XDH (xylose dehydrogenase) activity measurement

| Strain | Specific activity (μmol/min/mg-protein) | Relative activity |
|---|---|---|
| MG1655ΔsucA/pMW119 | ND | |
| MG1655ΔsucA/pMWccrNXA7513 | 21.5 | 1.0 |
| MG1655ΔsucA/pMW228 | ND | |
| MG1655ΔsucA/pMWccrNXA1110 | 140.4 | 6.5 |

ND: Not Detected
Note:
The relative activity was indicated as relative activity based on the specific activity of ccrNXA7513 taken as 1.

The medium copy number expression vector-introduced strain showed about 7 times higher XDH activity as compared to the low copy number expression vector-introduced strain. It had not been confirmed how xylose was actually distributed within the cells at the branching point of the xylose isomerase (XylA) characteristic to E. coli and XDH, and thus it was also still considered that the activity of XDH, which is the first enzyme of the NXA pathway, might be insufficient. However, since the increase of the XDH activity did not improve L-glutamic acid accumulation, and on the basis of accumulation of xylonic acid, and so forth, it was considered that either one or more of enzymes of the NXA pathway might be rate-limiting.

Therefore, the rate-limiting point of the NXA pathway was analyzed. Since xylonic acid accumulates as a metabolic intermediate, it was considered at least that the rate-limiting point might exist in the pathway from xylonic acid to αKG rather than the metabolic pathway from xylose to xylonic acid. Furthermore, in the structure of the ccrNXA operon, whereas the enzymes of the pathway from xylose to xylonic acid are encoded by the genes located at the third and fourth positions, the enzymes of the pathway from xylonic acid to αKG are encoded by the genes located at the first, second and fifth positions. The activity of XDH, of which gene is located at the third position in the operon, had been detected in vitro, and thus it was considered that if activity of the enzyme encoded by the gene located at the fifth position in the operon (XylD) could be further detected, it might serve as circumstantial evidence of transcription and translation of the whole NXA operon. Therefore, it was estimated that one of the three reactions from xylonic acid to αKG constituted a rate-limiting point, and the following experiments were conducted.

Plasmids pSTVPtac_xylD_Ttrp, pSTVPtac_xylX_Ttrp, and pSTVPtac_ccrxylA_Ttrp that express the xylD, xylX, and ccrxylA genes, respectively, were prepared as follows.

pSTV28-Ptac-xylX-Ttrp was prepared by constructing an xylX fragment by PCR using pUC18-xylX, which is a plasmid prepared by cloning xylX lacking the SfiI site into pUC18, as the template, as well as xylX-IFS-5742-10-1 (SEQ ID NO: 38) and xylX-IFA-5742-10-2 (SEQ ID NO: 39) as the primers, and cloning the obtained plasmid into pSTV28-Ptac-Ttrp which had been digested with SmaI by the in-fusion cloning method.

pSTV28-Ptac-ccrxylA-Ttrp was prepared by constructing a ccrxylA fragment by PCR using pUC18-ccrxylA, which is a plasmid prepared by cloning ccrxylA lacking the SfiI site into pUC18, as the template, as well as xylA_IFS_5742-10-3 (SEQ ID NO: 40) and xylA_IFA_5742-10-4 (SEQ ID NO: 41) as the primers, and cloning the obtained plasmid into pSTV28-Ptac-Ttrp digested with SmaI by the in-fusion cloning method.

pSTV28-Ptac-xylD-Ttrp was prepared by constructing an xylD fragment by PCR using pUC18-xylD, which is a plasmid prepared by cloning xylD lacking the SfiI site into pUC18, as the template, as well as xylD_IFS_5742-10-5 (SEQ ID NO: 42) and xylD_IFA_5742-10-6 (SEQ ID NO: 43) as the primers, and cloning the obtained plasmid into pSTV28-Ptac-Ttrp digested with SmaI by the in-fusion cloning method.

The aforementioned plasmids pUC18-xylX, pUC18-ccrxylA, and pUC18-xylD were prepared as described below, respectively.

By PCR using the genomic DNA of the *C. crescentus* CB-15 strain as the template, CC0823-01F_4691-87-1 (SEQ ID NO: 44) and CC0823-01R_4691-87-2 (SEQ ID NO: 45), as well as CC0823-02F_4691-87-3 (SEQ ID NO: 46) and CC0823-02R_4691-87-4 (SEQ ID NO: 47) as the primers, fragments of 900 bp and 280 bp were amplified, respectively. Then, pUC18 digested with SmaI, and two of the aforementioned amplified fragments were assembled by the in vitro assembly method (Nature Methods, 6(5), 343-345, 2009) to obtain pUC18-xylX in which the SfiI site was removed, and the xylX gene was inserted.

By PCR using the genomic DNA of the *C. crescentus* CB-15 strain as the template, CC0822-01F_4691-87-5 (SEQ ID NO: 48) and CC0822-01R_5659-8-7 (SEQ ID NO: 49), CC0822-02F_5659-8-8 (SEQ ID NO: 50) and CC0822-02R_5659-8-9 (SEQ ID NO: 51), CC0822-03F_5659-8-10 (SEQ ID NO: 52) and CC0822-03R_5659-8-11 (SEQ ID NO: 53), CC0822-04F_5659-8-12 (SEQ ID NO: 54) and CC0822-04R_5659-8-13 (SEQ ID NO: 55), as well as CC0822-05F_5659-8-14 (SEQ ID NO: 56) and CC0822-05R_4691-87-14 (SEQ ID NO: 57) as the primers, five fragments, 11v02 (175 bp), 12v02 (325 bp), 13v02 (260 bp), 14v02 (193 bp), and 15v02 (544 bp), were amplified, respectively. Then, two of the fragments, 11v02 and 12v02, were ligated by crossover PCR using these two fragments as the template, as well as CC0822-01F_4691-87-5 and CC0822-02R_5659-8-9 as the primers. Similarly, two of the fragments, 13v02 and 14v02, were ligated by crossover PCR using these two fragments as the template, as well as CC0822-03F_5659-8-12 and CC0822-04R_5659-8-13 as the primers. These two of fragments and the aforementioned 15v02 fragment were ligated by the in vitro assembly method (Nature Methods, 6(5), 343-345, 2009). The obtained ligated fragment was amplified by PCR using it as the template, as well as CC0822-01F_4691-87-5 and CC0822-05R_4691-87-14 as the primers. Then, pUC18 digested with SmaI, and the aforementioned ligated fragment was assembled by the in vitro assembly method (Nature Methods, 6(5), 343-345, 2009) to obtain pUC18-ccrxylA in which the SfiI site was removed, and the ccrxylA gene was inserted.

By PCR using the genomic DNA of the *C. crescentus* CB-15 strain as the template, CC0819-01F_4691-88-7 (SEQ ID NO: 17) and CC0819-01R_5659-9-1 (SEQ ID NO: 18), as well as CC0819-02F_5659-9-2 (SEQ ID NO: 19) and CC0819-02R_4691-88-10 (SEQ ID NO: 20) as the primers, fragments of 1130 bp and 653 bp were amplified, respectively. Then, pUC18 digested with SmaI, and two of the aforementioned amplified fragments were assembled by the in vitro assembly method (Nature Methods, 6(5), 343-345, 2009) to obtain pUC18-xylD in which the SfiI site was removed, and the xylD gene was inserted.

Crude enzyme extracts were prepared from the ccrNXA operon-expressing strain (MG1655ΔsucA/pTWV228Ptac_ccrNXA), and the strains harboring each of the plasmids expressing one of the aforementioned xylD, xylX, and ccrxylA genes, respectively (MG1655ΔsucA/pSTVPtac_xylD_Ttrp, MG1655ΔsucA/pSTVPtac_xylX_Ttrp, and MG1655ΔsucA/pSTVPtac_ccrxylA_Ttrp), and then each of the crude enzyme extracts of the strain harboring only the vector, or the strains expressing one of the xylD, xylX, and ccrxylA genes was added to the crude enzyme extract of the ccrNXA operon-expressing strain, and the activity for producing αKG from xylonic acid of each mixture was measured. The results are shown in Table 6. In Table 6, "1110" next to the strain name is the clone number.

TABLE 6

Measurement results of activity for producing αKG from xylonic acid

| CFE (①+②) | ① Δ sucA/pTWVPtac_ccrNXA_1110 ② JM109/pSTVPtac_Ttrp | | | |
|---|---|---|---|---|
| | None | xylD | xylX | ccrxylA |
| Specific activity (μmol/min/mg-protein) | 1.35 | 3.48 | 1.34 | 1.91 |
| | 1.0 | 2.6 | 1.0 | 1.4 |

Note:
The relative activity is indicated as relative activity based on the specific activity of the ccrNXA1110 and pSTV28-Ptac-Ttrp mixed system taken as 1.

When the crude enzyme extract of the strain expressing only the xylD gene was added to the system, an increase in the αKG-producing activity was observed. From this result, it was suggested that the xylonate dehydratase (XylD) encoded by the xylD gene constituted a rate-limiting point of the NXA pathway constructed in *E. coli* by heterogenous expression.

Since the metabolic flux of the whole pathway might be improved by further enhancing the xylD gene expression in the ccrNXA operon-expressing strain as suggested by the measurement of the enzymatic activity, a strain was constructed with increased expression of the xylD gene by introducing a xylD gene expression vector into the ccrNXA operon-expressing strain, and evaluating L-glutamic acid production using glucose and xylose as the carbon source. As the ccrNXA operon-expressing strain, MG1655ΔsucA/pMW119Ptac_ccrNXA and MG1655ΔsucA/pTWV228Ptac_ccrNXA were used.

The culture was performed in the same manner as that described in the aforementioned section (3).

The results are shown in Table 7. The strain with increased expression of the xylD gene showed markedly improved L-glutamic acid accumulation and yield. L-Glutamic acid accumulation was 23 to 25 g/L in contrast to 15 to 16 g/L in the control strain, and the yield based on the consumed saccharide reached 57 to 60% in contrast to 37 to 40% for the control strain. Xylonic acid, which is a metabolic intermediate, was not seen in the xylD gene expression-enhanced strain. On the other hand, the effect of enhancing xylD gene expression was seen only in the expression strain carrying a medium copy number type ccrNXA operon expression vector, and the effect was not seen in the expression strain carrying the low copy number type vector. From these results, it was considered that removal of the rate-limiting point of this pathway by increasing the activity of the whole NXA pathway by increasing the copy number of the vectors and further enhancement of xylD gene expression provided the improvement in the amount of L-glutamic acid produced. In addition, the activity for producing αKG from xylonic acid of the xylD gene expression-enhanced strain was increased about 10 times as compared to that observed before the enhancement (Table 8). The numerals "1110", "17" and "19" next to the strain names mentioned in Tables 7 and 8 are the clone numbers.

TABLE 7

Result of evaluation of ccrNXA operon + xylD expressing strain by L-Glu production culture

| Strain | L-Glu (g/L) | Yield (%) | O.D.600 |
| --- | --- | --- | --- |
| MG1655ΔsucA/pTWV228 | 15.7 | 37.6 | 23.9 |
| MG1655ΔsucA/pTWVccrNXA1110 | 16.3 | 39.2 | 16.6 |
| MG1655ΔsucA/pTWVccrNXA/pSTVPtacTtrp | 16.3 | 39.2 | 22.9 |
| MG1655ΔsucA/pTWVccrNXA/xylD17 | 25.4 | 61.1 | 14.3 |
| MG1655ΔsucA/pTWVccrNXA/xylD19 | 24.2 | 58.1 | 16.0 |

TABLE 8

Results of measurement of activity for producing αKG from xylonic acid

| Strain | Specific activity (μmol/min/mg-protein) | Relative activity |
| --- | --- | --- |
| MG1655ΔsucA/pTWV228/pSTVPtacTtrp | ND | |
| MG1655ΔsucA/pTWVccrNXA1110 | 1.9 | 1.0 |
| MG1655ΔsucA/pTWVccrNXA/pSTVxylD17 | 20.2 | 10.8 |
| MG1655ΔsucA/pTWVccrNXA/pSTVxylD19 | 17.1 | 9.2 |

Note:
The results for MG1655ΔsucA/pTWVccrNXA1110 are values obtained in experiments using different batches.
ND: Not Detected
Note:
The relative activity is indicated as relative activity based on the specific activity of ccrNXA1110 taken as 1.

Example 3

Introduction of NXA Pathway into *Corynebacterium glutamicum*

Construction of Plasmid pVK9Peftu_ccrNXA for Introduction of NXA Pathway

A plasmid having a sequence containing the promoter sequence of the elongation factor Tu (EF-Tu) gene, tuf (WO2008/114721, SEQ ID NO: 33, henceforth referred to as "Peftu") and xylD ligated downstream from the promoter sequence was constructed by using Clontech In-Fusion Cloning HD Kit (Clontech). First, PCR was performed by using the chromosomal DNA of the *C. glutamicum* ATCC 13869 strain as the template, as well as primers Peftu(Pst) (SEQ ID NO: 58) and Peftu_Rv (SEQ ID NO: 59) to obtain a fragment containing the Peftu sequence. This PCR was performed by using PrimeSTAR HS Polymerase according to the protocol attached to this enzyme.

Furthermore, PCR was performed by using pTWV228Ptac_ccrNXA as the template, as well as primers Peftu_xylXABCD_fw (SEQ ID NO: 60) and Peftu_xylXABCD_ry (SEQ ID NO: 61) to obtain a fragment containing the xylXABCD sequence of *C. crescentus*. This PCR was performed by using PrimeSTAR GXL Polymerase according to the protocol attached to this enzyme.

Then, the Peftu fragment and the fragment containing xylXABCD obtained above were mixed with pVK9 treated with PstI and BamHI, and used to perform the in-fusion reaction according to the protocol of Clontech In-fusion HD Cloning Kit. pVK9 is a shuttle vector obtained by blunt-ending pHSG299 (Takara Bio) at the AvaII site, and inserting a region autonomously replicable in coryneform bacteria contained in pHK4 (Japanese Patent Laid-open No. 05-007491), which was excised with BamHI and KpnI, and blunt-ended (Japanese Patent Laid-open No. 2007-97573, U.S. Patent Published Application No. 2005/0196846). *E. coli* JM109 was transformed with the in-fusion reaction mixture. The transformants were subjected to selection on an agar medium containing the LB medium supplemented with kanamycin at a final concentration of 50 mg/L. The target plasmid pVK9Peftu_ccrNXA was obtained from an obtained transformant.

(2) L-Glutamic Acid Production by *Corynebacterium glutamicum* Introduced with NXA Pathway The *C. glutamicum* ATCC 13869 strain was transformed with the aforementioned pVK9Peftu_ccrNXA by the electric pulse method (Japanese Patent Laid-open No. 2-207791). A strain introduced with pVK9Peftu_ccrNXA was selected on an agar medium comprising the CM-Dex medium supplemented with kanamycin at a final concentration of 25 mg/L. Furthermore, the *C. glutamicum* ATCC13869 strain transformed with pVK9 was also selected in a similar manner as a control strain.

Xylose-assimilating ability and L-glutamic acid-producing ability of the obtained transformants were verified by performing culture using a Sakaguchi flask. Cells of each transformant strain cultured at 31.5° C. for 24 hours on the CM-Dex agar medium supplemented with kanamycin at a final concentration of 25 mg/L were scraped off in an amount corresponding to ⅙ of the plate, and inoculated into 20 mL of the Glc medium contained in a Sakaguchi flask, 1 g of calcium carbonate sterilized beforehand with hot air was added, and shaking culture was performed at 31.5° C. and 120 rpm for 24 hours. The obtained culture medium in a volume of 1 mL was inoculated into 20 mL the Xyl medium (biotin restricted) contained in a Sakaguchi flask, 1 g of calcium carbonate sterilized beforehand with hot air was added, and shaking culture was performed at 31.5° C. and 120 rpm for 73 hours. The results are shown in Table 9.

The *C. glutamicum* ATCC 13869 strain introduced with pVK9 hardly grew in the Xyl medium, and did not produce L-glutamic acid, either. On the other hand, the *C. glutamicum* ATCC 13869 strain containing pVK9Peftu_ccrNXA grew in the Xyl medium, and produced L-glutamic acid. From these results, it was found that introduction of the NXA pathway into coryneform bacteria improved xylose-assimilating ability, and such a strain produced L-glutamic acid from xylose.

TABLE 9

| Strain | OD620 (x101) | Consumed Xyl (g/L) | Glu (g/L) | Yield (%) | Xylonic acid (g/L) |
|---|---|---|---|---|---|
| ATCC13869/pVK9 | 0.048 ± 0.013 | 0 | 0 | 0 | 0 |
| ATCC13869/ pVK9Peftu_ccrNXA | 0.404 ± 0.010 | 57.1 ± 0.22 | 2.5 ± 0.3 | 4.3 ± 0.5 | 44.5 ± 1.5 |

(3) Construction of Strain in which xylD Gene Expression is Further Enhanced

Since the *C. glutamicum* ATCC 13869 strain harboring pVK9Peftu_ccrNXA was able to produce xylonic acid, it was assumed that the activity of the xylD gene product was insufficient. Therefore, a plasmid expressing of the NXA pathway was constructed in which the xylD gene was further enhanced by introducing one more copy of xylD gene into the pVK9 Peftu_ccrNXA plasmid.

(4) Construction of Plasmid pVS7PmsrA_xylD for xylD Gene Expression

A plasmid having a sequence containing the promoter sequence of the msrA gene (peptide methionine sulfoxide reductase A) (henceforth referred to as "PmsrA") and the xylD gene of *C. crescentus* ligated downstream from the promoter sequence was constructed by using Clontech In-Fusion Cloning HD Kit.

First, PCR was performed by using the chromosomal DNA of the *C. glutamicum* ATCC 13869 strain as the template, as well as primers PmsrA(Pst) (SEQ ID NO: 62) and PmsrAR (SEQ ID NO: 63) to obtain a fragment containing the PmsrA sequence. Furthermore, PCR was performed by using pTWV228Ptac_ccrNXA as the template, as well as primers PmsrA_xylD_fw (SEQ ID NO: 64) and Peftu_xylXAB-CD_ry to obtain a fragment containing the xylD gene sequence of *C. crescentus*. These PCRs were performed by using PrimeSTAR HS Polymerase according to the protocol attached to this enzyme.

Then, the fragments containing the PmsrA fragment and the xylD gene obtained above were mixed with the shuttle vector pVS7 (construction method is shown below) treated with PstI and BamHI, and used to perform the in-fusion reaction according to the protocol of Clontech In-fusion HD Cloning Kit, and then *E. coli* JM109 was transformed with this reaction mixture. The transformants were subjected to selection on an agar medium containing the LB medium supplemented with spectinomycin at a final concentration of 25 mg/L. The target plasmid pVS7PmsrA_xylD was obtained from an obtained transformant.

pVS7 is a plasmid obtained by replacing the chloramphenicol resistance gene of pVC7 (Japanese Patent Laid-open No. 2000-201692, European Patent No. 1004671) with a spectinomycin resistance gene. The spectinomycin resistance gene can be obtained by preparing a plasmid pDG1726 from the *Escherichia coli* ECE101E strain sold by *Bacillus* Genetic Stock Center (BGSC), and taking out the resistance gene from the plasmid as a cassette. By PCR using pDG1726 as the template, as well as primers SpcR-F (SEQ ID NO: 65) and SpcR-R (SEQ ID NO: 66), the spectinomycin resistance gene was amplified. The obtained gene fragment was mixed with pVC7 treated with SmaI, a ligation reaction was performed according to the protocol of Ligation Mix <Mighty Mix> of Takara Bio, and *E. coli* JM109 was transformed with this reaction mixture. The transformants were subjected to selection on an agar medium containing the LB medium supplemented with spectinomycin at a final concentration of 25 mg/L. pVC7-spc containing pVC7 inserted with the spectinomycin resistance gene was obtained from an obtained transformant. Furthermore, PCR was performed by using pVC7-spc as the template, as well as primers spc(GTG start)-F (SEQ ID NO: 67) and spc(stop)-R (SEQ ID NO: 68) to amplify the spectinomycin resistance gene.

Separately, PCR was performed by using pVC7 as the template, as well as primers Spc-pVC7-Cm-F (SEQ ID NO: 69) and Spc-pVC7-Cm-R (SEQ ID NO: 70) to obtain a DNA fragment containing pVC7 in which the chloramphenicol resistance gene was removed. This DNA fragment and the DNA fragment of the spectinomycin resistance gene obtained above from pVC7-spc were mixed, and used to perform the in-fusion reaction according to the protocol of Clontech In-fusion HD Cloning Kit, and *E. coli* JM109 was transformed with the resulting reaction mixture. The transformants were subjected to selection on an agar medium containing the LB medium supplemented with spectinomycin at a final concentration of 25 mg/L. pVS7 was obtained from an obtained transformant.

(5) Construction of the Plasmid pVK9Peftu_ccrNXA+D in which the xylD Gene is Further Enhanced The DNA fragment containing the spectinomycin resistance gene (Spc) and PmsrA_xylD was amplified by using pVS7PmsrA_xylD as the template, as well as primers ME_Spc_fw (SEQ ID NO: 71) and ME_Peftu_xylXAB-CD_ry (SEQ ID NO: 72). The obtained DNA fragment was inserted into pVK9Peftu_ccrNXA in vitro according to the protocol of Ez-Tn5TM Custom Transposome Construction Kit (Epicentre), and the resultant was used to transform *E. coli* DH5a. The transformants were subjected to selection on an agar medium containing the LB agar medium supplemented with kanamycin and spectinomycin at a final concentration of 50 mg/L and 25 mg/L, respectively. Plasmids were extracted from the obtained transformants, and a plasmid for which it was confirmed that the insertion site of the Spc-PmsrA_xylD sequence was not on the Peftu_ccrNXA sequence by analysis of nucleotide sequence around the Spc-PmsrA_xylD sequence was designated pVK9Peftu_ccrNXA+D.

(6) L-Glutamic Acid Production by a Strain Containing the NXA Pathway and in which the xylD Gene is Further Enhanced pVK9Peftu_ccrNXA+D was introduced into the *C. glutamicum* ATCC 13869 strain by the electric pulse method, and the cells were applied to the CMDex agar medium containing 25 mg/L of kanamycin. L-Glutamic acid-producing ability of a strain grown after culture at 31.5° C. was verified in the same manner as that of the aforementioned section (2). The results are shown in Table 10.

The strain harboring pVK9Peftu_ccrNXA+D accumulated D-xylonic acid in a smaller amount, but accumulated L-glutamic acid in a larger amount as compared to the strain harboring pVK9Peftu_ccrNXA. By this result, it was demonstrated that L-glutamic acid could be more efficiently produced from D-xylose via the NXA pathway by further enhancing the xylD gene.

TABLE 10

L-Glutamic acid production of xylD gene-further enhanced NXA pathway-introduced strain

| Strain | OD620 (x101) | Consumed Xyl (g/L) | L-Glu (g/L) | Yield (%) | Xylonic acid (g/L) |
|---|---|---|---|---|---|
| ATCC13869/ pVK9Peftu_ccrNXA | 0.297 ± 0.004 | 58.3 ± 0.11 | 4.2 ± 0.1 | 7.1 ± 0.1 | 50.2 ± 0.1 |
| ATCC13869/ pVK9Peftu_ccrNXA$^{+D}$ | 0.351 ± 0.002 | 71.9 ± 0.66 | 27.5 ± 0.1 | 38.2 ± 0.4 | 22.7 ± 0.4 |

Example 4

Substitution of NXA Pathway Genes

In the aforementioned examples, by using the genes xylX, ccrxylA, ccrxylB, xylC, and xylD from the known bacterium *C. crescentus*, for which the NXA pathway has been reported, it is demonstrated that glutamic acid can be produced from xylose via the NXA pathway. In this example, homologue genes of xylD, xylX, and ccrxylA are obtained from biological species other than *C. crescentus*, and it is investigated whether these genes can replace the genes of *C. crescentus*. As the gene sources, the biological species described in Table 11 were chosen. The gene symbols of the genes (GenBank) are also shown. The sequence identification numbers of the nucleotide sequences of the genes and the amino acid sequences encoded by them used in Sequence Listing are shown in Table 12. In Table 12, "original" means nucleotide sequence of naturally occurring gene, and "optimized" means nucleotide sequence of which codons are optimized according to the codon usage in *E. coli*.

In the following descriptions, the enzymes encoded by homologues of the xylD, xylX, and xylA genes may be referred to as XylD, XylX, and XylA, respectively.

TABLE 11

| Organism | Classification | Abbreviation | Gene symbol |
|---|---|---|---|
| *Agrobacterium tumefaciens* 5A | α-proteobacteria | xylD(Atu) | EHJ96830 |
| *Herbaspirillum seropedicae* | β-proteobacteria | xylD(Hse) | Hsero_4498 |
| *Escherichia coli* | γ-proteobacteria | yjhG | ECK4286 |
| *Escherichia coli* | γ-proteobacteria | yagF | ECK0270 |
| *Actinoplanes missouriensis* | Actinobacteria | xylD(Amis) | AMIS_27920 |
| *Aspergillus oryzae* | Fungi | xylD(Aor) | AOR_1_412134 |
| *Agrobacterium tumefaciens* 5A | α-proteobacteria | xylX(Atu) | EHJ96825 |
| *Cupriavidus necator* | β-proteobacteria | xylX(Cne) | CNE_2c03420 |
| *Pseudomonas elodea* | γ-proteobacteria | xylX(Selo) | ZP_09955741 |
| *Zobellia galactanivorans* | Bacteroidetes | xylX(Zga) | zobellia_2318 |
| *Thermobacillus composti* | Firmicutes | xylX(Tco) | ZP_08919992.1 |
| *Arthrobacter globiformis* | Actinobacteria | xylX(Art) | ARGLB_037_02150 |
| *Azospirillum brasilense* | α-proteobacteria | xylA(Abr) | BAE94276.1 |
| *Halomonas boliviensis* | γ-proteobacteria | xylA(Hbo) | ZP_09188044.1 |
| *Bacillus subtilis* | Firmicutes | ycbD | BSU02470 |

TABLE 12

| Abbreviation | | SEQ ID NO (Nucleotide sequence) | SEQ ID NO (Amino acid sequence) |
|---|---|---|---|
| xylD(Atu) | original | 73 | 74 |
| | optimized | 75 | |
| xylD(Hse) | original | 76 | 77 |
| | optimized | 78 | |
| yjhG | | 34 | 35 |
| yagF | | 36 | 37 |
| xylD(Amis) | original | 79 | 80 |
| | optimized | 81 | |
| xylD(Aor) | original | 82 | 83 |
| | optimized | 84 | |
| xylX(Atu) | original | 85 | 86 |
| | optimized | 87 | |
| xylX(Cne) | original | 88 | 89 |
| | optimized | 90 | |
| xylX(Selo) | original | 91 | 92 |
| | optimized | 93 | |
| xylX(Zga) | original | 94 | 95 |
| | optimized | 96 | |
| xylX(Tco) | original | 97 | 98 |
| | optimized | 99 | |
| xylX(Art) | original | 100 | 101 |
| | optimized | 102 | |
| xylA(Abr) | original | 103 | 104 |
| | optimized | 105 | |
| xylA(Hbo) | original | 106 | 107 |
| | optimized | 108 | |
| ycbD | | 109 | 110 |

(2) Construction of Plasmids for Detecting XylD, XylX, and XylA Activities, pTWVPtac_ccrNXA_ΔxylD_Km, pTWVPtac_ccrNXA_ΔxylX_Km, and pTWVPtac_ccrNXA_ΔccrxylA_Km The construction was performed by using Clontech In-Fusion Cloning Kit.

First, by PCR using pTWVPtac_ccrNXA_Km as the template, as well as Ptac_xylXABC_F (SEQ ID NO: 111) and Ptac_xylXABC_R (SEQ ID NO: 112) as the primers, the DNA fragment except for xylD was amplified. The PCR product was used to perform the in-fusion reaction according to the protocol of Clontech In-fusion HD Cloning Kit, the *E.* coli JM109 strain was transformed with the reaction product, and the target plasmid pTWVPtac_ccrNXA_ΔxylD_Km was obtained from a transformant.

In the same manner as described above, pTWVPtac_ccrNXA_ΔxylX_Km was constructed by using Ptac_xylAB-CD_F (SEQ ID NO: 113) and Ptac_xylABCD_R (SEQ ID NO: 114) as the primers, and pTWVPtac_ccrNXA_Δccrxy-lA_Km was constructed by using Ptac_xylXBCD_F (SEQ ID NO: 115) and Ptac_xylXBCD_R (SEQ ID NO: 116) as the primers.

(3) Construction of *Pantoea ananatis* for Detecting XylD, XylX, and XylA Activities The *P. ananatis* NA1 strain was transformed with pTWVPtac_ccrNXA_ΔxylD_Km described above by the electroporation method. The constructed strain was referred to as *P. ananatis* NA2 ΔxylD. For the culture of the *P. ananatis* NA2 ΔxylD, a plate medium comprising LBGM9 to which kanamycin and tetracycline were added at final concentrations of 40 mg/L and 12.5 mg/L, respectively, was used.

In the same manner, the *P. ananatis* NA1 strain was transformed with pTWVPtac_ccrNXA_ΔxylX_Km or pTWVPtac_ccrNXA_ΔccrxylA_Km to construct *P. ananatis* NA2 ΔxylX strain and *P. ananatis* NA2 ΔccrxylA strain.

(4) Construction of xylD, xylX, and xylA Homologue Expression Plasmids

Plasmids for expression of yjhG or yagF, pSTV28-Ptac-yjhG-Ttrp and pSTV28-Ptac-yagF-Ttrp, were prepared as follows.

pSTV28-Ptac-yjhG-Ttrp was prepared by amplifying a yjhG fragment by PCR using the genomic DNA of the *E. coli* MG1655 strain as the template, as well as yjhG_F (SEQ ID NO: 117) and yjhG_R (SEQ ID NO: 118) as the primers, and cloning the amplified fragment into pSTV28-Ptac-Ttrp digested with SmaI according to the in-fusion cloning method.

pSTV28-Ptac-yagF-Ttrp was prepared in the same manner as that described above by using yagF_F (SEQ ID NO: 119) and yagF_R (SEQ ID NO: 120) as the primers.

A plasmid for expression of xylD(Hse), pSTV28-Ptac-xylD(Hse)-Ttrp, was prepared as follows. A DNA fragment having the sequences of tac promoter, xylD(Hse), and trp terminator (Ptac-xylD(Hse)-Ttrp) was synthesized, and ligated with the pUC57 vector (purchased from Thermo Fischer Scientific) digested with EcoRV to obtain pUC57-Ptac-xylD(Hse)-Ttrp. When the DNA fragment was synthesized, codons were optimized so that the fragment is suitable for expression in *E. coli*. Equal amounts of pSTV28 and pUC57-Ptac-xylD(Hse)-Ttrp, both of which were digested with EcoRI and KpnI, were mixed, and ligation reaction was performed. Then, JM109 was transformed with the ligation product, and a plasmid was extracted from a colony showing Cm resistance to obtain pSTV28-Ptac-xylD(Hse)-Ttrp.

Plasmids for expression of xylD(Amis), xylD(Aor), xylX (Cne), xylX(Zga), xylX(Tco), xylA(Abr), and ycbD, pSTV28-Ptac-xylD(Amis)-Ttrp, pSTV28-Ptac-xylD(Aor)-Ttrp, pSTV28-Ptac-xylX(Cne)-Ttrp, pSTV28-Ptac-xylX(Zga)-Ttrp, pSTV28-Ptac-xylX(Tco)-Ttrp, pSTV28-Ptac-xylA(Abr)-Ttrp, and pSTV28-Ptac-ycbD-Ttrp, respectively, were also prepared in the same manner. Codon optimization was not carried out for YcbD.

A plasmid for expression of xylD(Atu), pSTV28-Ptac-xylD(Atu)-Ttrp, was prepared as follows. A DNA fragment having the sequences of tac promoter, xylD(Atu), and trp terminator (Ptac-xylD(Atu)-Ttrp) was synthesized, and ligated with the pJET1.2 vector (purchased from Thermo Fischer Scientific) digested with EcoRV to obtain pJET1.2-Ptac-xylD(Atu)-Ttrp. When the DNA fragment was synthesized, codons were optimized so that the fragment is suitable for expression in *E. coli*. Equal amounts of pSTV28 and pJET1.2-Ptac-xylD(Atu)-Ttrp, both of which were digested with EcoRI and KpnI, were mixed, and a ligation reaction was performed. Then, JM109 was transformed with the ligation product, and a plasmid was extracted from a colony showing Cm resistance to obtain pSTV28-Ptac-xylD(Atu)-Ttrp.

Plasmids for expression of xylX(Atu) or xylA(Hbo), pSTV28-Ptac-xylX(Atu)-Ttrp and pSTV28-Ptac-xylA (Hbo)-Ttrp, were also prepared in the same manner.

A plasmid for expression of xylX(Art), pSTV28-Ptac-xylX(Art)-Ttrp, was prepared as follows. A DNA fragment having the sequences of tac promoter, xylX(Art), and trp terminator (Ptac-xylX(Art)-Ttrp) was synthesized, and ligated with the pCC1 vector (purchased from Epicentre) digested with EcoRV to obtain pCC1-Ptac-xylX(Art)-Ttrp. When the DNA fragment was synthesized, codons were optimized so that the fragment is suitable for expression in *E. coli*. Equal amounts of pSTV28 and pCC1-Ptac-xylX(Art)-Ttrp, both of which were digested with EcoRI and KpnI, were mixed, and ligation reaction was performed. Then, JM109 was transformed with the ligation product, and a plasmid was extracted from a colony showing Cm resistance to obtain pSTV28-Ptac-xylX(Art)-Ttrp.

(5) Detection of Activities of XylD Homologues

The *P. ananatis* NA2 ΔxylD strain was transformed with pSTV28-Ptac-Ttrp, pSTV28-Ptac-xylD-Ttrp, pSTV28-Ptac-xylD(Atu)-Ttrp, pSTV28-Ptac-xylD(Hse)-Ttrp, pSTV28-Ptac-yjhG-Ttrp, pSTV28-Ptac-yagF-Ttrp, pSTV28-Ptac-xylD(Amis)-Ttrp, or pSTV28-Ptac-xylD(Aor)-Ttrp by the electroporation method (refer to U.S. Pat. No. 6,682,912). For the culture of the transformants, a plate medium comprising LBGM9 to which kanamycin, tetracycline and chloramphenicol were added at final concentrations of 40 mg/L, 12.5 mg/L and 25 mg/L, respectively, was used.

Figure 5:
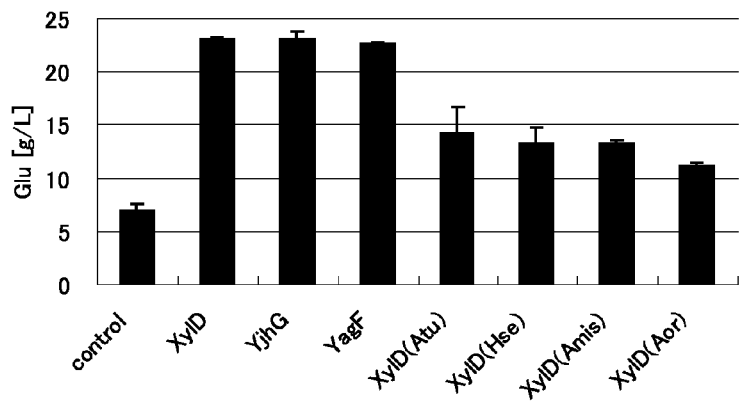
FIG. 5 depicts graphs showing results of L-glutamic acid production culture of xylD homologue gene-expressing strains derived from various kinds of microorganisms. Atu, Hse, Amis, and Aor represent *Agrobacterium tumefaciens, Herbaspirillum seropedicae, Actinoplanes missouriensis*, and *Aspergillus oryzae*, respectively.

Cells of each transformant cultured overnight at 34° C. on the LBGM9 plate to which the drugs were added were scraped off in an amount corresponding to ⅙ of the cells on the plate, inoculated into 5 ml of the MSII-SX medium contained in a large test tube, and cultured at 34° C. and 120 rpm for 48 hours, and amount of accumulated L-glutamic acid (Glu) was measured. The results are shown in FIG. 5.

Whereas the *P. ananatis* NA2 ΔxylD strain introduced with pSTV28-Ptac-Ttrp accumulated 6.9 g/L of L-glutamic acid, the other transformants accumulated 11.1 to 23.1 g/L of L-glutamic acid. In the strain introduced with pSTV28-Ptac-Ttrp, L-glutamic acid was hardly produced from xylose, and thus it was considered that L-glutamic acid was produced from xylose via the NXA pathway in the other transformants. That is, it was demonstrated that a xylD homologue derived from any of the biological species other than *C. crescentus* could substitute for xylD.

(6) Detection of Activities of XylX Homologues

The *P. ananatis* NA2 ΔxylX strain was transformed with pSTV28-Ptac-Ttrp, pSTV28-Ptac-xylX-Ttrp, pSTV28-Ptac-xylX(Art)-Ttrp, pSTV28-Ptac-xylX(Atu)-Ttrp, pSTV28-Ptac-xylX(Cne)-Ttrp, pSTV28-Ptac-xylX(Zga)-Ttrp, pSTV28-Ptac-xylX(Tco)-Ttrp, or pSTV28-Ptac-xylX(Selo)-Ttrp by the electroporation method. For the culture of the transformants, a plate medium comprising LBGM9 to which kanamycin, tetracycline and chloramphenicol were added at final concentrations of 40 mg/L, 12.5 mg/L and 25 mg/L, respectively, was used.

Figure 6:
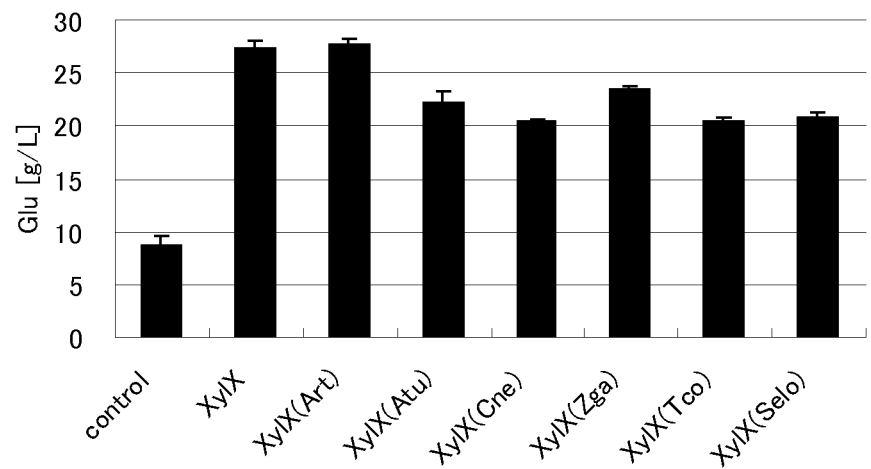
FIG. 6 depicts graphs showing results of L-glutamic acid production culture of xylX homologue-expressing strains derived from various kinds of microorganisms. Art, Atu, Cne, Zga, Tco, and Selo represent *Arthrobacter globiformis, Agrobacterium tumefaciens, Cupriavidus necator, Zobellia galactanivorans, Thermobacillus composti*, and *Pseudomonas elodea*, respectively.

Cells of each transformant cultured overnight at 34° C. on the LBGM9 plate to which the drugs were added were scraped off in an amount corresponding to ⅙ of the cells on the plate, inoculated into 5 ml of the MSII-SX medium contained in a large test tube, and cultured at 34° C. and 120 rpm for 48 hours, and the amount of accumulated L-glutamic acid (Glu) was measured. The results are shown in FIG. 6.

Whereas the *P. ananatis* NA2 ΔxylX strain introduced with pSTV28-Ptac-Ttrp accumulated 8.7 g/L of L-glutamic acid, the other transformants accumulated 20.5 to 27.8 g/L of L-glutamic acid. In the strain introduced with pSTV28-Ptac-Ttrp, L-glutamic acid was hardly produced from xylose, and thus it was considered that L-glutamic acid was produced from xylose via the NXA pathway in the other transformants. That is, it was demonstrated that a xylX homologue derived from any of the biological species other than *C. crescentus* could substitute for xylX.

(7) Detection of Activities of XylA Homologues

The *P. ananatis* NA2 ΔccrxylA strain was transformed with pSTV28-Ptac-Ttrp, pSTV28-Ptac-ccrxylA-Ttrp, pSTV28-Ptac-ycbD-Ttrp, pSTV28-Ptac-xylA(Hbo)-Ttrp, or pSTV28-Ptac-xylA(Abr)-Ttrp by the electroporation method. For the culture of the transformants, a plate medium containing LBGM9 to which kanamycin, tetracycline and chloramphenicol were added at final concentrations of 40 mg/L, 12.5 mg/L and 25 mg/L, respectively, was used.

Figure 7:
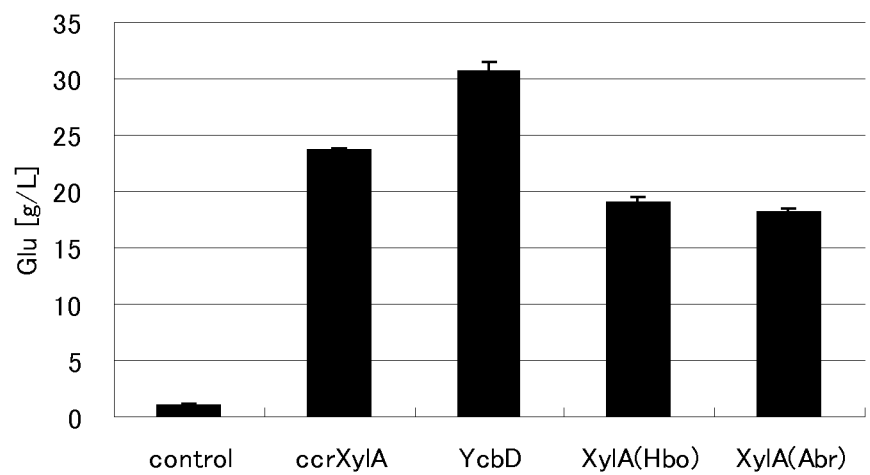
FIG. 7 depicts graphs showing results of L-glutamic acid production culture of xylA homologue-expressing strains derived from various kinds of microorganisms. Hbo and Abr represent *Halomonas boliviensis* and *Azospirillum brasilense*, respectively.

Cells of each transformant cultured overnight at 34° C. on the LBGM9 plate to which the drugs were added were scraped off in an amount corresponding to ⅙ of the cells on the plate, inoculated into 5 ml of the MSII-SX medium contained in a large test tube, and cultured at 34° C. and 120 rpm for 48 hours, and amount of accumulated L-glutamic acid (Glu) was measured. The results are shown in FIG. 7.

Whereas the *P. ananatis* NA2 ΔccrxylA strain introduced with pSTV28-Ptac-Ttrp accumulated 1.0 g/L of L-glutamic acid, the other transformants accumulated 18.1 to 30.7 g/L of L-glutamic acid. In the strain introduced with pSTV28-Ptac-Ttrp, L-glutamic acid was hardly produced from xylose, and thus it was considered that L-glutamic acid was produced from xylose via the NXA pathway in the other transformants. That is, it was demonstrated that a ccrxylA homologue derived from any of the biological species other than *C. crescentus* could substitute for xylA.

INDUSTRIAL APPLICABILITY

According to the present invention, a target substance can be efficiently produced by fermentation using a xylose raw material.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for producing a target substance comprising
A) culturing a bacterium belonging to the genus *Pantoea* or the genus *Corynebacterium* and having an ability to produce the target substance in a medium containing xylose wherein the bacterium is able to produce the target substance through conversion of xylonic acid produced from xylose into 2-ketoglutaric acid by xylonate dehydratase, 2-keto-3-deoxyxylonate dehydratase, and 2-ketoglutaric semialdehyde dehydrogenase,
B) allowing the bacterium to produce and secrete the target substance into the medium, and
C) collecting the target substance from the medium,
wherein the target substance is 2-ketoglutaric acid or a derivative thereof, the bacterium has an ability to produce xylonic acid from xylose, and activities of the enzymes xylonate dehydratase, 2-keto-3-deoxyxylonate dehydratase, and 2-ketoglutaric semialdehyde dehydrogenase have been imparted to or enhanced in the bacterium;
wherein the 2-ketoglutaric acid derivative is selected from the group consisting of L-glutamic acid, L-glutamine, L-arginine, L-citrulline, L-ornithine, L-proline, putrescine, and γ-aminobutyric acid,
wherein the bacterium can produce xylonic acid from xylose because of any one of the following characteristics:
(i) xylose dehydrogenase activity, or xylose dehydrogenase activity and xylonolactonase activity have been imparted to or enhanced in the bacterium, or
(ii) the bacterium has glucose dehydrogenase activity that can catalyze a reaction producing xylonic acid from xylose,
wherein said activities are imparted to or enhanced in the bacterium by introducing expressable forms of genes coding for the enzymes into the bacterium, wherein the genes are native to a microorganism belonging to a genus selected from the group consisting of *Caulobacter, Escherichia, Agrobacterium, Herbaspirillum, Actinoplanes, Cupriavidus, Pseudomonas, Zobellia, Thermobacillus, Arthrobacter, Azospirillum, Halomonas, Bacillus,* and *Aspergillus*.

2. The method according to claim 1, wherein the glucose dehydrogenase uses pyrroloquinoline quinone as a coenzyme, and the bacterium has glucose dehydrogenase activity because it has pyrroloquinoline quinone-producing ability, or it is cultured in a medium containing pyrroloquinoline quinone.

3. The method according to claim 1, wherein the bacterium has been further modified so that activity of 2-ketoglutarate dehydrogenase is reduced by a method selected from the group consisting of:
a) partially or totally eliminating the gene coding for the enzyme on the genome,
b) modifying an expression control sequence,
c) introducing a missense mutation, nonsense mutation, or a frame shift mutation into the regions coding for the enzyme on the genome,
d) introducing a transposon or IS factor into the gene, and
e) combinations thereof.

4. The method according to claim 1, wherein the bacterium has been further modified so that activity of succinate dehydrogenase is reduced by a method selected from the group consisting of:
a) partially or totally eliminating the gene coding for the enzyme on the genome,
b) modifying an expression control sequence,
c) introducing a missense mutation, nonsense mutation, or a frame shift mutation into the regions coding for the enzyme on the genome,
d) introducing a transposon or IS factor into the gene, and
e) combinations thereof.

5. The method according to claim 1, wherein the bacterium is *Pantoea ananatis*.

6. The method according to claim 1, wherein the bacterium is *Corynebacterium glutamicum*.

* * * * *

SEQUENCE LISTING

```
<160> NUMBER OF SEQ ID NOS: 120

<210> SEQ ID NO 1
<211> LENGTH: 40
<212> TYPE: DNA
<213> ORGANISM: Artificial Sequence
<220> FEATURE:
<223> OTHER INFORMATION: primer PtwvPtacf

<400> SEQUENCE: 1
gaattcgagc tcggtaccca gatctccctg ttgacaatta                40

<210> SEQ ID NO 2
<211> LENGTH: 40
<212> TYPE: DNA
<213> ORGANISM: Artificial Sequence
<220> FEATURE:
<223> OTHER INFORMATION: primer 0823Ptacr

<400> SEQUENCE: 2
aggaattcac tcacgcccac cctcctgtgt gaaattgtta                40

<210> SEQ ID NO 3
<211> LENGTH: 39
<212> TYPE: DNA
<213> ORGANISM: Artificial Sequence
<220> FEATURE:
<223> OTHER INFORMATION: primer Ptac0823f

<400> SEQUENCE: 3
taacaatttc acacaggagg gtgggcgtga gtgaattcc                 39

<210> SEQ ID NO 4
<211> LENGTH: 40
<212> TYPE: DNA
<213> ORGANISM: Artificial Sequence
<220> FEATURE:
<223> OTHER INFORMATION: primer 0819r
```

-continued

<400> SEQUENCE: 4
gcggggcgtg cggttagaca tggcggacct catgctgggg                           40

<210> SEQ ID NO 5
<211> LENGTH: 40
<212> TYPE: DNA
<213> ORGANISM: Artificial Sequence
<220> FEATURE:
<223> OTHER INFORMATION: primer 0819f

<400> SEQUENCE: 5
ccccagcatg aggtccgcca tgtctaaccg cacgccccgc                           40

<210> SEQ ID NO 6
<211> LENGTH: 36
<212> TYPE: DNA
<213> ORGANISM: Artificial Sequence
<220> FEATURE:
<223> OTHER INFORMATION: primer 219cc0819r

<400> SEQUENCE: 6
ctctagagga tccccttcag cgtttggcga cggaga                              36

<210> SEQ ID NO 7
<211> LENGTH: 21
<212> TYPE: DNA
<213> ORGANISM: Artificial Sequence
<220> FEATURE:
<223> OTHER INFORMATION: primer 219f

<400> SEQUENCE: 7
ggggatcctc tagagtcgac c                                              21

<210> SEQ ID NO 8
<211> LENGTH: 21
<212> TYPE: DNA
<213> ORGANISM: Artificial Sequence
<220> FEATURE:
<223> OTHER INFORMATION: primer 219r

<400> SEQUENCE: 8
gggtaccgag ctcgaattca c                                              21

<210> SEQ ID NO 9
<211> LENGTH: 35
<212> TYPE: DNA
<213> ORGANISM: Artificial Sequence
<220> FEATURE:
<223> OTHER INFORMATION: primer attL-F

<400> SEQUENCE: 9
tatattgatt cacttgaagt acgaaaaaaa ccggg                               35

<210> SEQ ID NO 10
<211> LENGTH: 45
<212> TYPE: DNA
<213> ORGANISM: Artificial Sequence
<220> FEATURE:
<223> OTHER INFORMATION: primer ntpII-R

<400> SEQUENCE: 10
cctgcaggcg gccgctcata gaaggcggcg gtggaatcga aatct                    45

<210> SEQ ID NO 11
<211> LENGTH: 45

```
<212> TYPE: DNA
<213> ORGANISM: Artificial Sequence
<220> FEATURE:
<223> OTHER INFORMATION: primer attR-F

<400> SEQUENCE: 11
gcggccgcct gcaggcccat gtaatgaata aaaagcagta attaa            45

<210> SEQ ID NO 12
<211> LENGTH: 30
<212> TYPE: DNA
<213> ORGANISM: Artificial Sequence
<220> FEATURE:
<223> OTHER INFORMATION: primer attR-R

<400> SEQUENCE: 12
tgaagcggcg cacgaaaaac gcgaaagcgt                             30

<210> SEQ ID NO 13
<211> LENGTH: 80
<212> TYPE: DNA
<213> ORGANISM: Artificial Sequence
<220> FEATURE:
<223> OTHER INFORMATION: primer Ap-Km-fw

<400> SEQUENCE: 13
ttaccaatgc ttaatcagtg aggcacctat ctcagcgatc tgtctatttc aagcttcacg   60
ctgccgcaag cactcagggc                                         80

<210> SEQ ID NO 14
<211> LENGTH: 80
<212> TYPE: DNA
<213> ORGANISM: Artificial Sequence
<220> FEATURE:
<223> OTHER INFORMATION: primer Ap-Km-rv

<400> SEQUENCE: 14
atgagtattc aacatttccg tgtcgccctt attccctttt ttgcggcatt cgctcataga   60
aggcggcggt ggaatcgaaa                                         80

<210> SEQ ID NO 15
<211> LENGTH: 40
<212> TYPE: DNA
<213> ORGANISM: Artificial Sequence
<220> FEATURE:
<223> OTHER INFORMATION: primer xylD_IFS_5742-10-5

<400> SEQUENCE: 15
acacaaggag actcccatgt ctaaccgcac gccccgccgg                  40

<210> SEQ ID NO 16
<211> LENGTH: 40
<212> TYPE: DNA
<213> ORGANISM: Artificial Sequence
<220> FEATURE:
<223> OTHER INFORMATION: primer xylD_IFS_5742-10-6

<400> SEQUENCE: 16
ggaactggcg gctccctcag tggttgtggc ggggcagctt                  40

<210> SEQ ID NO 17
<211> LENGTH: 45
<212> TYPE: DNA
<213> ORGANISM: Artificial Sequence
<220> FEATURE:
```

```
<223> OTHER INFORMATION: primer CC0819-01F_4691-88-7

<400> SEQUENCE: 17
gtcgactcta gaggatcccc atgtctaacc gcacgccccg ccggt                    45

<210> SEQ ID NO 18
<211> LENGTH: 24
<212> TYPE: DNA
<213> ORGANISM: Artificial Sequence
<220> FEATURE:
<223> OTHER INFORMATION: primer CC0819-01R_5659-9-1

<400> SEQUENCE: 18
aaccaggaac ccggccttct ctgc                                           24

<210> SEQ ID NO 19
<211> LENGTH: 24
<212> TYPE: DNA
<213> ORGANISM: Artificial Sequence
<220> FEATURE:
<223> OTHER INFORMATION: primer CC0819-02F_5659-9-2

<400> SEQUENCE: 19
tcccgtacca cgagccgctg gcag                                           24

<210> SEQ ID NO 20
<211> LENGTH: 44
<212> TYPE: DNA
<213> ORGANISM: Artificial Sequence
<220> FEATURE:
<223> OTHER INFORMATION: primer CC0819-02R_4691-88-10

<400> SEQUENCE: 20
cgaattcgag ctcggtaccc tcagtggttg tggcggggca gctt                     44

<210> SEQ ID NO 21
<211> LENGTH: 68
<212> TYPE: DNA
<213> ORGANISM: Artificial Sequence
<220> FEATURE:
<223> OTHER INFORMATION: primer xylA-H1P1-5742-5-1

<400> SEQUENCE: 21
acgacatcat ccatcacccg cggcattacc tgattatgga gttcaatatg tgaagcctgc    60
tttttat                                                              68

<210> SEQ ID NO 22
<211> LENGTH: 68
<212> TYPE: DNA
<213> ORGANISM: Artificial Sequence
<220> FEATURE:
<223> OTHER INFORMATION: primer xylA-H2P2-5742-5-2

<400> SEQUENCE: 22
atcgggccaa cggactgcac agttagccgt tatttgtcga acagataatg cgctcaagtt    60
agtataaa                                                             68

<210> SEQ ID NO 23
<211> LENGTH: 8296
<212> TYPE: DNA
<213> ORGANISM: Caulobacter crescentus
<220> FEATURE:
<221> NAME/KEY: CDS
<222> LOCATION: (1175)..(2329)
<220> FEATURE:
```

```
<221> NAME/KEY: CDS
<222> LOCATION: (2346)..(3782)
<220> FEATURE:
<221> NAME/KEY: CDS
<222> LOCATION: (3788)..(4534)
<220> FEATURE:
<221> NAME/KEY: CDS
<222> LOCATION: (4659)..(5528)

<400> SEQUENCE: 23
```

| | |
|---|---|
| caggacttca gacccgcgag gctgtagggg tcgtcaaagg ccttggccag gaccggcggc | 60 |
| acctcgcgct tggacaggcc gacgtcgcgc accggctggg tgccgatgtc gacggccttc | 120 |
| ttgcccgcct cgccccagcg gccggacggt tcctcgggct tggccggcgg cttgacctgg | 180 |
| gcgtgggcgc tggaggccag cagcacggcg gcggctccgg ccatgatcag cagcttgttc | 240 |
| ggcatcaaaa gcgccctccc gacaaaacac gccacgggaa cggcaagcct cgccgccggt | 300 |
| tcccgcccgc aagtccctcg gcacgaactc taaggcctgc gcacgatcca tcgccaccac | 360 |
| aaagcgtgtc atcccggccg aagcgcagcg gagagccggg acccaggcc acaagcacgg | 420 |
| cgcttcgtca cccctgggt cccggatagc gctccgcgct tccgggatga cacgggttta | 480 |
| agcacttggg tgagaagccc tagttcggcg cgccgcccgc ttccaggtcg aacgcggcgt | 540 |
| cgaaggcgtc gtcgccagga accgtccctt ccagggcggc gtcgaacagg tcttcgagcg | 600 |
| atgaccagat gaaggccatc tgctccatga tcgtcgggac gctggccgga tcgaagccgg | 660 |
| ggtagaggtc ttccaccagc cacaggcccg tgccgggatc gaaggcgaag cggcagccga | 720 |
| tcaggcggaa ctgggcgcgg gccatggtct cgaacagggc cgtcaggtcg cgggcggcgt | 780 |
| ccaggtcgtc gtggtccagc accaggcagc ggatctgcag ccagccgtgg tcgggcagca | 840 |
| ggtagaaggc gccctcgtcc tgatcctcgc ccgaaacctc cagcccccgg tcgatggctt | 900 |
| cgacgacata gccggccgcg cggcaggtgt cggtgagcgc ggccagcagg gcggcttcct | 960 |
| ggtcaggggt caggtcggtc atgggcaaga ggtccaggtc gtggtttgtc ggcggcttct | 1020 |
| agcatggacc gcccgcgccc gtgaggccga ggatttcgcg ctggtcagac aacctacttg | 1080 |
| ccgtccccac atgttagcgc taccaagtgc cgacgaacgc gcgccgccga cggtgtcggc | 1140 |

| | | |
|---|---|---|
| gcttcagacg ctcgagttt ggggagacga cgcc gtg ggc gtg agt gaa ttc ctg<br>                                                                                                                  Val Gly Val Ser Glu Phe Leu<br>                                                                                                                   1              5 | 1195 |
| ccg gaa gat tgg aaa gcc gcg acc ctg ctg ggg cgc atc gac ttt ggc<br>Pro Glu Asp Trp Lys Ala Ala Thr Leu Leu Gly Arg Ile Asp Phe Gly<br>     10                 15                 20 | 1243 |
| gaa ggc ccg acg ccg gtg ctg gtg cgc ggc ggc cgc gtc gag gac gtc<br>Glu Gly Pro Thr Pro Val Leu Val Arg Gly Gly Arg Val Glu Asp Val<br>25                  30                 35 | 1291 |
| tcg aag atc gcc ccc acc gtc gct gac ctg atg aac gcc ttc cag ccc<br>Ser Lys Ile Ala Pro Thr Val Ala Asp Leu Met Asn Ala Phe Gln Pro<br>40                      45                 50                     55 | 1339 |
| ggc gcg gtg atc ccg cgc ggc gag gac aag ggt ccg ctg gaa gcc ctc<br>Gly Ala Val Ile Pro Arg Gly Glu Asp Lys Gly Pro Leu Glu Ala Leu<br>                 60                     65                           70 | 1387 |
| gac atc cgc cca gtc tgg gaa gac ccg gac ggc gcg ccg gtc aag<br>Asp Ile Arg Pro Val Trp Glu Asp Pro Asp Gly Ala Ala Pro Val Lys<br>               75                     80                          85 | 1435 |
| ctg ttg gcc ccc gtc gac ctg caa tgc ctg aag gcc gcc ggc gtg acc<br>Leu Leu Ala Pro Val Asp Leu Gln Cys Leu Lys Ala Ala Gly Val Thr<br>   90                     95                          100 | 1483 |
| ttc gcg gtc tcg acc ctt gag cgg gtc atc gag gag cgc gcg cgc ggc<br>Phe Ala Val Ser Thr Leu Glu Arg Val Ile Glu Glu Arg Ala Arg Gly | 1531 |

-continued

|  |  |  |  |  |  |  |  |  |  |  |  |  |  |  |  |
|---|---|---|---|---|---|---|---|---|---|---|---|---|---|---|---|
|  | 105 |  |  |  | 110 |  |  |  | 115 |  |  |  |  |  |  |
| gac | gcc | ggc | gag | gcg | ctg | aag | atc | cgc | acc | ctg | ctg | gcc | gaa | cgc | atg | 1579 |
| Asp | Ala | Gly | Glu | Ala | Leu | Lys | Ile | Arg | Thr | Leu | Leu | Ala | Glu | Arg | Met |  |
| 120 |  |  |  |  | 125 |  |  |  |  | 130 |  |  |  |  | 135 |  |
| ggc | ggc | gac | ctc | aag | agc | gtc | gag | ccg | ggc | tcg | cag | ggc | gcc | cag | cgc | 1627 |
| Gly | Gly | Asp | Leu | Lys | Ser | Val | Glu | Pro | Gly | Ser | Gln | Gly | Ala | Gln | Arg |  |
|  |  |  |  | 140 |  |  |  |  | 145 |  |  |  |  | 150 |  |  |
| ctg | aag | gac | gcc | ctg | atc | gcc | gac | ggc | ctg | tgg | tcg | cag | tat | ctg | gaa | 1675 |
| Leu | Lys | Asp | Ala | Leu | Ile | Ala | Asp | Gly | Leu | Trp | Ser | Gln | Tyr | Leu | Glu |  |
|  |  |  | 155 |  |  |  |  | 160 |  |  |  |  | 165 |  |  |  |
| gtg | gcg | atc | ggc | ccg | gac | gcc | gag | atc | ttc | acc | aag | ggc | ccg | acc | ctg | 1723 |
| Val | Ala | Ile | Gly | Pro | Asp | Ala | Glu | Ile | Phe | Thr | Lys | Gly | Pro | Thr | Leu |  |
|  |  | 170 |  |  |  |  | 175 |  |  |  |  | 180 |  |  |  |  |
| tcc | tcg | atg | ggc | tgg | ggc | gac | cag | gtc | ggc | gtc | cgc | tat | gac | agc | cac | 1771 |
| Ser | Ser | Met | Gly | Trp | Gly | Asp | Gln | Val | Gly | Val | Arg | Tyr | Asp | Ser | His |  |
| 185 |  |  |  |  | 190 |  |  |  |  | 195 |  |  |  |  |  |  |
| tgg | aac | aat | ccc | gag | ccg | gaa | gtc | gtg | ctg | ctg | tgc | gac | ggt | tcg | ggc | 1819 |
| Trp | Asn | Asn | Pro | Glu | Pro | Glu | Val | Val | Leu | Leu | Cys | Asp | Gly | Ser | Gly |  |
| 200 |  |  |  |  | 205 |  |  |  |  | 210 |  |  |  |  | 215 |  |
| ctg | atc | cgc | ggc | gcg | gcg | ctg | ggc | aac | gac | gtc | aat | ctg | cgc | gac | ttc | 1867 |
| Leu | Ile | Arg | Gly | Ala | Ala | Leu | Gly | Asn | Asp | Val | Asn | Leu | Arg | Asp | Phe |  |
|  |  |  |  | 220 |  |  |  |  | 225 |  |  |  |  | 230 |  |  |
| gaa | ggt | cgt | tcg | gcc | ctg | ctg | ctc | agc | aag | gcc | aag | gac | aac | aac | gcc | 1915 |
| Glu | Gly | Arg | Ser | Ala | Leu | Leu | Leu | Ser | Lys | Ala | Lys | Asp | Asn | Asn | Ala |  |
|  |  |  | 235 |  |  |  |  | 240 |  |  |  |  | 245 |  |  |  |
| agc | tgc | gcc | atc | ggt | ccg | ttc | ttc | cgc | ctg | ttc | gac | gag | acc | ttc | ggc | 1963 |
| Ser | Cys | Ala | Ile | Gly | Pro | Phe | Phe | Arg | Leu | Phe | Asp | Glu | Thr | Phe | Gly |  |
|  |  | 250 |  |  |  |  | 255 |  |  |  |  | 260 |  |  |  |  |
| ctg | gac | gac | gtc | cgt | tcg | gcc | gag | gtc | gag | ctg | aag | atc | acc | ggc | cgc | 2011 |
| Leu | Asp | Asp | Val | Arg | Ser | Ala | Glu | Val | Glu | Leu | Lys | Ile | Thr | Gly | Arg |  |
| 265 |  |  |  |  | 270 |  |  |  |  | 275 |  |  |  |  |  |  |
| gac | aac | ttc | gtg | ctc | gac | ggc | aag | tcg | aac | atg | agc | ctg | atc | agc | cgc | 2059 |
| Asp | Asn | Phe | Val | Leu | Asp | Gly | Lys | Ser | Asn | Met | Ser | Leu | Ile | Ser | Arg |  |
| 280 |  |  |  |  | 285 |  |  |  |  | 290 |  |  |  |  | 295 |  |
| gac | ccg | gcc | gtg | ctg | gcc | gga | cag | gcc | tat | ggc | aag | cag | cac | cag | tat | 2107 |
| Asp | Pro | Ala | Val | Leu | Ala | Gly | Gln | Ala | Tyr | Gly | Lys | Gln | His | Gln | Tyr |  |
|  |  |  |  | 300 |  |  |  |  | 305 |  |  |  |  | 310 |  |  |
| ccg | gac | ggc | ttt | gct | ttg | ttc | ctg | ggc | acc | atg | ttc | gcc | ccg | atc | cag | 2155 |
| Pro | Asp | Gly | Phe | Ala | Leu | Phe | Leu | Gly | Thr | Met | Phe | Ala | Pro | Ile | Gln |  |
|  |  |  | 315 |  |  |  |  | 320 |  |  |  |  | 325 |  |  |  |
| gac | cgc | gac | acc | ccc | ggc | cag | ggt | ttc | acc | cac | aag | gtc | ggc | gac | cgc | 2203 |
| Asp | Arg | Asp | Thr | Pro | Gly | Gln | Gly | Phe | Thr | His | Lys | Val | Gly | Asp | Arg |  |
|  |  | 330 |  |  |  |  | 335 |  |  |  |  | 340 |  |  |  |  |
| gtg | cgt | gtc | tcg | acg | ccg | aag | ctg | ggc | gtg | ctc | gag | aac | gaa | gtc | acc | 2251 |
| Val | Arg | Val | Ser | Thr | Pro | Lys | Leu | Gly | Val | Leu | Glu | Asn | Glu | Val | Thr |  |
| 345 |  |  |  |  | 350 |  |  |  |  | 355 |  |  |  |  |  |  |
| acc | tgc | gac | aag | gcc | aag | ccg | tgg | acg | ttc | ggc | atc | tcg | gcc | ctg | atc | 2299 |
| Thr | Cys | Asp | Lys | Ala | Lys | Pro | Trp | Thr | Phe | Gly | Ile | Ser | Ala | Leu | Ile |  |
| 360 |  |  |  |  | 365 |  |  |  |  | 370 |  |  |  |  | 375 |  |
| cgc | aac | ctg | gcc | ggc | cgc | ggc | ctc | ctc | taa | tcgaaagctt | | cccgcg | atg | acc | 2351 |
| Arg | Asn | Leu | Ala | Gly | Arg | Gly | Leu | Leu |  |  |  |  | Met | Thr |  |
|  |  |  | 380 |  |  |  |  |  |  |  |  |  | 385 |  |  |  |
| gac | acc | ctg | cgc | cat | tac | atc | ggc | ggc | gaa | cgc | gtc | gcg | gcc | gac | gcc | 2399 |
| Asp | Thr | Leu | Arg | His | Tyr | Ile | Gly | Gly | Glu | Arg | Val | Ala | Ala | Asp | Ala |  |
|  |  |  | 390 |  |  |  |  | 395 |  |  |  |  | 400 |  |  |  |
| ccg | gcc | gag | agc | ctg | aac | ccg | tcc | aac | acc | aac | gac | gtc | gtc | gcc | aag | 2447 |
| Pro | Ala | Glu | Ser | Leu | Asn | Pro | Ser | Asn | Thr | Asn | Asp | Val | Val | Ala | Lys |  |
|  |  |  | 405 |  |  |  |  | 410 |  |  |  |  | 415 |  |  |  |
| gtc | ccg | atg | ggc | ggc | cag | gcc | gag | gtc | gac | gcc | gcc | gtc | gac | gcc | gcg | 2495 |

```
Val Pro Met Gly Gly Gln Ala Glu Val Asp Ala Ala Val Asp Ala Ala
    420                 425                 430 cgc aag gcc ttc ccg gcc tgg gcc gac gcc tcg ccg gag gtc cgc tcg      2543
Arg Lys Ala Phe Pro Ala Trp Ala Asp Ala Ser Pro Glu Val Arg Ser
435                 440                 445                 450 gac ctc ttg gac aag gtc ggt tcg acc atc atc gcc cgc agc gcc gac      2591
Asp Leu Leu Asp Lys Val Gly Ser Thr Ile Ile Ala Arg Ser Ala Asp
                455                 460                 465 atc ggc cgc ctg ctg gcc cgc gaa gag ggc aag acc ctg gcg gaa ggc      2639
Ile Gly Arg Leu Leu Ala Arg Glu Glu Gly Lys Thr Leu Ala Glu Gly
            470                 475                 480 atc ggc gag acc gtc cgc gcc ggc cgc atc ttc aag tac ttc gcc ggt      2687
Ile Gly Glu Thr Val Arg Ala Gly Arg Ile Phe Lys Tyr Phe Ala Gly
        485                 490                 495 gaa gcc ctg cgc cgt cac ggc cag aac ctg gaa agc acc cgt ccg ggc      2735
Glu Ala Leu Arg Arg His Gly Gln Asn Leu Glu Ser Thr Arg Pro Gly
    500                 505                 510 gtc gag atc cag acc tat cgt cag gcc gtg ggc gtc tat ggc ctg atc      2783
Val Glu Ile Gln Thr Tyr Arg Gln Ala Val Gly Val Tyr Gly Leu Ile
515                 520                 525                 530 acg ccc tgg aac ttc ccg atc gcc atc ccg gcc tgg aag gcc gcc ccg      2831
Thr Pro Trp Asn Phe Pro Ile Ala Ile Pro Ala Trp Lys Ala Ala Pro
                535                 540                 545 gcg ctc gcc ttc ggc aac acc gtg gtg atc aag ccg gcc ggc ccg acg      2879
Ala Leu Ala Phe Gly Asn Thr Val Val Ile Lys Pro Ala Gly Pro Thr
            550                 555                 560 ccc gcc acc gcc aac gtg ctg gcc gac atc atg gcc gag tgc ggc gcc      2927
Pro Ala Thr Ala Asn Val Leu Ala Asp Ile Met Ala Glu Cys Gly Ala
        565                 570                 575 ccg gcc ggc gtg ttc aac atg ctg ttt ggt cgc ggc tcg atg ggc gat      2975
Pro Ala Gly Val Phe Asn Met Leu Phe Gly Arg Gly Ser Met Gly Asp
    580                 585                 590 gcg ctg atc aag cac aag gac gtg gac ggc gtc tcg ttc acc ggc tcg      3023
Ala Leu Ile Lys His Lys Asp Val Asp Gly Val Ser Phe Thr Gly Ser
595                 600                 605                 610 cag ggc gtg ggc gcg cag gtc gcc gcc gcc gcc gtg gcc cgt cag gcc      3071
Gln Gly Val Gly Ala Gln Val Ala Ala Ala Ala Val Ala Arg Gln Ala
                615                 620                 625 cgc gtg cag ctg gag atg ggc ggc aag aac ccg ctg atc gtg ctg gac      3119
Arg Val Gln Leu Glu Met Gly Gly Lys Asn Pro Leu Ile Val Leu Asp
            630                 635                 640 gac gcc gac ctg gag cgc gcg gtc gcc atc gcc ctg gac ggc tcg ttc      3167
Asp Ala Asp Leu Glu Arg Ala Val Ala Ile Ala Leu Asp Gly Ser Phe
        645                 650                 655 ttc gcc acc ggc cag cgc tgc acc gcc agc tcg cgc ctg atc gtc cag      3215
Phe Ala Thr Gly Gln Arg Cys Thr Ala Ser Ser Arg Leu Ile Val Gln
    660                 665                 670 gac ggg att cac gac aag ttc gtg gcc ctg ctg gcc gag aag gtc gcc      3263
Asp Gly Ile His Asp Lys Phe Val Ala Leu Leu Ala Glu Lys Val Ala
675                 680                 685                 690 gcc ctg cgc gtg ggc gac gct ctg gac ccc aac acc cag atc ggc ccg      3311
Ala Leu Arg Val Gly Asp Ala Leu Asp Pro Asn Thr Gln Ile Gly Pro
                695                 700                 705 gcc gtc tcc gaa gac cag atg gag act tcg tac cgc tat atc gac atc      3359
Ala Val Ser Glu Asp Gln Met Glu Thr Ser Tyr Arg Tyr Ile Asp Ile
            710                 715                 720 gct gcc tcc gaa ggc ggc cgc gtg gtc acc ggc ggc gac cgc atc aag      3407
Ala Ala Ser Glu Gly Gly Arg Val Val Thr Gly Gly Asp Arg Ile Lys
        725                 730                 735
```

-continued

| | |
|---|---|
| ctc gac aat ccg ggc tgg tac gtg cgt ccg acc ctg atc gcc gac acg<br>Leu Asp Asn Pro Gly Trp Tyr Val Arg Pro Thr Leu Ile Ala Asp Thr<br>740                            745                      750 | 3455 |
| caa gcc ggc atg cgg atc aac aac gag gag gtc ttc ggc ccc gtc gcc<br>Gln Ala Gly Met Arg Ile Asn Asn Glu Glu Val Phe Gly Pro Val Ala<br>755                            760                      765                      770 | 3503 |
| tcg acc atc cgc gtc aag agc tac gaa gag gcg ctg gag atc gcc aac<br>Ser Thr Ile Arg Val Lys Ser Tyr Glu Glu Ala Leu Glu Ile Ala Asn<br>                      775                      780                      785 | 3551 |
| ggc gtc gag ttc ggc ctt tcg gcc ggc atc gcc acc acc tcg ctc aag<br>Gly Val Glu Phe Gly Leu Ser Ala Gly Ile Ala Thr Thr Ser Leu Lys<br>            790                      795                      800 | 3599 |
| cac gcc cgc cac ttc cag cgc tat gcc cgc gcg ggc atg acc atg gtc<br>His Ala Arg His Phe Gln Arg Tyr Ala Arg Ala Gly Met Thr Met Val<br>                  805                      810                      815 | 3647 |
| aat ctg gcc acg gcc ggc gtc gac tat cac gtg ccg ttc ggc ggc acg<br>Asn Leu Ala Thr Ala Gly Val Asp Tyr His Val Pro Phe Gly Gly Thr<br>820                            825                      830 | 3695 |
| aag agc agc tcg tac ggc gcc cgc gag cag ggc ttc gcg gcg gtc gag<br>Lys Ser Ser Ser Tyr Gly Ala Arg Glu Gln Gly Phe Ala Ala Val Glu<br>835                            840                      845                      850 | 3743 |
| ttc ttc acc cag acc aaa acc tcc tac tcg tgg tcg taa gcagc atg tcc<br>Phe Phe Thr Gln Thr Lys Thr Ser Tyr Ser Trp Ser            Met Ser<br>                      855                      860 | 3793 |
| tca gcc atc tat ccc agc ctg aag ggc aag cgc gtc gtc atc acc ggc<br>Ser Ala Ile Tyr Pro Ser Leu Lys Gly Lys Arg Val Val Ile Thr Gly<br>865                            870                      875                      880 | 3841 |
| ggc ggc tcg ggc atc ggg gcc ggc ctc acc gcc ggc ttc gcc cgt cag<br>Gly Gly Ser Gly Ile Gly Ala Gly Leu Thr Ala Gly Phe Ala Arg Gln<br>                      885                      890                      895 | 3889 |
| ggc gcg gag gtg atc ttc ctc gac atc gcc gac gag gac tcc agg gct<br>Gly Ala Glu Val Ile Phe Leu Asp Ile Ala Asp Glu Asp Ser Arg Ala<br>                900                      905                      910 | 3937 |
| ctt gag gcc gag ctg gcc ggc tcg ccg atc ccg ccg gtc tac aag cgc<br>Leu Glu Ala Glu Leu Ala Gly Ser Pro Ile Pro Pro Val Tyr Lys Arg<br>            915                      920                      925 | 3985 |
| tgc gac ctg atg aac ctc gag gcg atc aag gcg gtc ttc gcc gag atc<br>Cys Asp Leu Met Asn Leu Glu Ala Ile Lys Ala Val Phe Ala Glu Ile<br>930                            935                      940 | 4033 |
| ggc gac gtc gac gtg ctg gtc aac aac gcc ggc aat gac gac cgc cac<br>Gly Asp Val Asp Val Leu Val Asn Asn Ala Gly Asn Asp Asp Arg His<br>945                            950                      955                      960 | 4081 |
| aag ctg gcc gac gtg acc ggc gcc tat tgg gac gag cgg atc aac gtc<br>Lys Leu Ala Asp Val Thr Gly Ala Tyr Trp Asp Glu Arg Ile Asn Val<br>                      965                      970                      975 | 4129 |
| aac ctg cgc cac atg ctg ttc tgc acc cag gcc gtc gcg ccg ggc atg<br>Asn Leu Arg His Met Leu Phe Cys Thr Gln Ala Val Ala Pro Gly Met<br>            980                      985                      990 | 4177 |
| aag aag cgt ggc ggc ggg gcg gtg atc aac ttc ggt tcg atc agc tgg<br>Lys Lys Arg Gly Gly Gly Ala Val Ile Asn Phe Gly Ser Ile Ser Trp<br>            995                      1000                    1005 | 4225 |
| cac ctg ggg ctt gag gac ctc gtc ctc tac gaa acc gcc aag gcc<br>His Leu Gly Leu Glu Asp Leu Val Leu Tyr Glu Thr Ala Lys Ala<br>            1010                      1015                    1020 | 4270 |
| ggc atc gaa ggc atg acc cgc gcg ctg gcc cgg gag ctg ggt ccc<br>Gly Ile Glu Gly Met Thr Arg Ala Leu Ala Arg Glu Leu Gly Pro<br>1025                      1030                      1035 | 4315 |
| gac gac atc cgc gtc acc tgc gtg gtg ccg ggc aac gtc aag acc<br>Asp Asp Ile Arg Val Thr Cys Val Val Pro Gly Asn Val Lys Thr<br>1040                      1045                      1050 | 4360 |

```
aag cgc cag gag aag tgg tac acg ccc gaa ggc gag gcc cag atc       4405
Lys Arg Gln Glu Lys Trp Tyr Thr Pro Glu Gly Glu Ala Gln Ile
    1055            1060                1065 gtg gcg gcc caa tgc ctg aag ggc cgc atc gtc ccg gag aac gtc       4450
Val Ala Ala Gln Cys Leu Lys Gly Arg Ile Val Pro Glu Asn Val
1070            1075                1080 gcc gcg ctg gtg ctg ttc ctg gcc tcg gat gac gcg tcg ctc tgc       4495
Ala Ala Leu Val Leu Phe Leu Ala Ser Asp Asp Ala Ser Leu Cys
        1085            1090                1095 acc ggc cac gaa tac tgg atc gac gcc ggc tgg cgt tga cctaagaaaa   4544
Thr Gly His Glu Tyr Trp Ile Asp Ala Gly Trp Arg
1100                1105                1110 ctgtcatccc ggcccagcgt gaagcgcgcc gagccgggac cacggcaagc gccacgcgtc  4604
cggaggtccc ggctctccgc tgtgctacgg ccgggatgac agaggaatga ttgt atg    4661
                                                              Met acc gct caa gtc act tgc gta tgg gat ctg aag gcc acg ttg ggc       4706
Thr Ala Gln Val Thr Cys Val Trp Asp Leu Lys Ala Thr Leu Gly
    1115            1120                1125 gaa ggc ccg atc tgg cat ggc gac acc ctg tgg ttc gtc gac atc       4751
Glu Gly Pro Ile Trp His Gly Asp Thr Leu Trp Phe Val Asp Ile
1130            1135                1140 aag cag cgt aaa atc cac aac tac cac ccc gcc acc ggc gag cgc       4796
Lys Gln Arg Lys Ile His Asn Tyr His Pro Ala Thr Gly Glu Arg
        1145            1150                1155 ttc agc ttc gac gcg ccg gat cag gtg acc ttc ctc gcg ccg atc       4841
Phe Ser Phe Asp Ala Pro Asp Gln Val Thr Phe Leu Ala Pro Ile
1160            1165                1170 gtc ggc gcg acc ggc ttt gtc gtc ggt ctg aag acc ggg att cac       4886
Val Gly Ala Thr Gly Phe Val Val Gly Leu Lys Thr Gly Ile His
    1175            1180                1185 cgc ttc cac ccg gcc acg ggc ttc agc ctg ctg ctc gag gtc gag       4931
Arg Phe His Pro Ala Thr Gly Phe Ser Leu Leu Leu Glu Val Glu
1190            1195                1200 gac gcg gcg ctg aac aac cgc ccc aac gac gcc acg gtc gac gcg       4976
Asp Ala Ala Leu Asn Asn Arg Pro Asn Asp Ala Thr Val Asp Ala
        1205            1210                1215 caa ggc cgt ctg tgg ttc ggc acc atg cac gac ggg gaa gag aac       5021
Gln Gly Arg Leu Trp Phe Gly Thr Met His Asp Gly Glu Glu Asn
1220            1225                1230 aat agc ggc tcg ctc tat cgg atg gac ctc acc ggc gtc gcc cgg       5066
Asn Ser Gly Ser Leu Tyr Arg Met Asp Leu Thr Gly Val Ala Arg
    1235            1240                1245 atg gac cgc gac atc tgc atc acc aac ggc ccg tgc gtc tcg ccc       5111
Met Asp Arg Asp Ile Cys Ile Thr Asn Gly Pro Cys Val Ser Pro
1250            1255                1260 gac ggc aag acc ttc tac cac acc gac acc ctg gaa aag acg atc       5156
Asp Gly Lys Thr Phe Tyr His Thr Asp Thr Leu Glu Lys Thr Ile
        1265            1270                1275 tac gcc ttc gac ctg gcc gag gac ggc ctg ctg tcg aac aag cgc       5201
Tyr Ala Phe Asp Leu Ala Glu Asp Gly Leu Leu Ser Asn Lys Arg
1280            1285                1290 gtc ttc gtg cag ttc gcc ctg ggc gac gat gtc tat ccg gac ggt       5246
Val Phe Val Gln Phe Ala Leu Gly Asp Asp Val Tyr Pro Asp Gly
    1295            1300                1305 tcg gtc gtc gat tcc gaa ggc tat ctg tgg acc gcc ctg tgg ggc       5291
Ser Val Val Asp Ser Glu Gly Tyr Leu Trp Thr Ala Leu Trp Gly
1310            1315                1320 ggt ttc ggc gcg gtc cgc ttc tcg ccg caa ggc gac gcc gtg acg       5336
```

```
Gly Phe Gly Ala  Val Arg Phe Ser  Pro Gln Gly Asp  Ala Val Thr
        1325             1330             1335 cgc atc gaa ctg  ccc gcc ccc aac  gtc acc aag ccc  tgc ttc ggc         5381
Arg Ile Glu Leu  Pro Ala Pro Asn  Val Thr Lys Pro  Cys Phe Gly
        1340             1345             1350 ggg cct gac ctg  aag acc ctc tat  ttc acc acc gcc  cgc aag ggc         5426
Gly Pro Asp Leu  Lys Thr Leu Tyr  Phe Thr Thr Ala  Arg Lys Gly
        1355             1360             1365 ctg agc gac gag  acc ctg gcc cag  tac ccg ctg gcc  ggt ggt gtg         5471
Leu Ser Asp Glu  Thr Leu Ala Gln  Tyr Pro Leu Ala  Gly Gly Val
        1370             1375             1380 ttc gcc gtt ccg  gtc gat gtg gcc  ggc caa ccc cag  cat gag gtc         5516
Phe Ala Val Pro  Val Asp Val Ala  Gly Gln Pro Gln  His Glu Val
        1385             1390             1395 cgc ctt gtc taa ccgcacgccc cgccggttcc ggtcccgcga ttggttcgat            5568
Arg Leu Val aaccccgacc atatcgacat gaccgcgctc tatctggagc gcttcatgaa ctacgggatc      5628
acgccggagg agctgcgcag cggcaagccg atcatcggca tcgcccagac cggcagcgac      5688
atctcgccct gcaaccgcat ccacctggac ctggtccagc gggtgcggga cgggatccgc      5748
gacgccgggg gcatccccat ggagttcccg gtccatccga tcttcgagaa ctgccgtcgc      5808
ccgacggcgg cgctggaccg gaacctctcg tacctgggtc tcgtcgagac cctgcacggc      5868
tatccgatcg acgccgtggt tctgaccacc ggctgcgaca agaccacccc ggccgggatc      5928
atggccgcca ccacggtcaa tatcccggcc atcgtgctgt cgggcggccc gatgctggac      5988
ggctggcacg agaacgagct cgtgggctcg gcaccgtga tctggcgctc cgccgcaag       6048 ctggcggccg gcgagatcac cgaggaagag ttcatcgacc gcgccgccag ctcggcgccg      6108
tcggcgggcc actgcaacac catgggcacg gcctcgacca tgaacgccgt ggccgaggcg      6168
ctgggcctgt cgctgaccgg ctgcgcggcc atccccgccc cctaccgcga gcgcggccag      6228
atggcctaca agaccggcca gcgcatcgtc gatctggcct atgacgacgt caaaccgctc      6288
gacatcctga ccaagcaagc cttcgagaac gccatcgccc tggtggcggc ggccggcggc      6348
tcgaccaacg cccagccgca catcgtggcc atggcccgtc acgccggcgt cgagatcacc      6408
gccgacgact ggcgcgcggc ctatgacatc ccgctgatcg tcaacatgca gccggccggc      6468
aagtatctgg cgagcgcttc caccgagcc ggcggcgcgc cggcggtgct gtgggagctg       6528
ttgcagcaag gccgcctgca cggcgacgtg ctgaccgtca ccggcaagac gatgagcgag      6588
aacctgcaag gccgcgaaac cagcgaccgc gaggtgatct tccgtacca cgagccgctg       6648 gccgagaagg ccgggttcct ggttctcaag gcaacctct tcgacttcgc gatcatgaag       6708
tccagcgtga tcggcgagga gttccgcaag cgctacctgt cgcagcccgg ccaggaaggc      6768
gtgttcgaag cccgcgccat cgtgttcgac ggctcggacg actatcacaa gcggatcaac      6828
gatccgcccc tggagatcga cgagcgctgc atcctggtga tccgcggcgc gggtccgatc      6888
ggctggcccg gctcggccga ggtcgtcaac atgcagccgc cggatcacct tctgaagaag      6948
gggatcatga gcctgcccac cctgggcgat ggccgtcagt cgggcaccgc cgacagcccc      7008
tcgatcctga cgcctcgcc cgaaagcgcg atcggcggcg cctgtcgtg gctgcgcacc        7068 ggcgacacca tccgcatcga cctcaacacc ggccgctgcg acgccctggt cgacgaggcg      7128
acgatcgccg cgcgcaagca ggacggcatc ccggcggttc ccgccaccat gacgccctgg      7188
caggaaatct accgcgccca cgccagtcag ctcgacaccg cgggcgtgct ggagttcgcg      7248
gtcaagtacc aggacctggc ggccaagctg ccccgccaca accactgatg cgaagggcct     7308
```

-continued

```
tcggagcgat ccggaggccc ttttctttgc gccccccgga tcgcccgccc ccgcttcaca   7368
acacccagcc gaatcgcatt ttctccgtcg ccaaacgctg aaatgcgaag gggctggggg   7428
ggcgccatgg aactcaagga atactttctg ggcctgttgg ccatcatcac cggcctggcg   7488
atcaccgaca tgatcctgag cgtgcacggc ctgctacggc gcgtcagccg cgtacgatgg   7548
gattggctgc cgctcacggc cgccgccctg gttttcgtcg tcatcgtccg cagctggtgg   7608
atcgcctggg agcccgactg gatcaacacg ccgatgtggc agttcctgtt gatcctgatc   7668
cagctgacct gcctgttcct ggccgccaag tctgtgttgc cggacgacag cgacgccgaa   7728
gaggtcgacc tgatggctca ctactggtcg cagaaccggt tcgtctgggc gtccctgatc   7788
ggcatgatca cggcgttcgc cgccgcctcg gtcttcctgc gcatcaacga tccggcgagc   7848
ctgtcggcat ggttctggac gttcggttgg gagctgccgg tctactgctt gccgctggtg   7908
gtcctgatcc tcctgcagcg accgatcgtg catcgcgcgc tggttcccgc gctcctgctc   7968
gcctggctgg tcctgaacgg gacggacgtg atgcactaca gctagggctc ggcggctctg   8028
gtaaacaacc caaccccgat caacgaaggt ttagaaagct ttaagagaaa cgttgcgaat   8088
tgtaaaattc ttctctgggt tgaaacccat ttcgggtgta tcgatgaggt gtcgggccat   8148
ttattgagcg cggacaggat gttgtcagtg agccgagccc ttgatcaacg accggagtcg   8208
cccagcctgg tgatcgccac cacgatcctc cagcttggcc tcgttgttgt ggtttggctg   8268
gtggcgctga tccccgccgc gctggcgg                                      8296
```

<210> SEQ ID NO 24
<211> LENGTH: 384
<212> TYPE: PRT
<213> ORGANISM: Caulobacter crescentus

<400> SEQUENCE: 24

```
Val Gly Val Ser Glu Phe Leu Pro Glu Asp Trp Lys Ala Ala Thr Leu
1               5                   10                  15

Leu Gly Arg Ile Asp Phe Gly Glu Gly Pro Thr Pro Val Leu Val Arg
            20                  25                  30

Gly Gly Arg Val Glu Asp Val Ser Lys Ile Ala Pro Thr Val Ala Asp
        35                  40                  45

Leu Met Asn Ala Phe Gln Pro Gly Ala Val Ile Pro Arg Gly Glu Asp
    50                  55                  60

Lys Gly Pro Leu Glu Ala Leu Asp Ile Arg Pro Val Trp Glu Asp Pro
65                  70                  75                  80

Asp Gly Ala Ala Pro Val Lys Leu Leu Ala Pro Val Asp Leu Gln Cys
                85                  90                  95

Leu Lys Ala Gly Val Thr Phe Ala Val Ser Thr Leu Glu Arg Val
            100                 105                 110

Ile Glu Glu Arg Ala Arg Gly Asp Ala Gly Glu Ala Leu Lys Ile Arg
        115                 120                 125

Thr Leu Leu Ala Glu Arg Met Gly Gly Asp Leu Lys Ser Val Glu Pro
    130                 135                 140

Gly Ser Gln Gly Ala Gln Arg Leu Lys Asp Ala Leu Ile Ala Asp Gly
145                 150                 155                 160

Leu Trp Ser Gln Tyr Leu Glu Val Ala Ile Gly Pro Asp Ala Glu Ile
                165                 170                 175

Phe Thr Lys Gly Pro Thr Leu Ser Met Gly Trp Gly Asp Gln Val
            180                 185                 190
```

```
Gly Val Arg Tyr Asp Ser His Trp Asn Asn Pro Glu Pro Glu Val Val
            195                 200                 205

Leu Leu Cys Asp Gly Ser Gly Leu Ile Arg Gly Ala Ala Leu Gly Asn
    210                 215                 220

Asp Val Asn Leu Arg Asp Phe Glu Gly Arg Ser Ala Leu Leu Leu Ser
225                 230                 235                 240

Lys Ala Lys Asp Asn Asn Ala Ser Cys Ala Ile Gly Pro Phe Phe Arg
                245                 250                 255

Leu Phe Asp Glu Thr Phe Gly Leu Asp Asp Val Arg Ser Ala Glu Val
            260                 265                 270

Glu Leu Lys Ile Thr Gly Arg Asp Asn Phe Val Leu Asp Gly Lys Ser
        275                 280                 285

Asn Met Ser Leu Ile Ser Arg Asp Pro Ala Val Leu Ala Gly Gln Ala
    290                 295                 300

Tyr Gly Lys Gln His Gln Tyr Pro Asp Gly Phe Ala Leu Phe Leu Gly
305                 310                 315                 320

Thr Met Phe Ala Pro Ile Gln Asp Arg Asp Thr Pro Gly Gln Gly Phe
                325                 330                 335

Thr His Lys Val Gly Asp Arg Val Arg Val Ser Thr Pro Lys Leu Gly
            340                 345                 350

Val Leu Glu Asn Glu Val Thr Thr Cys Asp Lys Ala Lys Pro Trp Thr
        355                 360                 365

Phe Gly Ile Ser Ala Leu Ile Arg Asn Leu Ala Gly Arg Gly Leu Leu
    370                 375                 380

<210> SEQ ID NO 25
<211> LENGTH: 478
<212> TYPE: PRT
<213> ORGANISM: Caulobacter crescentus

<400> SEQUENCE: 25

Met Thr Asp Thr Leu Arg His Tyr Ile Gly Gly Glu Arg Val Ala Ala
1               5                   10                  15

Asp Ala Pro Ala Glu Ser Leu Asn Pro Ser Asn Thr Asn Asp Val Val
            20                  25                  30

Ala Lys Val Pro Met Gly Gly Gln Ala Glu Val Asp Ala Ala Val Asp
        35                  40                  45

Ala Ala Arg Lys Ala Phe Pro Ala Trp Ala Asp Ala Ser Pro Glu Val
    50                  55                  60

Arg Ser Asp Leu Leu Asp Lys Val Gly Ser Thr Ile Ile Ala Arg Ser
65                  70                  75                  80

Ala Asp Ile Gly Arg Leu Leu Ala Arg Glu Glu Gly Lys Thr Leu Ala
                85                  90                  95

Glu Gly Ile Gly Glu Thr Val Arg Ala Gly Arg Ile Phe Lys Tyr Phe
            100                 105                 110

Ala Gly Glu Ala Leu Arg Arg His Gly Gln Asn Leu Glu Ser Thr Arg
        115                 120                 125

Pro Gly Val Glu Ile Gln Thr Tyr Arg Gln Ala Val Gly Val Tyr Gly
    130                 135                 140

Leu Ile Thr Pro Trp Asn Phe Pro Ile Ala Ile Pro Ala Trp Lys Ala
145                 150                 155                 160

Ala Pro Ala Leu Ala Phe Gly Asn Thr Val Val Ile Lys Pro Ala Gly
                165                 170                 175

Pro Thr Pro Ala Thr Ala Asn Val Leu Ala Asp Ile Met Ala Glu Cys
            180                 185                 190
```

Gly Ala Pro Ala Gly Val Phe Asn Met Leu Phe Gly Arg Gly Ser Met
            195                 200                 205

Gly Asp Ala Leu Ile Lys His Lys Asp Val Asp Gly Val Ser Phe Thr
210                 215                 220

Gly Ser Gln Gly Val Gly Ala Gln Val Ala Ala Ala Val Ala Arg
225                 230                 235                 240

Gln Ala Arg Val Gln Leu Glu Met Gly Gly Lys Asn Pro Leu Ile Val
                245                 250                 255

Leu Asp Asp Ala Asp Leu Glu Arg Ala Val Ala Ile Ala Leu Asp Gly
            260                 265                 270

Ser Phe Phe Ala Thr Gly Gln Arg Cys Thr Ala Ser Ser Arg Leu Ile
        275                 280                 285

Val Gln Asp Gly Ile His Asp Lys Phe Val Ala Leu Leu Ala Glu Lys
    290                 295                 300

Val Ala Ala Leu Arg Val Gly Asp Ala Leu Asp Pro Asn Thr Gln Ile
305                 310                 315                 320

Gly Pro Ala Val Ser Glu Asp Gln Met Glu Thr Ser Tyr Arg Tyr Ile
                325                 330                 335

Asp Ile Ala Ala Ser Glu Gly Gly Arg Val Val Thr Gly Gly Asp Arg
            340                 345                 350

Ile Lys Leu Asp Asn Pro Gly Trp Tyr Val Arg Pro Thr Leu Ile Ala
        355                 360                 365

Asp Thr Gln Ala Gly Met Arg Ile Asn Asn Glu Glu Val Phe Gly Pro
    370                 375                 380

Val Ala Ser Thr Ile Arg Val Lys Ser Tyr Glu Glu Ala Leu Glu Ile
385                 390                 395                 400

Ala Asn Gly Val Glu Phe Gly Leu Ser Ala Gly Ile Ala Thr Thr Ser
                405                 410                 415

Leu Lys His Ala Arg His Phe Gln Arg Tyr Ala Arg Ala Gly Met Thr
            420                 425                 430

Met Val Asn Leu Ala Thr Ala Gly Val Asp Tyr His Val Pro Phe Gly
        435                 440                 445

Gly Thr Lys Ser Ser Tyr Gly Ala Arg Glu Gln Gly Phe Ala Ala
    450                 455                 460

Val Glu Phe Phe Thr Gln Thr Lys Thr Ser Tyr Ser Trp Ser
465                 470                 475

<210> SEQ ID NO 26
<211> LENGTH: 248
<212> TYPE: PRT
<213> ORGANISM: Caulobacter crescentus

<400> SEQUENCE: 26

Met Ser Ser Ala Ile Tyr Pro Ser Leu Lys Gly Lys Arg Val Ile
1               5                   10                  15

Thr Gly Gly Gly Ser Gly Ile Gly Ala Gly Leu Thr Ala Gly Phe Ala
            20                  25                  30

Arg Gln Gly Ala Glu Val Ile Phe Leu Asp Ile Ala Asp Glu Asp Ser
        35                  40                  45

Arg Ala Leu Glu Ala Glu Leu Ala Gly Ser Pro Ile Pro Pro Val Tyr
    50                  55                  60

Lys Arg Cys Asp Leu Met Asn Leu Glu Ala Ile Lys Ala Val Phe Ala
65                  70                  75                  80

Glu Ile Gly Asp Val Asp Val Leu Val Asn Asn Ala Gly Asn Asp Asp

```
                         85                  90                  95
Arg His Lys Leu Ala Asp Val Thr Gly Ala Tyr Trp Asp Glu Arg Ile
                100                 105                 110

Asn Val Asn Leu Arg His Met Leu Phe Cys Thr Gln Ala Val Ala Pro
                115                 120                 125

Gly Met Lys Lys Arg Gly Gly Ala Val Ile Asn Phe Gly Ser Ile
            130                 135                 140

Ser Trp His Leu Gly Leu Glu Asp Leu Val Leu Tyr Glu Thr Ala Lys
145                 150                 155                 160

Ala Gly Ile Glu Gly Met Thr Arg Ala Leu Ala Arg Glu Leu Gly Pro
                165                 170                 175

Asp Asp Ile Arg Val Thr Cys Val Val Pro Gly Asn Val Lys Thr Lys
                180                 185                 190

Arg Gln Glu Lys Trp Tyr Thr Pro Glu Gly Ala Gln Ile Val Ala
                195                 200                 205

Ala Gln Cys Leu Lys Gly Arg Ile Val Pro Glu Asn Val Ala Ala Leu
            210                 215                 220

Val Leu Phe Leu Ala Ser Asp Asp Ala Ser Leu Cys Thr Gly His Glu
225                 230                 235                 240

Tyr Trp Ile Asp Ala Gly Trp Arg
                245

<210> SEQ ID NO 27
<211> LENGTH: 289
<212> TYPE: PRT
<213> ORGANISM: Caulobacter crescentus

<400> SEQUENCE: 27

Met Thr Ala Gln Val Thr Cys Val Trp Asp Leu Lys Ala Thr Leu Gly
1               5                   10                  15

Glu Gly Pro Ile Trp His Gly Asp Thr Leu Trp Phe Val Asp Ile Lys
                20                  25                  30

Gln Arg Lys Ile His Asn Tyr His Pro Ala Thr Gly Glu Arg Phe Ser
            35                  40                  45

Phe Asp Ala Pro Asp Gln Val Thr Phe Leu Ala Pro Ile Val Gly Ala
        50                  55                  60

Thr Gly Phe Val Val Gly Leu Lys Thr Gly Ile His Arg Phe His Pro
65                  70                  75                  80

Ala Thr Gly Phe Ser Leu Leu Leu Glu Val Glu Asp Ala Ala Leu Asn
                85                  90                  95

Asn Arg Pro Asn Asp Ala Thr Val Asp Ala Gln Gly Arg Leu Trp Phe
                100                 105                 110

Gly Thr Met His Asp Gly Glu Glu Asn Asn Ser Gly Ser Leu Tyr Arg
            115                 120                 125

Met Asp Leu Thr Gly Val Ala Arg Met Asp Arg Asp Ile Cys Ile Thr
        130                 135                 140

Asn Gly Pro Cys Val Ser Pro Asp Gly Lys Thr Phe Tyr His Thr Asp
145                 150                 155                 160

Thr Leu Glu Lys Thr Ile Tyr Ala Phe Asp Leu Ala Glu Asp Gly Leu
                165                 170                 175

Leu Ser Asn Lys Arg Val Phe Val Gln Phe Ala Leu Gly Asp Asp Val
                180                 185                 190

Tyr Pro Asp Gly Ser Val Val Asp Ser Glu Gly Tyr Leu Trp Thr Ala
            195                 200                 205
```

```
Leu Trp Gly Gly Phe Gly Ala Val Arg Phe Ser Pro Gln Gly Asp Ala
    210                 215                 220

Val Thr Arg Ile Glu Leu Pro Ala Pro Asn Val Thr Lys Pro Cys Phe
225                 230                 235                 240

Gly Gly Pro Asp Leu Lys Thr Leu Tyr Phe Thr Ala Arg Lys Gly
                245                 250                 255

Leu Ser Asp Glu Thr Leu Ala Gln Tyr Pro Leu Ala Gly Gly Val Phe
                260                 265                 270

Ala Val Pro Val Asp Val Ala Gly Gln Pro Gln His Glu Val Arg Leu
                275                 280                 285

Val

<210> SEQ ID NO 28
<211> LENGTH: 1788
<212> TYPE: DNA
<213> ORGANISM: Caulobacter crescentus
<220> FEATURE:
<221> NAME/KEY: CDS
<222> LOCATION: (1)..(1788)

<400> SEQUENCE: 28 atg agg tcc gcc ttg tct aac cgc acg ccc cgc ggg ttc cgg tcc cgc       48
Met Arg Ser Ala Leu Ser Asn Arg Thr Pro Arg Arg Phe Arg Ser Arg
1               5                   10                  15 gat tgg ttc gat aac ccc gac cat atc gac atg acc gcg ctc tat ctg       96
Asp Trp Phe Asp Asn Pro Asp His Ile Asp Met Thr Ala Leu Tyr Leu
                20                  25                  30 gag cgc ttc atg aac tac ggg atc acg ccg gag gag ctg cgc agc ggc       144
Glu Arg Phe Met Asn Tyr Gly Ile Thr Pro Glu Glu Leu Arg Ser Gly
            35                  40                  45 aag ccg atc atc ggc atc gcc cag acc ggc agc gac atc tcg ccc tgc       192
Lys Pro Ile Ile Gly Ile Ala Gln Thr Gly Ser Asp Ile Ser Pro Cys
        50                  55                  60 aac cgc atc cac ctg gac ctg gtc cag cgg gtg cgg gac ggg atc cgc       240
Asn Arg Ile His Leu Asp Leu Val Gln Arg Val Arg Asp Gly Ile Arg
65                  70                  75                  80 gac gcc ggg ggc atc ccc atg gag ttc ccg gtc cat ccg atc ttc gag       288
Asp Ala Gly Gly Ile Pro Met Glu Phe Pro Val His Pro Ile Phe Glu
                85                  90                  95 aac tgc cgt cgc ccg acg gcg gcg ctg gac cgg aac ctc tcg tac ctg       336
Asn Cys Arg Arg Pro Thr Ala Ala Leu Asp Arg Asn Leu Ser Tyr Leu
            100                 105                 110 ggt ctc gtc gag acc ctg cac ggc tat ccg atc gac gcc gtg gtt ctg       384
Gly Leu Val Glu Thr Leu His Gly Tyr Pro Ile Asp Ala Val Val Leu
        115                 120                 125 acc acc ggc tgc gac aag acc acc ccg gcc ggg atc atg gcc gcc acc       432
Thr Thr Gly Cys Asp Lys Thr Thr Pro Ala Gly Ile Met Ala Ala Thr
    130                 135                 140 acg gtc aat atc ccg gcc atc gtg ctg tcg ggc ggc ccg atg ctg gac       480
Thr Val Asn Ile Pro Ala Ile Val Leu Ser Gly Gly Pro Met Leu Asp
145                 150                 155                 160 ggc tgg cac gag aac gag ctc gtg ggc tcg ggc acc gtg atc tgg cgc       528
Gly Trp His Glu Asn Glu Leu Val Gly Ser Gly Thr Val Ile Trp Arg
                165                 170                 175 tcg cgc cgc aag ctg gcg gcc ggc gag atc acc gag gaa gag ttc atc       576
Ser Arg Arg Lys Leu Ala Ala Gly Glu Ile Thr Glu Glu Glu Phe Ile
            180                 185                 190 gac cgc gcc gcc agc tcg gcg ccg tcg gcg ggc cac tgc aac acc atg       624
Asp Arg Ala Ala Ser Ser Ala Pro Ser Ala Gly His Cys Asn Thr Met
        195                 200                 205
```

```
ggc acg gcc tcg acc atg aac gcc gtg gcc gag gcg ctg ggc ctg tcg      672
Gly Thr Ala Ser Thr Met Asn Ala Val Ala Glu Ala Leu Gly Leu Ser
    210                 215                 220 ctg acc ggc tgc gcg gcc atc ccc gcc ccc tac cgc gag cgc ggc cag      720
Leu Thr Gly Cys Ala Ala Ile Pro Ala Pro Tyr Arg Glu Arg Gly Gln
225                 230                 235                 240 atg gcc tac aag acc ggc cag cgc atc gtc gat ctg gcc tat gac gac      768
Met Ala Tyr Lys Thr Gly Gln Arg Ile Val Asp Leu Ala Tyr Asp Asp
                245                 250                 255 gtc aaa ccg ctc gac atc ctg acc aag caa gcc ttc gag aac gcc atc      816
Val Lys Pro Leu Asp Ile Leu Thr Lys Gln Ala Phe Glu Asn Ala Ile
            260                 265                 270 gcc ctg gtg gcg gcg gcc ggc ggc tcg acc aac gcc cag ccg cac atc      864
Ala Leu Val Ala Ala Ala Gly Gly Ser Thr Asn Ala Gln Pro His Ile
        275                 280                 285 gtg gcc atg gcc cgt cac gcc ggc gtc gag atc acc gcc gac gac tgg      912
Val Ala Met Ala Arg His Ala Gly Val Glu Ile Thr Ala Asp Asp Trp
    290                 295                 300 cgc gcg gcc tat gac atc ccg ctg atc gtc aac atg cag ccg gcc ggc      960
Arg Ala Ala Tyr Asp Ile Pro Leu Ile Val Asn Met Gln Pro Ala Gly
305                 310                 315                 320 aag tat ctg ggc gag cgc ttc cac cga gcc ggc ggc gcg ccg gcg gtg     1008
Lys Tyr Leu Gly Glu Arg Phe His Arg Ala Gly Gly Ala Pro Ala Val
                325                 330                 335 ctg tgg gag ctg ttg cag caa ggc cgc ctg cac ggc gac gtg ctg acc     1056
Leu Trp Glu Leu Leu Gln Gln Gly Arg Leu His Gly Asp Val Leu Thr
            340                 345                 350 gtc acc ggc aag acg atg agc gag aac ctg caa ggc cgc gaa acc agc     1104
Val Thr Gly Lys Thr Met Ser Glu Asn Leu Gln Gly Arg Glu Thr Ser
        355                 360                 365 gac cgc gag gtg atc ttc ccg tac cac gag ccg ctg gcc gag aag gcc     1152
Asp Arg Glu Val Ile Phe Pro Tyr His Glu Pro Leu Ala Glu Lys Ala
    370                 375                 380 ggg ttc ctg gtt ctc aag ggc aac ctc ttc gac ttc gcg atc atg aag     1200
Gly Phe Leu Val Leu Lys Gly Asn Leu Phe Asp Phe Ala Ile Met Lys
385                 390                 395                 400 tcc agc gtg atc ggc gag gag ttc cgc aag cgc tac ctg tcg cag ccc     1248
Ser Ser Val Ile Gly Glu Glu Phe Arg Lys Arg Tyr Leu Ser Gln Pro
                405                 410                 415 ggc cag gaa ggc gtg ttc gaa gcc cgc gcc atc gtg ttc gac ggc tcg     1296
Gly Gln Glu Gly Val Phe Glu Ala Arg Ala Ile Val Phe Asp Gly Ser
            420                 425                 430 gac gac tat cac aag cgg atc aac gat ccg gcc ctg gag atc gac gag     1344
Asp Asp Tyr His Lys Arg Ile Asn Asp Pro Ala Leu Glu Ile Asp Glu
        435                 440                 445 cgc tgc atc ctg gtg atc cgc ggc gcg ggt ccg atc ggc tgg ccc ggc     1392
Arg Cys Ile Leu Val Ile Arg Gly Ala Gly Pro Ile Gly Trp Pro Gly
    450                 455                 460 tcg gcc gag gtc gtc aac atg cag ccg ccg gat cac ctt ctg aag aag     1440
Ser Ala Glu Val Val Asn Met Gln Pro Pro Asp His Leu Leu Lys Lys
465                 470                 475                 480 ggg atc atg agc ctg ccc acc ctg ggc gat ggc cgt cag tcg ggc acc     1488
Gly Ile Met Ser Leu Pro Thr Leu Gly Asp Gly Arg Gln Ser Gly Thr
                485                 490                 495 gcc gac agc ccc tcg atc ctg aac gcc tcg ccc gaa agc gcg atc ggc     1536
Ala Asp Ser Pro Ser Ile Leu Asn Ala Ser Pro Glu Ser Ala Ile Gly
            500                 505                 510 ggc ggc ctg tcg tgg ctg cgc acc ggc gac acc atc cgc atc gac ctc     1584
Gly Gly Leu Ser Trp Leu Arg Thr Gly Asp Thr Ile Arg Ile Asp Leu
```

```
                515                 520                 525
aac acc ggc cgc tgc gac gcc ctg gtc gac gag gcg acg atc gcc gcg     1632
Asn Thr Gly Arg Cys Asp Ala Leu Val Asp Glu Ala Thr Ile Ala Ala
    530                 535                 540 cgc aag cag gac ggc atc ccg gcg gtt ccc gcc acc atg acg ccc tgg     1680
Arg Lys Gln Asp Gly Ile Pro Ala Val Pro Ala Thr Met Thr Pro Trp
545                 550                 555                 560 cag gaa atc tac cgc gcc cac gcc agt cag ctc gac acc ggc ggc gtg     1728
Gln Glu Ile Tyr Arg Ala His Ala Ser Gln Leu Asp Thr Gly Gly Val
                565                 570                 575 ctg gag ttc gcg gtc aag tac cag gac ctg gcg gcc aag ctg ccc cgc     1776
Leu Glu Phe Ala Val Lys Tyr Gln Asp Leu Ala Ala Lys Leu Pro Arg
            580                 585                 590 cac aac cac tga                                                     1788
His Asn His
        595

<210> SEQ ID NO 29
<211> LENGTH: 595
<212> TYPE: PRT
<213> ORGANISM: Caulobacter crescentus

<400> SEQUENCE: 29

Met Arg Ser Ala Leu Ser Asn Arg Thr Pro Arg Arg Phe Arg Ser Arg
1               5                   10                  15

Asp Trp Phe Asp Asn Pro Asp His Ile Asp Met Thr Ala Leu Tyr Leu
            20                  25                  30

Glu Arg Phe Met Asn Tyr Gly Ile Thr Pro Glu Glu Leu Arg Ser Gly
        35                  40                  45

Lys Pro Ile Ile Gly Ile Ala Gln Thr Gly Ser Asp Ile Ser Pro Cys
    50                  55                  60

Asn Arg Ile His Leu Asp Leu Val Gln Arg Val Arg Asp Gly Ile Arg
65                  70                  75                  80

Asp Ala Gly Gly Ile Pro Met Glu Phe Pro Val His Pro Ile Phe Glu
                85                  90                  95

Asn Cys Arg Arg Pro Thr Ala Ala Leu Asp Arg Asn Leu Ser Tyr Leu
            100                 105                 110

Gly Leu Val Glu Thr Leu His Gly Tyr Pro Ile Asp Ala Val Val Leu
        115                 120                 125

Thr Thr Gly Cys Asp Lys Thr Thr Pro Ala Gly Ile Met Ala Ala Thr
    130                 135                 140

Thr Val Asn Ile Pro Ala Ile Val Leu Ser Gly Gly Pro Met Leu Asp
145                 150                 155                 160

Gly Trp His Glu Asn Glu Leu Val Gly Ser Gly Thr Val Ile Trp Arg
                165                 170                 175

Ser Arg Arg Lys Leu Ala Ala Gly Glu Ile Thr Glu Glu Phe Ile
            180                 185                 190

Asp Arg Ala Ala Ser Ser Ala Pro Ser Ala Gly His Cys Asn Thr Met
        195                 200                 205

Gly Thr Ala Ser Thr Met Asn Ala Val Ala Glu Ala Leu Gly Leu Ser
    210                 215                 220

Leu Thr Gly Cys Ala Ala Ile Pro Ala Pro Tyr Arg Glu Arg Gly Gln
225                 230                 235                 240

Met Ala Tyr Lys Thr Gly Gln Arg Ile Val Asp Leu Ala Tyr Asp Asp
                245                 250                 255

Val Lys Pro Leu Asp Ile Leu Thr Lys Gln Ala Phe Glu Asn Ala Ile
```

```
                      260                 265                 270
        Ala Leu Val Ala Ala Gly Gly Ser Thr Asn Ala Gln Pro His Ile
                275                 280                 285

Val Ala Met Ala Arg His Ala Gly Val Glu Ile Thr Ala Asp Asp Trp
            290                 295                 300

Arg Ala Ala Tyr Asp Ile Pro Leu Ile Val Asn Met Gln Pro Ala Gly
        305                 310                 315                 320

Lys Tyr Leu Gly Glu Arg Phe His Arg Ala Gly Ala Pro Ala Val
                        325                 330                 335

Leu Trp Glu Leu Leu Gln Gln Gly Arg Leu His Gly Asp Val Leu Thr
                    340                 345                 350

Val Thr Gly Lys Thr Met Ser Glu Asn Leu Gln Gly Arg Glu Thr Ser
                355                 360                 365

Asp Arg Glu Val Ile Phe Pro Tyr His Glu Pro Leu Ala Glu Lys Ala
            370                 375                 380

Gly Phe Leu Val Leu Lys Gly Asn Leu Phe Asp Phe Ala Ile Met Lys
        385                 390                 395                 400

Ser Ser Val Ile Gly Glu Glu Phe Arg Lys Arg Tyr Leu Ser Gln Pro
                        405                 410                 415

Gly Gln Glu Gly Val Phe Glu Ala Arg Ala Ile Val Phe Asp Gly Ser
                    420                 425                 430

Asp Asp Tyr His Lys Arg Ile Asn Asp Pro Ala Leu Glu Ile Asp Glu
                435                 440                 445

Arg Cys Ile Leu Val Ile Arg Gly Ala Gly Pro Ile Gly Trp Pro Gly
            450                 455                 460

Ser Ala Glu Val Val Asn Met Gln Pro Pro Asp His Leu Leu Lys Lys
        465                 470                 475                 480

Gly Ile Met Ser Leu Pro Thr Leu Gly Asp Gly Arg Gln Ser Gly Thr
                        485                 490                 495

Ala Asp Ser Pro Ser Ile Leu Asn Ala Ser Pro Glu Ser Ala Ile Gly
                    500                 505                 510

Gly Gly Leu Ser Trp Leu Arg Thr Gly Asp Thr Ile Arg Ile Asp Leu
                515                 520                 525

Asn Thr Gly Arg Cys Asp Ala Leu Val Asp Glu Ala Thr Ile Ala Ala
            530                 535                 540

Arg Lys Gln Asp Gly Ile Pro Ala Val Pro Ala Thr Met Thr Pro Trp
        545                 550                 555                 560

Gln Glu Ile Tyr Arg Ala His Ala Ser Gln Leu Asp Thr Gly Gly Val
                        565                 570                 575

Leu Glu Phe Ala Val Lys Tyr Gln Asp Leu Ala Ala Lys Leu Pro Arg
                    580                 585                 590

His Asn His
                595

<210> SEQ ID NO 30
<211> LENGTH: 1476
<212> TYPE: DNA
<213> ORGANISM: Escherichia coli
<220> FEATURE:
<221> NAME/KEY: CDS
<222> LOCATION: (1)..(1476)

<400> SEQUENCE: 30 atg aat acc cag tat aat tcc agt tat ata ttt tcg att acc tta gtc    48
Met Asn Thr Gln Tyr Asn Ser Ser Tyr Ile Phe Ser Ile Thr Leu Val
1               5                   10                  15
```

```
gct aca tta ggt ggt tta tta ttt ggc tac gac acc gcc gtt att tcc      96
Ala Thr Leu Gly Gly Leu Leu Phe Gly Tyr Asp Thr Ala Val Ile Ser
         20                  25                  30 ggt act gtt gag tca ctc aat acc gtc ttt gtt gct cca caa aac tta     144
Gly Thr Val Glu Ser Leu Asn Thr Val Phe Val Ala Pro Gln Asn Leu
             35                  40                  45 agt gaa tcc gct gcc aac tcc ctg tta ggg ttt tgc gtg gcc agc gct     192
Ser Glu Ser Ala Ala Asn Ser Leu Leu Gly Phe Cys Val Ala Ser Ala
 50                  55                  60 ctg att ggt tgc atc atc ggc ggt gcc ctc ggt ggt tat tgc agt aac     240
Leu Ile Gly Cys Ile Ile Gly Gly Ala Leu Gly Gly Tyr Cys Ser Asn
 65                  70                  75                  80 cgc ttc ggt cgt cgt gat tca ctt aag att gct gct gtc ctg ttt ttt     288
Arg Phe Gly Arg Arg Asp Ser Leu Lys Ile Ala Ala Val Leu Phe Phe
                 85                  90                  95 att tct ggt gta ggt tct gcc tgg cca gaa ctt ggt ttt acc tct ata     336
Ile Ser Gly Val Gly Ser Ala Trp Pro Glu Leu Gly Phe Thr Ser Ile
            100                 105                 110 aac ccg gac aac act gtg cct gtt tat ctg gca ggt tat gtc ccg gaa     384
Asn Pro Asp Asn Thr Val Pro Val Tyr Leu Ala Gly Tyr Val Pro Glu
        115                 120                 125 ttt gtt att tat cgc att att ggc ggt att ggc gtt ggt tta gcc tca     432
Phe Val Ile Tyr Arg Ile Ile Gly Gly Ile Gly Val Gly Leu Ala Ser
130                 135                 140 atg ctc tcg cca atg tat att gcg gaa ctg gct cca gct cat att cgc     480
Met Leu Ser Pro Met Tyr Ile Ala Glu Leu Ala Pro Ala His Ile Arg
145                 150                 155                 160 ggg aaa ctg gtc tct ttt aac cag ttt gcg att att ttc ggg caa ctt     528
Gly Lys Leu Val Ser Phe Asn Gln Phe Ala Ile Ile Phe Gly Gln Leu
                165                 170                 175 tta gtt tac tgc gta aac tat ttt att gcc cgt tcc ggt gat gcc agc     576
Leu Val Tyr Cys Val Asn Tyr Phe Ile Ala Arg Ser Gly Asp Ala Ser
            180                 185                 190 tgg ctg aat act gac ggc tgg cgt tat atg ttt gcc tcg gaa tgt atc     624
Trp Leu Asn Thr Asp Gly Trp Arg Tyr Met Phe Ala Ser Glu Cys Ile
        195                 200                 205 cct gca ctg ctg ttc tta atg ctg ctg tat acc gtg cca gaa agt cct     672
Pro Ala Leu Leu Phe Leu Met Leu Leu Tyr Thr Val Pro Glu Ser Pro
    210                 215                 220 cgc tgg ctg atg tcg cgc ggc aag caa gaa cag gcg gaa ggt atc ctg     720
Arg Trp Leu Met Ser Arg Gly Lys Gln Glu Gln Ala Glu Gly Ile Leu
225                 230                 235                 240 cgc aaa att atg ggc aac acg ctt gca act cag gca gta cag gaa att     768
Arg Lys Ile Met Gly Asn Thr Leu Ala Thr Gln Ala Val Gln Glu Ile
                245                 250                 255 aaa cac tcc ctg gat cat ggc cgc aaa acc ggt ggt cgt ctg ctg atg     816
Lys His Ser Leu Asp His Gly Arg Lys Thr Gly Gly Arg Leu Leu Met
            260                 265                 270 ttt ggc gtg ggc gtg att gta atc ggc gta atg ctc tcc atc ttc cag     864
Phe Gly Val Gly Val Ile Val Ile Gly Val Met Leu Ser Ile Phe Gln
        275                 280                 285 caa ttt gtc ggc atc aat gtg gtg ctg tac tac gcg ccg gaa gtg ttc     912
Gln Phe Val Gly Ile Asn Val Val Leu Tyr Tyr Ala Pro Glu Val Phe
    290                 295                 300 aaa acg ctg ggg gcc agc acg gat atc gcg ctg ttg cag acc att att     960
Lys Thr Leu Gly Ala Ser Thr Asp Ile Ala Leu Leu Gln Thr Ile Ile
305                 310                 315                 320 gtc gga gtt atc aac ctc acc ttc acc gtt ctg gca att atg acg gtg    1008
Val Gly Val Ile Asn Leu Thr Phe Thr Val Leu Ala Ile Met Thr Val
```

-continued

```
                    325                 330                 335
gat aaa ttt ggt cgt aag cca ctg caa att atc ggc gca ctc gga atg        1056
Asp Lys Phe Gly Arg Lys Pro Leu Gln Ile Ile Gly Ala Leu Gly Met
            340                 345                 350 gca atc ggt atg ttt agc ctc ggt acc gcg ttt tac act cag gca ccg        1104
Ala Ile Gly Met Phe Ser Leu Gly Thr Ala Phe Tyr Thr Gln Ala Pro
            355                 360                 365 ggt att gtg gcg cta ctg tcg atg ctg ttc tat gtt gcc gcc ttt gcc        1152
Gly Ile Val Ala Leu Leu Ser Met Leu Phe Tyr Val Ala Ala Phe Ala
            370                 375                 380 atg tcc tgg ggt ccg gta tgc tgg gta ctg ctg tcg gaa atc ttc ccg        1200
Met Ser Trp Gly Pro Val Cys Trp Val Leu Leu Ser Glu Ile Phe Pro
385                 390                 395                 400 aat gct att cgt ggt aaa gcg ctg gca atc gcg gtg gcg gcc cag tgg        1248
Asn Ala Ile Arg Gly Lys Ala Leu Ala Ile Ala Val Ala Ala Gln Trp
                405                 410                 415 ctg gcg aac tac ttc gtc tcc tgg acc ttc ccg atg atg gac aaa aac        1296
Leu Ala Asn Tyr Phe Val Ser Trp Thr Phe Pro Met Met Asp Lys Asn
            420                 425                 430 tcc tgg ctg gtg gcc cat ttc cac aac ggt ttc tcc tac tgg att tac        1344
Ser Trp Leu Val Ala His Phe His Asn Gly Phe Ser Tyr Trp Ile Tyr
            435                 440                 445 ggt tgt atg ggc gtt ctg gca gca ctg ttt atg tgg aaa ttt gtc ccg        1392
Gly Cys Met Gly Val Leu Ala Ala Leu Phe Met Trp Lys Phe Val Pro
450                 455                 460 gaa acc aaa ggt aaa acc ctt gag gag ctg gaa gcc ctc tgg gaa ccg        1440
Glu Thr Lys Gly Lys Thr Leu Glu Glu Leu Glu Ala Leu Trp Glu Pro
465                 470                 475                 480 gaa acg aag aaa aca caa caa act gct acg ctg taa                        1476
Glu Thr Lys Lys Thr Gln Gln Thr Ala Thr Leu
                485                 490

<210> SEQ ID NO 31
<211> LENGTH: 491
<212> TYPE: PRT
<213> ORGANISM: Escherichia coli

<400> SEQUENCE: 31

Met Asn Thr Gln Tyr Asn Ser Ser Tyr Ile Phe Ser Ile Thr Leu Val
1               5                   10                  15

Ala Thr Leu Gly Gly Leu Leu Phe Gly Tyr Asp Thr Ala Val Ile Ser
            20                  25                  30

Gly Thr Val Glu Ser Leu Asn Thr Val Phe Val Ala Pro Gln Asn Leu
        35                  40                  45

Ser Glu Ser Ala Ala Asn Ser Leu Leu Gly Phe Cys Val Ala Ser Ala
    50                  55                  60

Leu Ile Gly Cys Ile Ile Gly Gly Ala Leu Gly Tyr Cys Ser Asn
65                  70                  75                  80

Arg Phe Gly Arg Arg Asp Ser Leu Lys Ile Ala Ala Val Leu Phe Phe
                85                  90                  95

Ile Ser Gly Val Gly Ser Ala Trp Pro Glu Leu Gly Phe Thr Ser Ile
            100                 105                 110

Asn Pro Asp Asn Thr Val Pro Val Tyr Leu Ala Gly Tyr Val Pro Glu
        115                 120                 125

Phe Val Ile Tyr Arg Ile Ile Gly Gly Ile Gly Val Gly Leu Ala Ser
    130                 135                 140

Met Leu Ser Pro Met Tyr Ile Ala Glu Leu Ala Pro Ala His Ile Arg
145                 150                 155                 160
```

Gly Lys Leu Val Ser Phe Asn Gln Phe Ala Ile Ile Phe Gly Gln Leu
            165                 170                 175
Leu Val Tyr Cys Val Asn Tyr Phe Ile Ala Arg Ser Gly Asp Ala Ser
        180                 185                 190
Trp Leu Asn Thr Asp Gly Trp Arg Tyr Met Phe Ala Ser Glu Cys Ile
    195                 200                 205
Pro Ala Leu Leu Phe Leu Met Leu Leu Tyr Thr Val Pro Glu Ser Pro
210                 215                 220
Arg Trp Leu Met Ser Arg Gly Lys Gln Glu Gln Ala Glu Gly Ile Leu
225                 230                 235                 240
Arg Lys Ile Met Gly Asn Thr Leu Ala Thr Gln Ala Val Gln Glu Ile
            245                 250                 255
Lys His Ser Leu Asp His Gly Arg Lys Thr Gly Gly Arg Leu Leu Met
        260                 265                 270
Phe Gly Val Gly Val Ile Val Ile Gly Val Met Leu Ser Ile Phe Gln
    275                 280                 285
Gln Phe Val Gly Ile Asn Val Val Leu Tyr Tyr Ala Pro Glu Val Phe
290                 295                 300
Lys Thr Leu Gly Ala Ser Thr Asp Ile Ala Leu Leu Gln Thr Ile Ile
305                 310                 315                 320
Val Gly Val Ile Asn Leu Thr Phe Thr Val Leu Ala Ile Met Thr Val
            325                 330                 335
Asp Lys Phe Gly Arg Lys Pro Leu Gln Ile Ile Gly Ala Leu Gly Met
        340                 345                 350
Ala Ile Gly Met Phe Ser Leu Gly Thr Ala Phe Tyr Thr Gln Ala Pro
    355                 360                 365
Gly Ile Val Ala Leu Leu Ser Met Leu Phe Tyr Val Ala Ala Phe Ala
370                 375                 380
Met Ser Trp Gly Pro Val Cys Trp Val Leu Leu Ser Glu Ile Phe Pro
385                 390                 395                 400
Asn Ala Ile Arg Gly Lys Ala Leu Ala Ile Ala Val Ala Ala Gln Trp
            405                 410                 415
Leu Ala Asn Tyr Phe Val Ser Trp Thr Phe Pro Met Met Asp Lys Asn
        420                 425                 430
Ser Trp Leu Val Ala His Phe His Asn Gly Phe Ser Tyr Trp Ile Tyr
    435                 440                 445
Gly Cys Met Gly Val Leu Ala Ala Leu Phe Met Trp Lys Phe Val Pro
450                 455                 460
Glu Thr Lys Gly Lys Thr Leu Glu Glu Leu Glu Ala Leu Trp Glu Pro
465                 470                 475                 480
Glu Thr Lys Lys Thr Gln Gln Thr Ala Thr Leu
            485                 490

<210> SEQ ID NO 32
<211> LENGTH: 399
<212> TYPE: DNA
<213> ORGANISM: Artificial Sequence
<220> FEATURE:
<223> OTHER INFORMATION: synthetic DNA PtacTtrp

<400> SEQUENCE: 32
ggtaccagat ctccctgttg acaattaatc atcggctcta taatgtgtgg aatcgtgagc      60
ggataacaat ttcacacaag gagactcccg ggagccgcca gttccgctgg cggcatttta     120
actttcttta atgaagccgg aaaaatccta aattcattta atatttatct ttttaccgtt     180

```
tcgcttaccc cggtcgaacg tcaacttacg tcattttttcc gcccaacagt aatataatca    240
aacaaattaa tcccgcaaca taacaccagt aaaatcaata attttctcta agtcacttat    300
tcctcaggta attgttaata tatccagaat gttcctcaaa atatattttc cctctatctt    360
ctcgttgcgc ttaatttgac taattctcat tagggatcc                           399

<210> SEQ ID NO 33
<211> LENGTH: 362
<212> TYPE: DNA
<213> ORGANISM: Brevibacterium flavum

<400> SEQUENCE: 33
agatcgttta gatccgaagg aaaacgtcga aaagcaattt gcttttcgac gccccacccc     60
gcgcgtttta gcgtgtcagt aggcgcgtag ggtaagtggg gtagcggctt gttagatatc    120
ttgaaatcgg ctttcaacag cattgatttc gatgtattta gctggccgtt accctgcgaa    180
tgtccacagg gtagctggta gtttgaaaat caacgccgtt gcccttagga ttcagtaact    240
ggcacatttt gtaatgcgct agatctgtgt gctcagtctt ccaggctgct tatcacagtg    300
aaagcaaaac caattcgtgg ctgcgaaagt cgtagccacc acgaagtcca ggaggacata    360
ca                                                                   362

<210> SEQ ID NO 34
<211> LENGTH: 1968
<212> TYPE: DNA
<213> ORGANISM: Escherichia coli
<220> FEATURE:
<221> NAME/KEY: CDS
<222> LOCATION: (1)..(1968)

<400> SEQUENCE: 34 atg tct gtt cgc aat att ttt gct gac gag agc cac gat att tac acc      48
Met Ser Val Arg Asn Ile Phe Ala Asp Glu Ser His Asp Ile Tyr Thr
1               5                   10                  15 gtc aga acg cac gcc gat ggc ccg gac ggc gaa ctc cca tta acc gca      96
Val Arg Thr His Ala Asp Gly Pro Asp Gly Glu Leu Pro Leu Thr Ala
                20                  25                  30 gag atg ctt atc aac cgc ccg agc ggg gat ctg ttc ggt atg acc atg     144
Glu Met Leu Ile Asn Arg Pro Ser Gly Asp Leu Phe Gly Met Thr Met
            35                  40                  45 aat gcc gga atg ggt tgg tct ccg gac gag ctg gat cgg gac ggt att     192
Asn Ala Gly Met Gly Trp Ser Pro Asp Glu Leu Asp Arg Asp Gly Ile
        50                  55                  60 tta ctg ctc agt aca ctc ggt ggc tta cgc ggc gca gac ggt aaa ccc     240
Leu Leu Leu Ser Thr Leu Gly Gly Leu Arg Gly Ala Asp Gly Lys Pro
65                  70                  75                  80 gtg gcg ctg gcg ttg cac cag ggg cat tac gaa ctg gac atc cag atg     288
Val Ala Leu Ala Leu His Gln Gly His Tyr Glu Leu Asp Ile Gln Met
                85                  90                  95 aaa gcg gcg gcc gag gtt att aaa gcc aac cat gcc ctg ccc tat gcc     336
Lys Ala Ala Ala Glu Val Ile Lys Ala Asn His Ala Leu Pro Tyr Ala
                100                 105                 110 gtg tac gtc tcc gat cct tgt gac ggg cgt act cag ggt aca acg ggg     384
Val Tyr Val Ser Asp Pro Cys Asp Gly Arg Thr Gln Gly Thr Thr Gly
            115                 120                 125 atg ttt gat tcg cta cca tac cga aat gac gca tcg atg gta atg cgc     432
Met Phe Asp Ser Leu Pro Tyr Arg Asn Asp Ala Ser Met Val Met Arg
        130                 135                 140 cgc ctt att cgc tct ctg ccc gac gcg aaa gca gtt att ggt gtg gcg     480
```

```
Arg Leu Ile Arg Ser Leu Pro Asp Ala Lys Ala Val Ile Gly Val Ala
145                 150                 155                 160 agt tgc gat aag ggg ctt ccg gcc acc atg atg gca ctc gcc gcg cag      528
Ser Cys Asp Lys Gly Leu Pro Ala Thr Met Met Ala Leu Ala Ala Gln
                165                 170                 175 cac aac atc gca acc gtg ctg gtc ccc ggc ggc gcg acg ctg ccc gca      576
His Asn Ile Ala Thr Val Leu Val Pro Gly Gly Ala Thr Leu Pro Ala
            180                 185                 190 aag gat gga gaa gac aac ggc aag gtg caa acc att ggc gca cgc ttc      624
Lys Asp Gly Glu Asp Asn Gly Lys Val Gln Thr Ile Gly Ala Arg Phe
        195                 200                 205 gcc aat ggc gaa tta tct cta cag gac gca cgc cgt gcg ggc tgt aaa      672
Ala Asn Gly Glu Leu Ser Leu Gln Asp Ala Arg Arg Ala Gly Cys Lys
    210                 215                 220 gcc tgt gcc tct tcc ggc ggc ggc tgt caa ttt ttg ggc act gcc ggg      720
Ala Cys Ala Ser Ser Gly Gly Gly Cys Gln Phe Leu Gly Thr Ala Gly
225                 230                 235                 240 aca tct cag gtg gtg gcc gaa gga ttg gga ctg gca atc cca cat tca      768
Thr Ser Gln Val Val Ala Glu Gly Leu Gly Leu Ala Ile Pro His Ser
                245                 250                 255 gcc ctg gcc cct tcc ggt gag cct gtg tgg cgg gag atc gcc aga gct      816
Ala Leu Ala Pro Ser Gly Glu Pro Val Trp Arg Glu Ile Ala Arg Ala
            260                 265                 270 tcc gcg cga gct gcg ctg aac ctg agt caa aaa ggc atc acc acc cgg      864
Ser Ala Arg Ala Ala Leu Asn Leu Ser Gln Lys Gly Ile Thr Thr Arg
        275                 280                 285 gaa att ctc acc gat aaa gcg ata gag aat gcg atg acg gtc cat gcc      912
Glu Ile Leu Thr Asp Lys Ala Ile Glu Asn Ala Met Thr Val His Ala
    290                 295                 300 gcg ttc ggt ggt tca aca aac ctg ctg tta cac atc ccg gca att gct      960
Ala Phe Gly Gly Ser Thr Asn Leu Leu Leu His Ile Pro Ala Ile Ala
305                 310                 315                 320 cac cag gca ggt tgc cat atc ccg acc gtt gat gac tgg atc cgc atc     1008
His Gln Ala Gly Cys His Ile Pro Thr Val Asp Asp Trp Ile Arg Ile
                325                 330                 335 aac aag cgc gtg ccc cga ctg gtg agc gta ctg cct aat ggc ccg gtt     1056
Asn Lys Arg Val Pro Arg Leu Val Ser Val Leu Pro Asn Gly Pro Val
            340                 345                 350 tat cat cca acg gtc aat gcc ttt atg gca ggt ggt gtg ccg gaa gtc     1104
Tyr His Pro Thr Val Asn Ala Phe Met Ala Gly Gly Val Pro Glu Val
        355                 360                 365 atg ttg cat ctg cgc agc ctc gga ttg ttg cat gaa gac gtt atg acg     1152
Met Leu His Leu Arg Ser Leu Gly Leu Leu His Glu Asp Val Met Thr
    370                 375                 380 gtt acc ggc agc acg ctg aaa gaa aac ctc gac tgg tgg gag cac tcc     1200
Val Thr Gly Ser Thr Leu Lys Glu Asn Leu Asp Trp Trp Glu His Ser
385                 390                 395                 400 gaa cgg cgt cag cgg ttc aag caa ctc ctg ctc gat cag gaa caa atc     1248
Glu Arg Arg Gln Arg Phe Lys Gln Leu Leu Leu Asp Gln Glu Gln Ile
                405                 410                 415 aac gct gac gaa gtg atc atg tct ccg cag caa gca aaa gcg cgc gga     1296
Asn Ala Asp Glu Val Ile Met Ser Pro Gln Gln Ala Lys Ala Arg Gly
            420                 425                 430 tta acc tca act atc acc ttc ccg gtg ggc aat att gcg cca gaa ggt     1344
Leu Thr Ser Thr Ile Thr Phe Pro Val Gly Asn Ile Ala Pro Glu Gly
        435                 440                 445 tcg gtg atc aaa tcc acc gcc att gac ccc tcg atg att gat gag caa     1392
Ser Val Ile Lys Ser Thr Ala Ile Asp Pro Ser Met Ile Asp Glu Gln
    450                 455                 460
```

```
ggt atc tat tac cat aaa ggt gtg gcg aag gtt tat ctg tcc gag aaa      1440
Gly Ile Tyr Tyr His Lys Gly Val Ala Lys Val Tyr Leu Ser Glu Lys
465                 470                 475                 480 agt gcg att tac gat atc aaa cat gac aag atc aag gcg ggc gat att      1488
Ser Ala Ile Tyr Asp Ile Lys His Asp Lys Ile Lys Ala Gly Asp Ile
                485                 490                 495 ctg gtc att att ggc gtt gga cct tca ggt aca ggg atg gaa gaa acc      1536
Leu Val Ile Ile Gly Val Gly Pro Ser Gly Thr Gly Met Glu Glu Thr
500                 505                 510 tac cag gtt acc agt gcc ctg aag cat ctg tca tac ggt aag cat gtt      1584
Tyr Gln Val Thr Ser Ala Leu Lys His Leu Ser Tyr Gly Lys His Val
    515                 520                 525 tcg tta atc acc gat gca cgt ttc tcg ggc gtt tct act ggc gcg tgc      1632
Ser Leu Ile Thr Asp Ala Arg Phe Ser Gly Val Ser Thr Gly Ala Cys
530                 535                 540 atc ggc cat gtg ggg cca gaa gcg ctg gcc gga ggc ccc atc ggt aaa      1680
Ile Gly His Val Gly Pro Glu Ala Leu Ala Gly Gly Pro Ile Gly Lys
545                 550                 555                 560 tta cgc acc ggg gat tta att gaa att aaa att gat tgt cgc gag ctt      1728
Leu Arg Thr Gly Asp Leu Ile Glu Ile Lys Ile Asp Cys Arg Glu Leu
                565                 570                 575 cac ggc gaa gtc aat ttc ctc gga acc cgt agc gat gaa caa tta cct      1776
His Gly Glu Val Asn Phe Leu Gly Thr Arg Ser Asp Glu Gln Leu Pro
                580                 585                 590 tca cag gag gag gca act gca ata tta aat gcc aga ccc agc cat cag      1824
Ser Gln Glu Glu Ala Thr Ala Ile Leu Asn Ala Arg Pro Ser His Gln
            595                 600                 605 gat tta ctt ccc gat cct gaa ttg cca gat gat acc cgg cta tgg gca      1872
Asp Leu Leu Pro Asp Pro Glu Leu Pro Asp Asp Thr Arg Leu Trp Ala
610                 615                 620 atg ctt cag gcc gtg agt ggt ggg aca tgg acc ggt tgt att tat gat      1920
Met Leu Gln Ala Val Ser Gly Gly Thr Trp Thr Gly Cys Ile Tyr Asp
625                 630                 635                 640 gta aac aaa att ggc gcg gct ttg cgc gat ttt atg aat aaa aac tga      1968
Val Asn Lys Ile Gly Ala Ala Leu Arg Asp Phe Met Asn Lys Asn
                645                 650                 655

<210> SEQ ID NO 35
<211> LENGTH: 655
<212> TYPE: PRT
<213> ORGANISM: Escherichia coli

<400> SEQUENCE: 35

Met Ser Val Arg Asn Ile Phe Ala Asp Glu Ser His Asp Ile Tyr Thr
1               5                   10                  15

Val Arg Thr His Ala Asp Gly Pro Asp Gly Glu Leu Pro Leu Thr Ala
            20                  25                  30

Glu Met Leu Ile Asn Arg Pro Ser Gly Asp Leu Phe Gly Met Thr Met
        35                  40                  45

Asn Ala Gly Met Gly Trp Ser Pro Asp Glu Leu Asp Arg Asp Gly Ile
    50                  55                  60

Leu Leu Leu Ser Thr Leu Gly Gly Leu Arg Gly Ala Asp Gly Lys Pro
65                  70                  75                  80

Val Ala Leu Ala Leu His Gln Gly His Tyr Glu Leu Asp Ile Gln Met
                85                  90                  95

Lys Ala Ala Ala Glu Val Ile Lys Ala Asn His Ala Leu Pro Tyr Ala
            100                 105                 110

Val Tyr Val Ser Asp Pro Cys Asp Gly Arg Thr Gln Gly Thr Thr Gly
        115                 120                 125
```

```
Met Phe Asp Ser Leu Pro Tyr Arg Asn Asp Ala Ser Met Val Met Arg
        130                 135                 140

Arg Leu Ile Arg Ser Leu Pro Asp Ala Lys Ala Val Ile Gly Val Ala
145                 150                 155                 160

Ser Cys Asp Lys Gly Leu Pro Ala Thr Met Met Ala Leu Ala Ala Gln
                165                 170                 175

His Asn Ile Ala Thr Val Leu Val Pro Gly Ala Thr Leu Pro Ala
                180                 185                 190

Lys Asp Gly Glu Asp Asn Gly Lys Val Gln Thr Ile Gly Ala Arg Phe
                195                 200                 205

Ala Asn Gly Glu Leu Ser Leu Gln Asp Ala Arg Ala Gly Cys Lys
210                 215                 220

Ala Cys Ala Ser Ser Gly Gly Cys Gln Phe Leu Gly Thr Ala Gly
225                 230                 235                 240

Thr Ser Gln Val Val Ala Glu Gly Leu Gly Leu Ala Ile Pro His Ser
                245                 250                 255

Ala Leu Ala Pro Ser Gly Glu Pro Val Trp Arg Glu Ile Ala Arg Ala
                260                 265                 270

Ser Ala Arg Ala Ala Leu Asn Leu Ser Gln Lys Gly Ile Thr Thr Arg
                275                 280                 285

Glu Ile Leu Thr Asp Lys Ala Ile Glu Asn Ala Met Thr Val His Ala
                290                 295                 300

Ala Phe Gly Gly Ser Thr Asn Leu Leu Leu His Ile Pro Ala Ile Ala
305                 310                 315                 320

His Gln Ala Gly Cys His Ile Pro Thr Val Asp Trp Ile Arg Ile
                325                 330                 335

Asn Lys Arg Val Pro Arg Leu Val Ser Val Leu Pro Asn Gly Pro Val
                340                 345                 350

Tyr His Pro Thr Val Asn Ala Phe Met Ala Gly Gly Val Pro Glu Val
                355                 360                 365

Met Leu His Leu Arg Ser Leu Gly Leu Leu His Glu Asp Val Met Thr
                370                 375                 380

Val Thr Gly Ser Thr Leu Lys Glu Asn Leu Asp Trp Trp Glu His Ser
385                 390                 395                 400

Glu Arg Arg Gln Arg Phe Lys Gln Leu Leu Asp Gln Glu Gln Ile
                405                 410                 415

Asn Ala Asp Glu Val Ile Met Ser Pro Gln Gln Ala Lys Ala Arg Gly
                420                 425                 430

Leu Thr Ser Thr Ile Thr Phe Pro Val Gly Asn Ile Ala Pro Glu Gly
                435                 440                 445

Ser Val Ile Lys Ser Thr Ala Ile Asp Pro Ser Met Ile Asp Glu Gln
                450                 455                 460

Gly Ile Tyr Tyr His Lys Gly Val Ala Lys Val Tyr Leu Ser Glu Lys
465                 470                 475                 480

Ser Ala Ile Tyr Asp Ile Lys His Asp Lys Ile Lys Ala Gly Asp Ile
                485                 490                 495

Leu Val Ile Ile Gly Val Gly Pro Ser Gly Thr Gly Met Glu Glu Thr
                500                 505                 510

Tyr Gln Val Thr Ser Ala Leu Lys His Leu Ser Tyr Gly Lys His Val
                515                 520                 525

Ser Leu Ile Thr Asp Ala Arg Phe Ser Gly Val Ser Thr Gly Ala Cys
530                 535                 540
```

```
Ile Gly His Val Gly Pro Glu Ala Leu Ala Gly Pro Ile Gly Lys
545                 550                 555                 560

Leu Arg Thr Gly Asp Leu Ile Glu Ile Lys Ile Asp Cys Arg Glu Leu
                565                 570                 575

His Gly Glu Val Asn Phe Leu Gly Thr Arg Ser Asp Glu Gln Leu Pro
            580                 585                 590

Ser Gln Glu Glu Ala Thr Ala Ile Leu Asn Ala Arg Pro Ser His Gln
        595                 600                 605

Asp Leu Leu Pro Asp Pro Glu Leu Pro Asp Asp Thr Arg Leu Trp Ala
    610                 615                 620

Met Leu Gln Ala Val Ser Gly Gly Thr Trp Thr Gly Cys Ile Tyr Asp
625                 630                 635                 640

Val Asn Lys Ile Gly Ala Ala Leu Arg Asp Phe Met Asn Lys Asn
                645                 650                 655

<210> SEQ ID NO 36
<211> LENGTH: 1968
<212> TYPE: DNA
<213> ORGANISM: Escherichia coli
<220> FEATURE:
<221> NAME/KEY: CDS
<222> LOCATION: (1)..(1968)

<400> SEQUENCE: 36 atg acc att gag aaa att ttc acc ccg cag gac gac gcg ttt tat gcg      48
Met Thr Ile Glu Lys Ile Phe Thr Pro Gln Asp Asp Ala Phe Tyr Ala
1               5                   10                  15 gtg atc acc cac gcg gcg ggg ccg cag ggc gct ctg ccg ctg acc ccg      96
Val Ile Thr His Ala Ala Gly Pro Gln Gly Ala Leu Pro Leu Thr Pro
                20                  25                  30 cag atg ctg atg gaa tct ccc agc ggc aac ctg ttc ggc atg acg cag     144
Gln Met Leu Met Glu Ser Pro Ser Gly Asn Leu Phe Gly Met Thr Gln
            35                  40                  45 aac gcc ggg atg ggc tgg gac gcc aac aag ctc acc ggc aaa gag gtg     192
Asn Ala Gly Met Gly Trp Asp Ala Asn Lys Leu Thr Gly Lys Glu Val
        50                  55                  60 ctg att atc ggc act cag ggc ggc atc cgc gcc gga gac gga cgc cca     240
Leu Ile Ile Gly Thr Gln Gly Gly Ile Arg Ala Gly Asp Gly Arg Pro
65                  70                  75                  80 atc gcg ctg ggc tac cac acc ggg cat tgg gag atc ggc atg cag atg     288
Ile Ala Leu Gly Tyr His Thr Gly His Trp Glu Ile Gly Met Gln Met
                85                  90                  95 cag gcg gcg gcg aag gag atc acc cgc aat ggc ggg atc ccg ttc gcg     336
Gln Ala Ala Ala Lys Glu Ile Thr Arg Asn Gly Gly Ile Pro Phe Ala
            100                 105                 110 gcc ttc gtc agc gat ccg tgc gac ggg cgc tcg cag ggc acg cac ggt     384
Ala Phe Val Ser Asp Pro Cys Asp Gly Arg Ser Gln Gly Thr His Gly
        115                 120                 125 atg ttc gat tcc ctg ccg tac cgc aac gac gcg gcg atc gtg ttt cgc     432
Met Phe Asp Ser Leu Pro Tyr Arg Asn Asp Ala Ala Ile Val Phe Arg
    130                 135                 140 cgc ctg atc cgc tcc ctg ccg acg cgg cgg gcg gtg atc ggc gta gcg     480
Arg Leu Ile Arg Ser Leu Pro Thr Arg Arg Ala Val Ile Gly Val Ala
145                 150                 155                 160 acc tgc gat aaa ggg ctg ccc gcc acc atg att gcg ctg gcc gcg atg     528
Thr Cys Asp Lys Gly Leu Pro Ala Thr Met Ile Ala Leu Ala Ala Met
                165                 170                 175 cac gac ctg ccg act att ctg gtg ccg ggc ggg gcg acg ctg ccg ccg     576
His Asp Leu Pro Thr Ile Leu Val Pro Gly Gly Ala Thr Leu Pro Pro
            180                 185                 190
```

```
acc gtc ggg gaa gac gcg ggc aag gtg cag acc atc ggc gcg cgt ttc      624
Thr Val Gly Glu Asp Ala Gly Lys Val Gln Thr Ile Gly Ala Arg Phe
        195                 200                 205 gcc aac cac gaa ctc tcc ctg cag gag gcc gcc gaa ctg ggc tgt cgc      672
Ala Asn His Glu Leu Ser Leu Gln Glu Ala Ala Glu Leu Gly Cys Arg
    210                 215                 220 gcc tgc gcc tcg ccg ggc ggc ggg tgt cag ttc ctc ggc acg gcg ggc      720
Ala Cys Ala Ser Pro Gly Gly Gly Cys Gln Phe Leu Gly Thr Ala Gly
225                 230                 235                 240 acc tcg cag gtg gtc gcg gag gcg ctg ggt ctg gcg ctg ccg cac tcc      768
Thr Ser Gln Val Val Ala Glu Ala Leu Gly Leu Ala Leu Pro His Ser
                245                 250                 255 gcg ctg gcg ccg tcc ggg cag gcg gtg tgg ctg gag atc gcc cgc cag      816
Ala Leu Ala Pro Ser Gly Gln Ala Val Trp Leu Glu Ile Ala Arg Gln
            260                 265                 270 tcg gcg cgc gcg gtc agc gag ctg gat agc cgc ggc atc acc acg cgg      864
Ser Ala Arg Ala Val Ser Glu Leu Asp Ser Arg Gly Ile Thr Thr Arg
        275                 280                 285 gat atc ctc tcc gat aaa gcc atc gaa aac gcg atg gtg atc cac gcg      912
Asp Ile Leu Ser Asp Lys Ala Ile Glu Asn Ala Met Val Ile His Ala
    290                 295                 300 gcg ttc ggc ggc tcc acc aat tta ctg ctg cac att ccg gcc atc gcc      960
Ala Phe Gly Gly Ser Thr Asn Leu Leu Leu His Ile Pro Ala Ile Ala
305                 310                 315                 320 cac gcg gcg ggc tgc acg atc ccg gac gtt gag cac tgg acg cgc atc     1008
His Ala Ala Gly Cys Thr Ile Pro Asp Val Glu His Trp Thr Arg Ile
                325                 330                 335 aac cgt aaa gtg ccg cgt ctg gtg agc gtg ctg ccc aac ggc ccg gac     1056
Asn Arg Lys Val Pro Arg Leu Val Ser Val Leu Pro Asn Gly Pro Asp
            340                 345                 350 tat cac ccg acc gtg cgc gcc ttc ctc gcg ggc ggc gtg ccg gag gtg     1104
Tyr His Pro Thr Val Arg Ala Phe Leu Ala Gly Gly Val Pro Glu Val
        355                 360                 365 atg ctc cac ctg cgc gac ctc ggc ctg ctg cat ctg gac gcc atg acc     1152
Met Leu His Leu Arg Asp Leu Gly Leu Leu His Leu Asp Ala Met Thr
    370                 375                 380 gtg acc ggc cag acg gtg ggc gag aac ctt gaa tgg tgg cag gcg tcc     1200
Val Thr Gly Gln Thr Val Gly Glu Asn Leu Glu Trp Trp Gln Ala Ser
385                 390                 395                 400 gag cgc cgg gcg cgc ttc cgc cag tgc ctg cgc gag cag gac ggc gta     1248
Glu Arg Arg Ala Arg Phe Arg Gln Cys Leu Arg Glu Gln Asp Gly Val
                405                 410                 415 gag ccg gat gac gtg atc ctg ccg ccg gag aag gca aaa gcg aaa ggg     1296
Glu Pro Asp Asp Val Ile Leu Pro Pro Glu Lys Ala Lys Ala Lys Gly
            420                 425                 430 ctg acc tcg acg gtc tgc ttc ccg acg ggc aac atc gct ccg gaa ggt     1344
Leu Thr Ser Thr Val Cys Phe Pro Thr Gly Asn Ile Ala Pro Glu Gly
        435                 440                 445 tcg gtg atc aag gcc acg gcg atc gac ccg tcg gtg gtg ggc gaa gat     1392
Ser Val Ile Lys Ala Thr Ala Ile Asp Pro Ser Val Val Gly Glu Asp
    450                 455                 460 ggc gta tac cac cac acc ggc cgg gtg cgg gtg ttt gtc tcg gaa gcg     1440
Gly Val Tyr His His Thr Gly Arg Val Arg Val Phe Val Ser Glu Ala
465                 470                 475                 480 cag gcg atc aag gcg atc aag cgg gaa gag att gtg cag ggc gat atc     1488
Gln Ala Ile Lys Ala Ile Lys Arg Glu Glu Ile Val Gln Gly Asp Ile
                485                 490                 495 atg gtg gtg atc ggc ggg ggg ccg tcc ggc acc ggc atg gaa gag acc     1536
Met Val Val Ile Gly Gly Gly Pro Ser Gly Thr Gly Met Glu Glu Thr
```

```
                       500                 505                 510
tac cag ctc acc tcc gcg cta aag cat atc tcg tgg ggc aag acg gtg    1584
Tyr Gln Leu Thr Ser Ala Leu Lys His Ile Ser Trp Gly Lys Thr Val
            515                 520                 525 tcg ctc atc acc gat gcg cgc ttc tcg ggc gtg tcg acg ggc gcc tgc    1632
Ser Leu Ile Thr Asp Ala Arg Phe Ser Gly Val Ser Thr Gly Ala Cys
        530                 535                 540 ttc ggc cac gtg tcg ccg gag gcg ctg gcg ggc ggg ccg att ggc aag    1680
Phe Gly His Val Ser Pro Glu Ala Leu Ala Gly Gly Pro Ile Gly Lys
545                 550                 555                 560 ctg cgc gat aac gac atc atc gag att gcc gtg gat cgt ctg acg tta    1728
Leu Arg Asp Asn Asp Ile Ile Glu Ile Ala Val Asp Arg Leu Thr Leu
                565                 570                 575 act ggc agc gtg aac ttc atc ggc acc gcg gac aac ccg ctg acg ccg    1776
Thr Gly Ser Val Asn Phe Ile Gly Thr Ala Asp Asn Pro Leu Thr Pro
            580                 585                 590 gaa gag ggc gcg cgc gag ctg gcg cgg cgg cag acg cac ccg gac ctg    1824
Glu Glu Gly Ala Arg Glu Leu Ala Arg Arg Gln Thr His Pro Asp Leu
        595                 600                 605 cac gcc cac gac ttt ttg ccg gac gac acc cgg ctg tgg gcg gca ctg    1872
His Ala His Asp Phe Leu Pro Asp Asp Thr Arg Leu Trp Ala Ala Leu
610                 615                 620 cag tcg gtg agc ggc ggc acc tgg aaa ggc tgt att tat gac acc gat    1920
Gln Ser Val Ser Gly Gly Thr Trp Lys Gly Cys Ile Tyr Asp Thr Asp
625                 630                 635                 640 aaa att atc gag gta att aac gcc ggt aaa aaa gcg ctc gga att taa    1968
Lys Ile Ile Glu Val Ile Asn Ala Gly Lys Lys Ala Leu Gly Ile
                645                 650                 655

<210> SEQ ID NO 37
<211> LENGTH: 655
<212> TYPE: PRT
<213> ORGANISM: Escherichia coli

<400> SEQUENCE: 37

Met Thr Ile Glu Lys Ile Phe Thr Pro Gln Asp Asp Ala Phe Tyr Ala
1               5                   10                  15

Val Ile Thr His Ala Ala Gly Pro Gln Gly Ala Leu Pro Leu Thr Pro
            20                  25                  30

Gln Met Leu Met Glu Ser Pro Ser Gly Asn Leu Phe Gly Met Thr Gln
        35                  40                  45

Asn Ala Gly Met Gly Trp Asp Ala Asn Lys Leu Thr Gly Lys Glu Val
    50                  55                  60

Leu Ile Ile Gly Thr Gln Gly Gly Ile Arg Ala Gly Asp Gly Arg Pro
65                  70                  75                  80

Ile Ala Leu Gly Tyr His Thr Gly His Trp Glu Ile Gly Met Gln Met
                85                  90                  95

Gln Ala Ala Ala Lys Glu Ile Thr Arg Asn Gly Gly Ile Pro Phe Ala
            100                 105                 110

Ala Phe Val Ser Asp Pro Cys Asp Gly Arg Ser Gln Gly Thr His Gly
        115                 120                 125

Met Phe Asp Ser Leu Pro Tyr Arg Asn Asp Ala Ala Ile Val Phe Arg
    130                 135                 140

Arg Leu Ile Arg Ser Leu Pro Thr Arg Arg Ala Val Ile Gly Val Ala
145                 150                 155                 160

Thr Cys Asp Lys Gly Leu Pro Ala Thr Met Ile Ala Leu Ala Ala Met
                165                 170                 175
```

```
His Asp Leu Pro Thr Ile Leu Val Pro Gly Ala Thr Leu Pro Pro
                180                 185                 190
Thr Val Gly Glu Asp Ala Gly Lys Val Gln Thr Ile Gly Ala Arg Phe
            195                 200                 205
Ala Asn His Glu Leu Ser Leu Gln Glu Ala Ala Glu Leu Gly Cys Arg
        210                 215                 220
Ala Cys Ala Ser Pro Gly Gly Cys Gln Phe Leu Gly Thr Ala Gly
225                 230                 235                 240
Thr Ser Gln Val Val Ala Glu Ala Leu Gly Leu Ala Leu Pro His Ser
                245                 250                 255
Ala Leu Ala Pro Ser Gly Gln Ala Val Trp Leu Glu Ile Ala Arg Gln
            260                 265                 270
Ser Ala Arg Ala Val Ser Glu Leu Asp Ser Arg Gly Ile Thr Thr Arg
        275                 280                 285
Asp Ile Leu Ser Asp Lys Ala Ile Glu Asn Ala Met Val Ile His Ala
290                 295                 300
Ala Phe Gly Gly Ser Thr Asn Leu Leu Leu His Ile Pro Ala Ile Ala
                305                 310                 315                 320
His Ala Ala Gly Cys Thr Ile Pro Asp Val Glu His Trp Thr Arg Ile
            325                 330                 335
Asn Arg Lys Val Pro Arg Leu Val Ser Val Leu Pro Asn Gly Pro Asp
        340                 345                 350
Tyr His Pro Thr Val Arg Ala Phe Leu Ala Gly Gly Val Pro Glu Val
        355                 360                 365
Met Leu His Leu Arg Asp Leu Gly Leu Leu His Leu Asp Ala Met Thr
    370                 375                 380
Val Thr Gly Gln Thr Val Gly Glu Asn Leu Glu Trp Trp Gln Ala Ser
385                 390                 395                 400
Glu Arg Arg Ala Arg Phe Arg Gln Cys Leu Arg Glu Gln Asp Gly Val
                405                 410                 415
Glu Pro Asp Asp Val Ile Leu Pro Pro Glu Lys Ala Lys Ala Lys Gly
            420                 425                 430
Leu Thr Ser Thr Val Cys Phe Pro Thr Gly Asn Ile Ala Pro Glu Gly
        435                 440                 445
Ser Val Ile Lys Ala Thr Ala Ile Asp Pro Ser Val Val Gly Glu Asp
    450                 455                 460
Gly Val Tyr His His Thr Gly Arg Val Arg Val Phe Val Ser Glu Ala
465                 470                 475                 480
Gln Ala Ile Lys Ala Ile Lys Arg Glu Glu Ile Val Gln Gly Asp Ile
                485                 490                 495
Met Val Val Ile Gly Gly Pro Ser Gly Thr Gly Met Glu Glu Thr
            500                 505                 510
Tyr Gln Leu Thr Ser Ala Leu Lys His Ile Ser Trp Gly Lys Thr Val
        515                 520                 525
Ser Leu Ile Thr Asp Ala Arg Phe Ser Gly Val Ser Thr Gly Ala Cys
    530                 535                 540
Phe Gly His Val Ser Pro Glu Ala Leu Ala Gly Gly Pro Ile Gly Lys
545                 550                 555                 560
Leu Arg Asp Asn Asp Ile Ile Glu Ile Ala Val Asp Arg Leu Thr Leu
                565                 570                 575
Thr Gly Ser Val Asn Phe Ile Gly Thr Ala Asp Asn Pro Leu Thr Pro
            580                 585                 590
Glu Glu Gly Ala Arg Glu Leu Ala Arg Arg Gln Thr His Pro Asp Leu
```

```
                    595                 600                 605
His Ala His Asp Phe Leu Pro Asp Asp Thr Arg Leu Trp Ala Ala Leu
        610                 615                 620

Gln Ser Val Ser Gly Gly Thr Trp Lys Gly Cys Ile Tyr Asp Thr Asp
625                 630                 635                 640

Lys Ile Ile Glu Val Ile Asn Ala Gly Lys Lys Ala Leu Gly Ile
                645                 650                 655
```

<210> SEQ ID NO 38
<211> LENGTH: 40
<212> TYPE: DNA
<213> ORGANISM: Artificial Sequence
<220> FEATURE:
<223> OTHER INFORMATION: primer xylX_IFS_5742-10-1

<400> SEQUENCE: 38
acacaaggag actcccatgg gcgtgagtga attcctgccg                            40

<210> SEQ ID NO 39
<211> LENGTH: 40
<212> TYPE: DNA
<213> ORGANISM: Artificial Sequence
<220> FEATURE:
<223> OTHER INFORMATION: primer xylX_IFA_5742-10-2

<400> SEQUENCE: 39
ggaactggcg gctcccttag aggaggccgc ggccggccag                            40

<210> SEQ ID NO 40
<211> LENGTH: 40
<212> TYPE: DNA
<213> ORGANISM: Artificial Sequence
<220> FEATURE:
<223> OTHER INFORMATION: primer xylA_IFS_5742-10-3

<400> SEQUENCE: 40
acacaaggag actcccatga ccgacaccct gcgccattac                            40

<210> SEQ ID NO 41
<211> LENGTH: 40
<212> TYPE: DNA
<213> ORGANISM: Artificial Sequence
<220> FEATURE:
<223> OTHER INFORMATION: primer xylA_IFA_5742-10-4

<400> SEQUENCE: 41
ggaactggcg gctcccttac gaccacgagt aggaggtttt                            40

<210> SEQ ID NO 42
<211> LENGTH: 40
<212> TYPE: DNA
<213> ORGANISM: Artificial Sequence
<220> FEATURE:
<223> OTHER INFORMATION: primer xylD_IFS_5742-10-5

<400> SEQUENCE: 42
acacaaggag actcccatgt ctaaccgcac gccccgccgg                            40

<210> SEQ ID NO 43
<211> LENGTH: 40
<212> TYPE: DNA
<213> ORGANISM: Artificial Sequence
<220> FEATURE:
<223> OTHER INFORMATION: primer xylD-IFA_5742-10-6

```
<400> SEQUENCE: 43
ggaactggcg gctccctcag tggttgtggc ggggcagctt                          40

<210> SEQ ID NO 44
<211> LENGTH: 44
<212> TYPE: DNA
<213> ORGANISM: Artificial Sequence
<220> FEATURE:
<223> OTHER INFORMATION: primer CC0823-01F_4691-87-1

<400> SEQUENCE: 44
gtcgactcta gaggatcccc gtgggcgtga gtgaattcct gccg                     44

<210> SEQ ID NO 45
<211> LENGTH: 24
<212> TYPE: DNA
<213> ORGANISM: Artificial Sequence
<220> FEATURE:
<223> OTHER INFORMATION: primer CC0823-01R_4691-87-2

<400> SEQUENCE: 45
tatgcctgtc ctgccagcac tgcc                                           24

<210> SEQ ID NO 46
<211> LENGTH: 24
<212> TYPE: DNA
<213> ORGANISM: Artificial Sequence
<220> FEATURE:
<223> OTHER INFORMATION: primer CC0823-02F_4691-87-3

<400> SEQUENCE: 46
ggcagtgctg gcaggacagg cata                                           24

<210> SEQ ID NO 47
<211> LENGTH: 44
<212> TYPE: DNA
<213> ORGANISM: Artificial Sequence
<220> FEATURE:
<223> OTHER INFORMATION: primer CC0823-02R_4691-87-4

<400> SEQUENCE: 47
cgaattcgag ctcggtaccc ttagaggagg ccgcggccgg ccag                     44

<210> SEQ ID NO 48
<211> LENGTH: 44
<212> TYPE: DNA
<213> ORGANISM: Artificial Sequence
<220> FEATURE:
<223> OTHER INFORMATION: primer CC0822-01F_4691-87-5

<400> SEQUENCE: 48
gtcgactcta gaggatcccc atgaccgaca ccctgcgcca ttac                     44

<210> SEQ ID NO 49
<211> LENGTH: 24
<212> TYPE: DNA
<213> ORGANISM: Artificial Sequence
<220> FEATURE:
<223> OTHER INFORMATION: primer CC0822-01R_5659-8-7

<400> SEQUENCE: 49
gcgtcggccc aggccgggaa tgcc                                           24

<210> SEQ ID NO 50
<211> LENGTH: 24
```

```
<212> TYPE: DNA
<213> ORGANISM: Artificial Sequence
<220> FEATURE:
<223> OTHER INFORMATION: primer CC0822-02F_5659-8-8

<400> SEQUENCE: 50
gtcgacgccg cgcgcaaggc attc                                    24

<210> SEQ ID NO 51
<211> LENGTH: 24
<212> TYPE: DNA
<213> ORGANISM: Artificial Sequence
<220> FEATURE:
<223> OTHER INFORMATION: primer CC0822-02R_5659-8-9

<400> SEQUENCE: 51
gagcgccggg gcggccttcc atgc                                    24

<210> SEQ ID NO 52
<211> LENGTH: 24
<212> TYPE: DNA
<213> ORGANISM: Artificial Sequence
<220> FEATURE:
<223> OTHER INFORMATION: primer CC0822-03F_5659-8-10

<400> SEQUENCE: 52
cttcccgatc gccatcccgg catg                                    24

<210> SEQ ID NO 53
<211> LENGTH: 24
<212> TYPE: DNA
<213> ORGANISM: Artificial Sequence
<220> FEATURE:
<223> OTHER INFORMATION: primer CC0822-03R_5659-8-11

<400> SEQUENCE: 53
cagctgcacg cgggcctgac gtgc                                    24

<210> SEQ ID NO 54
<211> LENGTH: 24
<212> TYPE: DNA
<213> ORGANISM: Artificial Sequence
<220> FEATURE:
<223> OTHER INFORMATION: primer CC0822-04F_5659-8-12

<400> SEQUENCE: 54
ggtcgccgcc gccgccgtgg cacg                                    24

<210> SEQ ID NO 55
<211> LENGTH: 24
<212> TYPE: DNA
<213> ORGANISM: Artificial Sequence
<220> FEATURE:
<223> OTHER INFORMATION: primer CC0822-04R_5659-8-13

<400> SEQUENCE: 55
ggcgaccttc tcggccagca gtgc                                    24

<210> SEQ ID NO 56
<211> LENGTH: 24
<212> TYPE: DNA
<213> ORGANISM: Artificial Sequence
<220> FEATURE:
<223> OTHER INFORMATION: primer CC0822-05F_5659-8-14

<400> SEQUENCE: 56
```

```
ggattcacga caagttcgtg gcac                                            24

<210> SEQ ID NO 57
<211> LENGTH: 44
<212> TYPE: DNA
<213> ORGANISM: Artificial Sequence
<220> FEATURE:
<223> OTHER INFORMATION: primer CC0822-05R_4691-87-14

<400> SEQUENCE: 57
cgaattcgag ctcggtaccc ttacgaccac gagtaggagg tttt                     44

<210> SEQ ID NO 58
<211> LENGTH: 35
<212> TYPE: DNA
<213> ORGANISM: Artificial Sequence
<220> FEATURE:
<223> OTHER INFORMATION: primer Peftu(Pst)

<400> SEQUENCE: 58
ccaagcttgc atgccagatc gtttagatcc gaagg                               35

<210> SEQ ID NO 59
<211> LENGTH: 22
<212> TYPE: DNA
<213> ORGANISM: Artificial Sequence
<220> FEATURE:
<223> OTHER INFORMATION: primer Peftu_Rv

<400> SEQUENCE: 59
tgtatgtcct cctggacttc gt                                             22

<210> SEQ ID NO 60
<211> LENGTH: 52
<212> TYPE: DNA
<213> ORGANISM: Artificial Sequence
<220> FEATURE:
<223> OTHER INFORMATION: primer Peftu_xylXABCD_fw

<400> SEQUENCE: 60
ccaggaggac atacaatggg cgtgagtgaa ttcctgccgg aagattggaa ag             52

<210> SEQ ID NO 61
<211> LENGTH: 39
<212> TYPE: DNA
<213> ORGANISM: Artificial Sequence
<220> FEATURE:
<223> OTHER INFORMATION: primer eftu_xylXABCD_rv

<400> SEQUENCE: 61
cggtacccgg ggatctcagt ggttgtggcg gggcagctt                           39

<210> SEQ ID NO 62
<211> LENGTH: 38
<212> TYPE: DNA
<213> ORGANISM: Artificial Sequence
<220> FEATURE:
<223> OTHER INFORMATION: primer PmsrA(Pst)

<400> SEQUENCE: 62
ccaagcttgc atgccatttg cgcctgcaac gtaggttg                            38

<210> SEQ ID NO 63
<211> LENGTH: 23
<212> TYPE: DNA
<213> ORGANISM: Artificial Sequence
```

```
<220> FEATURE:
<223> OTHER INFORMATION: primer PmsrAR

<400> SEQUENCE: 63
aacaggaatg ttcctttcga aaa                                         23

<210> SEQ ID NO 64
<211> LENGTH: 41
<212> TYPE: DNA
<213> ORGANISM: Artificial Sequence
<220> FEATURE:
<223> OTHER INFORMATION: primer PmsrA_xylD_fw

<400> SEQUENCE: 64
aggaacattc ctgttatgtc taaccgcacg ccccgccggt t                     41

<210> SEQ ID NO 65
<211> LENGTH: 25
<212> TYPE: DNA
<213> ORGANISM: Artificial Sequence
<220> FEATURE:
<223> OTHER INFORMATION: primer SpcR-F

<400> SEQUENCE: 65
ctaataacgt aacgtgactg gcaag                                       25

<210> SEQ ID NO 66
<211> LENGTH: 23
<212> TYPE: DNA
<213> ORGANISM: Artificial Sequence
<220> FEATURE:
<223> OTHER INFORMATION: primer SpcR-R

<400> SEQUENCE: 66
ataagtaaga ttaaccatta gtc                                         23

<210> SEQ ID NO 67
<211> LENGTH: 30
<212> TYPE: DNA
<213> ORGANISM: Artificial Sequence
<220> FEATURE:
<223> OTHER INFORMATION: primer spc(GTG start)-F

<400> SEQUENCE: 67
gtgaggagga tatatttgaa tacatacgaa                                  30

<210> SEQ ID NO 68
<211> LENGTH: 35
<212> TYPE: DNA
<213> ORGANISM: Artificial Sequence
<220> FEATURE:
<223> OTHER INFORMATION: primer spc(stop)-R

<400> SEQUENCE: 68 taatttttt aatctgttat ttaaatagtt tatag                             35

<210> SEQ ID NO 69
<211> LENGTH: 42
<212> TYPE: DNA
<213> ORGANISM: Artificial Sequence
<220> FEATURE:
<223> OTHER INFORMATION: primer Spc-pVC7-Cm-F

<400> SEQUENCE: 69
atatatcctc ctcactttag cttccttagc tcctgaaaat ct                    42
```

<210> SEQ ID NO 70
<211> LENGTH: 45
<212> TYPE: DNA
<213> ORGANISM: Artificial Sequence
<220> FEATURE:
<223> OTHER INFORMATION: primer Spc-pVC7-Cm-R

<400> SEQUENCE: 70
agattaaaaa aattataatt tttttaaggc agttattggt gccct    45

<210> SEQ ID NO 71
<211> LENGTH: 54
<212> TYPE: DNA
<213> ORGANISM: Artificial Sequence
<220> FEATURE:
<223> OTHER INFORMATION: primer ME_Spc_fw

<400> SEQUENCE: 71
ctgtctctta tacacatctc caagcttgca tgccgcggcc tggttggttg ggtt    54

<210> SEQ ID NO 72
<211> LENGTH: 58
<212> TYPE: DNA
<213> ORGANISM: Artificial Sequence
<220> FEATURE:
<223> OTHER INFORMATION: primer ME_Peftu_xylXABCD_rv

<400> SEQUENCE: 72
ctgtctctta tacacatctc ggtacccggg gatctcagtg gttgtggcgg ggcagctt    58

<210> SEQ ID NO 73
<211> LENGTH: 1785
<212> TYPE: DNA
<213> ORGANISM: Agrobacterium tumefaciens
<220> FEATURE:
<221> NAME/KEY: CDS
<222> LOCATION: (1)..(1785)

<400> SEQUENCE: 73

| | | | | | | | | | | | | | | | |
|---|---|---|---|---|---|---|---|---|---|---|---|---|---|---|---|
| atg | agc | gac | gac | aag | aca | ccc | gtg | cgg | cgg | ctg | cga | tcc | cag | gac | tgg | 48 |
| Met | Ser | Asp | Asp | Lys | Thr | Pro | Val | Arg | Arg | Leu | Arg | Ser | Gln | Asp | Trp | |
| 1 | | | | 5 | | | | | 10 | | | | | 15 | | |

| ttc | gac | aac | cct | gac | cat | ctc | gac | atg | acg | gcg | ctc | tat | ctg | gag | cgc | 96 |
| Phe | Asp | Asn | Pro | Asp | His | Leu | Asp | Met | Thr | Ala | Leu | Tyr | Leu | Glu | Arg | |
| | | | 20 | | | | | 25 | | | | | 30 | | | |

| ttc | atg | aat | tat | ggc | gtg | acg | ccg | gaa | gag | ctg | cgt | tcc | ggc | aag | ccg | 144 |
| Phe | Met | Asn | Tyr | Gly | Val | Thr | Pro | Glu | Glu | Leu | Arg | Ser | Gly | Lys | Pro | |
| | | 35 | | | | | 40 | | | | | 45 | | | | |

| gtc | atc | ggc | atc | gcg | cag | agc | ggc | agc | gac | ctg | acg | ccc | tgc | aac | cgc | 192 |
| Val | Ile | Gly | Ile | Ala | Gln | Ser | Gly | Ser | Asp | Leu | Thr | Pro | Cys | Asn | Arg | |
| 50 | | | | | 55 | | | | | 60 | | | | | | |

| gtc | cat | gtc | gaa | ctg | gtc | aag | cgg | gtg | cgc | gat | ggt | atc | cgt | gat | gcg | 240 |
| Val | His | Val | Glu | Leu | Val | Lys | Arg | Val | Arg | Asp | Gly | Ile | Arg | Asp | Ala | |
| 65 | | | | 70 | | | | | 75 | | | | | 80 | | |

| ggc | ggc | atc | ccc | atc | gag | ttt | ccg | acc | cat | ccg | atg | ttc | gaa | aac | tgc | 288 |
| Gly | Gly | Ile | Pro | Ile | Glu | Phe | Pro | Thr | His | Pro | Met | Phe | Glu | Asn | Cys | |
| | | | | 85 | | | | | 90 | | | | | 95 | | |

| aag | cga | ccg | aca | gcg | gcg | ctt | gac | cgc | aat | ctt | gcc | tat | ctc | agc | ctg | 336 |
| Lys | Arg | Pro | Thr | Ala | Ala | Leu | Asp | Arg | Asn | Leu | Ala | Tyr | Leu | Ser | Leu | |
| | | | 100 | | | | | 105 | | | | | 110 | | | |

| gtg | gaa | gtg | ctt | tac | ggt | tat | cca | ctc | gat | ggc | gtc | gtg | ttg | acc | acg | 384 |
| Val | Glu | Val | Leu | Tyr | Gly | Tyr | Pro | Leu | Asp | Gly | Val | Val | Leu | Thr | Thr | |
| | | | | 115 | | | | | 120 | | | | | 125 | | |

-continued

| | |
|---|---|
| ggc tgc gac aag acc acg cct tcg gcg ctg atg gcg gca agc acg gtt<br>Gly Cys Asp Lys Thr Thr Pro Ser Ala Leu Met Ala Ala Ser Thr Val<br>130                          135                          140 | 432 |
| gat att ccg gct atc gtc tta tcc ggc ggg ccg atg ctc gac gga tat<br>Asp Ile Pro Ala Ile Val Leu Ser Gly Gly Pro Met Leu Asp Gly Tyr<br>145                        150                        155                        160 | 480 |
| cat gac ggc gat ctg gtt ggt tcc ggc acg gtc atc tgg cgc atg cgc<br>His Asp Gly Asp Leu Val Gly Ser Gly Thr Val Ile Trp Arg Met Arg<br>                      165                        170                        175 | 528 |
| cgc aaa tac ggc gcc ggc gaa atc acc cgc gag gaa ttc ctg cag gcg<br>Arg Lys Tyr Gly Ala Gly Glu Ile Thr Arg Glu Glu Phe Leu Gln Ala<br>                  180                        185                        190 | 576 |
| gcg ctc gaa tcc gct cct tcg gtc ggt cac tgc aac acc atg ggc acg<br>Ala Leu Glu Ser Ala Pro Ser Val Gly His Cys Asn Thr Met Gly Thr<br>      195                        200                        205 | 624 |
| gcc tct acc atg aat gcc att gcc gaa gcg ctc ggc atg tcg ctg acc<br>Ala Ser Thr Met Asn Ala Ile Ala Glu Ala Leu Gly Met Ser Leu Thr<br>210                          215                          220 | 672 |
| ggc tgc ggc gca atc ccg gcc gct tac cgc gaa cgc ggc cag atg gcc<br>Gly Cys Gly Ala Ile Pro Ala Ala Tyr Arg Glu Arg Gly Gln Met Ala<br>225                          230                        235                        240 | 720 |
| tat cgc acc ggc cgc cgc gcc gtc gaa ctg gtt gtc gag aat atc aag<br>Tyr Arg Thr Gly Arg Arg Ala Val Glu Leu Val Val Glu Asn Ile Lys<br>                  245                        250                        255 | 768 |
| cct tcg gat atc atg acg cgc gag gcg ttt ttg aac gcg atc cgc gtc<br>Pro Ser Asp Ile Met Thr Arg Glu Ala Phe Leu Asn Ala Ile Arg Val<br>                    260                        265                        270 | 816 |
| aat tcg gca atc ggc ggt tcg aca aat gcc cag ccg cat ctg gcg gcg<br>Asn Ser Ala Ile Gly Gly Ser Thr Asn Ala Gln Pro His Leu Ala Ala<br>                      275                        280                        285 | 864 |
| atg gcg aaa cat gcg ggc gtc gaa ctt cgc gag gaa gac tgg cag gtt<br>Met Ala Lys His Ala Gly Val Glu Leu Arg Glu Glu Asp Trp Gln Val<br>290                          295                          300 | 912 |
| cac ggt tat gac att ccg ctc atc gcc aat gtc cag ccc gcc gga aaa<br>His Gly Tyr Asp Ile Pro Leu Ile Ala Asn Val Gln Pro Ala Gly Lys<br>305                          310                        315                        320 | 960 |
| tgg ctg ggc gag aaa tat cac cgt gcc ggc ggt acg ccc gcc atc atg<br>Trp Leu Gly Glu Lys Tyr His Arg Ala Gly Gly Thr Pro Ala Ile Met<br>                  325                        330                        335 | 1008 |
| tgg gag ctt ctg aag gca ggc aag ctt gat ggg agc tgt ccg acc gtg<br>Trp Glu Leu Leu Lys Ala Gly Lys Leu Asp Gly Ser Cys Pro Thr Val<br>                    340                        345                        350 | 1056 |
| acc ggc aag acc gtg gcg gaa aat ctg gac ggg cgg gaa tcg acc gac<br>Thr Gly Lys Thr Val Ala Glu Asn Leu Asp Gly Arg Glu Ser Thr Asp<br>                  355                        360                        365 | 1104 |
| cgc gac gtg atc ctt cct tac gat aag ccg ctc aag gaa cgg gcc ggt<br>Arg Asp Val Ile Leu Pro Tyr Asp Lys Pro Leu Lys Glu Arg Ala Gly<br>370                          375                        380 | 1152 |
| ttc ctc gtc ctc aag ggc aat ctg ttc gat ttc gcc atc atg aag acg<br>Phe Leu Val Leu Lys Gly Asn Leu Phe Asp Phe Ala Ile Met Lys Thr<br>385                          390                        395                        400 | 1200 |
| agt gtg atc tcg gcg gaa ttc cgg cag cgt tat ctg agt gag ccg ggt<br>Ser Val Ile Ser Ala Glu Phe Arg Gln Arg Tyr Leu Ser Glu Pro Gly<br>                    405                        410                        415 | 1248 |
| cga gag ggg att ttc gag ggc aaa tgt gtg gtt ttc gat ggt tcg gaa<br>Arg Glu Gly Ile Phe Glu Gly Lys Cys Val Val Phe Asp Gly Ser Glu<br>                    420                        425                        430 | 1296 |
| gac tat cac gcc cgt atc aac gat ccg tct ctc gat atc gat gag cgc<br>Asp Tyr His Ala Arg Ile Asn Asp Pro Ser Leu Asp Ile Asp Glu Arg<br>                    435                        440                        445 | 1344 |

```
acc att ctc gtc att cgc ggg gcc gga ccg ctc ggc tgg ccg ggt tcg       1392
Thr Ile Leu Val Ile Arg Gly Ala Gly Pro Leu Gly Trp Pro Gly Ser
    450                 455                 460 gct gag gtc gtc aac atg cag ccg ccg gac gcg ctg ttg aaa aaa ggc       1440
Ala Glu Val Val Asn Met Gln Pro Pro Asp Ala Leu Leu Lys Lys Gly
465                 470                 475                 480 ata acc agc ctg ccg aca atc ggc gac ggc cgg caa tcg gga acc gcg       1488
Ile Thr Ser Leu Pro Thr Ile Gly Asp Gly Arg Gln Ser Gly Thr Ala
                485                 490                 495 gac agc ccg tcg atc ctc aat gcc tcg cca gaa agt gcc gcc ggt gga       1536
Asp Ser Pro Ser Ile Leu Asn Ala Ser Pro Glu Ser Ala Ala Gly Gly
            500                 505                 510 gga ctg gca tgg ctt cgc acg ggt gat gta atc cgc atc gac ttc aat       1584
Gly Leu Ala Trp Leu Arg Thr Gly Asp Val Ile Arg Ile Asp Phe Asn
        515                 520                 525 cag ggc aag tgc gac gcg ttg gta ccg gat gca gag ctt gct gcc cga       1632
Gln Gly Lys Cys Asp Ala Leu Val Pro Asp Ala Glu Leu Ala Ala Arg
    530                 535                 540 aag gcc gat ggc att cct gcg gtg cct gcg gat gcc acg ccc tgg cag       1680
Lys Ala Asp Gly Ile Pro Ala Val Pro Ala Asp Ala Thr Pro Trp Gln
545                 550                 555                 560 cgc atc tat cgt caa tcg gtg acc cag ctt tcg gac ggt gcg gtt ctg       1728
Arg Ile Tyr Arg Gln Ser Val Thr Gln Leu Ser Asp Gly Ala Val Leu
                565                 570                 575 gaa ggg gcc gcg gat ttc cgc cgg att gcc gag aag atg ccc cgg cac       1776
Glu Gly Ala Ala Asp Phe Arg Arg Ile Ala Glu Lys Met Pro Arg His
            580                 585                 590 aac cat tga                                                           1785
Asn His <210> SEQ ID NO 74
<211> LENGTH: 594
<212> TYPE: PRT
<213> ORGANISM: Agrobacterium tumefaciens

<400> SEQUENCE: 74

Met Ser Asp Asp Lys Thr Pro Val Arg Arg Leu Arg Ser Gln Asp Trp
1               5                   10                  15

Phe Asp Asn Pro Asp His Leu Asp Met Thr Ala Leu Tyr Leu Glu Arg
            20                  25                  30

Phe Met Asn Tyr Gly Val Thr Pro Glu Glu Leu Arg Ser Gly Lys Pro
        35                  40                  45

Val Ile Gly Ile Ala Gln Ser Gly Ser Asp Leu Thr Pro Cys Asn Arg
    50                  55                  60

Val His Val Glu Leu Val Lys Arg Val Arg Asp Gly Ile Arg Asp Ala
65                  70                  75                  80

Gly Gly Ile Pro Ile Glu Phe Pro Thr His Pro Met Phe Glu Asn Cys
                85                  90                  95

Lys Arg Pro Thr Ala Ala Leu Asp Arg Asn Leu Ala Tyr Leu Ser Leu
            100                 105                 110

Val Glu Val Leu Tyr Gly Tyr Pro Leu Asp Gly Val Val Leu Thr Thr
        115                 120                 125

Gly Cys Asp Lys Thr Thr Pro Ser Ala Leu Met Ala Ser Thr Val
    130                 135                 140

Asp Ile Pro Ala Ile Val Leu Ser Gly Gly Pro Met Leu Asp Gly Tyr
145                 150                 155                 160

His Asp Gly Asp Leu Val Gly Ser Gly Thr Val Ile Trp Arg Met Arg
```

```
                165                 170                 175
Arg Lys Tyr Gly Ala Gly Glu Ile Thr Arg Glu Glu Phe Leu Gln Ala
                180                 185                 190

Ala Leu Glu Ser Ala Pro Ser Val Gly His Cys Asn Thr Met Gly Thr
                195                 200                 205

Ala Ser Thr Met Asn Ala Ile Ala Glu Ala Leu Gly Met Ser Leu Thr
    210                 215                 220

Gly Cys Gly Ala Ile Pro Ala Ala Tyr Arg Glu Arg Gly Gln Met Ala
225                 230                 235                 240

Tyr Arg Thr Gly Arg Arg Ala Val Glu Leu Val Val Glu Asn Ile Lys
                245                 250                 255

Pro Ser Asp Ile Met Thr Arg Glu Ala Phe Leu Asn Ala Ile Arg Val
                260                 265                 270

Asn Ser Ala Ile Gly Gly Ser Thr Asn Ala Gln Pro His Leu Ala Ala
                275                 280                 285

Met Ala Lys His Ala Gly Val Glu Leu Arg Glu Glu Asp Trp Gln Val
            290                 295                 300

His Gly Tyr Asp Ile Pro Leu Ile Ala Asn Val Gln Pro Ala Gly Lys
305                 310                 315                 320

Trp Leu Gly Glu Lys Tyr His Arg Ala Gly Thr Pro Ala Ile Met
                325                 330                 335

Trp Glu Leu Leu Lys Ala Gly Lys Leu Asp Gly Ser Cys Pro Thr Val
                340                 345                 350

Thr Gly Lys Thr Val Ala Glu Asn Leu Asp Gly Arg Glu Ser Thr Asp
            355                 360                 365

Arg Asp Val Ile Leu Pro Tyr Asp Lys Pro Leu Lys Glu Arg Ala Gly
    370                 375                 380

Phe Leu Val Leu Lys Gly Asn Leu Phe Asp Phe Ala Ile Met Lys Thr
385                 390                 395                 400

Ser Val Ile Ser Ala Glu Phe Arg Gln Arg Tyr Leu Ser Glu Pro Gly
                405                 410                 415

Arg Glu Gly Ile Phe Glu Gly Lys Cys Val Val Phe Asp Gly Ser Glu
                420                 425                 430

Asp Tyr His Ala Arg Ile Asn Asp Pro Ser Leu Asp Ile Asp Glu Arg
            435                 440                 445

Thr Ile Leu Val Ile Arg Gly Ala Gly Pro Leu Gly Trp Pro Gly Ser
    450                 455                 460

Ala Glu Val Val Asn Met Gln Pro Pro Asp Ala Leu Leu Lys Lys Gly
465                 470                 475                 480

Ile Thr Ser Leu Pro Thr Ile Gly Asp Gly Arg Gln Ser Gly Thr Ala
                485                 490                 495

Asp Ser Pro Ser Ile Leu Asn Ala Ser Pro Glu Ser Ala Ala Gly Gly
            500                 505                 510

Gly Leu Ala Trp Leu Arg Thr Gly Asp Val Ile Arg Ile Asp Phe Asn
        515                 520                 525

Gln Gly Lys Cys Asp Ala Leu Val Pro Asp Ala Glu Leu Ala Ala Arg
530                 535                 540

Lys Ala Asp Gly Ile Pro Ala Val Pro Ala Asp Ala Thr Pro Trp Gln
545                 550                 555                 560

Arg Ile Tyr Arg Gln Ser Val Thr Gln Leu Ser Asp Gly Ala Val Leu
                565                 570                 575

Glu Gly Ala Ala Asp Phe Arg Arg Ile Ala Glu Lys Met Pro Arg His
            580                 585                 590
```

Asn His

<210> SEQ ID NO 75
<211> LENGTH: 1785
<212> TYPE: DNA
<213> ORGANISM: Artificial Sequence
<220> FEATURE:
<223> OTHER INFORMATION: synthetic DNA

<400> SEQUENCE: 75

```
atgagcgatg ataaaacccc ggtgcgtcgc ctgcgttctc aggattggtt tgataacccg      60
gatcatctgg atatgacggc gctgtatctg aacgcttta tgaattatgg tgtgaccccg     120
gaagaactgc gcagcggtaa accggttatt ggcatcgccc agagcggttc tgatctgacc     180
ccgtgcaacc gtgtgcatgt tgaactggtg aaacgtgttc gcgatggtat tcgcgatgca     240
ggcggtattc cgatcgaatt tccgacgcac ccgatgttcg aaaactgtaa acgtccgacc     300
gcggccctgg atcgtaatct ggcctatctg agcctggtgg aagttctgta tggctacccg     360
ctggatggtg tggttctgac cacgggctgc gataaaacca ccccgagtgc cctgatggca     420
gccagcaccg tggatattcc ggcaatcgtt ctgagcggcg gtccgatgct ggatggttat     480
catgatggcg atctggtggg ttctggcacg gttatttggc gtatgcgtcg caaatacggt     540
gccggcgaaa tcacccgcga agaatttctg caggccgcac tggaatctgc gccgagtgtg     600
ggccactgca acaccatggg tacggcctct accatgaatg ccattgcaga gccctgggt     660
atgagtctga ccggttgtgg tgccatcccg gccgcatatc gtgaacgtgg ccagatggcc     720
tatcgcaccg gtcgtcgcgc ggtggaactg gtggttgaaa acattaaacc gagcgatatc     780
atgacgcgtg aagcatttct gaacgcgatt cgcgttaatt ctgcaatcgg cggtagtacc     840
aatgcgcagc cgcatctggc agcgatggcg aaacacgccg cgtgaaact gcgtgaagaa     900
gattggcagg ttcatggtta tgatattccg ctgatcgcca atgtgcagcc ggccggtaaa     960
tggctgggcg aaaaatatca ccgtgcgggc ggcaccccgg caattatgtg ggaactgctg    1020
aaagccggta actggatgg cagttgtccg accgtgacgg gcaaaacggt tgcagaaaac    1080
ctggatggtc gtgaaagcac cgatcgcgat gttatcctgc cgtatgataa accgctgaaa    1140
gaacgtgcgg gctttctggt gctgaaaggt aatctgtttg atttcgcgat tatgaaaacc    1200
agcgttatct ctgccgaatt tcgtcagcgt tatctgtctg aaccgggtcg tgaaggcatt    1260
tttgaaggca atgcgtggt tttcgatggt agtgaagatt accacgcccg cattaacgat    1320
ccgagcctgg atatcgatga acgtaccatt ctggtgattc gcggtgcagg tccgctgggt    1380
tggccgggca gcgcggaagt ggttaatatg cagccgccag atgcgctgct gaaaaaaggc    1440
attacgtctc tgccgaccat cggtgatggc cgccagagtg gtacgccga tagtccgagc    1500
atcctgaatg caagtccgga aagcgccgca ggcggtggcc tggcctggct gcgtaccggt    1560
gatgtgattc gcatcgattt taatcagggt aaatgtgatg cactggttcc ggatgcggaa    1620
ctggcggccc gtaaagccga tggcattccg gcagttccgg cggatgcaac cccgtggcag    1680
cgtatctacc gccagagcgt gacccagctg tctgatggcg cagttctgga aggtgcagcg    1740
gatttccgtc gcattgcgga aaaaatgccg cgccataacc actga                  1785
```

<210> SEQ ID NO 76
<211> LENGTH: 1785
<212> TYPE: DNA
<213> ORGANISM: Herbaspirillum seropedicae
<220> FEATURE:

-continued

<210> NAME/KEY: CDS
<222> LOCATION: (1)..(1785)

<400> SEQUENCE: 76

```
atg aac aag cca aac gcc acc ccc cgt cgc ttc cgc tcc cag gac tgg      48
Met Asn Lys Pro Asn Ala Thr Pro Arg Arg Phe Arg Ser Gln Asp Trp
1               5                   10                  15 ttc gac aac ccg gac cac atc gac atg acc gcg ctc tac ctg gag cgc      96
Phe Asp Asn Pro Asp His Ile Asp Met Thr Ala Leu Tyr Leu Glu Arg
            20                  25                  30 ttc atg aac tac ggc atc acg gcc gag gag ctg cgc tcg gga cgt ccc     144
Phe Met Asn Tyr Gly Ile Thr Ala Glu Glu Leu Arg Ser Gly Arg Pro
        35                  40                  45 atc atc ggc atc gcc cag agc ggc agc gac atc agc ccc tgc aac cgc     192
Ile Ile Gly Ile Ala Gln Ser Gly Ser Asp Ile Ser Pro Cys Asn Arg
    50                  55                  60 atc cac ctg gag ctg gcc aag cgg gtg cgc gat ggc atc cgc gat gcc     240
Ile His Leu Glu Leu Ala Lys Arg Val Arg Asp Gly Ile Arg Asp Ala
65                  70                  75                  80 ggc ggc att ccc atg gaa ttc ccg ctg cat ccc atc ttc gag aac tgc     288
Gly Gly Ile Pro Met Glu Phe Pro Leu His Pro Ile Phe Glu Asn Cys
                85                  90                  95 cgc cgc ccc acc gcc gcc atc gac cgc aac ctg gcc tac ctg ggc ctg     336
Arg Arg Pro Thr Ala Ala Ile Asp Arg Asn Leu Ala Tyr Leu Gly Leu
            100                 105                 110 gtg gaa atc ctg cac ggc tat ccc atc gac gcc gtg gtg ctc acc acc     384
Val Glu Ile Leu His Gly Tyr Pro Ile Asp Ala Val Val Leu Thr Thr
        115                 120                 125 ggc tgc gac aag acc acg ccc tcg cag atc atg gcc gca gcc acc gtc     432
Gly Cys Asp Lys Thr Thr Pro Ser Gln Ile Met Ala Ala Ala Thr Val
    130                 135                 140 gat atc ccc gcc atc gtg ctc tcc ggc ggc ccc atg ctg gac ggc tgg     480
Asp Ile Pro Ala Ile Val Leu Ser Gly Gly Pro Met Leu Asp Gly Trp
145                 150                 155                 160 atg gat ggc gaa ctg gtc ggc tcc ggc tcg gcc atc tgg aag ggc cgc     528
Met Asp Gly Glu Leu Val Gly Ser Gly Ser Ala Ile Trp Lys Gly Arg
                165                 170                 175 aag ctg ctc tcg gca ggc agc atc gac aac gag aaa ttc ctg gag atc     576
Lys Leu Leu Ser Ala Gly Ser Ile Asp Asn Glu Lys Phe Leu Glu Ile
            180                 185                 190 gcg gcg gcc tcc gcg ccc tcg tcc ggc cac tgc aac acc atg ggc acc     624
Ala Ala Ala Ser Ala Pro Ser Ser Gly His Cys Asn Thr Met Gly Thr
        195                 200                 205 gcc tcc acc atg aac gcc atg gcc gag gcc ctg ggc atg tcg ctg acc     672
Ala Ser Thr Met Asn Ala Met Ala Glu Ala Leu Gly Met Ser Leu Thr
    210                 215                 220 ggc tgc tcg gcc att ccc gcg ccc tac cgc gaa cgc ggc cag atg gcc     720
Gly Cys Ser Ala Ile Pro Ala Pro Tyr Arg Glu Arg Gly Gln Met Ala
225                 230                 235                 240 tat gag acg ggc cgg cgc atc gtc ggc atg gcc tac gaa gac ctg cgt     768
Tyr Glu Thr Gly Arg Arg Ile Val Gly Met Ala Tyr Glu Asp Leu Arg
                245                 250                 255 cct tcc gcc atc ctc acg cgc gac gcc ttc ctc gac gcc atc gtg gtc     816
Pro Ser Ala Ile Leu Thr Arg Asp Ala Phe Leu Asp Ala Ile Val Val
            260                 265                 270 aat gcc gcc atc ggc ggc tcc acc aat gcc cag ccg cac atc atg gcc     864
Asn Ala Ala Ile Gly Gly Ser Thr Asn Ala Gln Pro His Ile Met Ala
        275                 280                 285 atg gcg cgc cat gcg ggc gtg gaa ctg cag tcg gaa gac tgg atg aag     912
Met Ala Arg His Ala Gly Val Glu Leu Gln Ser Glu Asp Trp Met Lys
```

```
                  290                 295                 300
tac  ggc  tac  gac  gtg  cca  ctg  ctg  ctg  aac  atg  cag  ccg  gcc  ggc  aag         960
Tyr  Gly  Tyr  Asp  Val  Pro  Leu  Leu  Leu  Asn  Met  Gln  Pro  Ala  Gly  Lys
305                      310                 315                      320 tac  ctg  ggc  gaa  cgc  ttc  cac  cgc  gcc  ggc  ggc  gtg  ccg  gcc  atc  atg        1008
Tyr  Leu  Gly  Glu  Arg  Phe  His  Arg  Ala  Gly  Gly  Val  Pro  Ala  Ile  Met
               325                      330                      335 tgg  gaa  ctg  cag  cag  gcc  ggc  aag  ctg  cgc  gcc  gag  cgc  atc  acc  gct        1056
Trp  Glu  Leu  Gln  Gln  Ala  Gly  Lys  Leu  Arg  Ala  Glu  Arg  Ile  Thr  Ala
          340                      345                      350 acc  ggc  aag  acc  atg  gcc  gag  aac  ctg  cag  ggc  cgg  gca  tcg  aac  gac        1104
Thr  Gly  Lys  Thr  Met  Ala  Glu  Asn  Leu  Gln  Gly  Arg  Ala  Ser  Asn  Asp
                    355                      360                      365 cgg  gaa  atg  att  tac  cca  ttt  gcc  gcc  ccg  ctg  cgc  gag  cgc  gcc  ggc        1152
Arg  Glu  Met  Ile  Tyr  Pro  Phe  Ala  Ala  Pro  Leu  Arg  Glu  Arg  Ala  Gly
     370                      375                      380 ttc  ctg  gtg  ttg  aag  ggc  aac  ctg  ttc  gac  ttc  gcc  atc  atg  aag  acc        1200
Phe  Leu  Val  Leu  Lys  Gly  Asn  Leu  Phe  Asp  Phe  Ala  Ile  Met  Lys  Thr
385                      390                      395                      400 agc  gtc  atc  tcg  gaa  acc  ttc  cgc  gaa  cgc  tat  ctc  agc  acg  ccc  ggc        1248
Ser  Val  Ile  Ser  Glu  Thr  Phe  Arg  Glu  Arg  Tyr  Leu  Ser  Thr  Pro  Gly
                         405                      410                      415 cag  gag  aac  atc  ttc  gaa  tgc  cgc  gcc  gtg  gtc  ttc  gat  ggt  tcg  gac        1296
Gln  Glu  Asn  Ile  Phe  Glu  Cys  Arg  Ala  Val  Val  Phe  Asp  Gly  Ser  Asp
               420                      425                      430 gac  tat  cac  gcc  cgc  atc  aac  gac  ccg  gcg  ctc  aag  atc  gac  gag  aac        1344
Asp  Tyr  His  Ala  Arg  Ile  Asn  Asp  Pro  Ala  Leu  Lys  Ile  Asp  Glu  Asn
          435                      440                      445 acc  ctg  ctg  gcc  atc  cgt  ggc  gcc  ggc  ccg  gtg  ggc  tgg  ccc  ggt  tcg        1392
Thr  Leu  Leu  Ala  Ile  Arg  Gly  Ala  Gly  Pro  Val  Gly  Trp  Pro  Gly  Ser
     450                      455                      460 gcc  gag  gta  gtc  aac  atg  caa  ccg  ccc  gac  gcc  ctg  atc  aag  cgc  ggt        1440
Ala  Glu  Val  Val  Asn  Met  Gln  Pro  Pro  Asp  Ala  Leu  Ile  Lys  Arg  Gly
465                      470                      475                      480 gta  tcg  acc  ctg  ccg  acg  ctg  ggc  gat  ggc  cgc  cag  tcg  ggc  acc  tcc        1488
Val  Ser  Thr  Leu  Pro  Thr  Leu  Gly  Asp  Gly  Arg  Gln  Ser  Gly  Thr  Ser
                    485                      490                      495 gac  agc  ccc  tcc  atc  ctc  aac  gcc  tcc  ccc  gag  agc  gcc  gtc  ggt  ggc        1536
Asp  Ser  Pro  Ser  Ile  Leu  Asn  Ala  Ser  Pro  Glu  Ser  Ala  Val  Gly  Gly
               500                      505                      510 ggc  ctg  gcc  tac  ctg  cgc  gat  ggc  gac  cgc  gtg  cgc  atc  gac  ctc  aac        1584
Gly  Leu  Ala  Tyr  Leu  Arg  Asp  Gly  Asp  Arg  Val  Arg  Ile  Asp  Leu  Asn
          515                      520                      525 acc  ggc  gag  tgc  aac  atg  ctg  gtc  agc  gag  gaa  gag  ctg  gcg  cgc  cgc        1632
Thr  Gly  Glu  Cys  Asn  Met  Leu  Val  Ser  Glu  Glu  Glu  Leu  Ala  Arg  Arg
     530                      535                      540 aag  agc  gag  ggc  atc  ccg  ccg  gtg  ccg  ccc  agc  cag  acg  ccc  tgg  cag        1680
Lys  Ser  Glu  Gly  Ile  Pro  Pro  Val  Pro  Pro  Ser  Gln  Thr  Pro  Trp  Gln
545                      550                      555                      560 gaa  atc  tat  cgc  agc  acg  gtc  ggc  cag  ctg  gag  acc  ggc  gcc  tgc  atg        1728
Glu  Ile  Tyr  Arg  Ser  Thr  Val  Gly  Gln  Leu  Glu  Thr  Gly  Ala  Cys  Met
                    565                      570                      575 gaa  ctg  gcc  ttg  aag  tac  cag  ggt  gtg  gcc  cag  acc  ctg  ccc  cgg  cac        1776
Glu  Leu  Ala  Leu  Lys  Tyr  Gln  Gly  Val  Ala  Gln  Thr  Leu  Pro  Arg  His
               580                      585                      590 aat  cac  tga                                                                          1785
Asn  His
```

<210> SEQ ID NO 77

<211> LENGTH: 594
<212> TYPE: PRT
<213> ORGANISM: Herbaspirillum seropedicae

<400> SEQUENCE: 77

```
Met Asn Lys Pro Asn Ala Thr Pro Arg Arg Phe Arg Ser Gln Asp Trp
 1               5                  10                  15

Phe Asp Asn Pro Asp His Ile Asp Met Thr Ala Leu Tyr Leu Glu Arg
            20                  25                  30

Phe Met Asn Tyr Gly Ile Thr Ala Glu Glu Leu Arg Ser Gly Arg Pro
        35                  40                  45

Ile Ile Gly Ile Ala Gln Ser Gly Ser Asp Ile Ser Pro Cys Asn Arg
50                  55                  60

Ile His Leu Glu Leu Ala Lys Arg Val Arg Asp Gly Ile Arg Asp Ala
65                  70                  75                  80

Gly Gly Ile Pro Met Glu Phe Pro Leu His Pro Ile Phe Glu Asn Cys
                85                  90                  95

Arg Arg Pro Thr Ala Ala Ile Asp Arg Asn Leu Ala Tyr Leu Gly Leu
            100                 105                 110

Val Glu Ile Leu His Gly Tyr Pro Ile Asp Ala Val Val Leu Thr Thr
        115                 120                 125

Gly Cys Asp Lys Thr Thr Pro Ser Gln Ile Met Ala Ala Ala Thr Val
130                 135                 140

Asp Ile Pro Ala Ile Val Leu Ser Gly Gly Pro Met Leu Asp Gly Trp
145                 150                 155                 160

Met Asp Gly Glu Leu Val Gly Ser Gly Ser Ala Ile Trp Lys Gly Arg
                165                 170                 175

Lys Leu Leu Ser Ala Gly Ser Ile Asp Asn Glu Lys Phe Leu Glu Ile
            180                 185                 190

Ala Ala Ala Ser Ala Pro Ser Ser Gly His Cys Asn Thr Met Gly Thr
        195                 200                 205

Ala Ser Thr Met Asn Ala Met Ala Glu Ala Leu Gly Met Ser Leu Thr
210                 215                 220

Gly Cys Ser Ala Ile Pro Ala Pro Tyr Arg Glu Arg Gly Gln Met Ala
225                 230                 235                 240

Tyr Glu Thr Gly Arg Arg Ile Val Gly Met Ala Tyr Glu Asp Leu Arg
                245                 250                 255

Pro Ser Ala Ile Leu Thr Arg Asp Ala Phe Leu Asp Ala Ile Val Val
            260                 265                 270

Asn Ala Ala Ile Gly Gly Ser Thr Asn Ala Gln Pro His Ile Met Ala
        275                 280                 285

Met Ala Arg His Ala Gly Val Glu Leu Gln Ser Glu Asp Trp Met Lys
290                 295                 300

Tyr Gly Tyr Asp Val Pro Leu Leu Leu Asn Met Gln Pro Ala Gly Lys
305                 310                 315                 320

Tyr Leu Gly Glu Arg Phe His Arg Ala Gly Val Pro Ala Ile Met
                325                 330                 335

Trp Glu Leu Gln Gln Ala Gly Lys Leu Arg Ala Glu Arg Ile Thr Ala
            340                 345                 350

Thr Gly Lys Thr Met Ala Glu Leu Gln Gly Arg Ala Ser Asn Asp
        355                 360                 365

Arg Glu Met Ile Tyr Pro Phe Ala Ala Pro Leu Arg Glu Arg Ala Gly
370                 375                 380

Phe Leu Val Leu Lys Gly Asn Leu Phe Asp Phe Ala Ile Met Lys Thr
```

```
                385                 390                 395                 400
        Ser Val Ile Ser Glu Thr Phe Arg Glu Arg Tyr Leu Ser Thr Pro Gly
                        405                 410                 415
        Gln Glu Asn Ile Phe Glu Cys Arg Ala Val Val Phe Asp Gly Ser Asp
                        420                 425                 430
        Asp Tyr His Ala Arg Ile Asn Asp Pro Ala Leu Lys Ile Asp Glu Asn
                        435                 440                 445
        Thr Leu Leu Ala Ile Arg Gly Ala Gly Pro Val Gly Trp Pro Gly Ser
                450                 455                 460
        Ala Glu Val Val Asn Met Gln Pro Pro Asp Ala Leu Ile Lys Arg Gly
        465                 470                 475                 480
        Val Ser Thr Leu Pro Thr Leu Gly Asp Gly Arg Gln Ser Gly Thr Ser
                        485                 490                 495
        Asp Ser Pro Ser Ile Leu Asn Ala Ser Pro Glu Ser Ala Val Gly Gly
                        500                 505                 510
        Gly Leu Ala Tyr Leu Arg Asp Gly Asp Arg Val Arg Ile Asp Leu Asn
                        515                 520                 525
        Thr Gly Glu Cys Asn Met Leu Val Ser Glu Glu Leu Ala Arg Arg
                530                 535                 540
        Lys Ser Glu Gly Ile Pro Pro Val Pro Pro Ser Gln Thr Pro Trp Gln
        545                 550                 555                 560
        Glu Ile Tyr Arg Ser Thr Val Gly Gln Leu Gly Thr Gly Ala Cys Met
                        565                 570                 575
        Glu Leu Ala Leu Lys Tyr Gln Gly Val Ala Gln Thr Leu Pro Arg His
                        580                 585                 590
        Asn His
```

<210> SEQ ID NO 78
<211> LENGTH: 1785
<212> TYPE: DNA
<213> ORGANISM: Artificial Sequence
<220> FEATURE:
<223> OTHER INFORMATION: synthetic DNA

<400> SEQUENCE: 78

```
atgaacaaac cgaatgccac cccgcgtcgc tttcgtagcc aggattggtt cgataacccg      60
gatcatattg atatgacggc gctgtatctg aacgctttta tgaattacgg cattaccgcc     120
gaagaactgc gtagcggtcg cccgattatc ggcatcgcac agagtggtag cgatatttct     180
ccgtgcaacc gtatccatct ggaactggca aaacgtgttc gcgatggtat tcgcgatgcg     240
ggcggtatcc cgatggaatt tccgctgcac ccgattttcg aaaattgccg tcgcccgacc     300
gccgcaattg atcgtaatct ggcatatctg gcctggtgg aaattctgca tggttacccg     360
atcgatgcgg tggttctgac cacgggctgc gataaaacca cgccgagtca gattatggca     420
gcggccaccg tggatattcc ggcgatcgtt ctgagcggcg tccgatgct ggatggttgg     480
atggatggcg aactggttgg ttctggcagt gccatctgga aggccgcaa actgctgagc     540
gcaggttcta tcgataacga aaagttcctg gaaattgcag ccgcatctgc cccgagctct     600
ggtcactgca acaccatggg tacggcaagt accatgaatg cgatggccga agcactgggc     660
atgagcctga cgggttgttc tgcaattccg gcgccgtatc gtgaacgcgg ccagatggcc     720
tacgaaaccg gccgtcgcat tgtgggtatg gcgtatgaag atctgcgccc gagcgccatc     780
ctgacccgtg atgcctttct ggatgcaatt gtggttaacg cagcgatcgg cggtagcacc     840
aatgcacagc cgcatattat ggcgatggcc cgtcacgcgg gcgttgaact gcagtctgaa     900
```

-continued

```
gattggatga aatatggtta cgatgtgccg ctgctgctga acatgcagcc ggccggtaaa    960
tatctgggcg aacgctttca tcgcgcaggc ggtgttccgg cgattatgtg gaactgcag    1020
caggccggta aactgcgtgc agaacgcatc accgcgacgg gcaaaaccat ggccgaaaac   1080
ctgcagggtc gtgcaagcaa tgatcgcgaa atgatttacc cgtttgccgc accgctgcgt   1140
gaacgtgccg gcttcctggt tctgaaaggt aacctgtttg atttcgccat tatgaaaacg   1200
agtgtgatca gcgaaacctt tcgtgaacgc tatctgtcta cgccgggcca ggaaaatatc   1260
tttgaatgtc gtgcggtggt tttcgatggt agtgatgatt accacgcacg cattaacgat   1320
ccggcgctga aaatcgatga aaataccctg ctggccattc gtggtgccgg tccggttggt   1380
tggccgggta gcgcggaagt ggttaacatg cagccgccag atgccctgat caaacgtggc   1440
gtgagtacgc tgccgaccct gggtgatggc cgccagagcg gcaccagcga ttctccgagt   1500
attctgaatg cctctccgga aagtgcagtg ggcggtggcc tggcatatct gcgtgatggc   1560
gatcgtgttc gcatcgatct gaacacgggt gaatgtaata tgctggtgag tgaagaagaa   1620
ctggcgcgtc gcaaaagcga aggcattccg ccggttccgc cgtctcagac cccgtggcag   1680
gaaatctatc gtagcacggt gggccagctg gaaaccggtg cgtgcatgga actggccctg   1740
aaatatcagg gtgtggccca gaccctgccg cgtcataatc actga                  1785
```

```
<210> SEQ ID NO 79
<211> LENGTH: 1755
<212> TYPE: DNA
<213> ORGANISM: Actinoplanes missouriensis
<220> FEATURE:
<221> NAME/KEY: CDS
<222> LOCATION: (1)..(1755)

<400> SEQUENCE: 79
```

| | | | | | | | | | | | | | | | | |
|---|---|---|---|---|---|---|---|---|---|---|---|---|---|---|---|---|
| atg | gac | cta | cac | agg | ccc | cgg | aag | tta | cga | agg | agg | ctg | gcg | atg | cag | 48 |
| Met | Asp | Leu | His | Arg | Pro | Arg | Lys | Leu | Arg | Arg | Arg | Leu | Ala | Met | Gln | |
| 1 | | | | 5 | | | | | 10 | | | | | 15 | | |

| cga | cgc | agt | gca | cag | tgg | tac | gcc | ggt | gac | gac | cgg | aac | agc | tac | atc | 96 |
|---|---|---|---|---|---|---|---|---|---|---|---|---|---|---|---|---|
| Arg | Arg | Ser | Ala | Gln | Trp | Tyr | Ala | Gly | Asp | Asp | Arg | Asn | Ser | Tyr | Ile | |
| | | | 20 | | | | | 25 | | | | | 30 | | | |

| cac | cgc | gcc | tgg | atg | cgc | cgg | ggc | ctg | ccg | gcc | gac | gcg | ttc | gac | ggg | 144 |
|---|---|---|---|---|---|---|---|---|---|---|---|---|---|---|---|---|
| His | Arg | Ala | Trp | Met | Arg | Arg | Gly | Leu | Pro | Ala | Asp | Ala | Phe | Asp | Gly | |
| | | 35 | | | | | 40 | | | | | 45 | | | | |

| cgc | ccg | cac | atc | gcc | atc | gcc | aac | acc | gcc | tcg | gac | ctg | acc | ccg | tgc | 192 |
|---|---|---|---|---|---|---|---|---|---|---|---|---|---|---|---|---|
| Arg | Pro | His | Ile | Ala | Ile | Ala | Asn | Thr | Ala | Ser | Asp | Leu | Thr | Pro | Cys | |
| | 50 | | | | | 55 | | | | | 60 | | | | | |

| aac | gcc | cac | ttc | gac | gag | gtc | gcc | cgc | agc | gtc | gcc | gac | ggc | atc | cac | 240 |
|---|---|---|---|---|---|---|---|---|---|---|---|---|---|---|---|---|
| Asn | Ala | His | Phe | Asp | Glu | Val | Ala | Arg | Ser | Val | Ala | Asp | Gly | Ile | His | |
| 65 | | | | | 70 | | | | | 75 | | | | | 80 | |

| cgg | gcg | ggc | ggc | gtc | gcg | ctg | aac | ctg | ccc | gtc | gtg | tcg | atc | ggc | gag | 288 |
|---|---|---|---|---|---|---|---|---|---|---|---|---|---|---|---|---|
| Arg | Ala | Gly | Gly | Val | Ala | Leu | Asn | Leu | Pro | Val | Val | Ser | Ile | Gly | Glu | |
| | | | | 85 | | | | | 90 | | | | | 95 | | |

| acc | cag | gtc | cgg | ccc | acc | gcg | atg | ctg | tgg | cga | aac | atg | gcc | gcg | atg | 336 |
|---|---|---|---|---|---|---|---|---|---|---|---|---|---|---|---|---|
| Thr | Gln | Val | Arg | Pro | Thr | Ala | Met | Leu | Trp | Arg | Asn | Met | Ala | Ala | Met | |
| | | | 100 | | | | | 105 | | | | | 110 | | | |

| gcg | atc | gag | gag | atg | ctc | cgc | gcc | aac | ccg | atc | gac | ggc | gtc | gtc | ctg | 384 |
|---|---|---|---|---|---|---|---|---|---|---|---|---|---|---|---|---|
| Ala | Ile | Glu | Glu | Met | Leu | Arg | Ala | Asn | Pro | Ile | Asp | Gly | Val | Val | Leu | |
| | | 115 | | | | | 120 | | | | | 125 | | | | |

| ctc | ggc | ggc | tgc | gac | aag | acc | atc | ccc | gcg | ctg | ctc | atg | ggc | gcc | gcc | 432 |
|---|---|---|---|---|---|---|---|---|---|---|---|---|---|---|---|---|
| Leu | Gly | Gly | Cys | Asp | Lys | Thr | Ile | Pro | Ala | Leu | Leu | Met | Gly | Ala | Ala | |
| | 130 | | | | | 135 | | | | | 140 | | | | | |

| tcg | gtc | gac | ctg | ccg | gcc | gtc | gtg | atg | ccc | ggc | ggc | ccg | atg | ctg | acc | 480 |
|---|---|---|---|---|---|---|---|---|---|---|---|---|---|---|---|---|
| Ser | Val | Asp | Leu | Pro | Ala | Val | Val | Met | Pro | Gly | Gly | Pro | Met | Leu | Thr | |

```
Ser Val Asp Leu Pro Ala Val Val Met Pro Gly Gly Pro Met Leu Thr
145                 150                 155                 160 ggc acc ttc cgg ggc gtg ccg ctc ggc tgc ggc acc gac gtg tgg aag      528
Gly Thr Phe Arg Gly Val Pro Leu Gly Cys Gly Thr Asp Val Trp Lys
                165                 170                 175 ctg agc gag gag gtc cgg gcc ggc acc ctg agc gcc gcc gag ttc acc      576
Leu Ser Glu Glu Val Arg Ala Gly Thr Leu Ser Ala Ala Glu Phe Thr
                180                 185                 190 cgc tcc gag tca tcg atg atc agg agc aag ggc cac tgc aac acc atg      624
Arg Ser Glu Ser Ser Met Ile Arg Ser Lys Gly His Cys Asn Thr Met
            195                 200                 205 ggt acg gcg tcg acc atg ggc ctg ctc gcc gaa gtg ctc ggc atg acc      672
Gly Thr Ala Ser Thr Met Gly Leu Leu Ala Glu Val Leu Gly Met Thr
        210                 215                 220 ctg ccg ggg gtg gcc ggc acg ccc gcc ccg gac agc cgg ctg ctg gag      720
Leu Pro Gly Val Ala Gly Thr Pro Ala Pro Asp Ser Arg Leu Leu Glu
225                 230                 235                 240 gcc gcc cac gcg acc ggg gtg ctc gcc gtc ggc ctg gtc gac gcg gac      768
Ala Ala His Ala Thr Gly Val Leu Ala Val Gly Leu Val Asp Ala Asp
                245                 250                 255 cgc cgc ccg agc cag gtg atg acc cgc ggc tcg ttc ctc aac gcg atc      816
Arg Arg Pro Ser Gln Val Met Thr Arg Gly Ser Phe Leu Asn Ala Ile
                260                 265                 270 gtc gcg ctc gcc gcc ctg ggc ggc tcc acc aac gcc gtc gtg cac ctg      864
Val Ala Leu Ala Ala Leu Gly Gly Ser Thr Asn Ala Val Val His Leu
            275                 280                 285 ctg gcc atc gcc ggc cgg ctc ggc gtg ccg ctg tcc cag gac gac ttc      912
Leu Ala Ile Ala Gly Arg Leu Gly Val Pro Leu Ser Gln Asp Asp Phe
        290                 295                 300 gac acc acc ggc gcc gac gtt ccg ctg ctg gtc gac ctg ctc ccg gcc      960
Asp Thr Thr Gly Ala Asp Val Pro Leu Leu Val Asp Leu Leu Pro Ala
305                 310                 315                 320 ggc cgc ttc ctg atg gac gac ctc tac cgc gcc ggc ggt ctg cac gcc     1008
Gly Arg Phe Leu Met Asp Asp Leu Tyr Arg Ala Gly Gly Leu His Ala
                325                 330                 335 gtc ctc gcc gag gtc cgt gac ctg ctc gac ccg tcc gcg atc acg gtc     1056
Val Leu Ala Glu Val Arg Asp Leu Leu Asp Pro Ser Ala Ile Thr Val
                340                 345                 350 acc ggc cgg ccg ctg acc gag cac ctc ggc gac gcc cgc gtc cac gac     1104
Thr Gly Arg Pro Leu Thr Glu His Leu Gly Asp Ala Arg Val His Asp
            355                 360                 365 cgc gag gtg atc cgg ccg cgg gcc gaa ccg ttg ctg ccg cac gcc ggg     1152
Arg Glu Val Ile Arg Pro Arg Ala Glu Pro Leu Leu Pro His Ala Gly
        370                 375                 380 atc gcg gtc ctc tac ggc aac ctg gcg ccg gac ggc gcg gtc gtc aaa     1200
Ile Ala Val Leu Tyr Gly Asn Leu Ala Pro Asp Gly Ala Val Val Lys
385                 390                 395                 400 ccg gcc gcc gcg tcc gag cac ttg ctc cgc cac cgg ggt ccg gcc gtg     1248
Pro Ala Ala Ala Ser Glu His Leu Leu Arg His Arg Gly Pro Ala Val
                405                 410                 415 gtc ttc gac tcc gtc gag gac ctg cac gcc cgg ctc gac gac ccg gac     1296
Val Phe Asp Ser Val Glu Asp Leu His Ala Arg Leu Asp Asp Pro Asp
                420                 425                 430 ctg gac gtc acc gcc gac tcg gtg ctg gtg ctg cgc ggc tgc ggt ccc     1344
Leu Asp Val Thr Ala Asp Ser Val Leu Val Leu Arg Gly Cys Gly Pro
            435                 440                 445 aag ggc tat ccg ggc atg ccg gag gtg tcc aac atg ccg ctg ccg gcg     1392
Lys Gly Tyr Pro Gly Met Pro Glu Val Ser Asn Met Pro Leu Pro Ala
        450                 455                 460
```

```
aaa ctc ctc gaa cag ggg gtc cgc gac atg gtc cgg gtc tgc gac ggg    1440
Lys Leu Leu Glu Gln Gly Val Arg Asp Met Val Arg Val Cys Asp Gly
465                 470                 475                 480 cgg atg tcg ggt acg gcg tac ggc acg gtg gtc ctg cac gtc gcc ccg    1488
Arg Met Ser Gly Thr Ala Tyr Gly Thr Val Val Leu His Val Ala Pro
                485                 490                 495 gaa gcc gcg gcg ggg ggg ccg ctc gcc cgg gtc cgc acc ggc gac atg    1536
Glu Ala Ala Ala Gly Gly Pro Leu Ala Arg Val Arg Thr Gly Asp Met
        500                 505                 510 atc atc ctc gac gtc gcg aac cgg cgc ctc gac gcc gac gtc ccg gcc    1584
Ile Ile Leu Asp Val Ala Asn Arg Arg Leu Asp Ala Asp Val Pro Ala
        515                 520                 525 gag gag tgg gcc gcc cgc gag ccg tca ccg gag gcg gcg aaa gcc tac    1632
Glu Glu Trp Ala Ala Arg Glu Pro Ser Pro Glu Ala Ala Lys Ala Tyr
530                 535                 540 gcg gcg ccg tcc cgc ggc tgg gag cgt ctc tac gtc gac acc gtc ggc    1680
Ala Ala Pro Ser Arg Gly Trp Glu Arg Leu Tyr Val Asp Thr Val Gly
545                 550                 555                 560 cag gcc gac acc ggc gcc gac tgc gac ttc ctg cgc ggc gcg agc ggc    1728
Gln Ala Asp Thr Gly Ala Asp Cys Asp Phe Leu Arg Gly Ala Ser Gly
                565                 570                 575 gac cgc gtc tcc cgc gag tcc cac tga                                1755
Asp Arg Val Ser Arg Glu Ser His
                580

<210> SEQ ID NO 80
<211> LENGTH: 584
<212> TYPE: PRT
<213> ORGANISM: Actinoplanes missouriensis

<400> SEQUENCE: 80

Met Asp Leu His Arg Pro Arg Lys Leu Arg Arg Arg Leu Ala Met Gln
1               5                   10                  15

Arg Arg Ser Ala Gln Trp Tyr Ala Gly Asp Asp Arg Asn Ser Tyr Ile
            20                  25                  30

His Arg Ala Trp Met Arg Arg Gly Leu Pro Ala Asp Ala Phe Asp Gly
        35                  40                  45

Arg Pro His Ile Ala Ile Ala Asn Thr Ala Ser Asp Leu Thr Pro Cys
    50                  55                  60

Asn Ala His Phe Asp Glu Val Ala Arg Ser Val Ala Asp Gly Ile His
65                  70                  75                  80

Arg Ala Gly Gly Val Ala Leu Asn Leu Pro Val Val Ser Ile Gly Glu
                85                  90                  95

Thr Gln Val Arg Pro Thr Ala Met Leu Trp Arg Asn Met Ala Ala Met
            100                 105                 110

Ala Ile Glu Glu Met Leu Arg Ala Asn Pro Ile Asp Gly Val Val Leu
        115                 120                 125

Leu Gly Gly Cys Asp Lys Thr Ile Pro Ala Leu Leu Met Gly Ala Ala
    130                 135                 140

Ser Val Asp Leu Pro Ala Val Val Met Pro Gly Gly Pro Met Leu Thr
145                 150                 155                 160

Gly Thr Phe Arg Gly Val Pro Leu Gly Cys Gly Thr Asp Val Trp Lys
                165                 170                 175

Leu Ser Glu Glu Val Arg Ala Gly Thr Leu Ser Ala Ala Glu Phe Thr
            180                 185                 190

Arg Ser Glu Ser Ser Met Ile Arg Ser Lys Gly His Cys Asn Thr Met
        195                 200                 205
```

```
Gly Thr Ala Ser Thr Met Gly Leu Leu Ala Glu Val Leu Gly Met Thr
            210                 215                 220

Leu Pro Gly Val Ala Gly Thr Pro Ala Pro Asp Ser Arg Leu Leu Glu
225                 230                 235                 240

Ala Ala His Ala Thr Gly Val Leu Ala Val Gly Leu Val Asp Ala Asp
                245                 250                 255

Arg Arg Pro Ser Gln Val Met Thr Arg Gly Ser Phe Leu Asn Ala Ile
            260                 265                 270

Val Ala Leu Ala Ala Leu Gly Gly Ser Thr Asn Ala Val His Leu
    275                 280                 285

Leu Ala Ile Ala Gly Arg Leu Gly Val Pro Leu Ser Gln Asp Asp Phe
290                 295                 300

Asp Thr Thr Gly Ala Asp Val Pro Leu Leu Val Asp Leu Leu Pro Ala
305                 310                 315                 320

Gly Arg Phe Leu Met Asp Asp Leu Tyr Arg Ala Gly Leu His Ala
            325                 330                 335

Val Leu Ala Glu Val Arg Asp Leu Leu Asp Pro Ser Ala Ile Thr Val
                340                 345                 350

Thr Gly Arg Pro Leu Thr Glu His Leu Gly Asp Ala Arg Val His Asp
            355                 360                 365

Arg Glu Val Ile Arg Pro Arg Ala Glu Pro Leu Leu Pro His Ala Gly
370                 375                 380

Ile Ala Val Leu Tyr Gly Asn Leu Ala Pro Asp Gly Ala Val Val Lys
385                 390                 395                 400

Pro Ala Ala Ala Ser Glu His Leu Leu Arg His Arg Gly Pro Ala Val
                405                 410                 415

Val Phe Asp Ser Val Glu Asp Leu His Ala Arg Leu Asp Asp Pro Asp
            420                 425                 430

Leu Asp Val Thr Ala Asp Ser Val Leu Val Leu Arg Gly Cys Gly Pro
            435                 440                 445

Lys Gly Tyr Pro Gly Met Pro Glu Val Ser Asn Met Pro Leu Pro Ala
    450                 455                 460

Lys Leu Leu Glu Gln Gly Val Arg Asp Met Val Arg Val Cys Asp Gly
465                 470                 475                 480

Arg Met Ser Gly Thr Ala Tyr Gly Thr Val Val Leu His Val Ala Pro
                485                 490                 495

Glu Ala Ala Ala Gly Gly Pro Leu Ala Arg Val Arg Thr Gly Asp Met
            500                 505                 510

Ile Ile Leu Asp Val Ala Asn Arg Arg Leu Asp Ala Asp Val Pro Ala
            515                 520                 525

Glu Glu Trp Ala Ala Arg Glu Pro Ser Pro Glu Ala Ala Lys Ala Tyr
530                 535                 540

Ala Ala Pro Ser Arg Gly Trp Glu Arg Leu Tyr Val Asp Thr Val Gly
545                 550                 555                 560

Gln Ala Asp Thr Gly Ala Asp Cys Asp Phe Leu Arg Gly Ala Ser Gly
                565                 570                 575

Asp Arg Val Ser Arg Glu Ser His
            580
```

<210> SEQ ID NO 81
<211> LENGTH: 1755
<212> TYPE: DNA
<213> ORGANISM: Artificial Sequence
<220> FEATURE:
<223> OTHER INFORMATION: synthetic DNA

<400> SEQUENCE: 81

```
atggatctgc atcgtccgcg taaactgcgt cgccgtctgg ccatgcagcg ccgtagcgcc      60
cagtggtatg caggcgatga tcgcaactct tacattcatc gtgcatggat gcgccgtggt     120
ctgccggcag atgcatttga tggccgtccg cacattgcga tcgccaacac ggcgtctgat     180
ctgaccccgt gcaatgccca tttcgatgaa gttgcgcgca gtgtggccga tggtattcac     240
cgtgcaggcg gtgttgcgct gaatctgccg gtggttagca ttggtgaaac ccaagtgcgt     300
ccgaccgcca tgctgtggcg taacatggcg gccatggcaa ttgaagaaat gctgcgtgcg     360
aatccgatcg atggtgtggt tctgctgggc ggttgtgata aaacgattcc ggccctgctg     420
atgggcgcag cgagtgttga tctgccggca gtggttatgc cggcggtcc gatgctgacc      480
ggcacgtttc gcgtgtgcc gctgggttgt ggcaccgatg tttggaaact gagcgaagaa      540
gtgcgtgcgg gtacgctgtc tgccgcagaa tttacccgca gtgaaagctc tatgatccgt     600
agcaaaggtc attgtaacac catgggcacg gcaagcacca tgggtctgct ggcagaagtt     660
ctgggcatga cgctgccggg tgtggcgggc accccggcac cggattctcg tctgctggaa     720
gccgcacatg ccaccggtgt gctggcggtt ggcctggtgg atgccgatcg ccgtccgtct     780
caggttatga cgcgtggcag ttttctgaat gcaattgtgg cactggcggc gctgggcggc     840
agtaccaatg cagtggttca tctgctggca attgccggcc gcctgggtgt gccgctgagc     900
caggatgatt ttgataccac gggtgccgat gttccgctgc tggttgatct gctgccggca     960
ggccgcttcc tgatggatga tctgtatcgt gcgggcggtc tgcatgcggt tctggcagaa    1020
gtgcgcgatc tgctggatcc gagcgcgatc accgtgaccg gtcgtccgct gaccgaacat    1080
ctgggcgatg cgcgcgttca cgatcgtgaa gtgattcgtc cgcgtgcgga accgctgctg    1140
ccgcatgcag gtattgcggt gctgtacggt aatctggccc cggatggtgc ggtggttaaa    1200
ccggcggcag ccagcgaaca tctgctgcgt caccgtggtc cggcggtggt tttcgattct    1260
gttgaagatc tgcacgcacg cctggatgat ccggatctgg atgtgaccgc ggattctgtg    1320
ctggttctgc gtggctgcgg tccgaaaggc tatccgggta tgccggaagt tagtaacatg    1380
ccgctgccgg cgaaactgct ggaacagggt gtgcgcgata tggtgcgtgt ttgtgatggc    1440
cgtatgtctg gtacggcata cggcaccgtg gttctgcatg ttgccccgga agcggcagcg    1500
ggcggtccgc tggcacgcgt gcgtaccggc gatatgatta cctgatgt tgccaatcgc     1560
cgtctggatg cagatgtgcc ggccgaagaa tgggcggcac gtgaaccgag tccggaagcc    1620
gcaaaagcct atgcggcccc gagccgtggt tgggaacgtc tgtacgttga tacggtgggt    1680
caggccgata ccggcgcaga ttgcgatttt ctgcgtggcg cgagcggtga tcgcgtgagt    1740
cgtgaaagcc actga                                                     1755
```

<210> SEQ ID NO 82
<211> LENGTH: 1962
<212> TYPE: DNA
<213> ORGANISM: Aspergillus oryzae
<220> FEATURE:
<221> NAME/KEY: CDS
<222> LOCATION: (1)..(1962)

<400> SEQUENCE: 82

```
atg tcg tgt cag tca cgc acc tcg tgt gaa ggc tgc tcc tgc agt gac    48
Met Ser Cys Gln Ser Arg Thr Ser Cys Glu Gly Cys Ser Cys Ser Asp
1               5                   10                  15 ggg ggc agc cgg cca cca gtg aac atc gag gac tgt gag agc gaa ctg    96
```

```
Gly Gly Ser Arg Pro Val Asn Ile Glu Asp Cys Glu Ser Glu Leu
             20              25              30 ctt gcc ctt cgg agg cgt aca gtg gag ctc gag aaa act cta gca tca      144
Leu Ala Leu Arg Arg Arg Thr Val Glu Leu Glu Lys Thr Leu Ala Ser
         35              40              45 atg caa gat ggc cgg cca cat gct aat gca tca agg gcc cgg aag tta      192
Met Gln Asp Gly Arg Pro His Ala Asn Ala Ser Arg Ala Arg Lys Leu
 50              55              60 cgg tcg gcc aac tgg ttc aac tgc gag agc gat ccg ggc atg atg gcc      240
Arg Ser Ala Asn Trp Phe Asn Cys Glu Ser Asp Pro Gly Met Met Ala
 65              70              75              80 ctc tac att gag cgg tac ctc aac tat ggt atc acc cgg gaa gaa ctg      288
Leu Tyr Ile Glu Arg Tyr Leu Asn Tyr Gly Ile Thr Arg Glu Glu Leu
             85              90              95 atg tct ggt aaa cca ata atc gga ata gca cag tcc ggg tcc gac ttg      336
Met Ser Gly Lys Pro Ile Ile Gly Ile Ala Gln Ser Gly Ser Asp Leu
            100             105             110 tct cca tgc aac cgc cat cac ctc gag ttg gcg aaa cgg gtt cga gaa      384
Ser Pro Cys Asn Arg His His Leu Glu Leu Ala Lys Arg Val Arg Glu
        115             120             125 ggt atc agg tcc gcc gga ggg atc gcc ttt gaa ttc ccc acg cat cct      432
Gly Ile Arg Ser Ala Gly Gly Ile Ala Phe Glu Phe Pro Thr His Pro
130             135             140 att cag gag act agc agg aga ccc act gct tgt att gac cga aat cta      480
Ile Gln Glu Thr Ser Arg Arg Pro Thr Ala Cys Ile Asp Arg Asn Leu
145             150             155             160 tcg tat ctg ggc ctg gta gaa att ctc ttc gga tat ccc ttg gac ggt      528
Ser Tyr Leu Gly Leu Val Glu Ile Leu Phe Gly Tyr Pro Leu Asp Gly
            165             170             175 gta gtc ctc ctg acg ggc tgc gac aag act act ccc gcc gct ctg atg      576
Val Val Leu Leu Thr Gly Cys Asp Lys Thr Thr Pro Ala Ala Leu Met
        180             185             190 gcc gcg gct aca gtg aat atc cca gca ata tgc ttg aat gtc ggc cca      624
Ala Ala Ala Thr Val Asn Ile Pro Ala Ile Cys Leu Asn Val Gly Pro
    195             200             205 atg ctt aac ggt tac gtg aag aag gac ctg gcg ggg tcc gga atg gta      672
Met Leu Asn Gly Tyr Val Lys Lys Asp Leu Ala Gly Ser Gly Met Val
210             215             220 ttg tgg acg ggt aga gag atg tat gcg gca ggt gag atc aac aag gag      720
Leu Trp Thr Gly Arg Glu Met Tyr Ala Ala Gly Glu Ile Asn Lys Glu
225             230             235             240 gaa ttc att gac tat gtg tcc aaa ggt aca cca tca gtg gga cat tgt      768
Glu Phe Ile Asp Tyr Val Ser Lys Gly Thr Pro Ser Val Gly His Cys
            245             250             255 aac acg atg gga aca gca tca act atg aat gct ttg gca gaa gcg ctt      816
Asn Thr Met Gly Thr Ala Ser Thr Met Asn Ala Leu Ala Glu Ala Leu
        260             265             270 gga atg gcc cta cct ggg tcg gct gcc ata ccg gct ccg tat cgt gaa      864
Gly Met Ala Leu Pro Gly Ser Ala Ala Ile Pro Ala Pro Tyr Arg Glu
    275             280             285 cgt ggc caa tgt gct tac gaa aca ggt ttg cgt att gtc gaa atg gtt      912
Arg Gly Gln Cys Ala Tyr Glu Thr Gly Leu Arg Ile Val Glu Met Val
290             295             300 cat tcc gat cgg aag ccc agc gat att atg act cga gag gct ttc gag      960
His Ser Asp Arg Lys Pro Ser Asp Ile Met Thr Arg Glu Ala Phe Glu
305             310             315             320 aat gtt att gta gtt aat act gct atc ggc ggc agt acc aat gcc cct      1008
Asn Val Ile Val Val Asn Thr Ala Ile Gly Gly Ser Thr Asn Ala Pro
            325             330             335
```

```
att cat atc aac gcc att gcc aaa cat att ggg gtt gag gtt tca ctg    1056
Ile His Ile Asn Ala Ile Ala Lys His Ile Gly Val Glu Val Ser Leu
            340                 345                 350 gat gac tgg gac cga ctt gga ttt cat att cca cta ctg cta aac atg    1104
Asp Asp Trp Asp Arg Leu Gly Phe His Ile Pro Leu Leu Leu Asn Met
        355                 360                 365 caa cca gcc ggt gaa ctg ctg gga gag gaa tac tat cgg gcg ggc ggg    1152
Gln Pro Ala Gly Glu Leu Leu Gly Glu Glu Tyr Tyr Arg Ala Gly Gly
    370                 375                 380 cta ccc gcg att atg gcg gag ctg cta gat gct agg aag ctg aac ccg    1200
Leu Pro Ala Ile Met Ala Glu Leu Leu Asp Ala Arg Lys Leu Asn Pro
385                 390                 395                 400 gat gct tta aca tgc aat ggt tac aca gta gcc gag aat gtc cgg gac    1248
Asp Ala Leu Thr Cys Asn Gly Tyr Thr Val Ala Glu Asn Val Arg Asp
                405                 410                 415 aaa cat acc tgg gac cgt cga atg atc aag ccg tac aat gag cca ctt    1296
Lys His Thr Trp Asp Arg Arg Met Ile Lys Pro Tyr Asn Glu Pro Leu
            420                 425                 430 ctg gaa gat gcc ggt ttt ctc cat ctt caa ggc agt ctg ttc cgg tct    1344
Leu Glu Asp Ala Gly Phe Leu His Leu Gln Gly Ser Leu Phe Arg Ser
        435                 440                 445 gct atc atg aag aca tgt gtg ata tcg gag cct ttc cga caa aag ttc    1392
Ala Ile Met Lys Thr Cys Val Ile Ser Glu Pro Phe Arg Gln Lys Phe
    450                 455                 460 ttg gag aat ccc aag gac ccg aat gca ttt gaa ggt acg gtt gta gta    1440
Leu Glu Asn Pro Lys Asp Pro Asn Ala Phe Glu Gly Thr Val Val Val
465                 470                 475                 480 ttt gat gga ccg gag gat tat cat cac cga ctt gag gac cct tcc acc    1488
Phe Asp Gly Pro Glu Asp Tyr His His Arg Leu Glu Asp Pro Ser Thr
                485                 490                 495 ccc atc gac gac aga agt atc ctg gtg atg cgc ggt gct ggc cca ttg    1536
Pro Ile Asp Asp Arg Ser Ile Leu Val Met Arg Gly Ala Gly Pro Leu
            500                 505                 510 gga tat cca ggt gcc gcc gag gtc gtc aac atg cac cca cct gga cgg    1584
Gly Tyr Pro Gly Ala Ala Glu Val Val Asn Met His Pro Pro Gly Arg
        515                 520                 525 ctt tta cga caa ggg gtc aaa tcg ctt ccg tgc att gga gac ggg cga    1632
Leu Leu Arg Gln Gly Val Lys Ser Leu Pro Cys Ile Gly Asp Gly Arg
    530                 535                 540 caa tcg gga act tcc ggc tca cca tca atc ctc aat gct agt ccc gag    1680
Gln Ser Gly Thr Ser Gly Ser Pro Ser Ile Leu Asn Ala Ser Pro Glu
545                 550                 555                 560 gca gcg gcg ggt ggt aat cta gcc ctt ctt caa gat ggg gac aga ctc    1728
Ala Ala Ala Gly Gly Asn Leu Ala Leu Leu Gln Asp Gly Asp Arg Leu
                565                 570                 575 cgt gtt gat cta aat aaa cgg cgc gtt gac atc ctt gtt tcc acg gag    1776
Arg Val Asp Leu Asn Lys Arg Arg Val Asp Ile Leu Val Ser Thr Glu
            580                 585                 590 gaa ctg gaa aag cgg aga aag aca cta gaa gcc caa gga ggt tat gat    1824
Glu Leu Glu Lys Arg Arg Lys Thr Leu Glu Ala Gln Gly Gly Tyr Asp
        595                 600                 605 gtg ccg gaa agt caa act cca tgg cag gaa ctg ttc agg agg gag acg    1872
Val Pro Glu Ser Gln Thr Pro Trp Gln Glu Leu Phe Arg Arg Glu Thr
    610                 615                 620 aca cag ttg agt gat ggt atg gtc ctc cga gac gcg gta aaa tac caa    1920
Thr Gln Leu Ser Asp Gly Met Val Leu Arg Asp Ala Val Lys Tyr Gln
625                 630                 635                 640 cga ctt gcc cag cga tat gag aac ccc cgg cac aat cat tga            1962
Arg Leu Ala Gln Arg Tyr Glu Asn Pro Arg His Asn His
                645                 650
```

<210> SEQ ID NO 83
<211> LENGTH: 653
<212> TYPE: PRT
<213> ORGANISM: Aspergillus oryzae

<400> SEQUENCE: 83

```
Met Ser Cys Gln Ser Arg Thr Ser Cys Glu Gly Cys Ser Cys Ser Asp
1               5                   10                  15

Gly Gly Ser Arg Pro Pro Val Asn Ile Glu Asp Cys Glu Ser Glu Leu
            20                  25                  30

Leu Ala Leu Arg Arg Arg Thr Val Glu Leu Glu Lys Thr Leu Ala Ser
        35                  40                  45

Met Gln Asp Gly Arg Pro His Ala Asn Ala Ser Arg Ala Arg Lys Leu
    50                  55                  60

Arg Ser Ala Asn Trp Phe Asn Cys Glu Ser Asp Pro Gly Met Met Ala
65                  70                  75                  80

Leu Tyr Ile Glu Arg Tyr Leu Asn Tyr Gly Ile Thr Arg Glu Glu Leu
                85                  90                  95

Met Ser Gly Lys Pro Ile Ile Gly Ile Ala Gln Ser Gly Ser Asp Leu
            100                 105                 110

Ser Pro Cys Asn Arg His His Leu Glu Leu Ala Lys Arg Val Arg Glu
        115                 120                 125

Gly Ile Arg Ser Ala Gly Gly Ile Ala Phe Glu Phe Pro Thr His Pro
    130                 135                 140

Ile Gln Glu Thr Ser Arg Arg Pro Thr Ala Cys Ile Asp Arg Asn Leu
145                 150                 155                 160

Ser Tyr Leu Gly Leu Val Glu Ile Leu Phe Gly Tyr Pro Leu Asp Gly
                165                 170                 175

Val Val Leu Leu Thr Gly Cys Asp Lys Thr Thr Pro Ala Ala Leu Met
            180                 185                 190

Ala Ala Ala Thr Val Asn Ile Pro Ala Ile Cys Leu Asn Val Gly Pro
        195                 200                 205

Met Leu Asn Gly Tyr Val Lys Lys Asp Leu Ala Gly Ser Gly Met Val
    210                 215                 220

Leu Trp Thr Gly Arg Glu Met Tyr Ala Ala Gly Glu Ile Asn Lys Glu
225                 230                 235                 240

Glu Phe Ile Asp Tyr Val Ser Lys Gly Thr Pro Ser Val Gly His Cys
                245                 250                 255

Asn Thr Met Gly Thr Ala Ser Thr Met Asn Ala Leu Ala Glu Ala Leu
            260                 265                 270

Gly Met Ala Leu Pro Gly Ser Ala Ala Ile Pro Ala Pro Tyr Arg Glu
        275                 280                 285

Arg Gly Gln Cys Ala Tyr Glu Thr Gly Leu Arg Ile Val Glu Met Val
    290                 295                 300

His Ser Asp Arg Lys Pro Ser Asp Ile Met Thr Arg Glu Ala Phe Glu
305                 310                 315                 320

Asn Val Ile Val Val Asn Thr Ala Ile Gly Gly Ser Thr Asn Ala Pro
                325                 330                 335

Ile His Ile Asn Ala Ile Ala Lys His Ile Gly Val Glu Val Ser Leu
            340                 345                 350

Asp Asp Trp Asp Arg Leu Gly Phe His Ile Pro Leu Leu Leu Asn Met
        355                 360                 365

Gln Pro Ala Gly Glu Leu Leu Gly Glu Glu Tyr Tyr Arg Ala Gly Gly
```

Leu Pro Ala Ile Met Ala Glu Leu Leu Asp Ala Arg Lys Leu Asn Pro
385                 390                 395                 400

Asp Ala Leu Thr Cys Asn Gly Tyr Thr Val Ala Glu Asn Val Arg Asp
            405                 410                 415

Lys His Thr Trp Asp Arg Arg Met Ile Lys Pro Tyr Asn Glu Pro Leu
        420                 425                 430

Leu Glu Asp Ala Gly Phe Leu His Leu Gln Gly Ser Leu Phe Arg Ser
    435                 440                 445

Ala Ile Met Lys Thr Cys Val Ile Ser Glu Pro Phe Arg Gln Lys Phe
450                 455                 460

Leu Glu Asn Pro Lys Asp Pro Asn Ala Phe Glu Gly Thr Val Val Val
465                 470                 475                 480

Phe Asp Gly Pro Glu Asp Tyr His His Arg Leu Glu Asp Pro Ser Thr
                485                 490                 495

Pro Ile Asp Asp Arg Ser Ile Leu Val Met Arg Gly Ala Gly Pro Leu
            500                 505                 510

Gly Tyr Pro Gly Ala Ala Glu Val Val Asn Met His Pro Pro Gly Arg
        515                 520                 525

Leu Leu Arg Gln Gly Val Lys Ser Leu Pro Cys Ile Gly Asp Gly Arg
    530                 535                 540

Gln Ser Gly Thr Ser Gly Ser Pro Ser Ile Leu Asn Ala Ser Pro Glu
545                 550                 555                 560

Ala Ala Ala Gly Gly Asn Leu Ala Leu Leu Gln Asp Gly Asp Arg Leu
                565                 570                 575

Arg Val Asp Leu Asn Lys Arg Val Asp Ile Leu Val Ser Thr Glu
            580                 585                 590

Glu Leu Glu Lys Arg Arg Lys Thr Leu Glu Ala Gln Gly Gly Tyr Asp
        595                 600                 605

Val Pro Glu Ser Gln Thr Pro Trp Gln Glu Leu Phe Arg Arg Glu Thr
    610                 615                 620

Thr Gln Leu Ser Asp Gly Met Val Leu Arg Asp Ala Val Lys Tyr Gln
625                 630                 635                 640

Arg Leu Ala Gln Arg Tyr Glu Asn Pro Arg His Asn His
                645                 650

<210> SEQ ID NO 84
<211> LENGTH: 1962
<212> TYPE: DNA
<213> ORGANISM: Artificial Sequence
<220> FEATURE:
<223> OTHER INFORMATION: synthetic DNA

<400> SEQUENCE: 84
atgtcttgcc agagtcgcac cagctgtgaa ggttgcagct gttctgatgg cggttctcgt    60
ccgccggtta atattgaaga ttgcgaaagt gaactgctgg ccctgcgtcg ccgtacggtg   120
gaactggaaa aaccctggc atctatgcag gatggccgtc gcatgcaaa tgcctctcgt    180 gcacgtaaac tgcgtagtgc aaactggttt aattgtgaaa gtgatccggg tatgatggcg   240
ctgtatattg aacgctatct gaattacggc atcacccgtg aagaactgat gagtggcaaa   300
ccgattatcg gtattgcaca gagtggcagc gatctgagcc cgtgcaaccg ccatcacctg   360
gaactggcga acgtgtgcg tgaaggtatt cgtagcgcag gcggtatcgc gtttgaattt   420
ccgacccacc cgattcagga aacgagccgc cgtccgaccg cgtgtatcga tcgtaatctg   480

-continued

| | |
|---|---|
| tcttatctgg gtctggtgga atcctgtttt ggttacccgc tggatggcgt ggttctgctg | 540 |
| accggttgtg ataaaaccac cccggcggcc ctgatggcag ccgcaaccgt taacattccg | 600 |
| gccatctgtc tgaacgtggg tccgatgctg aatggctatg tgaaaaaaga tctggcaggc | 660 |
| agcggtatgg tgctgtggac gggtcgcgaa atgtatgcag cgggcgaaat caacaaagaa | 720 |
| gaatttatcg attacgttag caaaggcacc ccgtctgtgg gccattgcaa taccatgggc | 780 |
| acggcgtcta ccatgaacgc cctggcagaa gccctgggta tggccctgcc gggtagtgcc | 840 |
| gcaattccgg ccccgtatcg cgaacgtggc cagtgtgcat acgaaacggg cctgcgcatt | 900 |
| gttgaaatgg tgcacagtga tcgcaaaccg agcgatatca tgacccgtga agcctttgaa | 960 |
| aacgtgattg tggttaatac ggcgatcggc ggtagtacca acgccccgat tcatatcaat | 1020 |
| gccattgcaa acacatcgg tgttgaagtg agcctggatg attgggatcg tctgggcttc | 1080 |
| catattccgc tgctgctgaa tatgcagccg gcgggcgaac tgctgggtga agaatattat | 1140 |
| cgtgccggcg gtctgccggc catcatggcc gaactgctgg atgcacgtaa actgaacccg | 1200 |
| gatgcgctga cgtgcaatgg ttataccgtt gcggaaaacg tgcgcgataa acatacgtgg | 1260 |
| gatcgccgta tgatcaaacc gtacaacgaa ccgctgctgg aagatgcggg ttttctgcac | 1320 |
| ctgcagggct ctctgttccg cagtgccatt atgaaaacct gcgtgatcag cgaaccgttt | 1380 |
| cgtcagaaat tcctggaaaa cccgaaagat ccgaatgcgt ttgaaggtac ggtggtggtg | 1440 |
| tttgatggcc cggaagatta tcatcaccgc ctggaagatc cgagcacccc gattgatgat | 1500 |
| cgctctattc tggttatgcg tggcgccggt ccgctgggct acccgggtgc ggccgaagtt | 1560 |
| gtgaatatgc atccgccggg tcgcctgctg cgtcagggtg tgaaaagtct gccgtgcatt | 1620 |
| ggcgatggtc gtcagagcgg cacctctggt agtccgagca tcctgaacgc gagcccggaa | 1680 |
| gcagccgccg gcgtaaccct ggcgctgctg caggatggtg atcgcctgcg tgttgatctg | 1740 |
| aacaaacgcc gtgttgatat tctggtgtct acggaagaac tggaaaaacg ccgtaaaacc | 1800 |
| ctggaagcgc agggcggtta tgatgtgccg gaaagccaga cccgtggca ggaactgttt | 1860 |
| cgccgtgaaa ccacgcagct gtctgatggc atggttctgc gcgatgccgt gaaatatcag | 1920 |
| cgcctggcac agcgttacga aaacccgcgt cataatcact ga | 1962 |

<210> SEQ ID NO 85
<211> LENGTH: 1161
<212> TYPE: DNA
<213> ORGANISM: Agrobacterium tumefaciens
<220> FEATURE:
<221> NAME/KEY: CDS
<222> LOCATION: (1)..(1161)

<400> SEQUENCE: 85

| | |
|---|---|
| atg acc ggc tca agg tcc atc gac gct acc gct att ttg cct gaa gac<br>Met Thr Gly Ser Arg Ser Ile Asp Ala Thr Ala Ile Leu Pro Glu Asp<br>1               5                   10                  15 | 48 |
| ttt gaa aac gcc ctg ctc gtc ggc cgc gta tgg tcg aaa agc gaa ggc<br>Phe Glu Asn Ala Leu Leu Val Gly Arg Val Trp Ser Lys Ser Glu Gly<br>            20                  25                  30 | 96 |
| ggc ccc tgc ccc gtt ctg cta aaa ggc ggc gtg ctt tac gac ctc acc<br>Gly Pro Cys Pro Val Leu Leu Lys Gly Gly Val Leu Tyr Asp Leu Thr<br>        35                  40                  45 | 144 |
| tct att tcg ccg acc atg tct gaa ctt ctg gaa aag acg gat ctg gtg<br>Ser Ile Ser Pro Thr Met Ser Glu Leu Leu Glu Lys Thr Asp Leu Val<br>    50                  55                  60 | 192 |
| gag ctg ctt gca gac acc ggc aca ttc gtg gcg ctt ggc gcg ctc gag<br>Glu Leu Leu Ala Asp Thr Gly Thr Phe Val Ala Leu Gly Ala Leu Glu | 240 |

```
                                                            -continued 65                     70                     75                     80 gcc ttt ctg gat ggc tcc gct ggt gaa ctt ctc gcc ccc aac gat att        288
Ala Phe Leu Asp Gly Ser Ala Gly Glu Leu Leu Ala Pro Asn Asp Ile
                85                     90                     95 cag gcc gtg aag gct gca ggc gtg acc ttc gcc gac agc atg ctg gaa        336
Gln Ala Val Lys Ala Ala Gly Val Thr Phe Ala Asp Ser Met Leu Glu
            100                    105                    110 cgc gtg atc gag gag cag gcc aag ggc gat cca ctt cgc gcg cag gaa        384
Arg Val Ile Glu Glu Gln Ala Lys Gly Asp Pro Leu Arg Ala Gln Glu
        115                    120                    125 ata cgc gga cgg ctg gcg ccg gtt ctc ggc gac aat ctc aag gga ctt        432
Ile Arg Gly Arg Leu Ala Pro Val Leu Gly Asp Asn Leu Lys Gly Leu
    130                    135                    140 gag gcc ggt tcg gaa aaa gca gcc gaa gtg aag aaa ctg ctg cag gaa        480
Glu Ala Gly Ser Glu Lys Ala Ala Glu Val Lys Lys Leu Leu Gln Glu
145                    150                    155                    160 atg ggc ctg tgg tcg caa tat ctg gaa gtt ggc atc ggt ccg gat gcg        528
Met Gly Leu Trp Ser Gln Tyr Leu Glu Val Gly Ile Gly Pro Asp Ala
                165                    170                    175 gag ata ttc tcc aag gcg cag gcc atg gcc tcc gtc ggc tgc ggc gcg        576
Glu Ile Phe Ser Lys Ala Gln Ala Met Ala Ser Val Gly Cys Gly Ala
            180                    185                    190 ctg atc ggc gtt cac ccg aaa tcg cag tgg aac aac ccg gag ccg gaa        624
Leu Ile Gly Val His Pro Lys Ser Gln Trp Asn Asn Pro Glu Pro Glu
        195                    200                    205 gtg gtg ctg gcc att gcc tcc gac ggc cgt atc gtt ggc gcg acg ctt        672
Val Val Leu Ala Ile Ala Ser Asp Gly Arg Ile Val Gly Ala Thr Leu
    210                    215                    220 ggc aac gac gtc aac ctg cgt gac ttc gag ggc cgc tcc gcc ctc ctg        720
Gly Asn Asp Val Asn Leu Arg Asp Phe Glu Gly Arg Ser Ala Leu Leu
225                    230                    235                    240 ctc agc aag gca aaa gac aac aac gca tcc tgc gca atc ggt ccc ttc        768
Leu Ser Lys Ala Lys Asp Asn Asn Ala Ser Cys Ala Ile Gly Pro Phe
                245                    250                    255 atc cgc ctg ttt gat gga cgc ttt acc atc gaa gac gtg aag aag gcg        816
Ile Arg Leu Phe Asp Gly Arg Phe Thr Ile Glu Asp Val Lys Lys Ala
            260                    265                    270 cag ata tcg ctt ctg gtc gaa ggc gag gac ggc ttc acc atg acc ggt        864
Gln Ile Ser Leu Leu Val Glu Gly Glu Asp Gly Phe Thr Met Thr Gly
        275                    280                    285 gca agc gca atg cag gcg atc agc cgc acg ccg gaa aac ctc gct tcc        912
Ala Ser Ala Met Gln Ala Ile Ser Arg Thr Pro Glu Asn Leu Ala Ser
    290                    295                    300 cag ctc ttg aac cgc aac cat cag tat cct gac ggc gcc gtc ttt ttc        960
Gln Leu Leu Asn Arg Asn His Gln Tyr Pro Asp Gly Ala Val Phe Phe
305                    310                    315                    320 ctt ggt acg atg ttc gcg ccg gta aag gac cgc cat ggc ccg ggt ctc       1008
Leu Gly Thr Met Phe Ala Pro Val Lys Asp Arg His Gly Pro Gly Leu
                325                    330                    335 ggc ttc acc cac tcc aag ggc gac cgt gtc gaa atc tcc acg ccc aag       1056
Gly Phe Thr His Ser Lys Gly Asp Arg Val Glu Ile Ser Thr Pro Lys
            340                    345                    350 ctc ggc aag ctg atc aac tgg gtc acg acg aca gac gaa tgc ccg gaa       1104
Leu Gly Lys Leu Ile Asn Trp Val Thr Thr Thr Asp Glu Cys Pro Glu
        355                    360                    365 tgg aca ttc ggc acc gcg gcc ctc atg cgc aac ctg gcg aaa cgc ggg       1152
Trp Thr Phe Gly Thr Ala Ala Leu Met Arg Asn Leu Ala Lys Arg Gly
    370                    375                    380 ctg ctc tag                                                            1161
```

Leu Leu
385

<210> SEQ ID NO 86
<211> LENGTH: 386
<212> TYPE: PRT
<213> ORGANISM: Agrobacterium tumefaciens

<400> SEQUENCE: 86

```
Met Thr Gly Ser Arg Ser Ile Asp Ala Thr Ala Ile Leu Pro Glu Asp
1               5                  10                  15

Phe Glu Asn Ala Leu Leu Val Gly Arg Val Trp Ser Lys Ser Glu Gly
            20                  25                  30

Gly Pro Cys Pro Val Leu Leu Lys Gly Gly Val Leu Tyr Asp Leu Thr
        35                  40                  45

Ser Ile Ser Pro Thr Met Ser Glu Leu Leu Glu Lys Thr Asp Leu Val
50                  55                  60

Glu Leu Leu Ala Asp Thr Gly Thr Phe Val Ala Leu Gly Ala Leu Glu
65                  70                  75                  80

Ala Phe Leu Asp Gly Ser Ala Gly Glu Leu Leu Ala Pro Asn Asp Ile
            85                  90                  95

Gln Ala Val Lys Ala Ala Gly Val Thr Phe Ala Asp Ser Met Leu Glu
        100                 105                 110

Arg Val Ile Glu Glu Gln Ala Lys Gly Asp Pro Leu Arg Ala Gln Glu
    115                 120                 125

Ile Arg Gly Arg Leu Ala Pro Val Leu Gly Asp Asn Leu Lys Gly Leu
130                 135                 140

Glu Ala Gly Ser Glu Lys Ala Ala Glu Val Lys Lys Leu Leu Gln Glu
145                 150                 155                 160

Met Gly Leu Trp Ser Gln Tyr Leu Glu Val Gly Ile Gly Pro Asp Ala
            165                 170                 175

Glu Ile Phe Ser Lys Ala Gln Ala Met Ala Ser Val Gly Cys Gly Ala
        180                 185                 190

Leu Ile Gly Val His Pro Lys Ser Gln Trp Asn Asn Pro Glu Pro Glu
    195                 200                 205

Val Val Leu Ala Ile Ala Ser Asp Gly Arg Ile Val Gly Ala Thr Leu
210                 215                 220

Gly Asn Asp Val Asn Leu Arg Asp Phe Glu Gly Arg Ser Ala Leu Leu
225                 230                 235                 240

Leu Ser Lys Ala Lys Asp Asn Asn Ala Ser Cys Ala Ile Gly Pro Phe
            245                 250                 255

Ile Arg Leu Phe Asp Gly Arg Phe Thr Ile Glu Asp Val Lys Lys Ala
        260                 265                 270

Gln Ile Ser Leu Leu Val Glu Gly Glu Asp Gly Phe Thr Met Thr Gly
    275                 280                 285

Ala Ser Ala Met Gln Ala Ile Ser Arg Thr Pro Glu Asn Leu Ala Ser
290                 295                 300

Gln Leu Leu Asn Arg Asn His Gln Tyr Pro Asp Gly Ala Val Phe Phe
305                 310                 315                 320

Leu Gly Thr Met Phe Ala Pro Val Lys Asp Arg His Gly Pro Gly Leu
            325                 330                 335

Gly Phe Thr His Ser Lys Gly Asp Arg Val Glu Ile Ser Thr Pro Lys
        340                 345                 350

Leu Gly Lys Leu Ile Asn Trp Val Thr Thr Thr Asp Glu Cys Pro Glu
    355                 360                 365
```

Trp Thr Phe Gly Thr Ala Ala Leu Met Arg Asn Leu Ala Lys Arg Gly
370                 375                 380

Leu Leu
385

<210> SEQ ID NO 87
<211> LENGTH: 1161
<212> TYPE: DNA
<213> ORGANISM: Artificial Sequence
<220> FEATURE:
<223> OTHER INFORMATION: synthetic DNA

<400> SEQUENCE: 87

```
atgacgggca gccgttctat tgatgcgacc gccatcctgc cggaagattt cgaaaacgcg      60
ctgctggttg ccgcgtttg gagtaaaagc gaaggcggtc cgtgcccggt gctgctgaaa     120
ggcggtgttc tgtatgatct gaccagcatt agtccgacca tgagcgaact gctggaaaaa     180
accgatctgg tggaactgct ggccgatacc ggcaccttcg ttgcgctggg tgccctggaa     240
gcatttctgg atggtagcgc aggcgaactg ctggcgccga cgatatcca ggcagtgaaa      300
gcggccggcg ttaccttcgc ggattctatg ctggaacgtg tgattgaaga acaggcgaaa     360
ggtgatccgc tgcgtgcaca ggaaattcgc ggccgcctgg caccggtgct gggtgataat     420
ctgaaaggtc tggaagcggg ctctgaaaaa gcagcggaag tgaaaaaact gctgcaggaa     480
atgggcctgt ggagtcagta cctggaagtt ggcattggtc cggatgccga atctttttct     540
aaagcacagg cgatggccag tgtgggctgc ggtgcactga ttggtgttca tccgaaaagt     600
cagtggaaca atccggaacc ggaagtggtt ctggcaattg cgagcgatgg tcgtatcgtg     660
ggcgcgacgc tgggtaacga tgttaatctg cgtgatttcg aaggccgcag cgccctgctg     720
ctgtctaaag caaagataa caatgcgagt gtgccattg gcccgtttat ccgtctgttc      780
gatggtcgct ttaccattga agatgtgaaa aaagcccaga tctctctgct ggttgaaggt     840
gaagatggct ttacgatgac cggtgccagt gcaatgcagg ccattagccg tacgccggaa     900
aatctggcaa gccagctgct gaaccgcaat caccagtatc cggatggcgc ggtgttttc      960
ctgggcacca tgttcgcccc ggttaaagat cgtcatggcc cgggtctggg ctttacgcac    1020
agcaaaggcg atcgcgtgga atttctaccc cgaaactgg gtaaactgat caactgggtt    1080
accacgaccg atgaatgtcc ggaatggacc tttggcaccg ccgcactgat gcgtaatctg    1140
gcgaaacgcg gtctgctgta g                                              1161
```

<210> SEQ ID NO 88
<211> LENGTH: 1200
<212> TYPE: DNA
<213> ORGANISM: Cupriavidus necator
<220> FEATURE:
<221> NAME/KEY: CDS
<222> LOCATION: (1)..(1200)

<400> SEQUENCE: 88

```
atg gca ttg ccg ctc acg ctc agc gct acg caa acg ctt cct gcc gac     48
Met Ala Leu Pro Leu Thr Leu Ser Ala Thr Gln Thr Leu Pro Ala Asp
1               5                   10                  15 ggg ctg gcg ggg acg ctg gtc ggc cgc gca tgg atc ccg gcc ggt gac     96
Gly Leu Ala Gly Thr Leu Val Gly Arg Ala Trp Ile Pro Ala Gly Asp
            20                  25                  30 ggc gtt ccg gcc ggc ccg gct gtc gtg gtc ttg cgg ccg gat ggt gta    144
Gly Val Pro Ala Gly Pro Ala Val Val Val Leu Arg Pro Asp Gly Val
        35                  40                  45
```

| | | | | | | | | | | | | | | | |
|---|---|---|---|---|---|---|---|---|---|---|---|---|---|---|---|
| ttc | gac | att | tcc | gat | gtc | gcc | ccg | acc | atg | agc | acc | ctg | ctc | gaa | cag | 192 |
| Phe | Asp | Ile | Ser | Asp | Val | Ala | Pro | Thr | Met | Ser | Thr | Leu | Leu | Glu | Gln | |
| | | 50 | | | 55 | | | | | 60 | | | | | | |

| gac | gac | ccg | ctc | acg | gtg | gtg | cac | aat | gcg | ccc | ggg | cgc | tgg | atc | ggc | 240 |
| Asp | Asp | Pro | Leu | Thr | Val | Val | His | Asn | Ala | Pro | Gly | Arg | Trp | Ile | Gly |
| 65 | | | | 70 | | | | | 75 | | | | | | 80 |

| aag | ctg | gac | gac | ctg | ctg | gcc | aac | acg | gcc | gat | ccg | cac | ggc | agc | aac | 288 |
| Lys | Leu | Asp | Asp | Leu | Leu | Ala | Asn | Thr | Ala | Asp | Pro | His | Gly | Ser | Asn |
| | | | | 85 | | | | | 90 | | | | | 95 | |

| ggc | gtg | gcc | cgc | ctg | ctg | gcg | cca | tgc | gac | ctg | cag | gtg | atc | aag | gcg | 336 |
| Gly | Val | Ala | Arg | Leu | Leu | Ala | Pro | Cys | Asp | Leu | Gln | Val | Ile | Lys | Ala |
| | | 100 | | | | | 105 | | | | | 110 | | | | |

| gca | ggc | gtg | acc | ttt | gcc | ggc | agc | ctg | gtc | gag | cgt | gtc | atc | gaa | gag | 384 |
| Ala | Gly | Val | Thr | Phe | Ala | Gly | Ser | Leu | Val | Glu | Arg | Val | Ile | Glu | Glu |
| | | | 115 | | | | | 120 | | | | | 125 | | | |

| cag | acc | aag | ggc | gac | ccg | caa | ggc | gcc | gcc | gag | gtc | cgc | aac | cgg | atc | 432 |
| Gln | Thr | Lys | Gly | Asp | Pro | Gln | Gly | Ala | Ala | Glu | Val | Arg | Asn | Arg | Ile |
| 130 | | | | | 135 | | | | | 140 | | | | | | |

| cag | gcg | ctg | gtg | ggc | gag | cgc | ctg | tcc | cgg | atc | cgg | ccg | ggt | tcc | cgc | 480 |
| Gln | Ala | Leu | Val | Gly | Glu | Arg | Leu | Ser | Arg | Ile | Arg | Pro | Gly | Ser | Arg |
| 145 | | | | 150 | | | | | 155 | | | | | 160 | |

| gag | gcg | ggc | gaa | ctc | aag | gcc | ttg | ctg | atc | gag | cat | ggc | atg | tgg | tcg | 528 |
| Glu | Ala | Gly | Glu | Leu | Lys | Ala | Leu | Leu | Ile | Glu | His | Gly | Met | Trp | Ser |
| | | | | 165 | | | | | 170 | | | | | 175 | |

| caa | tac | ctt | gag | gtg | ggc | atc | ggc | ccg | gac | gcc | gag | atc | ttc | acc | aag | 576 |
| Gln | Tyr | Leu | Glu | Val | Gly | Ile | Gly | Pro | Asp | Ala | Glu | Ile | Phe | Thr | Lys |
| | | | | 180 | | | | | 185 | | | | | 190 | |

| gca | ccg | ctg | ctt | tcc | gcg | ctt | ggc | acc | ggt | acg | gaa | atc | gga | ctg | cat | 624 |
| Ala | Pro | Leu | Leu | Ser | Ala | Leu | Gly | Thr | Gly | Thr | Glu | Ile | Gly | Leu | His |
| | | 195 | | | | | 200 | | | | | 205 | | | | |

| ccc | ggc | tcg | gca | tgg | aac | aat | ccg | gaa | ccc | gag | atc | gtg | ctg | gcc | atc | 672 |
| Pro | Gly | Ser | Ala | Trp | Asn | Asn | Pro | Glu | Pro | Glu | Ile | Val | Leu | Ala | Ile |
| 210 | | | | | 215 | | | | | 220 | | | | | | |

| aac | agc | cgc | ggt | gat | gtg | ctc | ggc | gcc | acg | ctg | ggt | aat | gac | gtc | aac | 720 |
| Asn | Ser | Arg | Gly | Asp | Val | Leu | Gly | Ala | Thr | Leu | Gly | Asn | Asp | Val | Asn |
| 225 | | | | 230 | | | | | 235 | | | | | 240 | |

| ctg | cgc | gac | ttc | gag | ggc | cgc | agt | gcg | ttg | ctg | ctg | ggc | aag | gcc | aag | 768 |
| Leu | Arg | Asp | Phe | Glu | Gly | Arg | Ser | Ala | Leu | Leu | Leu | Gly | Lys | Ala | Lys |
| | | | | 245 | | | | | 250 | | | | | 255 | |

| gac | aat | aac | ggc | tcc | tgc | gcg | atc | ggt | ccg | ttc | ctg | cgc | ctg | ttc | gac | 816 |
| Asp | Asn | Asn | Gly | Ser | Cys | Ala | Ile | Gly | Pro | Phe | Leu | Arg | Leu | Phe | Asp |
| | | | 260 | | | | | 265 | | | | | 270 | | |

| cag | agt | ttc | tcg | ctc | gac | gac | gtg | cgg | cgg | gcg | acg | gtg | gat | ctg | cgt | 864 |
| Gln | Ser | Phe | Ser | Leu | Asp | Asp | Val | Arg | Arg | Ala | Thr | Val | Asp | Leu | Arg |
| | | 275 | | | | | 280 | | | | | 285 | | | | |

| gtc | gat | ggc | ctg | gac | ggc | ttc | gtg | ttg | tcc | ggc | acc | agc | tcg | atg | gac | 912 |
| Val | Asp | Gly | Leu | Asp | Gly | Phe | Val | Leu | Ser | Gly | Thr | Ser | Ser | Met | Asp |
| | 290 | | | | | 295 | | | | | 300 | | | | | |

| cag | atc | acg | cgc | gac | ccg | ctg | gag | ctg | gcc | gag | cag | gca | atg | ggg | gcg | 960 |
| Gln | Ile | Thr | Arg | Asp | Pro | Leu | Glu | Leu | Ala | Glu | Gln | Ala | Met | Gly | Ala |
| 305 | | | | | 310 | | | | | 315 | | | | | 320 | |

| acc | cac | cag | tat | ccc | gat | ggc | gcc | atg | ctg | ttc | ctc | ggc | acg | ctg | ttc | 1008 |
| Thr | His | Gln | Tyr | Pro | Asp | Gly | Ala | Met | Leu | Phe | Leu | Gly | Thr | Leu | Phe |
| | | | | 325 | | | | | 330 | | | | | 335 | |

| gcg | ccg | gtg | gaa | gac | cgc | gac | acc | gcg | ggc | ggc | ggc | ttc | acc | cac | aag | 1056 |
| Ala | Pro | Val | Glu | Asp | Arg | Asp | Thr | Ala | Gly | Gly | Gly | Phe | Thr | His | Lys |
| | | | 340 | | | | | 345 | | | | | 350 | | |

| ggt | ggt | gat | ctt | gtc | acc | atc | tcc | agc | cgc | cag | ctc | ggc | agc | ctg | gtc | 1104 |
| Gly | Gly | Asp | Leu | Val | Thr | Ile | Ser | Ser | Arg | Gln | Leu | Gly | Ser | Leu | Val |

```
                355                 360                 365
aac cgc gtg ggc cgc agc gac cgt atc gct ccg tgg acg ttc ggc gta      1152
Asn Arg Val Gly Arg Ser Asp Arg Ile Ala Pro Trp Thr Phe Gly Val
    370                 375                 380 cgc gcc ctg atg gcc aac ctg gcc gca cgt ggc cac acc act ttc tga      1200
Arg Ala Leu Met Ala Asn Leu Ala Ala Arg Gly His Thr Thr Phe
385                 390                 395

<210> SEQ ID NO 89
<211> LENGTH: 399
<212> TYPE: PRT
<213> ORGANISM: Cupriavidus necator

<400> SEQUENCE: 89

Met Ala Leu Pro Leu Thr Leu Ser Ala Thr Gln Thr Leu Pro Ala Asp
1               5                   10                  15

Gly Leu Ala Gly Thr Leu Val Gly Arg Ala Trp Ile Pro Ala Gly Asp
            20                  25                  30

Gly Val Pro Ala Gly Pro Ala Val Val Leu Arg Pro Asp Gly Val
        35                  40                  45

Phe Asp Ile Ser Asp Val Ala Pro Thr Met Ser Thr Leu Leu Glu Gln
50                  55                  60

Asp Asp Pro Leu Thr Val Val His Asn Ala Pro Gly Arg Trp Ile Gly
65                  70                  75                  80

Lys Leu Asp Asp Leu Leu Ala Asn Thr Ala Asp Pro His Gly Ser Asn
                85                  90                  95

Gly Val Ala Arg Leu Leu Ala Pro Cys Asp Leu Gln Val Ile Lys Ala
            100                 105                 110

Ala Gly Val Thr Phe Ala Gly Ser Leu Val Glu Arg Val Ile Glu Glu
        115                 120                 125

Gln Thr Lys Gly Asp Pro Gln Gly Ala Ala Glu Val Arg Asn Arg Ile
130                 135                 140

Gln Ala Leu Val Gly Glu Arg Leu Ser Arg Ile Arg Pro Gly Ser Arg
145                 150                 155                 160

Glu Ala Gly Glu Leu Lys Ala Leu Leu Ile Glu His Gly Met Trp Ser
                165                 170                 175

Gln Tyr Leu Glu Val Gly Ile Gly Pro Asp Ala Glu Ile Phe Thr Lys
            180                 185                 190

Ala Pro Leu Leu Ser Ala Leu Gly Thr Gly Thr Glu Ile Gly Leu His
        195                 200                 205

Pro Gly Ser Ala Trp Asn Asn Pro Glu Pro Glu Ile Val Leu Ala Ile
    210                 215                 220

Asn Ser Arg Gly Asp Val Leu Gly Ala Thr Leu Gly Asn Asp Val Asn
225                 230                 235                 240

Leu Arg Asp Phe Glu Gly Arg Ser Ala Leu Leu Gly Lys Ala Lys
                245                 250                 255

Asp Asn Asn Gly Ser Cys Ala Ile Gly Pro Phe Leu Arg Leu Phe Asp
            260                 265                 270

Gln Ser Phe Ser Leu Asp Asp Val Arg Arg Ala Thr Val Asp Leu Arg
        275                 280                 285

Val Asp Gly Leu Asp Gly Phe Val Leu Ser Gly Thr Ser Ser Met Asp
    290                 295                 300

Gln Ile Thr Arg Asp Pro Leu Glu Leu Ala Glu Gln Ala Met Gly Ala
305                 310                 315                 320

Thr His Gln Tyr Pro Asp Gly Ala Met Leu Phe Leu Gly Thr Leu Phe
```

Ala Pro Val Glu Asp Arg Asp Thr Ala Gly Gly Gly Phe Thr His Lys
            340                 345                 350

Gly Gly Asp Leu Val Thr Ile Ser Ser Arg Gln Leu Gly Ser Leu Val
        355                 360                 365

Asn Arg Val Gly Arg Ser Asp Arg Ile Ala Pro Trp Thr Phe Gly Val
370                 375                 380

Arg Ala Leu Met Ala Asn Leu Ala Ala Arg Gly His Thr Thr Phe
385                 390                 395

<210> SEQ ID NO 90
<211> LENGTH: 1200
<212> TYPE: DNA
<213> ORGANISM: Artificial Sequence
<220> FEATURE:
<223> OTHER INFORMATION: synthetic DNA

<400> SEQUENCE: 90

| | |
|---|---|
| atggcgctgc cgctgaccct gagcgccacc cagacgctgc cggccgatgg tctgccggc | 60 |
| accctggtgg ccgtgcatg gattccggcc ggtgatggcg ttccggccgg tccggccgtg | 120 |
| gttgtgctgc gtccggatgg tgttttcgat atcagtgatg tggcgccgac catgagcacg | 180 |
| ctgctggaac aggatgatcc gctgaccgtt gtgcataacg ccccgggtcg ctggattggc | 240 |
| aaactggatg atctgctggc aaacacggcg gatccgcacg gttctaatgg tgtggcacgt | 300 |
| ctgctggcac gtgcgatct gcaggttatt aaagcggccg gcgtgacctt gccggtagt | 360 |
| ctggttgaac gcgtgatcga agaacagacg aaaggtgatc gcagggcgc agcggaagtt | 420 |
| cgtaatcgta ttcaggcgct ggttggcgaa cgcctgagcc gtatccgccc gggttctcgt | 480 |
| gaagccggtg aactgaaagc cctgctgatt gaacatggca tgtggagcca gtatctggaa | 540 |
| gtgggtattg cccggatgc cgaaatcttc accaaagcac cgctgctgag tgcgctgggc | 600 |
| accggcacga aaatcggtct gcacccgggc agcgcatgga caatccgga accggaaatt | 660 |
| gttctggcca tcaactctcg cggtgatgtg ctgggcgcaa ccctgggtaa cgatgttaat | 720 |
| ctgcgcgatt tcgaaggccg tagcgccctg ctgctgggta agcaaaaga taacaatggc | 780 |
| tcttgtgcaa ttggtccgtt tctgcgcctg ttcgatcagt cttttagtct ggatgatgtg | 840 |
| cgtcgcgcga ccgttgatct gcgtgtggat ggtctggatg ctttgttct gagcggcacc | 900 |
| agctctatgg atcagatcac gcgtgatccg ctggaactgg ccgaacaggc aatgggtgcg | 960 |
| acccatcagt acccggatgg cgcgatgctg ttcctgggta cgctgtttgc accggtggaa | 1020 |
| gatcgcgata ccgcgggcgg tggctttacg cacaaaggtg gcgatctggt taccattagt | 1080 |
| agccgtcagc tgggctctct ggttaaccgt gtgggtcgca gtgatcgtat tgccccgtgg | 1140 |
| accttcggcg tgcgcgccct gatggcaaat ctggccgcac gtggtcatac cacgttttga | 1200 |

<210> SEQ ID NO 91
<211> LENGTH: 1113
<212> TYPE: DNA
<213> ORGANISM: Pseudomonas elodea
<220> FEATURE:
<221> NAME/KEY: CDS
<222> LOCATION: (1)..(1113)

<400> SEQUENCE: 91

| | |
|---|---|
| atg ctg cct gcc gat cat gcg cag gcg att ctg gtc ggc cgt gtg cag | 48 |
| Met Leu Pro Ala Asp His Ala Gln Ala Ile Leu Val Gly Arg Val Gln | |
| 1               5                   10                  15 | |

| | |
|---|---|
| acc ccg gcg ggc ccg agc ccc gtt ctc ctc cgc gat ggc cag gtg atc<br>Thr Pro Ala Gly Pro Ser Pro Val Leu Leu Arg Asp Gly Gln Val Ile<br>          20                    25                    30 | 96 |
| gac gtt tcg gcg atc gcg ccg acc gtc gcc gac ctg ctg gaa cgc gac<br>Asp Val Ser Ala Ile Ala Pro Thr Val Ala Asp Leu Leu Glu Arg Asp<br>          35                    40                    45 | 144 |
| gac atc gcg acg ctg agc ggc acg gtg ctg tgc agc gtc gac gcg ctc<br>Asp Ile Ala Thr Leu Ser Gly Thr Val Leu Cys Ser Val Asp Ala Leu<br>50                    55                    60 | 192 |
| ggc acc gag tcg gcg ccg cag gtg ctg gct ccg gtc gac ctg cag tgc<br>Gly Thr Glu Ser Ala Pro Gln Val Leu Ala Pro Val Asp Leu Gln Cys<br>65                    70                    75                    80 | 240 |
| gtg aag gcc gcc ggc gtc acc ttc gcc gtc tcg gcg ctg gag cgc gtg<br>Val Lys Ala Ala Gly Val Thr Phe Ala Val Ser Ala Leu Glu Arg Val<br>                    85                    90                    95 | 288 |
| atc gag gaa cgc gcc cgc ggc gat tcc gcc aag gcc gcc gag att cgc<br>Ile Glu Glu Arg Ala Arg Gly Asp Ser Ala Lys Ala Ala Glu Ile Arg<br>                100                 105              110 | 336 |
| ggc gac ctc gaa gcc aag gtg ggt tcg ggc atc cgc tcg gtc gtc ccc<br>Gly Asp Leu Glu Ala Lys Val Gly Ser Gly Ile Arg Ser Val Val Pro<br>       115                    120                 125 | 384 |
| ggt acc gcc gag gcc gcg gcg ctc aag gcc gcg ctg atc gag gcg ggc<br>Gly Thr Ala Glu Ala Ala Ala Leu Lys Ala Ala Leu Ile Glu Ala Gly<br>130                    135                 140 | 432 |
| atg tgg tcg caa tat ctc gaa gtg gcc atc ggg ccg gac gcg gag gtg<br>Met Trp Ser Gln Tyr Leu Glu Val Ala Ile Gly Pro Asp Ala Glu Val<br>145                    150                 155              160 | 480 |
| ttc acc aag gcg ccg gtt ctg tcg gcg atg ggc tgg ggc gcc gag atc<br>Phe Thr Lys Ala Pro Val Leu Ser Ala Met Gly Trp Gly Ala Glu Ile<br>                    165                 170              175 | 528 |
| ggc atc cgc tcg gac agc gac tgg aac aat ccg gag ccg gaa gtg gtg<br>Gly Ile Arg Ser Asp Ser Asp Trp Asn Asn Pro Glu Pro Glu Val Val<br>                180                 185              190 | 576 |
| ctg gtg gtc gac cgg aat ggt gcg atc aag ggc gcg acg ctc ggc aac<br>Leu Val Val Asp Arg Asn Gly Ala Ile Lys Gly Ala Thr Leu Gly Asn<br>       195                    200                 205 | 624 |
| gac gtc aac ctg cgc gac ttc gag ggc cgc agc gcg ctg ctg ctg ggc<br>Asp Val Asn Leu Arg Asp Phe Glu Gly Arg Ser Ala Leu Leu Leu Gly<br>210                    215                 220 | 672 |
| aag gcg aag gac aac aat gcc tct acc gcg atc ggc ccg ttc atc cgc<br>Lys Ala Lys Asp Asn Asn Ala Ser Thr Ala Ile Gly Pro Phe Ile Arg<br>225                    230                 235              240 | 720 |
| ctg ttc gat gac ggc ttc acg atg gac gac gtg cgt agc gcg gtg gtc<br>Leu Phe Asp Asp Gly Phe Thr Met Asp Asp Val Arg Ser Ala Val Val<br>                    245                 250              255 | 768 |
| gac ctc acc atc gac ggg ccg gag ggc tat cgc ctc tcg ggc acc aac<br>Asp Leu Thr Ile Asp Gly Pro Glu Gly Tyr Arg Leu Ser Gly Thr Asn<br>                260                 265              270 | 816 |
| aag atg agc gag atc agc cga gat ccg acc gag ctc gtg cgc cag acg<br>Lys Met Ser Glu Ile Ser Arg Asp Pro Thr Glu Leu Val Arg Gln Thr<br>       275                    280                 285 | 864 |
| ctg agc gag cac cag tat ccg gac ggc ttc gcg ctg ttc ctc ggc acg<br>Leu Ser Glu His Gln Tyr Pro Asp Gly Phe Ala Leu Phe Leu Gly Thr<br>290                    295                 300 | 912 |
| ctg ttc gcg ccg gtg cag gat cgc gac cat ccc ggc cgc ggc ttc act<br>Leu Phe Ala Pro Val Gln Asp Arg Asp His Pro Gly Arg Gly Phe Thr<br>305                    310                 315              320 | 960 |
| cac aag ccc ggc gat att gtc cgc att tcc acg ccg aag ctc ggc acg<br>His Lys Pro Gly Asp Ile Val Arg Ile Ser Thr Pro Lys Leu Gly Thr<br>                    325                 330              335 | 1008 |

```
ctc gtc aac cgc gtc acc acg tcc aag gcc gcc gcg ccc tgg acg ttc     1056
Leu Val Asn Arg Val Thr Thr Ser Lys Ala Ala Ala Pro Trp Thr Phe
            340                 345                 350 ggc atc cgc gat ctg atg cgc aat ctc gcc gcc cgc ggc ctt ctc tcg     1104
Gly Ile Arg Asp Leu Met Arg Asn Leu Ala Ala Arg Gly Leu Leu Ser
        355                 360                 365 cat tcc taa                                                          1113
His Ser
    370

<210> SEQ ID NO 92
<211> LENGTH: 370
<212> TYPE: PRT
<213> ORGANISM: Pseudomonas elodea

<400> SEQUENCE: 92

Met Leu Pro Ala Asp His Ala Gln Ala Ile Leu Val Gly Arg Val Gln
1               5                   10                  15

Thr Pro Ala Gly Pro Ser Pro Val Leu Leu Arg Asp Gly Gln Val Ile
            20                  25                  30

Asp Val Ser Ala Ile Ala Pro Thr Val Ala Asp Leu Leu Glu Arg Asp
        35                  40                  45

Asp Ile Ala Thr Leu Ser Gly Thr Val Leu Cys Ser Val Asp Ala Leu
    50                  55                  60

Gly Thr Glu Ser Ala Pro Gln Val Leu Ala Pro Val Asp Leu Gln Cys
65                  70                  75                  80

Val Lys Ala Ala Gly Val Thr Phe Ala Val Ser Ala Leu Glu Arg Val
                85                  90                  95

Ile Glu Glu Arg Ala Arg Gly Asp Ser Ala Lys Ala Ala Glu Ile Arg
            100                 105                 110

Gly Asp Leu Glu Ala Lys Val Gly Ser Gly Ile Arg Ser Val Val Pro
        115                 120                 125

Gly Thr Ala Glu Ala Ala Ala Leu Lys Ala Ala Leu Ile Glu Ala Gly
    130                 135                 140

Met Trp Ser Gln Tyr Leu Glu Val Ala Ile Gly Pro Asp Ala Glu Val
145                 150                 155                 160

Phe Thr Lys Ala Pro Val Leu Ser Ala Met Gly Trp Gly Ala Glu Ile
                165                 170                 175

Gly Ile Arg Ser Asp Ser Asp Trp Asn Asn Pro Glu Pro Glu Val Val
            180                 185                 190

Leu Val Val Asp Arg Asn Gly Ala Ile Lys Gly Ala Thr Leu Gly Asn
        195                 200                 205

Asp Val Asn Leu Arg Asp Phe Glu Gly Arg Ser Ala Leu Leu Leu Gly
    210                 215                 220

Lys Ala Lys Asp Asn Asn Ala Ser Thr Ala Ile Gly Pro Phe Ile Arg
225                 230                 235                 240

Leu Phe Asp Asp Gly Phe Thr Met Asp Asp Val Arg Ser Ala Val Val
                245                 250                 255

Asp Leu Thr Ile Asp Gly Pro Glu Gly Tyr Arg Leu Ser Gly Thr Asn
            260                 265                 270

Lys Met Ser Glu Ile Ser Arg Asp Pro Thr Glu Leu Val Arg Gln Thr
        275                 280                 285

Leu Ser Glu His Gln Tyr Pro Asp Gly Phe Ala Leu Phe Leu Gly Thr
    290                 295                 300

Leu Phe Ala Pro Val Gln Asp Arg Asp His Pro Gly Arg Gly Phe Thr
```

```
305                310               315               320
His Lys Pro Gly Asp Ile Val Arg Ile Ser Thr Pro Lys Leu Gly Thr
              325                330               335

Leu Val Asn Arg Val Thr Thr Ser Lys Ala Ala Ala Pro Trp Thr Phe
              340                345               350

Gly Ile Arg Asp Leu Met Arg Asn Leu Ala Ala Arg Gly Leu Leu Ser
              355                360               365

His Ser
    370

<210> SEQ ID NO 93
<211> LENGTH: 1113
<212> TYPE: DNA
<213> ORGANISM: Artificial Sequence
<220> FEATURE:
<223> OTHER INFORMATION: synthetic DNA

<400> SEQUENCE: 93
atgctgccgg cggatcatgc ccaagcaatc ctggtcggtc gcgtccaaac cccggctggc      60
ccgtccccgg tcctgctgcg tgatggtcag gtcattgatg tgtccgcaat cgcaccgacc     120
gtggcagacc tgctggaacg tgatgacatt gccaccctga gcggtacggt gctgtgctct     180
gttgatgccc tgggcacgga agcgcaccg caggtcctgg caccggtgga cctgcaatgt     240
gtcaaagcg ccggtgttac cttcgcagtc tcagctctgg aacgcgtgat cgaagaacgt     300
gcacgcggtg attcggctaa agcagctgaa attcgtggcg acctggaagc gaaagtgggc     360
tcaggtatcc gctcggtggt tccgggcacg gcagaagcgg ccgcactgaa agctgcgctg     420
attgaagcgg gcatgtggtc acagtatctg gaagttgcga tcggcccgga tgccgaagtg     480
ttcaccaagg caccggttct gtcggctatg ggctggggtg cggaaattgg tatccgtagc     540
gattctgact ggaacaatcc ggaaccggaa gtcgtgctgg ttgtcgatcg caacggcgca     600
attaaaggtg ctacgctggg caacgatgtt aatctgcgtg actttgaagg tcgcagtgcc     660
ctgctgctgg gcaaagcaaa ggataacaat gcgtccaccg ccattggtcc gtttatccgt     720
ctgttcgatg acggctttac catggatgac gtgcgcagtg ccgtggttga tctgacgatt     780
gacggcccgg aaggttatcg tctgtccggc accaacaaga tgagtgaaat ctcccgtgat     840
ccgaccgaac tggttcgcca gacgctgagc gaacatcaat accgggatgg ttttgctctg     900
ttcctgggca cgctgttcgc accggttcaa gatcgtgacc atccgggccg cggttttacc     960
cacaaaccgg gtgatattgt ccgtatcagc accccgaagc tgggcacgct ggttaatcgc    1020
gtcaccacgt ctaaagccgc agctccgtgg accttcggta ttcgtgacct gatgcgtaat    1080
ctggcggctc gtggcctgct gtctcattcg tga                                1113

<210> SEQ ID NO 94
<211> LENGTH: 1194
<212> TYPE: DNA
<213> ORGANISM: Zobellia galactanivorans
<220> FEATURE:
<221> NAME/KEY: CDS
<222> LOCATION: (1)..(1194)

<400> SEQUENCE: 94 atg aat tat atc gat tta aac cgc ctc ata ccg gaa tta gcg gaa aca       48
Met Asn Tyr Ile Asp Leu Asn Arg Leu Ile Pro Glu Leu Ala Glu Thr
1               5                   10                  15 ggc aca tgg ata ggc agg tgc atg gta ccg gca caa aaa gcg tac aat       96
Gly Thr Trp Ile Gly Arg Cys Met Val Pro Ala Gln Lys Ala Tyr Asn
```

```
                        20                  25                  30
ggt ata gct ggg ccc cac gtg gtg atg gcc cgc aaa gga aaa atc tac      144
Gly Ile Ala Gly Pro His Val Val Met Ala Arg Lys Gly Lys Ile Tyr
         35                  40                  45 gac cta tcg gcc cac ttc aac tcc aca agt gag cta ttc aac tgt aag      192
Asp Leu Ser Ala His Phe Asn Ser Thr Ser Glu Leu Phe Asn Cys Lys
 50                  55                  60 aac ccg gtt tcc cgc tta aaa gcc tta aac gat tta ccg gaa cta ggc      240
Asn Pro Val Ser Arg Leu Lys Ala Leu Asn Asp Leu Pro Glu Leu Gly
 65                  70                  75                  80 agc ctg aaa gat gcc ttg aaa aac gcc cta tac ttc aat cag aat cca      288
Ser Leu Lys Asp Ala Leu Lys Asn Ala Leu Tyr Phe Asn Gln Asn Pro
             85                  90                  95 cta ctc ccc tac atc ata gcg cca aac gat ata caa gcc gta aaa gcc      336
Leu Leu Pro Tyr Ile Ile Ala Pro Asn Asp Ile Gln Ala Val Lys Ala
                100                 105                 110 tgt ggt gta act ttt atc aaa agc ttg ctc gag agg gtc att gaa gaa      384
Cys Gly Val Thr Phe Ile Lys Ser Leu Leu Glu Arg Val Ile Glu Glu
            115                 120                 125 aaa gca aaa ggc gat gcc cta gta gcg aac gac ata cgt caa acc att      432
Lys Ala Lys Gly Asp Ala Leu Val Ala Asn Asp Ile Arg Gln Thr Ile
130                 135                 140 tac gat acc tta ggc aac gac ttg agc aag gtt acc ccc ggt tca ccg      480
Tyr Asp Thr Leu Gly Asn Asp Leu Ser Lys Val Thr Pro Gly Ser Pro
145                 150                 155                 160 gaa acc gaa aag ctc aag gag gaa tta cag aaa aaa ggc cta tgg tcg      528
Glu Thr Glu Lys Leu Lys Glu Glu Leu Gln Lys Lys Gly Leu Trp Ser
                165                 170                 175 caa tac ctc gaa gtg ggc att ggc aag gat gcc gag gtt ttc acc aag      576
Gln Tyr Leu Glu Val Gly Ile Gly Lys Asp Ala Glu Val Phe Thr Lys
            180                 185                 190 gcc caa ccc ttg tct gcc gtt ggt ttc gga gcg gag ata ggc gtt cta      624
Ala Gln Pro Leu Ser Ala Val Gly Phe Gly Ala Glu Ile Gly Val Leu
        195                 200                 205 aag agt tcc aaa tgg aac aat ccg gaa cct gaa atc gtg ctc gcc gta      672
Lys Ser Ser Lys Trp Asn Asn Pro Glu Pro Glu Ile Val Leu Ala Val
    210                 215                 220 tcc tcc tcg gga aaa atc gtc ggg gcc aca ctc ggc aac gac gta aac      720
Ser Ser Ser Gly Lys Ile Val Gly Ala Thr Leu Gly Asn Asp Val Asn
225                 230                 235                 240 ctt cgc gat tac gaa ggt cgc agc gcc cta ttg ctc ggt gag gcg aaa      768
Leu Arg Asp Tyr Glu Gly Arg Ser Ala Leu Leu Leu Gly Glu Ala Lys
                245                 250                 255 gac caa aac gga tct tgt gcc att ggc ccc ttg ttt cgc ttg ttc gat      816
Asp Gln Asn Gly Ser Cys Ala Ile Gly Pro Leu Phe Arg Leu Phe Asp
            260                 265                 270 gag act ttt tcc cta gat gac gta aag gat tgc gat gta atg ttt tct      864
Glu Thr Phe Ser Leu Asp Asp Val Lys Asp Cys Asp Val Met Phe Ser
        275                 280                 285 atg aag ggg aag gac aat ttc gcc act tcc gga agc aat aag atg aaa      912
Met Lys Gly Lys Asp Asn Phe Ala Thr Ser Gly Ser Asn Lys Met Lys
    290                 295                 300 gag att agc cgt agt cct gaa aat tta gtg gcc cag gtc ata gga aaa      960
Glu Ile Ser Arg Ser Pro Glu Asn Leu Val Ala Gln Val Ile Gly Lys
305                 310                 315                 320 aac cat caa tac cca gac ggg ctc gtg ctt ttc tta ggt act atg ttc     1008
Asn His Gln Tyr Pro Asp Gly Leu Val Leu Phe Leu Gly Thr Met Phe
                325                 330                 335 gcc cct acg gaa gac cgc aat gga aaa ggt ttg ggt ttc acc cac aaa     1056
```

```
Ala Pro Thr Glu Asp Arg Asn Gly Lys Gly Leu Gly Phe Thr His Lys
                340                 345                 350 aag gga gat caa gtc aac atc tct tct tcg cat ttg ggc aca ctc atc    1104
Lys Gly Asp Gln Val Asn Ile Ser Ser Ser His Leu Gly Thr Leu Ile
            355                 360                 365 aat tgg gtg aac act tgt gac caa ata cca aag tgg gaa ttc ggc att    1152
Asn Trp Val Asn Thr Cys Asp Gln Ile Pro Lys Trp Glu Phe Gly Ile
370                 375                 380 ggt gct ttt acg aac tat att gta aaa cgg aat tta aaa tag            1194
Gly Ala Phe Thr Asn Tyr Ile Val Lys Arg Asn Leu Lys
385                 390                 395

<210> SEQ ID NO 95
<211> LENGTH: 397
<212> TYPE: PRT
<213> ORGANISM: Zobellia galactanivorans

<400> SEQUENCE: 95

Met Asn Tyr Ile Asp Leu Asn Arg Leu Ile Pro Glu Leu Ala Glu Thr
1               5                   10                  15

Gly Thr Trp Ile Gly Arg Cys Met Val Pro Ala Gln Lys Ala Tyr Asn
            20                  25                  30

Gly Ile Ala Gly Pro His Val Met Ala Arg Lys Gly Lys Ile Tyr
        35                  40                  45

Asp Leu Ser Ala His Phe Asn Ser Thr Ser Glu Leu Phe Asn Cys Lys
    50                  55                  60

Asn Pro Val Ser Arg Leu Lys Ala Leu Asn Asp Leu Pro Glu Leu Gly
65                  70                  75                  80

Ser Leu Lys Asp Ala Leu Lys Asn Ala Leu Tyr Phe Asn Gln Asn Pro
                85                  90                  95

Leu Leu Pro Tyr Ile Ile Ala Pro Asn Asp Ile Gln Ala Val Lys Ala
            100                 105                 110

Cys Gly Val Thr Phe Ile Lys Ser Leu Leu Glu Arg Val Ile Glu Glu
        115                 120                 125

Lys Ala Lys Gly Asp Ala Leu Val Ala Asn Asp Ile Arg Gln Thr Ile
    130                 135                 140

Tyr Asp Thr Leu Gly Asn Asp Leu Ser Lys Val Thr Pro Gly Ser Pro
145                 150                 155                 160

Glu Thr Glu Lys Leu Lys Glu Glu Leu Gln Lys Lys Gly Leu Trp Ser
                165                 170                 175

Gln Tyr Leu Glu Val Gly Ile Gly Lys Asp Ala Glu Val Phe Thr Lys
            180                 185                 190

Ala Gln Pro Leu Ser Ala Val Gly Phe Gly Ala Glu Ile Gly Val Leu
        195                 200                 205

Lys Ser Ser Lys Trp Asn Asn Pro Glu Pro Glu Ile Val Leu Ala Val
    210                 215                 220

Ser Ser Ser Gly Lys Ile Val Gly Ala Thr Leu Gly Asn Asp Val Asn
225                 230                 235                 240

Leu Arg Asp Tyr Glu Gly Arg Ser Ala Leu Leu Leu Gly Glu Ala Lys
                245                 250                 255

Asp Gln Asn Gly Ser Cys Ala Ile Gly Pro Leu Phe Arg Leu Phe Asp
            260                 265                 270

Glu Thr Phe Ser Leu Asp Asp Val Lys Asp Cys Asp Val Met Phe Ser
        275                 280                 285

Met Lys Gly Lys Asp Asn Phe Ala Thr Ser Gly Ser Asn Lys Met Lys
    290                 295                 300
```

| Glu | Ile | Ser | Arg | Ser | Pro | Glu | Asn | Leu | Val | Ala | Gln | Val | Ile | Gly | Lys |
|---|---|---|---|---|---|---|---|---|---|---|---|---|---|---|---|
| 305 | | | | 310 | | | | 315 | | | | 320 | | | |

| Asn | His | Gln | Tyr | Pro | Asp | Gly | Leu | Val | Leu | Phe | Leu | Gly | Thr | Met | Phe |
|---|---|---|---|---|---|---|---|---|---|---|---|---|---|---|---|
| | | | | 325 | | | | | 330 | | | | | 335 | |

| Ala | Pro | Thr | Glu | Asp | Arg | Asn | Gly | Lys | Gly | Leu | Gly | Phe | Thr | His | Lys |
|---|---|---|---|---|---|---|---|---|---|---|---|---|---|---|---|
| | | | 340 | | | | | 345 | | | | | 350 | | |

| Lys | Gly | Asp | Gln | Val | Asn | Ile | Ser | Ser | Ser | His | Leu | Gly | Thr | Leu | Ile |
|---|---|---|---|---|---|---|---|---|---|---|---|---|---|---|---|
| | 355 | | | | | 360 | | | | | 365 | | | | |

| Asn | Trp | Val | Asn | Thr | Cys | Asp | Gln | Ile | Pro | Lys | Trp | Glu | Phe | Gly | Ile |
|---|---|---|---|---|---|---|---|---|---|---|---|---|---|---|---|
| 370 | | | | | 375 | | | | | 380 | | | | | |

| Gly | Ala | Phe | Thr | Asn | Tyr | Ile | Val | Lys | Arg | Asn | Leu | Lys |
|---|---|---|---|---|---|---|---|---|---|---|---|---|
| 385 | | | | | 390 | | | | | 395 | | |

<210> SEQ ID NO 96
<211> LENGTH: 1194
<212> TYPE: DNA
<213> ORGANISM: Artificial Sequence
<220> FEATURE:
<223> OTHER INFORMATION: synthetic DNA

<400> SEQUENCE: 96

```
atgaactata ttgatctgaa tcgtctgatc ccggaactgg cggaaaccgg tacgtggatt      60
ggccgctgca tggtgccggc ccagaaagcc tataacggta tcgccggccc gcatgtggtt     120
atggcacgta aaggcaaaat ttacgatctg agcgcccact taatagtac cagcgaactg      180
ttcaactgta aaaatccggt tagccgcctg aaagcactga acgatctgcc ggaactgggt     240
tctctgaaag atgcgctgaa aaatgccctg tattttaacc agaatccgct gctgccgtac     300
attatcgcgc cgaacgatat tcaggcagtg aaagcgtgcg cgttaccctt catcaaaagc     360
ctgctggaac gtgtgattga agaaaaagcc aaaggtgatg ccctggttgc aaacgatatt     420
cgccagacca tctatgatac gctgggcaat gatctgagta agtgaccccc gggtagcccg     480
gaaacggaaa aactgaaaga gaactgcag aaaaaaggcc tgtggtctca gtacctggaa      540
gtgggcatcg gtaaagatgc cgaagttttt accaaagcac agccgctgag cgcggtgggt     600
tttggtgcag aaattggtgt tctgaaaagc tctaaatgga caatccgga accggaaatc      660
gtgctggcgg ttagtagctc tggtaaaatt gtgggcgcca ccctgggtaa cgatgttaat     720
ctgcgtgatt acgaaggccg cagtgcactg ctgctgggtg aagcgaaaga tcagaatggc     780
agctgcgcga ttggtccgct gtttcgtctg ttcgatgaaa ccttttctct ggatgatgtg     840
aaggattgtg atgttatgtt cagtatgaag ggcaaggata cttcgcaac gtctggtagt     900
aacaagatga aggaaatcag ccgttctccg gaaaacctgg tggcgcaggt tattggcaaa     960
aatcatcagt atccggatgg cctggtgctg tttctgggca ccatgttcgc accgacggaa    1020
gatcgcaacg gcaaaggtct gggctttacc cataaaaaag gcgatcaagt gaatatcagt    1080
agctctcacc tgggcaccct gattaactgg gttaatacgt gtgatcagat tccgaaatgg    1140
gaatttggta tcggcgcgtt cacgaactac attgttaaac gcaatctgaa atag          1194
```

<210> SEQ ID NO 97
<211> LENGTH: 897
<212> TYPE: DNA
<213> ORGANISM: Thermobacillus composti
<220> FEATURE:
<221> NAME/KEY: CDS
<222> LOCATION: (1)..(897)

<400> SEQUENCE: 97

-continued

```
atg cgc att att cgt tac atc ggg gac gac gga gct gcg cgc ctc gcg      48
Met Arg Ile Ile Arg Tyr Ile Gly Asp Asp Gly Ala Ala Arg Leu Ala
1               5                   10                  15 gcg gtg acc gac gag gag cag gct ttc ccg ctc cgg tcg ccg gat ttc      96
Ala Val Thr Asp Glu Glu Gln Ala Phe Pro Leu Arg Ser Pro Asp Phe
                20                  25                  30 atg gcg ctg gtg cgg gaa gcg gac gag gcg ggg atc acg ccg ctg gaa     144
Met Ala Leu Val Arg Glu Ala Asp Glu Ala Gly Ile Thr Pro Leu Glu
            35                  40                  45 gcg gtg cgc cgt cag atc gcg ggc gca cag ccg ctg ccc ggc gac tgg     192
Ala Val Arg Arg Gln Ile Ala Gly Ala Gln Pro Leu Pro Gly Asp Trp
        50                  55                  60 cgc gag ttg aac ctg ctg acg ccg gtg gat gcg ccc gag gtg tgg gcg     240
Arg Glu Leu Asn Leu Leu Thr Pro Val Asp Ala Pro Glu Val Trp Ala
65                  70                  75                  80 gcc ggc gtc act tat gag cgc agc aaa gaa gcg cgc aac gag gag tcg     288
Ala Gly Val Thr Tyr Glu Arg Ser Lys Glu Ala Arg Asn Glu Glu Ser
                85                  90                  95 aag ggc gcc gca acc ggc gac gaa acg ttc tac gac aag gtg tac cgg     336
Lys Gly Ala Ala Thr Gly Asp Glu Thr Phe Tyr Asp Lys Val Tyr Arg
            100                 105                 110 gcc gag cgg ccg gag att ttc ttc aag tcg acg agc gcc cgc acg gcg     384
Ala Glu Arg Pro Glu Ile Phe Phe Lys Ser Thr Ser Ala Arg Thr Ala
        115                 120                 125 cgg ccg ggc aca ccc gtc tgc atc cgc agc gac tcg gac tgg cag gtg     432
Arg Pro Gly Thr Pro Val Cys Ile Arg Ser Asp Ser Asp Trp Gln Val
130                 135                 140 ccc gag ccg gaa ctc ggc atc gtg ctg gac cgc ggc ggc cgc atc ctc     480
Pro Glu Pro Glu Leu Gly Ile Val Leu Asp Arg Gly Gly Arg Ile Leu
145                 150                 155                 160 ggc tac acg gtc ggc aac gac atg agc tgc cgc gac atc gag ggc gag     528
Gly Tyr Thr Val Gly Asn Asp Met Ser Cys Arg Asp Ile Glu Gly Glu
                165                 170                 175 aac ccg ctc tat ctg ccg cag gcg aaa atc tgg cgc cgc tcc tgt tcc     576
Asn Pro Leu Tyr Leu Pro Gln Ala Lys Ile Trp Arg Arg Ser Cys Ser
            180                 185                 190 atc ggt ccg gcg atc cgg ctg gcc gaa acc gtg ccg aat ccg tat gac     624
Ile Gly Pro Ala Ile Arg Leu Ala Glu Thr Val Pro Asn Pro Tyr Asp
        195                 200                 205 ctg acg atc acc tgc cgc atc tat cgg gac ggt caa ttg gcg gtg aac     672
Leu Thr Ile Thr Cys Arg Ile Tyr Arg Asp Gly Gln Leu Ala Val Asn
210                 215                 220 gag acg gcc aat acg ggg cag ctc cgg cgg aag ctg gac gaa ctg gcg     720
Glu Thr Ala Asn Thr Gly Gln Leu Arg Arg Lys Leu Asp Glu Leu Ala
225                 230                 235                 240 tcc ttc ctc gtg cgg gac aac gtc gtg ttc gac ggc acc gtg ctg ctg     768
Ser Phe Leu Val Arg Asp Asn Val Val Phe Asp Gly Thr Val Leu Leu
                245                 250                 255 acc ggc acc tgc atc gtg ccg ccc gac cgg ttc acg ctg cag ccc ggc     816
Thr Gly Thr Cys Ile Val Pro Pro Asp Arg Phe Thr Leu Gln Pro Gly
            260                 265                 270 gac cgc atc gag atc gac att tcc ggc atc ggc acc ctg atc aac cct     864
Asp Arg Ile Glu Ile Asp Ile Ser Gly Ile Gly Thr Leu Ile Asn Pro
        275                 280                 285 gtc gcg gcg gcg gac gcc gca atc cag gat taa                         897
Val Ala Ala Ala Asp Ala Ala Ile Gln Asp
290                 295
```

<210> SEQ ID NO 98

<211> LENGTH: 298
<212> TYPE: PRT
<213> ORGANISM: Thermobacillus composti

<400> SEQUENCE: 98

Met Arg Ile Ile Arg Tyr Ile Gly Asp Asp Gly Ala Ala Arg Leu Ala
1               5                   10                  15

Ala Val Thr Asp Glu Glu Gln Ala Phe Pro Leu Arg Ser Pro Asp Phe
            20                  25                  30

Met Ala Leu Val Arg Glu Ala Asp Glu Ala Gly Ile Thr Pro Leu Glu
        35                  40                  45

Ala Val Arg Arg Gln Ile Ala Gly Ala Gln Pro Leu Pro Gly Asp Trp
    50                  55                  60

Arg Glu Leu Asn Leu Leu Thr Pro Val Asp Ala Pro Glu Val Trp Ala
65                  70                  75                  80

Ala Gly Val Thr Tyr Glu Arg Ser Lys Glu Ala Arg Asn Glu Glu Ser
                85                  90                  95

Lys Gly Ala Ala Thr Gly Asp Glu Thr Phe Tyr Asp Lys Val Tyr Arg
            100                 105                 110

Ala Glu Arg Pro Glu Ile Phe Phe Lys Ser Thr Ser Ala Arg Thr Ala
        115                 120                 125

Arg Pro Gly Thr Pro Val Cys Ile Arg Ser Asp Ser Asp Trp Gln Val
    130                 135                 140

Pro Glu Pro Glu Leu Gly Ile Val Leu Asp Arg Gly Gly Arg Ile Leu
145                 150                 155                 160

Gly Tyr Thr Val Gly Asn Asp Met Ser Cys Arg Asp Ile Glu Gly Glu
                165                 170                 175

Asn Pro Leu Tyr Leu Pro Gln Ala Lys Ile Trp Arg Arg Ser Cys Ser
            180                 185                 190

Ile Gly Pro Ala Ile Arg Leu Ala Glu Thr Val Pro Asn Pro Tyr Asp
        195                 200                 205

Leu Thr Ile Thr Cys Arg Ile Tyr Arg Asp Gly Gln Leu Ala Val Asn
    210                 215                 220

Glu Thr Ala Asn Thr Gly Gln Leu Arg Arg Lys Leu Asp Glu Leu Ala
225                 230                 235                 240

Ser Phe Leu Val Arg Asp Asn Val Val Phe Asp Gly Thr Val Leu Leu
                245                 250                 255

Thr Gly Thr Cys Ile Val Pro Pro Asp Arg Phe Thr Leu Gln Pro Gly
            260                 265                 270

Asp Arg Ile Glu Ile Asp Ile Ser Gly Ile Gly Thr Leu Ile Asn Pro
        275                 280                 285

Val Ala Ala Ala Asp Ala Ala Ile Gln Asp
    290                 295

<210> SEQ ID NO 99
<211> LENGTH: 897
<212> TYPE: DNA
<213> ORGANISM: Artificial Sequence
<220> FEATURE:
<223> OTHER INFORMATION: synthetic DNA

<400> SEQUENCE: 99
atgcgtatta tccgctatat tggtgatgat ggtgccgcac gtctggcagc cgttaccgat      60
gaagaacagg catttccgct gcgttctccg gatttcatgg cgctggttcg cgaagcggat     120
gaagcgggta tcacgccgct ggaagcggtg cgtcgccaga ttgcgggtgc acagccgctg     180

-continued

```
ccgggtgatt ggcgcgaact gaacctgctg accccggtgg atgcaccgga agtttgggca    240
gcaggtgtga cgtacgaacg tagcaaagaa gcacgcaatg aagaatctaa aggcgcggcc    300
accggtgatg aaacctttta tgataaagtt taccgtgcgg aacgcccgga atcttttttc    360
aaaagcacct ctgcacgtac cgcccgtccg ggcaccccgg tgtgcattcg tagtgatagc    420
gattggcagg ttccggaacc ggaactgggt atcgtgctgg atcgtggcgg tcgcattctg    480
ggctataccg tgggtaacga tatgagctgc cgtgatatcg aaggcgaaaa tccgctgtac    540
ctgccgcagg ccaaaatttg cgtcgctct tgtagtatcg gtccggccat cgcctggca    600 gaaaccgttc cgaacccgta tgatctgacc atcacgtgcc gtatttaccg cgatggccag    660
ctggcggtga acgaaaccgc caatacgggt cagctgcgtc gcaaactgga tgaactggcg    720
agttttctgg ttcgcgataa cgtggttttc gatggcaccg ttctgctgac cggtacgtgc    780
atcgtgccgc cggatcgttt caccctgcag ccgggcgatc gcattgaaat cgatattagc    840
ggcatcggca ccctgattaa tccggtggca gcggccgatg cagcgattca ggattaa      897
```

<210> SEQ ID NO 100
<211> LENGTH: 1227
<212> TYPE: DNA
<213> ORGANISM: Arthrobacter globiformis
<220> FEATURE:
<221> NAME/KEY: CDS
<222> LOCATION: (1)..(1227)

<400> SEQUENCE: 100

```
gtg acc gcg ccg ccg att ccc ggg agt tcc gtt cct ccg gta acc tct         48
Val Thr Ala Pro Pro Ile Pro Gly Ser Ser Val Pro Pro Val Thr Ser
 1               5                  10                  15 gtc ctt ccg gat gac gct ggc cag gcg ctg ctg gtt ggc cgg atc tgg         96
Val Leu Pro Asp Asp Ala Gly Gln Ala Leu Leu Val Gly Arg Ile Trp
             20                  25                  30 gac ccc gcc acc ggc ggt ccc cgg gtg gtg gct ctc agc ggg gac tcc        144
Asp Pro Ala Thr Gly Gly Pro Arg Val Val Ala Leu Ser Gly Asp Ser
         35                  40                  45 gcc gtc gac ctg acg cgc ctg gcc gga acc gtc tcg gaa ctg ctc gaa        192
Ala Val Asp Leu Thr Arg Leu Ala Gly Thr Val Ser Glu Leu Leu Glu
     50                  55                  60 ctg cct gat cca gcc gcg gca gtc cgt gcg gcg ctc ctt gac ccg gca        240
Leu Pro Asp Pro Ala Ala Ala Val Arg Ala Ala Leu Leu Asp Pro Ala
 65                  70                  75                  80 ctg ggg gta cag cgg tgg gcg acg gcc gac gtc gtc gcc gcc tcg ctg        288
Leu Gly Val Gln Arg Trp Ala Thr Ala Asp Val Val Ala Ala Ser Leu
                 85                  90                  95 gcc ggt gac gca gca cgc ccg cac ctg ctc gca ccg gtt gac ctg cag        336
Ala Gly Asp Ala Ala Arg Pro His Leu Leu Ala Pro Val Asp Leu Gln
            100                 105                 110 gtc atc aag gcc tgc ggc gtg acg ttt gtg gac agc atg atc gaa cgg        384
Val Ile Lys Ala Cys Gly Val Thr Phe Val Asp Ser Met Ile Glu Arg
        115                 120                 125 gtg atc gag gaa agg tgc gcc ggc gac gcc gct cgg gcg gcc gag atg        432
Val Ile Glu Glu Arg Cys Ala Gly Asp Ala Ala Arg Ala Ala Glu Met
    130                 135                 140 cgc gag ctt gtc ggg aag gcg ctc ggc gga agc atc gcc acg gtc cgg        480
Arg Glu Leu Val Gly Lys Ala Leu Gly Gly Ser Ile Ala Thr Val Arg
145                 150                 155                 160 ccg ggg tcc ccg gag gcg gcc gag gcc aag cgc gtc ctg att gcc gag        528
Pro Gly Ser Pro Glu Ala Ala Glu Ala Lys Arg Val Leu Ile Ala Glu
                165                 170                 175
```

```
ggg ctc tgg tcg cag tat ctc gag gtg ggc atc ggg ccg gac ccg gag    576
Gly Leu Trp Ser Gln Tyr Leu Glu Val Gly Ile Gly Pro Asp Pro Glu
            180                 185                 190 gtg ttc acg aag gcg ccg gtg ctg tcc tcg gtg ggc ctg ggc gcg ggc    624
Val Phe Thr Lys Ala Pro Val Leu Ser Ser Val Gly Leu Gly Ala Gly
        195                 200                 205 atc ggg att ccg cgg ttc tcc tcc tgg aac aac ccg gag ccg gaa ctg    672
Ile Gly Ile Pro Arg Phe Ser Ser Trp Asn Asn Pro Glu Pro Glu Leu
    210                 215                 220 gtg ctg atc gtg acg tcc cgc ggc gag gtg gtg ggc gcc act ctg ggc    720
Val Leu Ile Val Thr Ser Arg Gly Glu Val Val Gly Ala Thr Leu Gly
225                 230                 235                 240 aac gac gtc aac ctg cgc gac gtt gag ggc cgc agc gcc ctg ctg ctg    768
Asn Asp Val Asn Leu Arg Asp Val Glu Gly Arg Ser Ala Leu Leu Leu
                245                 250                 255 ggc aag gcc aag gac aac aac gcg tcc agt gcc ctc gga cca ctg atc    816
Gly Lys Ala Lys Asp Asn Asn Ala Ser Ser Ala Leu Gly Pro Leu Ile
            260                 265                 270 agg ctc ttc gac ggc agc ttc acg gtg gac acc ctc cgt gag gag gag    864
Arg Leu Phe Asp Gly Ser Phe Thr Val Asp Thr Leu Arg Glu Glu Glu
        275                 280                 285 atc ctg ctg cgt gtc gaa ggc ctg gac ggc tac ctg ctg gag ggg cgg    912
Ile Leu Leu Arg Val Glu Gly Leu Asp Gly Tyr Leu Leu Glu Gly Arg
    290                 295                 300 aac acg ctg gcg agg atc agc agg ccc ttc gag gag ctc gtg gcg gcc    960
Asn Thr Leu Ala Arg Ile Ser Arg Pro Phe Glu Glu Leu Val Ala Ala
305                 310                 315                 320 acc cgc ggc agg cac cac cag tat ccg gac ggc ttc gca ctg ttc acc   1008
Thr Arg Gly Arg His His Gln Tyr Pro Asp Gly Phe Ala Leu Phe Thr
                325                 330                 335 ggc acg ctt ttc gca ccg acc cag gac cgc gac gag ccg ggg cag ggg   1056
Gly Thr Leu Phe Ala Pro Thr Gln Asp Arg Asp Glu Pro Gly Gln Gly
            340                 345                 350 ttc acg cac aag cac ggg gat gtt gtg acc atc cgg agc cgc cac ctg   1104
Phe Thr His Lys His Gly Asp Val Val Thr Ile Arg Ser Arg His Leu
        355                 360                 365 ggt gcc ctc atc aac cgg gtg ggc acg gca gag gag ctc ccg gag tgg   1152
Gly Ala Leu Ile Asn Arg Val Gly Thr Ala Glu Glu Leu Pro Glu Trp
    370                 375                 380 acc ttc ggc ctg cgg cag ctg ttc ggc tac ctc gcg gag cag cgg cag   1200
Thr Phe Gly Leu Arg Gln Leu Phe Gly Tyr Leu Ala Glu Gln Arg Gln
385                 390                 395                 400 gcg gag cta gct cag atg cag gag tag                               1227
Ala Glu Leu Ala Gln Met Gln Glu
                405
```

<210> SEQ ID NO 101
<211> LENGTH: 408
<212> TYPE: PRT
<213> ORGANISM: Arthrobacter globiformis

<400> SEQUENCE: 101

```
Val Thr Ala Pro Pro Ile Pro Gly Ser Ser Val Pro Val Thr Ser
1               5                   10                  15

Val Leu Pro Asp Asp Ala Gly Gln Ala Leu Leu Val Gly Arg Ile Trp
            20                  25                  30

Asp Pro Ala Thr Gly Gly Pro Arg Val Val Ala Leu Ser Gly Asp Ser
        35                  40                  45

Ala Val Asp Leu Thr Arg Leu Ala Gly Thr Val Ser Glu Leu Leu Glu
    50                  55                  60
```

Leu Pro Asp Pro Ala Ala Val Arg Ala Ala Leu Leu Asp Pro Ala
65                  70                  75                  80

Leu Gly Val Gln Arg Trp Ala Thr Ala Asp Val Val Ala Ala Ser Leu
            85                  90                  95

Ala Gly Asp Ala Ala Arg Pro His Leu Leu Ala Pro Val Asp Leu Gln
        100                 105                 110

Val Ile Lys Ala Cys Gly Val Thr Phe Val Asp Ser Met Ile Glu Arg
    115                 120                 125

Val Ile Glu Glu Arg Cys Ala Gly Asp Ala Ala Arg Ala Ala Glu Met
130                 135                 140

Arg Glu Leu Val Gly Lys Ala Leu Gly Gly Ser Ile Ala Thr Val Arg
145                 150                 155                 160

Pro Gly Ser Pro Glu Ala Ala Glu Ala Lys Arg Val Leu Ile Ala Glu
                165                 170                 175

Gly Leu Trp Ser Gln Tyr Leu Glu Val Gly Ile Gly Pro Asp Pro Glu
            180                 185                 190

Val Phe Thr Lys Ala Pro Val Leu Ser Ser Val Gly Leu Gly Ala Gly
        195                 200                 205

Ile Gly Ile Pro Arg Phe Ser Ser Trp Asn Asn Pro Glu Pro Glu Leu
    210                 215                 220

Val Leu Ile Val Thr Ser Arg Gly Glu Val Val Gly Ala Thr Leu Gly
225                 230                 235                 240

Asn Asp Val Asn Leu Arg Asp Val Glu Gly Arg Ser Ala Leu Leu Leu
                245                 250                 255

Gly Lys Ala Lys Asp Asn Asn Ala Ser Ser Ala Leu Gly Pro Leu Ile
            260                 265                 270

Arg Leu Phe Asp Gly Ser Phe Thr Val Asp Thr Leu Arg Glu Glu Glu
        275                 280                 285

Ile Leu Leu Arg Val Glu Gly Leu Asp Gly Tyr Leu Leu Glu Gly Arg
    290                 295                 300

Asn Thr Leu Ala Arg Ile Ser Arg Pro Phe Glu Glu Leu Val Ala Ala
305                 310                 315                 320

Thr Arg Gly Arg His His Gln Tyr Pro Asp Gly Phe Ala Leu Phe Thr
                325                 330                 335

Gly Thr Leu Phe Ala Pro Thr Gln Asp Arg Asp Glu Pro Gly Gln Gly
            340                 345                 350

Phe Thr His Lys His Gly Asp Val Val Thr Ile Arg Ser Arg His Leu
        355                 360                 365

Gly Ala Leu Ile Asn Arg Val Gly Thr Ala Glu Glu Leu Pro Glu Trp
    370                 375                 380

Thr Phe Gly Leu Arg Gln Leu Phe Gly Tyr Leu Ala Glu Gln Arg Gln
385                 390                 395                 400

Ala Glu Leu Ala Gln Met Gln Glu
                405

<210> SEQ ID NO 102
<211> LENGTH: 1227
<212> TYPE: DNA
<213> ORGANISM: Artificial Sequence
<220> FEATURE:
<223> OTHER INFORMATION: synthetic DNA

<400> SEQUENCE: 102
atgaccgccc cgccgatccc gggttcgtcc gtgccgccgg tgacctctgt tctgccggat      60

```
gatgctggcc aagctctgct ggttggtcgt atttgggacc cggcaaccgg cggtccgcgt    120
gtggttgccc tgagcggtga tagcgcggtg gacctgaccc gtctggcagg cacggtgtct    180
gaactgctgg aactgccgga cccggcggcg gcggtgcgtg ctgcgctgct ggacccggcc    240
ctgggcgtcc agcgttgggc aaccgcagat gtcgtggcag caagcctggc aggtgacgct    300
gcacgtccgc atctgctggc accggtggat ctgcaagtta ttaaagcgtg cggcgtcacg    360
tttgtggact ctatgattga acgtgtgatc gaagaacgtt gtgcaggtga tgcagcacgt    420
gctgcggaaa tgcgcgaact ggtgggcaaa gctctgggcg gtagtatcgc aaccgttcgt    480
ccgggttccc cggaagccgc agaagcaaaa cgcgttctga ttgcagaagg tctgtggagc    540
cagtatctgg aagtgggcat cggtccggac ccggaagttt ttaccaaagc tccggtcctg    600
agctctgtgg gtctgggtgc aggtattggt atcccgcgtt tcagttcctg aacaatccg    660 gaaccggaac tggttctgat tgtcacctca cgcggcgaag ttgtcggtgc aacgctgggc    720
aacgatgtta atctgcgtga cgtcgaaggt cgctcggctc tgctgctggg caaagcgaaa    780
gataacaatg cttcatcggc gctgggtccg ctgattcgtc tgtttgatgg cagtttcacc    840
gtggacacgc tgcgtgaaga agaaatcctg ctgcgcgttg aaggcctgga tggttatctg    900
ctggaaggtc gtaacaccct ggcacgtatc tcccgcccgt ttgaagaact ggtggctgcg    960
acgcgtggtc gccatcacca ataccgga ggttttgccc tgttcaccgg cacgctgttt    1020
gcaccgaccc aggatcgtga cgaaccgggc caaggtttca cccataaaca cggcgacgtg    1080
gttacgattc gtagtcgcca cctgggtgct ctgatcaatc gtgtgggcac cgcggaagaa    1140
ctgccggaat ggacgttcgg tctgcgccaa ctgtttggtt atctggcgga caacgtcaa    1200 gcggaactgg ctcaaatgca ggaatga                                        1227
```

<210> SEQ ID NO 103
<211> LENGTH: 1446
<212> TYPE: DNA
<213> ORGANISM: Azospirillum brasilense
<220> FEATURE:
<221> NAME/KEY: CDS
<222> LOCATION: (1)..(1446)

<400> SEQUENCE: 103

```
atg gct aac gtg act tat acg gat acg caa ctg ctg atc gac ggc gag    48
Met Ala Asn Val Thr Tyr Thr Asp Thr Gln Leu Leu Ile Asp Gly Glu
1               5                  10                  15 tgg gtc gac gcc gcg agc ggc aag acg atc gac gtc gtg aac ccg gcg    96
Trp Val Asp Ala Ala Ser Gly Lys Thr Ile Asp Val Val Asn Pro Ala
            20                  25                  30 acc ggc aag ccg atc ggc agg gtg gcc cat gcg ggc atc gcc gat ctc   144
Thr Gly Lys Pro Ile Gly Arg Val Ala His Ala Gly Ile Ala Asp Leu
        35                  40                  45 gac cgt gcg ctc gcc gcc gcg caa agc ggc ttc gag gca tgg cgc aag   192
Asp Arg Ala Leu Ala Ala Ala Gln Ser Gly Phe Glu Ala Trp Arg Lys
    50                  55                  60 gtg ccc gcg cac gag cgc gcg gcg acg atg cgc aag gcg gcc gcg ctg   240
Val Pro Ala His Glu Arg Ala Ala Thr Met Arg Lys Ala Ala Ala Leu
65                  70                  75                  80 gtg cgt gaa cgc gcc gac gcg atc gcg cag ctg atg acg cag gag cag   288
Val Arg Glu Arg Ala Asp Ala Ile Ala Gln Leu Met Thr Gln Glu Gln
                85                  90                  95 ggc aag ccg ctc acc gaa gcg cgc gtc gaa gtg ctg tcg gcg gcg gac   336
Gly Lys Pro Leu Thr Glu Ala Arg Val Glu Val Leu Ser Ala Ala Asp
            100                 105                 110
```

```
                                   -continued atc atc gaa tgg ttc gcg gac gaa ggc cgc cgc gtg tac ggc cgg atc       384
Ile Ile Glu Trp Phe Ala Asp Glu Gly Arg Arg Val Tyr Gly Arg Ile
        115                 120                 125 gtg ccg ccg cgc aac ctc ggc gca cag cag acg gtg aag gag ccg           432
Val Pro Pro Arg Asn Leu Gly Ala Gln Gln Thr Val Val Lys Glu Pro
130                 135                 140 gtc ggc ccg gtc gcc gcg ttc acg ccg tgg aat ttc ccg gtc aac cag       480
Val Gly Pro Val Ala Ala Phe Thr Pro Trp Asn Phe Pro Val Asn Gln
145                 150                 155                 160 gtc gtg cgc aag ctg agc gcc gcg ctg gca acc ggc tgt tcg ttc ctc       528
Val Val Arg Lys Leu Ser Ala Ala Leu Ala Thr Gly Cys Ser Phe Leu
                165                 170                 175 gtg aaa gcg ccg gaa gaa acc ccc gcg tcg ccg gcc gcg ctg ctg cgc       576
Val Lys Ala Pro Glu Glu Thr Pro Ala Ser Pro Ala Ala Leu Leu Arg
            180                 185                 190 gcc ttc gtc gac gca ggc gtg ccg gcc ggc gtg atc ggc ctc gtg tac       624
Ala Phe Val Asp Ala Gly Val Pro Ala Gly Val Ile Gly Leu Val Tyr
        195                 200                 205 ggc gat ccg gcc gaa atc tcg tcg tac ctg atc ccg cac ccg gtg atc       672
Gly Asp Pro Ala Glu Ile Ser Ser Tyr Leu Ile Pro His Pro Val Ile
210                 215                 220 cgc aag gtc acg ttc acg ggt tcg acg ccg gtc ggc aag cag ctc gcc       720
Arg Lys Val Thr Phe Thr Gly Ser Thr Pro Val Gly Lys Gln Leu Ala
225                 230                 235                 240 tcg ctg gcg ggc ctg cac atg aag cgc gcg acg atg gag ctg ggc ggg       768
Ser Leu Ala Gly Leu His Met Lys Arg Ala Thr Met Glu Leu Gly Gly
                245                 250                 255 cac gca ccg gtg atc gtg gcc gaa gac gcc gac gtt gcg ctc gcg gtg       816
His Ala Pro Val Ile Val Ala Glu Asp Ala Asp Val Ala Leu Ala Val
            260                 265                 270 aaa gcg gcc ggc ggc gcg aag ttc cgc aac gcg ggg cag gtc tgc atc       864
Lys Ala Ala Gly Gly Ala Lys Phe Arg Asn Ala Gly Gln Val Cys Ile
        275                 280                 285 tcg ccg acg cgc ttc ctc gtg cac aac agc atc cgc gac gaa ttc acg       912
Ser Pro Thr Arg Phe Leu Val His Asn Ser Ile Arg Asp Glu Phe Thr
    290                 295                 300 cgc gcg ctg gtc aag cat gcc gaa ggg ctg aag gtc ggc aac ggc ctc       960
Arg Ala Leu Val Lys His Ala Glu Gly Leu Lys Val Gly Asn Gly Leu
305                 310                 315                 320 gag gaa ggc acg acg ctc ggc gcg ctc gcg aac ccg cgc cgg ctg acc      1008
Glu Glu Gly Thr Thr Leu Gly Ala Leu Ala Asn Pro Arg Arg Leu Thr
                325                 330                 335 gcg atg gcg tcg gtc atc gac aac gcg cgc aag gtc ggt gcg agc atc      1056
Ala Met Ala Ser Val Ile Asp Asn Ala Arg Lys Val Gly Ala Ser Ile
            340                 345                 350 gaa acc ggc ggc gag cgg atc ggc tcg gaa ggc aac ttc ttc gcg ccg      1104
Glu Thr Gly Gly Glu Arg Ile Gly Ser Glu Gly Asn Phe Phe Ala Pro
        355                 360                 365 acc gtg atc gcg aac gtg ccg ctc gat gcg gac gtg ttc aac aac gag      1152
Thr Val Ile Ala Asn Val Pro Leu Asp Ala Asp Val Phe Asn Asn Glu
    370                 375                 380 ccg ttc ggc ccg gtc gcg gcg att cgc ggt ttc gac aag ctc gaa gag      1200
Pro Phe Gly Pro Val Ala Ala Ile Arg Gly Phe Asp Lys Leu Glu Glu
385                 390                 395                 400 gcg atc gcg gaa gcg aac cgt ttg ccg ttc ggt ctt gcc ggc tac gcg      1248
Ala Ile Ala Glu Ala Asn Arg Leu Pro Phe Gly Leu Ala Gly Tyr Ala
                405                 410                 415 ttc acg cgt tcg ttc gcg aac gtg cac ctg ctc acg cag cgc ctc gaa      1296
Phe Thr Arg Ser Phe Ala Asn Val His Leu Leu Thr Gln Arg Leu Glu
            420                 425                 430
```

```
gtc ggg atg ctg tgg atc aac cag ccg gcg acg ccg tgg ccg gaa atg    1344
Val Gly Met Leu Trp Ile Asn Gln Pro Ala Thr Pro Trp Pro Glu Met
        435                 440                 445 ccg ttc ggc ggc gtg aag gac tcg ggc tac ggt tcg gaa ggc ggc ccg    1392
Pro Phe Gly Gly Val Lys Asp Ser Gly Tyr Gly Ser Glu Gly Gly Pro
450                 455                 460 gaa gcg ctc gag ccg tac ctg gtc acg aag tcg gtg acg gtg atg gcc    1440
Glu Ala Leu Glu Pro Tyr Leu Val Thr Lys Ser Val Thr Val Met Ala
465                 470                 475                 480 gtc tga                                                             1446
Val

<210> SEQ ID NO 104
<211> LENGTH: 481
<212> TYPE: PRT
<213> ORGANISM: Azospirillum brasilense

<400> SEQUENCE: 104

Met Ala Asn Val Thr Tyr Thr Asp Thr Gln Leu Leu Ile Asp Gly Glu
1               5                   10                  15

Trp Val Asp Ala Ala Ser Gly Lys Thr Ile Asp Val Val Asn Pro Ala
            20                  25                  30

Thr Gly Lys Pro Ile Gly Arg Val Ala His Ala Gly Ile Ala Asp Leu
        35                  40                  45

Asp Arg Ala Leu Ala Ala Ala Gln Ser Gly Phe Glu Ala Trp Arg Lys
    50                  55                  60

Val Pro Ala His Glu Arg Ala Ala Thr Met Arg Lys Ala Ala Ala Leu
65                  70                  75                  80

Val Arg Glu Arg Ala Asp Ala Ile Ala Gln Leu Met Thr Gln Glu Gln
                85                  90                  95

Gly Lys Pro Leu Thr Glu Ala Arg Val Glu Val Leu Ser Ala Ala Asp
            100                 105                 110

Ile Ile Glu Trp Phe Ala Asp Glu Gly Arg Arg Val Tyr Gly Arg Ile
        115                 120                 125

Val Pro Pro Arg Asn Leu Gly Ala Gln Gln Thr Val Val Lys Glu Pro
    130                 135                 140

Val Gly Pro Val Ala Ala Phe Thr Pro Trp Asn Phe Pro Val Asn Gln
145                 150                 155                 160

Val Val Arg Lys Leu Ser Ala Ala Leu Ala Thr Gly Cys Ser Phe Leu
                165                 170                 175

Val Lys Ala Pro Glu Glu Thr Pro Ala Ser Pro Ala Ala Leu Leu Arg
            180                 185                 190

Ala Phe Val Asp Ala Gly Val Pro Ala Gly Val Ile Gly Leu Val Tyr
        195                 200                 205

Gly Asp Pro Ala Glu Ile Ser Ser Tyr Leu Ile Pro His Pro Val Ile
    210                 215                 220

Arg Lys Val Thr Phe Thr Gly Ser Thr Pro Val Gly Lys Gln Leu Ala
225                 230                 235                 240

Ser Leu Ala Gly Leu His Met Lys Arg Ala Thr Met Glu Leu Gly Gly
                245                 250                 255

His Ala Pro Val Ile Val Ala Glu Asp Ala Asp Val Ala Leu Ala Val
            260                 265                 270

Lys Ala Ala Gly Gly Ala Lys Phe Arg Asn Ala Gly Gln Val Cys Ile
        275                 280                 285

Ser Pro Thr Arg Phe Leu Val His Asn Ser Ile Arg Asp Glu Phe Thr
```

```
        290                 295                 300
Arg Ala Leu Val Lys His Ala Glu Gly Leu Lys Val Gly Asn Gly Leu
305                 310                 315                 320

Glu Glu Gly Thr Thr Leu Gly Ala Leu Ala Asn Pro Arg Arg Leu Thr
                325                 330                 335

Ala Met Ala Ser Val Ile Asp Asn Ala Arg Lys Val Gly Ala Ser Ile
            340                 345                 350

Glu Thr Gly Gly Glu Arg Ile Gly Ser Glu Gly Asn Phe Phe Ala Pro
        355                 360                 365

Thr Val Ile Ala Asn Val Pro Leu Asp Ala Asp Val Phe Asn Asn Glu
    370                 375                 380

Pro Phe Gly Pro Val Ala Ala Ile Arg Gly Phe Asp Lys Leu Glu Glu
385                 390                 395                 400

Ala Ile Ala Glu Ala Asn Arg Leu Pro Phe Gly Leu Ala Gly Tyr Ala
                405                 410                 415

Phe Thr Arg Ser Phe Ala Asn Val His Leu Leu Thr Gln Arg Leu Glu
            420                 425                 430

Val Gly Met Leu Trp Ile Asn Gln Pro Ala Thr Pro Trp Pro Glu Met
        435                 440                 445

Pro Phe Gly Gly Val Lys Asp Ser Gly Tyr Gly Ser Glu Gly Gly Pro
    450                 455                 460

Glu Ala Leu Glu Pro Tyr Leu Val Thr Lys Ser Val Thr Val Met Ala
465                 470                 475                 480

Val

<210> SEQ ID NO 105
<211> LENGTH: 1446
<212> TYPE: DNA
<213> ORGANISM: Artificial Sequence
<220> FEATURE:
<223> OTHER INFORMATION: synthetic DNA

<400> SEQUENCE: 105
atggccaatg tgacctatac ggatacccag ctgctgatcg atggcgaatg ggttgatgcg     60
gccagcggta aaacgattga tgtggttaac ccggcgaccg gcaaaccgat cggtcgtgtg    120
gcccatgcag gcattgccga tctggatcgc gccctggcag ccgcacagtc tggttttgaa    180
gcctggcgta aagtgccggc acacgaacgt gcggccacca tgcgtaaagc ggcggcgctg    240
gtgcgtgaac gtgccgatgc catcgcacag ctgatgacgc aggaacaggg caaaccgctg    300
accgaagccc gcgtggaagt tctgtctgcc gcagatatta tcgaatggtt tgcggatgaa    360
ggccgtcgcg tgtacggtcg tattgttccg ccgcgcaatc tgggtgccca gcagaccgtg    420 gttaagaac cggtgggtcc ggttgccgca tttaccccgt ggaacttccc ggtgaatcag    480
gtggttcgta aactgagcgc ggcgctggcc accggttgca gttttctggt taaagcgccg    540
gaagaaaccc cggcaagccc ggccgcactg ctgcgcgcgt tgtggatgc gggcgttccg    600 gcaggtgtga ttggtctggt ttatggtgat ccggcggaaa ttagctctta cctgatcccg    660
catccggtga ttcgtaaagt tacgtttacc ggcagcaccc cggtgggtaa acagctggcg    720
tctctggccg gtctgcatat gaaacgcgca accatggaac tgggcggtca cgcgccggtg    780
attgttgcag aagatgcgga tgtggcgctg gcggttaaag ccgccggcgg tgcaaaattc    840
cgtaatgccg gtcaggtgtg catcagtccg accgcttc tggttcataa cagcattcgt    900
gatgaattta cccgcgccct ggtgaaacac gcagaaggtc tgaaagttgg caacggtctg    960
```

-continued

```
gaagaaggca ccacgctggg tgcactggcc aatccgcgtc gcctgaccgc aatggcaagc    1020
gtgatcgata acgcgcgtaa agttggcgcc tctatcgaaa cgggcggtga acgcattggc    1080
agtgagggta acttttctcgc accgaccgtg attgcgaatg ttccgctgga tgcggatgtt    1140
```
```
gaagaaggca ccacgctggg tgcactggcc aatccgcgtc gcctgaccgc aatggcaagc    1020
gtgatcgata acgcgcgtaa agttggcgcc tctatcgaaa cgggcggtga acgcattggc    1080
agtgagggta acttttttcgc accgaccgtg attgcgaatg ttccgctgga tgcggatgtt    1140
tttaacaatg aaccgtttgg cccggttgca gcgatccgtg ttttgataa actggaagaa     1200 gcgattgccg aagcaaaccg cctgccgttt ggcctggccg ttatgcatt tacgcgtagt     1260 ttcgccaatg tgcacctgct gacccagcgc ctggaagttg gtatgctgtg atcaatcag     1320 ccggccaccc cgtggccgga aatgccgttt ggcggtgtga agatagtgg ctatggtagc     1380 gaaggcggtc cggaagccct ggaaccgtac ctggtgacga aaagcgtgac cgttatggca    1440
gtttga                                                               1446

<210> SEQ ID NO 106
<211> LENGTH: 1440
<212> TYPE: DNA
<213> ORGANISM: Halomonas boliviensis
<220> FEATURE:
<221> NAME/KEY: CDS
<222> LOCATION: (1)..(1440)

<400> SEQUENCE: 106 atg ggc gaa atg aac aac aat tta atc ggt ggc gta tgg cgc gag gcc     48
Met Gly Glu Met Asn Asn Asn Leu Ile Gly Gly Val Trp Arg Glu Ala
1               5                  10                  15 gat gat gtc tca gaa aac act aac ccc tcc gat gtg acg gat ctg atc     96
Asp Asp Val Ser Glu Asn Thr Asn Pro Ser Asp Val Thr Asp Leu Ile
            20                  25                  30 ggg ctt tat gcc cgc ggc ggt gcc cag gat gtg acc gat gcc gcc gaa   144
Gly Leu Tyr Ala Arg Gly Gly Ala Gln Asp Val Thr Asp Ala Ala Glu
        35                  40                  45 gcg gca gag gtc gca atg ccc gcc tgg gcc ggc gcg acc cct cag ctg   192
Ala Ala Glu Val Ala Met Pro Ala Trp Ala Gly Ala Thr Pro Gln Leu
    50                  55                  60 cgc gct gat ctg ctg gac cgc gtg gcc gca gag atc acc cgc cgc gaa   240
Arg Ala Asp Leu Leu Asp Arg Val Ala Ala Glu Ile Thr Arg Arg Glu
65                  70                  75                  80 gat gag att gcg acg atg ctg gcc tgc gaa gag ggt aag gtt ctg tta   288
Asp Glu Ile Ala Thr Met Leu Ala Cys Glu Glu Gly Lys Val Leu Leu
                85                  90                  95 gaa gcg ctg gga gaa gtt cgc cgc gcc gcg cat gtg ttt cgt ttt ttc   336
Glu Ala Leu Gly Glu Val Arg Arg Ala Ala His Val Phe Arg Phe Phe
            100                 105                 110 gcc gga gag gcg cta cgt ctg acg ggg gat gcc ctg gcc tcg gtg cga   384
Ala Gly Glu Ala Leu Arg Leu Thr Gly Asp Ala Leu Ala Ser Val Arg
        115                 120                 125 ccc ggc gtg gat gtg gag gtg acc cgc gag ccg tta ggc att gtc ggt   432
Pro Gly Val Asp Val Glu Val Thr Arg Glu Pro Leu Gly Ile Val Gly
    130                 135                 140 atc atc acc ccg tgg aac ttc ccc atc gcg att cct gcg tgg aaa att   480
Ile Ile Thr Pro Trp Asn Phe Pro Ile Ala Ile Pro Ala Trp Lys Ile
145                 150                 155                 160 gcc cct gcc tta gct tat ggc aac tgc gtg atc ttt aag cca gcg gaa   528
Ala Pro Ala Leu Ala Tyr Gly Asn Cys Val Ile Phe Lys Pro Ala Glu
                165                 170                 175 cag acg ccg ggc tca gcc cac ata ttg acc cag att att cat gag gcg   576
Gln Thr Pro Gly Ser Ala His Ile Leu Thr Gln Ile Ile His Glu Ala
            180                 185                 190 ggc tgc ccg gcg ggt gtt ttc aat ctc gtt atg ggg cgt ggc tcc gtc   624
Gly Cys Pro Ala Gly Val Phe Asn Leu Val Met Gly Arg Gly Ser Val
        195                 200                 205
```

| | | |
|---|---|---|
| gtc ggt gag gcg atg acc acg gat ccg cgc atc tcg gga att tcc ttt<br>Val Gly Glu Ala Met Thr Thr Asp Pro Arg Ile Ser Gly Ile Ser Phe<br>    210                            215                          220 | 672 |
| acc ggg tcg gtg cag gta ggg cgg cag ctg gct ggc gcc tgc gcg gcg<br>Thr Gly Ser Val Gln Val Gly Arg Gln Leu Ala Gly Ala Cys Ala Ala<br>225                            230                          235                      240 | 720 |
| aac atg aaa aaa ctt cag cta gag atg ggc ggt aag aac ccg gtg atc<br>Asn Met Lys Lys Leu Gln Leu Glu Met Gly Gly Lys Asn Pro Val Ile<br>                        245                          250                          255 | 768 |
| gtg atg gac gac gcc gat ctg gaa acc gct gtt tct gtc tgt ctc aac<br>Val Met Asp Asp Ala Asp Leu Glu Thr Ala Val Ser Val Cys Leu Asn<br>            260                            265                          270 | 816 |
| ggt gcc ttt tac cag acg ggg cag cgc tgt acc gca tcg tcg cgt cta<br>Gly Ala Phe Tyr Gln Thr Gly Gln Arg Cys Thr Ala Ser Ser Arg Leu<br>                        275                          280                          285 | 864 |
| atc gta cag tcg ggc atc cat gat gcc ttt atc gcg gaa ctc agt cgc<br>Ile Val Gln Ser Gly Ile His Asp Ala Phe Ile Ala Glu Leu Ser Arg<br>            290                            295                          300 | 912 |
| cag atg cag gcg ctc aag gtg ggg cat gcg ctc gcc gag ggg atg cag<br>Gln Met Gln Ala Leu Lys Val Gly His Ala Leu Ala Glu Gly Met Gln<br>305                            310                          315                      320 | 960 |
| att ggc ccc gtc gcc gcc cgg agt cag ctc gaa agc aat ctt tac tac<br>Ile Gly Pro Val Ala Ala Arg Ser Gln Leu Glu Ser Asn Leu Tyr Tyr<br>                            325                          330                          335 | 1008 |
| gtg gcg ctc gcc gct gaa gag ggc tgc gat gta ttg ggt gga gag cag<br>Val Ala Leu Ala Ala Glu Glu Gly Cys Asp Val Leu Gly Gly Glu Gln<br>                      340                          345                          350 | 1056 |
| ctc aca cgc gac act gaa ggg tat ttc cag gca ccc gca ctt ttc ctt<br>Leu Thr Arg Asp Thr Glu Gly Tyr Phe Gln Ala Pro Ala Leu Phe Leu<br>                            355                          360                          365 | 1104 |
| ggg gcg agt aat gcc atg cgt agc gcc cgt gaa gag atc ttc ggc ccc<br>Gly Ala Ser Asn Ala Met Arg Ser Ala Arg Glu Glu Ile Phe Gly Pro<br>        370                            375                          380 | 1152 |
| tgt gcc agc gtg att cgt gtc gat gac ttt gaa gaa gca gta gcg ctg<br>Cys Ala Ser Val Ile Arg Val Asp Asp Phe Glu Glu Ala Val Ala Leu<br>385                            390                          395                      400 | 1200 |
| gcc aat gac acc cag ttc ggt ctg tcg tcg ggg att tgt acc acc aat<br>Ala Asn Asp Thr Gln Phe Gly Leu Ser Ser Gly Ile Cys Thr Thr Asn<br>                            405                          410                          415 | 1248 |
| cta cgc tat gcg cgg gag ttc aag cgc cgt tct gcc gct ggc atg gtg<br>Leu Arg Tyr Ala Arg Glu Phe Lys Arg Arg Ser Ala Ala Gly Met Val<br>                    420                          425                          430 | 1296 |
| atg ctc aac ttg ccg acc gcg ggc gtg gat tat cac gtg ccc ttt ggc<br>Met Leu Asn Leu Pro Thr Ala Gly Val Asp Tyr His Val Pro Phe Gly<br>                  435                          440                          445 | 1344 |
| ggg cgt aaa gcg tcg agc ttc ggg tca cgt gag cag ggt agc tat gca<br>Gly Arg Lys Ala Ser Ser Phe Gly Ser Arg Glu Gln Gly Ser Tyr Ala<br>        450                            455                          460 | 1392 |
| gcc gaa ttc tat aca tcg gtg aaa acc gcc tat acg tat gcc ggt taa<br>Ala Glu Phe Tyr Thr Ser Val Lys Thr Ala Tyr Thr Tyr Ala Gly<br>465                            470                          475 | 1440 |

<210> SEQ ID NO 107
<211> LENGTH: 479
<212> TYPE: PRT
<213> ORGANISM: Halomonas boliviensis

<400> SEQUENCE: 107

Met Gly Glu Met Asn Asn Asn Leu Ile Gly Gly Val Trp Arg Glu Ala

```
  1               5                  10                 15
Asp Asp Val Ser Glu Asn Thr Asn Pro Ser Asp Val Thr Asp Leu Ile
             20                 25                 30
Gly Leu Tyr Ala Arg Gly Gly Ala Gln Asp Val Thr Asp Ala Ala Glu
             35                 40                 45
Ala Ala Glu Val Ala Met Pro Ala Trp Ala Gly Ala Thr Pro Gln Leu
 50                 55                 60
Arg Ala Asp Leu Leu Asp Arg Val Ala Ala Glu Ile Thr Arg Arg Glu
 65                 70                 75                 80
Asp Glu Ile Ala Thr Met Leu Ala Cys Glu Glu Gly Lys Val Leu Leu
                 85                 90                 95
Glu Ala Leu Gly Glu Val Arg Arg Ala Ala His Val Phe Arg Phe Phe
             100                105                110
Ala Gly Glu Ala Leu Arg Leu Thr Gly Asp Ala Leu Ala Ser Val Arg
             115                120                125
Pro Gly Val Asp Val Glu Val Thr Arg Glu Pro Leu Gly Ile Val Gly
             130                135                140
Ile Ile Thr Pro Trp Asn Phe Pro Ile Ala Ile Pro Ala Trp Lys Ile
145                150                155                160
Ala Pro Ala Leu Ala Tyr Gly Asn Cys Val Ile Phe Lys Pro Ala Glu
                 165                170                175
Gln Thr Pro Gly Ser Ala His Ile Leu Thr Gln Ile Ile His Glu Ala
             180                185                190
Gly Cys Pro Ala Gly Val Phe Asn Leu Val Met Gly Arg Gly Ser Val
             195                200                205
Val Gly Glu Ala Met Thr Thr Asp Pro Arg Ile Ser Gly Ile Ser Phe
210                215                220
Thr Gly Ser Val Gln Val Gly Arg Gln Leu Ala Gly Ala Cys Ala Ala
225                230                235                240
Asn Met Lys Lys Leu Gln Leu Glu Met Gly Gly Lys Asn Pro Val Ile
                 245                250                255
Val Met Asp Asp Ala Asp Leu Glu Thr Ala Val Ser Val Cys Leu Asn
             260                265                270
Gly Ala Phe Tyr Gln Thr Gly Gln Arg Cys Thr Ala Ser Ser Arg Leu
             275                280                285
Ile Val Gln Ser Gly Ile His Asp Ala Phe Ile Ala Glu Leu Ser Arg
             290                295                300
Gln Met Gln Ala Leu Lys Val Gly His Ala Leu Ala Glu Gly Met Gln
305                310                315                320
Ile Gly Pro Val Ala Ala Arg Ser Gln Leu Glu Ser Asn Leu Tyr Tyr
                 325                330                335
Val Ala Leu Ala Ala Glu Glu Gly Cys Asp Val Leu Gly Gly Glu Gln
             340                345                350
Leu Thr Arg Asp Thr Glu Gly Tyr Phe Gln Ala Pro Ala Leu Phe Leu
             355                360                365
Gly Ala Ser Asn Ala Met Arg Ser Ala Arg Glu Glu Ile Phe Gly Pro
             370                375                380
Cys Ala Ser Val Ile Arg Val Asp Asp Phe Glu Glu Ala Val Ala Leu
385                390                395                400
Ala Asn Asp Thr Gln Phe Gly Leu Ser Ser Gly Ile Cys Thr Thr Asn
                 405                410                415
Leu Arg Tyr Ala Arg Glu Phe Lys Arg Arg Ser Ala Ala Gly Met Val
             420                425                430
```

```
Met Leu Asn Leu Pro Thr Ala Gly Val Asp Tyr His Val Pro Phe Gly
        435                 440                 445

Gly Arg Lys Ala Ser Ser Phe Gly Ser Arg Glu Gln Gly Ser Tyr Ala
    450                 455                 460

Ala Glu Phe Tyr Thr Ser Val Lys Thr Ala Tyr Thr Tyr Ala Gly
465                 470                 475
```

<210> SEQ ID NO 108
<211> LENGTH: 1440
<212> TYPE: DNA
<213> ORGANISM: Artificial Sequence
<220> FEATURE:
<223> OTHER INFORMATION: synthetic DNA

<400> SEQUENCE: 108

| | | |
|---|---|---|
| atgggcgaaa tgaacaataa cctgatcggc ggtgtttggc gtgaagccga tgatgtgagt | 60 |
| gaaaatacca acccgagcga tgtgacggat ctgattggcc tgtatgcccg cggcggtgca | 120 |
| caggatgtta ccgatgcggc cgaagcggcc gaagtggcaa tgccggcctg gcaggtgca | 180 |
| acgccgcagc tgcgtgcgga tctgctggat cgcgttgccg cagaaatcac ccgtcgcgaa | 240 |
| gatgaaattg cgacgatgct ggcctgcgaa gaaggcaaag tgctgctgga agccctgggt | 300 |
| gaagttcgtc gcgcggccca tgttttcgt ttctttgcag gtgaagccct cgtctgacc | 360 |
| ggtgatgccc tggcatctgt tcgtccgggc gtggatgttg aagtgacccg gaaccgctg | 420 |
| ggcatcgtgg gtattatcac gccgtggaat ttcccgattg ccatcccggc atggaaaatc | 480 |
| gcaccggcgc tggcctatgg caactgcgtt attttaaac cggcagaaca gaccccgggt | 540 |
| agcgcgcata ttctgacgca gattatccac gaagcaggct gtccggcggg tgttttcaat | 600 |
| ctggtgatgg gccgtggtag cgtggttggt gaagcgatga ccacggatcc gcgcattagc | 660 |
| ggcatctctt ttaccggttc tgttcaagtg ggccgtcagc tggcaggtgc ctgcgcagcg | 720 |
| aatatgaaaa aactgcagct ggaaatgggc ggtaaaaacc cggttatcgt gatggatgat | 780 |
| gcggatctgg aaaccgccgt tagcgtgtgc ctgaacggcg cgttctatca gaccggtcag | 840 |
| cgttgtacgg ccagctctcg cctgattgtg cagtctggca tccatgatgc gtttattgcc | 900 |
| gaactgagtc gtcagatgca gccctgaaa gttggtcacg ccctggcaga aggcatgcag | 960 |
| attggtccgg tggccgcacg cagtcagctg gaaagcaatc tgtattacgt tgcgctggcg | 1020 |
| gccgaagaag gctgtgatgt gctgggcggt gaacagctga cccgtgatac ggaaggctac | 1080 |
| tttcaggcgc cggccctgtt cctgggtgca tctaacgcga tgcgtagtgc cgcgaagaa | 1140 |
| atctttggtc cgtgcgcaag tgttattcgc gtggatgatt cgaagaagc agttgcgctg | 1200 |
| gccaatgata cccagtttgg cctgagtagc ggtatttgta ccacgaacct gcgttatgcg | 1260 |
| cgcgaattta acgtcgcag cgcagcgggc atggtgatgc tgaatctgcc gaccgccggt | 1320 |
| gttgattacc acgtgccgtt tggcggtcgt aaagcgtcta gtttcggcag ccgcgaacag | 1380 |
| ggttcttatg ccgcagaatt ttacaccagc gtgaaaaccg cctatacgta cgcaggttaa | 1440 |

<210> SEQ ID NO 109
<211> LENGTH: 1467
<212> TYPE: DNA
<213> ORGANISM: Bacillus subtilis
<220> FEATURE:
<221> NAME/KEY: CDS
<222> LOCATION: (1)..(1467)

<400> SEQUENCE: 109

| | | |
|---|---|---|
| atg tct gtg atc acg gaa caa aac acg tac ctc aac ttt att aac gga<br>Met Ser Val Ile Thr Glu Gln Asn Thr Tyr Leu Asn Phe Ile Asn Gly<br>1               5                   10                  15 | | 48 |
| gag tgg gtt aag tct caa tca ggc gat atg gtc aaa gtc gaa aac cct<br>Glu Trp Val Lys Ser Gln Ser Gly Asp Met Val Lys Val Glu Asn Pro<br>            20                  25                  30 | | 96 |
| gcc gat gtg aat gat att gtc gga tat gta cag aat tca acg gct gaa<br>Ala Asp Val Asn Asp Ile Val Gly Tyr Val Gln Asn Ser Thr Ala Glu<br>        35                  40                  45 | | 144 |
| gat gtg gaa cgt gcc gtc acc gcc gcc aat gaa gcc aaa acg gct tgg<br>Asp Val Glu Arg Ala Val Thr Ala Ala Asn Glu Ala Lys Thr Ala Trp<br>    50                  55                  60 | | 192 |
| aga aag ctg acg ggt gcc gag cgc ggc caa tac tta tac aaa aca gcg<br>Arg Lys Leu Thr Gly Ala Glu Arg Gly Gln Tyr Leu Tyr Lys Thr Ala<br>65                  70                  75                  80 | | 240 |
| gat atc atg gag cag cgc ttg gag gaa atc gcc gcc tgt gca acg cgt<br>Asp Ile Met Glu Gln Arg Leu Glu Glu Ile Ala Ala Cys Ala Thr Arg<br>                85                  90                  95 | | 288 |
| gaa atg ggt aaa aca ttg ccg gaa gcg aag gga gaa aca gcc cgg ggg<br>Glu Met Gly Lys Thr Leu Pro Glu Ala Lys Gly Glu Thr Ala Arg Gly<br>            100                 105                 110 | | 336 |
| att gcc att ctg cgc tat tac gcc gga gag ggc atg cga aaa acg ggt<br>Ile Ala Ile Leu Arg Tyr Tyr Ala Gly Glu Gly Met Arg Lys Thr Gly<br>        115                 120                 125 | | 384 |
| gac gtc att ccg tct act gac aaa gac gcg ctc atg ttt acc acc cgt<br>Asp Val Ile Pro Ser Thr Asp Lys Asp Ala Leu Met Phe Thr Thr Arg<br>    130                 135                 140 | | 432 |
| gtt ccg ctc ggt gtg gtc ggt gtg att tct ccg tgg aac ttc cca gtg<br>Val Pro Leu Gly Val Val Gly Val Ile Ser Pro Trp Asn Phe Pro Val<br>145                 150                 155                 160 | | 480 |
| gcg att ccg att tgg aaa atg gcg ccg gca ttg gta tac ggc aat acc<br>Ala Ile Pro Ile Trp Lys Met Ala Pro Ala Leu Val Tyr Gly Asn Thr<br>                165                 170                 175 | | 528 |
| gtt gtc atc aaa ccg gcg aca gaa aca gct gtg aca tgc gcg aag atc<br>Val Val Ile Lys Pro Ala Thr Glu Thr Ala Val Thr Cys Ala Lys Ile<br>            180                 185                 190 | | 576 |
| att gcc tgc ttt gag gaa gcg ggg ctc ccg gca ggg gtc atc aat ttg<br>Ile Ala Cys Phe Glu Glu Ala Gly Leu Pro Ala Gly Val Ile Asn Leu<br>        195                 200                 205 | | 624 |
| gtg aca ggc ccg ggt tct gtt gtc ggg cag ggg ctt gct gag cat gac<br>Val Thr Gly Pro Gly Ser Val Val Gly Gln Gly Leu Ala Glu His Asp<br>    210                 215                 220 | | 672 |
| ggt gta aac gcc gtt acg ttt acc ggt tca aat caa gtc gga aaa atc<br>Gly Val Asn Ala Val Thr Phe Thr Gly Ser Asn Gln Val Gly Lys Ile<br>225                 230                 235                 240 | | 720 |
| atc ggg caa gcc gct tta gcg agg gga gcc aaa tat cag ctt gag atg<br>Ile Gly Gln Ala Ala Leu Ala Arg Gly Ala Lys Tyr Gln Leu Glu Met<br>                245                 250                 255 | | 768 |
| ggc ggc aaa aac cct gtc atc gta gct gat gac gct gac ctt gaa gct<br>Gly Gly Lys Asn Pro Val Ile Val Ala Asp Asp Ala Asp Leu Glu Ala<br>            260                 265                 270 | | 816 |
| gcg gca gaa gct gtc ata acg ggg gcc ttc cgt tca acc ggc cag aaa<br>Ala Ala Glu Ala Val Ile Thr Gly Ala Phe Arg Ser Thr Gly Gln Lys<br>        275                 280                 285 | | 864 |
| tgc acc gcg aca agc cgt gtc atc gta caa agc gga att tac gag cgc<br>Cys Thr Ala Thr Ser Arg Val Ile Val Gln Ser Gly Ile Tyr Glu Arg<br>    290                 295                 300 | | 912 |
| ttt aaa gaa aaa ctg ctc cag cgc aca aaa gat att aca atc gga gac<br>Phe Lys Glu Lys Leu Leu Gln Arg Thr Lys Asp Ile Thr Ile Gly Asp<br>305                 310                 315                 320 | | 960 |

```
agc tta aaa gag gat gtc tgg atg gga ccg ata gcc agc aag aat cag    1008
Ser Leu Lys Glu Asp Val Trp Met Gly Pro Ile Ala Ser Lys Asn Gln
            325                 330                 335 ctt gat aac tgc ctg tca tac att gag aaa ggc aaa cag gag ggc gct    1056
Leu Asp Asn Cys Leu Ser Tyr Ile Glu Lys Gly Lys Gln Glu Gly Ala
        340                 345                 350 tcc ctt tta ata gga gga gaa aag ctg gag aac gga aag tat caa aac    1104
Ser Leu Leu Ile Gly Gly Glu Lys Leu Glu Asn Gly Lys Tyr Gln Asn
    355                 360                 365 ggc tat tat gtt cag cct gcc atc ttt gac aat gtg aca tct gag atg    1152
Gly Tyr Tyr Val Gln Pro Ala Ile Phe Asp Asn Val Thr Ser Glu Met
370                 375                 380 aca att gcc cag gag gaa att ttc ggt ccg gtg atc gcc ttg atc aag    1200
Thr Ile Ala Gln Glu Glu Ile Phe Gly Pro Val Ile Ala Leu Ile Lys
385                 390                 395                 400 gtg gac tcg ata gag gag gcg ctg aac atc gcc aat gat gtg aag ttc    1248
Val Asp Ser Ile Glu Glu Ala Leu Asn Ile Ala Asn Asp Val Lys Phe
                405                 410                 415 ggt tta agt gca tcc atc ttc acg gaa aac atc ggc cga atg ctt tct    1296
Gly Leu Ser Ala Ser Ile Phe Thr Glu Asn Ile Gly Arg Met Leu Ser
            420                 425                 430 ttc att gat gaa atc gat gcc ggg ctg gtt cgg atc aat gca gaa agc    1344
Phe Ile Asp Glu Ile Asp Ala Gly Leu Val Arg Ile Asn Ala Glu Ser
        435                 440                 445 gca ggt gtt gag ctg cag gcg cct ttt ggc ggc atg aag cag tcg agc    1392
Ala Gly Val Glu Leu Gln Ala Pro Phe Gly Gly Met Lys Gln Ser Ser
    450                 455                 460 tcc cac tcc cga gaa cag ggt gag gca gcg aag gac ttt ttc aca gcg    1440
Ser His Ser Arg Glu Gln Gly Glu Ala Ala Lys Asp Phe Phe Thr Ala
465                 470                 475                 480 atc aaa act gtt ttt gtg aag ccg taa                                1467
Ile Lys Thr Val Phe Val Lys Pro
                485

<210> SEQ ID NO 110
<211> LENGTH: 488
<212> TYPE: PRT
<213> ORGANISM: Bacillus subtilis

<400> SEQUENCE: 110

Met Ser Val Ile Thr Glu Gln Asn Thr Tyr Leu Asn Phe Ile Asn Gly
1               5                   10                  15

Glu Trp Val Lys Ser Gln Ser Gly Asp Met Val Lys Val Glu Asn Pro
            20                  25                  30

Ala Asp Val Asn Asp Ile Val Gly Tyr Val Gln Asn Ser Thr Ala Glu
        35                  40                  45

Asp Val Glu Arg Ala Val Thr Ala Ala Asn Glu Ala Lys Thr Ala Trp
    50                  55                  60

Arg Lys Leu Thr Gly Ala Glu Arg Gly Gln Tyr Leu Tyr Lys Thr Ala
65                  70                  75                  80

Asp Ile Met Glu Gln Arg Leu Glu Glu Ile Ala Ala Cys Ala Thr Arg
                85                  90                  95

Glu Met Gly Lys Thr Leu Pro Glu Ala Lys Gly Glu Thr Ala Arg Gly
            100                 105                 110

Ile Ala Ile Leu Arg Tyr Tyr Ala Gly Glu Gly Met Arg Lys Thr Gly
        115                 120                 125

Asp Val Ile Pro Ser Thr Asp Lys Asp Ala Leu Met Phe Thr Thr Arg
    130                 135                 140
```

```
Val Pro Leu Gly Val Gly Val Ile Ser Pro Trp Asn Phe Pro Val
145                 150                 155                 160

Ala Ile Pro Ile Trp Lys Met Ala Pro Ala Leu Val Tyr Gly Asn Thr
            165                 170                 175

Val Val Ile Lys Pro Ala Thr Glu Thr Ala Val Thr Cys Ala Lys Ile
            180                 185                 190

Ile Ala Cys Phe Glu Glu Ala Gly Leu Pro Ala Gly Val Ile Asn Leu
            195                 200                 205

Val Thr Gly Pro Gly Ser Val Gly Gln Gly Leu Ala Glu His Asp
            210                 215                 220

Gly Val Asn Ala Val Thr Phe Thr Gly Ser Asn Gln Val Gly Lys Ile
225                 230                 235                 240

Ile Gly Gln Ala Ala Leu Ala Arg Gly Ala Lys Tyr Gln Leu Glu Met
            245                 250                 255

Gly Gly Lys Asn Pro Val Ile Val Ala Asp Asp Ala Asp Leu Glu Ala
            260                 265                 270

Ala Ala Glu Ala Val Ile Thr Gly Ala Phe Arg Ser Thr Gly Gln Lys
            275                 280                 285

Cys Thr Ala Thr Ser Arg Val Ile Val Gln Ser Gly Ile Tyr Glu Arg
290                 295                 300

Phe Lys Glu Lys Leu Leu Gln Arg Thr Lys Asp Ile Thr Ile Gly Asp
305                 310                 315                 320

Ser Leu Lys Glu Asp Val Trp Met Gly Pro Ile Ala Ser Lys Asn Gln
            325                 330                 335

Leu Asp Asn Cys Leu Ser Tyr Ile Glu Lys Gly Lys Gln Glu Gly Ala
            340                 345                 350

Ser Leu Leu Ile Gly Gly Glu Lys Leu Glu Asn Gly Lys Tyr Gln Asn
            355                 360                 365

Gly Tyr Tyr Val Gln Pro Ala Ile Phe Asp Asn Val Thr Ser Glu Met
            370                 375                 380

Thr Ile Ala Gln Glu Glu Ile Phe Gly Pro Val Ile Ala Leu Ile Lys
385                 390                 395                 400

Val Asp Ser Ile Glu Glu Ala Leu Asn Ile Ala Asn Asp Val Lys Phe
            405                 410                 415

Gly Leu Ser Ala Ser Ile Phe Thr Glu Asn Ile Gly Arg Met Leu Ser
            420                 425                 430

Phe Ile Asp Glu Ile Asp Ala Gly Leu Val Arg Ile Asn Ala Glu Ser
            435                 440                 445

Ala Gly Val Glu Leu Gln Ala Pro Phe Gly Gly Met Lys Gln Ser Ser
            450                 455                 460

Ser His Ser Arg Glu Gln Gly Glu Ala Ala Lys Asp Phe Phe Thr Ala
465                 470                 475                 480

Ile Lys Thr Val Phe Val Lys Pro
                485

<210> SEQ ID NO 111
<211> LENGTH: 30
<212> TYPE: DNA
<213> ORGANISM: Artificial Sequence
<220> FEATURE:
<223> OTHER INFORMATION: primer Ptac_xylXABC_F

<400> SEQUENCE: 111
tgcgaagggc cttcggagcg atccggaggc                                    30
```

<210> SEQ ID NO 112
<211> LENGTH: 36
<212> TYPE: DNA
<213> ORGANISM: Artificial Sequence
<220> FEATURE:
<223> OTHER INFORMATION: primer Ptac_xylXABC_R

<400> SEQUENCE: 112
cgaaggccct tcgcattaga catggcggac ctcatg                                36

<210> SEQ ID NO 113
<211> LENGTH: 36
<212> TYPE: DNA
<213> ORGANISM: Artificial Sequence
<220> FEATURE:
<223> OTHER INFORMATION: primer Ptac_xylABCD_F

<400> SEQUENCE: 113
caatttcaca caggaggatg accgacaccc tgcgcc                                36

<210> SEQ ID NO 114
<211> LENGTH: 30
<212> TYPE: DNA
<213> ORGANISM: Artificial Sequence
<220> FEATURE:
<223> OTHER INFORMATION: primer Ptac_xylABCD_R

<400> SEQUENCE: 114
cctcctgtgt gaaattgtta tccgctcacg                                       30

<210> SEQ ID NO 115
<211> LENGTH: 35
<212> TYPE: DNA
<213> ORGANISM: Artificial Sequence
<220> FEATURE:
<223> OTHER INFORMATION: primer Ptac_xylXBCD_F

<400> SEQUENCE: 115
cgaaagcttc ccgcgatgtc ctcagccatc tatcc                                 35

<210> SEQ ID NO 116
<211> LENGTH: 30
<212> TYPE: DNA
<213> ORGANISM: Artificial Sequence
<220> FEATURE:
<223> OTHER INFORMATION: primer Ptac_xylXBCD_R

<400> SEQUENCE: 116
cgcgggaagc tttcgattag aggaggccgc                                       30

<210> SEQ ID NO 117
<211> LENGTH: 37
<212> TYPE: DNA
<213> ORGANISM: Artificial Sequence
<220> FEATURE:
<223> OTHER INFORMATION: primer yjhG_F

<400> SEQUENCE: 117
cacaaggaga ctcccatgtc tgttcgcaat atttttg                               37

<210> SEQ ID NO 118
<211> LENGTH: 36
<212> TYPE: DNA
<213> ORGANISM: Artificial Sequence
<220> FEATURE:
<223> OTHER INFORMATION: primer yjhG_R

```
<400> SEQUENCE: 118
gaactggcgg ctccctcagt ttttattcat aaaatc                        36

<210> SEQ ID NO 119
<211> LENGTH: 36
<212> TYPE: DNA
<213> ORGANISM: Artificial Sequence
<220> FEATURE:
<223> OTHER INFORMATION: primer yagF_F

<400> SEQUENCE: 119
cacaaggaga ctcccatgac cattgagaaa attttc                        36

<210> SEQ ID NO 120
<211> LENGTH: 38
<212> TYPE: DNA
<213> ORGANISM: Artificial Sequence
<220> FEATURE:
<223> OTHER INFORMATION: primer yagF_R

<400> SEQUENCE: 120
gaactggcgg ctcccttaaa ttccgagcgc tttttac                       38
```